US011718832B2

(12) United States Patent
Kim et al.

(10) Patent No.: US 11,718,832 B2
(45) Date of Patent: Aug. 8, 2023

(54) METHOD TO REDUCE ONCOGENIC POTENTIAL OF INDUCED PLURIPOTENT STEM CELLS FROM AGED DONORS

(71) Applicant: MEMORIAL SLOAN-KETTERING CANCER CENTER, New York, NY (US)

(72) Inventors: Kitai Kim, New York, NY (US); Maria Skamagki, New York, NY (US); Yildirim Dogan, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 678 days.

(21) Appl. No.: 15/517,014

(22) PCT Filed: Oct. 6, 2015

(86) PCT No.: PCT/US2015/054319
§ 371 (c)(1),
(2) Date: Apr. 5, 2017

(87) PCT Pub. No.: WO2016/057574
PCT Pub. Date: Apr. 14, 2016

(65) Prior Publication Data

US 2018/0282701 A1 Oct. 4, 2018

Related U.S. Application Data

(60) Provisional application No. 62/060,532, filed on Oct. 6, 2014, provisional application No. 62/121,463, filed on Feb. 26, 2015, provisional application No. 62/121,460, filed on Feb. 26, 2015.

(51) Int. Cl.

| | |
|---|---|
| ***C12N 5/074*** | (2010.01) |
| ***C07K 14/47*** | (2006.01) |
| ***C12N 5/10*** | (2006.01) |
| ***C12N 15/85*** | (2006.01) |

(52) U.S. Cl.
CPC ........ *C12N 5/0696* (2013.01); *C07K 14/4702* (2013.01); *C12N 5/10* (2013.01); *C12N 15/85* (2013.01); *C12N 2501/50* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/71* (2013.01); *C12N 2501/998* (2013.01); *C12N 2510/00* (2013.01)

(58) Field of Classification Search
CPC ........ C12N 5/0696; C12N 5/10; C12N 15/85; C12N 2501/50; C12N 2501/602; C12N 2501/603; C12N 2501/604; C12N 2501/605; C12N 2501/606; C12N 2501/608; C12N 2501/71; C12N 2501/998; C12N 2510/00; C07K 14/4702
USPC ............... 435/325, 455, 320.1, 377; 530/350
See application file for complete search history.

(56) References Cited

U.S. PATENT DOCUMENTS 8,071,378 B2 * 12/2011 Snyder .................. A61P 35/00 435/377
2012/0142094 A1 6/2012 Duan
2014/0056860 A1 2/2014 Prieur et al.

FOREIGN PATENT DOCUMENTS

JP 2010-521990 A 7/2010
WO WO 2013/177228 11/2013

OTHER PUBLICATIONS

Barcena et al. (2014) Nat. Cell. Biol., vol. 19(9), 1012-1013.*
Miller et al. (2013) Cell Stem Cell., vol. 13(6), 691 -705.*
Wang et al. (2007) Stem Cells, vol. 25, 2173-2182.*
Han et al. (2011) Antioxidants & Redox Signaling, vol. 15 (7), 1799-1820.*
Park et al., "Reprogramming of human somatic cells to pluripotency with defined factors," Nature, vol. 451, pp. 2-8 (Jan. 2008).
Yu et al., "Zfp206, Oct4 and Sox2 are integrated components of a transcriptional regulatory network in embryonic stem cells," Journal of Biological Chemistry, vol. 284, No. 45, pp. 31327-31335 (Nov. 6, 2008).
Yu, Hong-Bing et al., "Zfp206, Oct4, and Sox2 are integrated components of a transcriptional regulatory network in embryonic stem cells", The Journal of Biological Chemistry, Epub. Sep. 9, 2009, vol. 284, No. 45, pp. 31323-31335.
Prigione, Alessandro et al., "Mitochondrial-associated cell death mechanisms are reset to an embryonic-like state in aged donor-derived iPS cells harboring chromosomal aberrations", Plos One, Epub. Nov. 14, 2011, vol. 6, No. 111, Article No. e27352 (internal pp. 1-15).

(Continued)

*Primary Examiner* — Anne Marie S Wehbe
(74) *Attorney, Agent, or Firm* — Foley & Lardner LLP

(57) ABSTRACT

Disclosed are findings that: (a) induced pluripotent stem cells derived from aged donors (A-iPSC) show increased genomic instability, a defect in apoptosis, a defect in glucose metabolism, and a blunted DNA damage response are compared to those derived from young donors (Y-iPSC); and (b) inhibition of excessive glutathione-mediated $H_2O_2$ scavenging activity, found to be associated with A-iPSC and in turn inhibiting DNA damage response and apoptosis, substantially rescues these defects and reduces the oncogenic potential of A-iPSC. Supplementation of pluripotency factor ZSCAN10 (shown to be poorly activated in A-iPSC and to act upstream of glutathione involvement), e.g., by expression as an adjunct to the four Yamanaka iPSC reprogramming factors, led to substantial recovery of genomic stability, DNA damage response, and apoptosis in A-iPSC through enhancing GLUT3 and normalizing homeostasis of glutathione/$H_2O_2$; GLUT3 (a pluripotent stem cell-specific glucose transporter acting upstream of glutathione and also poorly activated in A-iPSC) has similar effects, indicating that inhibition of glutathione/$H_2O_2$ notably through delivery of ZSCAN 10 and/or GLUT3 and/or an exosome subunit will be clinically useful, resulting in A-iPSC of improved properties and reduced oncogenic potential.

15 Claims, 27 Drawing Sheets

Specification includes a Sequence Listing.

(56) References Cited

OTHER PUBLICATIONS

Kim, Kitai et al., "Donor cell type can influence the epigenome and differentiation potential of human induced pluripotent stem cells", Nature Biotechnology, Nov. 27, 2011, vol. 29, No. 12, pp. 1117-1119.
International Search Report and Written Opinion in corresponding PCT Application No. PCT/US2015/054319, dated Jan. 25, 2016.
Takahashi et al., "Induction of Pluripotent Stem Cells from Mouse Embryonic and Adult Fibroblast Cultures by Defined Factors", Cell 126: 663-676, Aug. 25, 2006.
Gonzalez, F. et al., "Methods for making induced pluripotent stem cells: reprogramming à la carte", Nature Reviews Genetics 12: 231-242 (Apr. 1, 2011).
Park et al., "Disease-specific induced pluripotent stem (iPS) cells", Cell 134:877-86, Sep. 5, 2008.
Kim et al., "Donor cell type can influence the epigenome and differentiation potential of human induced pluripotent stem cells", Nat Biotechnol 29(12): 1117-1119, 2011, Jun. 1, 2012.
Kim et al., "Epigenetic memory in induced pluripotent stem cells", Nature 467(7313):285-290, 2010, Aug. 5, 2011.
Nakagawa, M. et al., "Generation of induced pluripotent stem cells without Myc from mouse and human fibroblasts", Nat Biotechnol. Jan. 2008; 26(1): 101-6.
Chen IP et al., "Induced Pluripotent Stem Cell Reprogramming by Integration-Free Sendai Virus Vectors from Peripheral Blood of Patients with Craniometaphyseal Dysplasia", Cell Reprogram. Dec. 2013;15(6):503-13.
Lieu PT et al., "Generation of Induced Pluripotent Stem Cells with CytoTune, a Non-Integrating Sendai Virus", (Apr. 2013) Generation of Induced Pluripotent Stem Cells with CytoTune, a Non- Integrating Sendai Virus, Methods Mol. Biol. 2013;997:45-56.
"EBioscience." EBioscience Reagents for Immunology, Multicolor Flow Cytometry, and Biological System Analysis. N.p., n.d. Web. <http://www.ebioscience.com/knowledge-center/cell-type/induced-pluripotent-stem-cells.htm#benefits%20of%20rna>. Copyright 2007.
Warren, L. et al., "Feeder-Free Derivation of Human Induced Pluripotent Stem Cells with Messenger RNA", Nature Scientific reports, 2:#657 (Sep. 14, 2012).
Kim, D. et al., "Generation of human induced pluripotent stem cells by direct delivery of reprogramming proteins", Cell Stem Cell. Jun. 5, 2009; 4(6):472-6.
Stoll EA, Horner PJ, Rostomily RC, "The impact of age on oncogenic potential: tumorinitiating cells and the brain microenvironment", Aging Cell. Oct. 2013; 12(5):733-41. PMID: 23711239.
Liu, J. C. et al., "High mitochondrial priming sensitizes hESCs to DNA-damage-induced Apoptosis", Cell stem cell 13, 483-491, doi: 10.1016/j.stem.2013.07.018 ( Oct. 2013).
Donnerstag, B. et al., "Reduced glutathione and S-acetylglutathione as selective apoptosisinducing agents in cancer therapy", Cancer Lett. Dec. 2, 19960; 110(1-2):63-70.
Database, GeneCards Human Gene. "ZSCAN10 Gene(Protein Coding)." GeneCards Is a Searchable, Integrative Database That Provides Comprehensive, User-friendly Information on All Annotated and Predicted Human Genes. N.p., n.d. Web. Feb. 24, 2015. <http://www.genecards.org/cgi-bin/carddisp.pl?gene=ZSCAN10>.
DNASU plasmid Repository at Tempe Arizona http://dnasu.org/DNASU/GetCloneDetail.do?cloneid=295134; last visited Feb. 24, 2015.
Zhou H, et al., "Generation of induced pluripotent stem cells using recombinant proteins", Cell Stem Cell 4: 381-384, May 8, 2009.
Singh, VK et al., Induced pluripotent stem cells: applications in regenerative medicine, disease modeling, and drug discovery, Front. In Dev. Biol. 3(2): 1-18, Feb. 2015.
Yu, J., Vodyanik, M. A., Smuga-Otto, K., Antosiewicz-Bourget, J., Frane, J. L., Tian, S., et al., "Induced pluripotent stem cell lines derived from human somatic cells", Science 318, 1917-1920. doi: 10.126/science.151526. Dec. 21, 2007.
Huangfu, D., Macht, R., Guo, W., Eijkelenboom, A., Snitow, M., Chen, A. E., et al., "Induction of pluripotent stem cells by defined factors is greatly improved by small-molecule compounds", Nat. Biotechnol. 26, 795-1797. doi:10.1038/nbtl418, Jul. 2008.
Dimos, J. T., Rodolfa, K. T., Niakan, K. K., Weisenthal, L. M., Mitsumoto, FL, Chung, W., et al., "Induced pluripotent stem cells generated from patients with ALS can be differentiated into motor neurons", Aug. 29, 2008 Science 321, 1218-1221. doi: 10.1126/science.1158799.
Hanna, J., Markoulaki, S., Schorderet, P., Carey, B. W., Beard, C, Wernig, M., et al., "Direct reprogramming of terminally differentiated mature B Lymphocytes to pluripotency", Cell 133, 250-264. doi: 10.1016/J.cell2008.03.028, Apr. 18, 2008.
Mali, P., Ye, Z., Hommond, H. FL, Yu, X., Lin, J., Chen, G., et al., "Improved efficiency and pace of generating induced pluripotent stem cells from human adult and fetal fibroblasts", Aug. 2008, Stem Cells 26, 1998- 2005. doi: 10.11634/stemcells.2008-0346.
Marson, A., Foreman, R., Chevalier, B., Bilodeau, S., Kahn, M., Young, R. A., et al., "Wnt signaling promotes reprogramming of somatic cells to pluripotency", Aug. 7, 2008, Cell Stem Cell 3, 132-135. doi: 10.1016/j.stem.2008.06.019.
Mikkelsen, T. S., Hanna, J., Zhang, X., Ku, M., Wernig., M., Schorderet, P., et al., "Dissecting direct reprogramming through integrative genomic analysis", Jul. 3, 2008, Nature 454, 49-55. doi: 10.1038/nature 07056.
Park, I. H. Zhao, R., West, J. A., Yabuchi, A., Huo, H., Ince, T. A., et al., "Reprogramming of human somatic cells to pluripotency with defined factors", Jan. 10, 2008, Nature 451, 141-146. doi: 10.1038/nature 06534.
Shi, Y., Desponts, C, Do, J. T. Hahm, H. S., Scholer, H. R., and Ding, S., "Induction of pluripotent stem cells from mouse embryonic fibroblasts by Oct4 and Klf4 with small-molecule compounds", Nov. 6, 2008, Cell Stem Cell 3, 568-574. doi: 10.1016/J.stem.2008.10.004.
Shi, Y., Do, J. T. Desponts, C, Hahm, H. S., Scholer, H. R., and Ding, S., "A combined chemical and genetic approach for the generation of induced pluripotent stem cells", Jun. 2008, Cell Stem Cell !, 525-528. doi: 10.1016j.stem.2008.05.011.
Takahashi, K et al., "Induction of Pluripotent Stem Cells from Adult Human Fibroblasts by Defined Factors", Cell. Nov. 30, 2007;131(5):861-72.
"SLC2A3 Solute Carrier Family 2 Member 3 [Homo Sapiens (human)]—Gene—NCBI." National Center for Biotechnology Information. U.S. National Library of Medicine, n.d. Web. Jun. 15, 2016. <https://www.ncbi.nlm.nih.gov/gene/6515>.
"MyBioSource: Your source for antibodies, proteins, ELISA kits and so much more!." MyBioSource.com. N.p., n.d. Web. <http://www.mybiosource.com/datasheet.php?products_id=1214582+>. (last visited Feb. 25, 2015).
Bagci, H. et al., "DNA Demethylation in Pluripotency and Reprogramming: The Role of Tet Proteins and Cell Division", Cell Stem Cell 3,:265-269 (Sep. 5, 2013).
Schmid et al., "The exosome: a multipurpose RNA-decay machine", Sep. 9, 2008, Trends in Biochemical Sciences vol. 33 No. 10, pp. 501-510.
Singh et al., "Glutathione Peroxidase 2, the Major Cigarette Smoke-Inducible Isoform of GPX in Lungs, Is Regulated by Nrf2", Am J Respir Cell Mol Biol. 35(6):639-50 (Jun. 1, 2006).
Yu et al., "Zfp206, Oct4, and Sox2 Are Integrated Components of a Transcriptional Regulatory Network in Embryonic Stem Cells", J Biol Chem. 284(45): 31327-31335 (Sep. 4, 2009).
"World's Largest Collection of CDNA Clones." OriGene—CDNA Clones. N.p., n.d. Web. 2017. <http://www.origene.com/cDNA/default.mspx>.
Sander and Joung, "CRISPR-Cas systems for genome editing, regulation and targeting", Nature Biotechnology 32, 347-355 (Apr. 2014).
Vanoni MA and Curti B, "Structure-Function Studies of Glutamate Synthases: A Class of Self-regulated Iron-sulfur Flavoenzymes Essential for Nitrogen Assimilation", IUBMB Life. 60(5):287-300 (May 2008).
Hensley et al., "Glutamine and cancer: cell biology, physiology, and clinical opportunities", J Clin Invest. 123(9):3678-84 (Sep. 2013).

(56) References Cited

OTHER PUBLICATIONS

Koh et al., “Novel retroviral vectors to facilitate expression screens in mammalian cells”, Nucleic Acids Res. 30: e142, 2000. Accepted Nov. 2, 2002.
Kim et al., “An extended transcriptional network for pluripotency of embryonic stem cells”, Cell 132(6) 1049-61(Mar. 21, 2008).
Harvard PlasmID Database. N.p., n.d. Web. <https://plasmid.med.harvard.edu/PLASMID/>. 2004-2017.
Abm. Source for MiRNA, Stem Cell, Viral Vector, Antibody, PCR and More. N.p., n.d. Web. Oct. 6, 2015. <https://www.abmgood.com/>.
Tsuda et al., “The mammalian exosome mediates the efficient degradation of mRNAs that contain AU-rich elements”, AATEX 11 (2), 118-128, Sep. 27, 2005.
Schoenberg et al., “Regulation of cytoplasmic mRNA decay”, Nat Rev Genet. 13 (4): 246-259 (Oct. 1, 2012).
Mukherjee et al., “The mammalian exosome mediates the efficient degradation of mRNAs that contain AU-rich elements”, EMBO J. 21(1-2): 165-174 (Jan. 15, 2002).
Johnson et al., “Dysregulation of Glutathione Homeostasis in Neurodegenerative Diseases”, Nutrients.4(10):1399-440 (Oct. 9, 2012).
Flavahan, WA, et al., “Brain Tumor Initiating Cells Adapt to Restricted Nutrition through Preferential Glucose Uptake”, Nature Neuroscience 16: 1373-1382 (Oct. 2013).
“FU-tet-o-hOct4 (Plasmid #19778).” Addgene. N.p., n.d. Web. Feb. 25, 2015. <http://www.addgene.org/19778/>.
“Haematoxylin Eosin (H&E) Staining.” Protocols Online. N.p., Oct. 3, 2016. Web. <http://www.protocolsonline.com/histology/dyes-and-stains/haematoxylin-eosin-he-staining/>.
National Society for Histotechnology. “Guidelines for Hematoxylin & Eosin Staining.” (n.d.): n. pag. Web. Jul. 2001.
“S1c2a3 Solute Carrier Family 2 (facilitated Glucose Transporter), Member 3 [Mus Musculus (house Mouse)]—Gene—NCBI.” National Center for Biotechnology Information. U.S. National Library of Medicine, n.d. Web. Last updated Apr. 3, 2017. <https://www.ncbi.nlm.nih.gov/gene/20527>.
“S1c2a3 Solute Carrier Family 2 (facilitated Glucose Transporter), Member 3 [Rattus Norvegicus (Norway Rat)]—Gene—NCBI.” National Center for Biotechnology Information. U.S. National Library of Medicine, n.d. Web. Last updated Apr. 9, 2017. <https://www.ncbi.nlm.nih.gov/gene/25551>.
Dannenmann, B et al., “High Glutathione and Glutathione Peroxidase-2 Levels Mediate Cell-Type-Specific DNA Damage Protection in Human Induced Pluripotent Stem Cells,” Stem Cell Reports, vol. 4, No. 5, pp. 886-898 (May 1, 2015).
Hussein, S. et al., “Copy number variation and selection during reprogramming to pluripotency,” Nature, vol. 471, No. 7336, pp. 58-62 (Mar. 3, 2011).
Lapasset, L. et al., “Rejuvenating senescent and centenarian human cells by reprogramming through the pluripotent state,” Genes & Development, Cold Spring Harbor Laboratory Press, vol. 25, pp. 2248-2253 (Nov. 1, 2011).

* cited by examiner

E

F

G

A
Number of colonies that defective on HPRT promoter activity after 6-TG selection / 10⁶ cells
100
90
80
70
60
50
40
30
20
10
0
p=0.457
p=0.007
p=0.007
ESC
Y-iPSC
A-iPSC
A-iPSC ZSCAN10
B
ESC (n=6)
C
Y-iPSC (n=12)
D
A-iPSC (n=28, 48%)
E
A-iPSC (n=30, 52%)

D
ATM-/- H2AX-/- ESC
A-iPSC
Y-iPSC
Y-iPSC-shZSCAN10
PHLEO
p-ATM
pH2AX
β-actin
p53-/- iPSC
p53
E
Endogenous ZSCAN10 levels normalized to β actin
1.5
1
0.5
0
p=0.0061
Fibroblast
ESC
Y-iPSC
Y-iPSC shRNA ZSCAN10
F
Y-PSC
PHLEO
10 Gy
0 Gy
A-iPSC-ZSCAN10
p53 -/- iPSC
Phleo
β-ACTIN
G
H2O2
A-iPSC ZSCAN10
pATM

A

B

E

C
O2 consumption rate (pmol/min/10,000)
120
100
80
60
40
20
0
p=0.036
p=8.9e-5
p=9e-6
ESC
Y-iPSC
A-iPSC
A-iPSC-ZSCAN10
A-iPSC-GLUT3
D
ESC-ATM-/-
ESC
Y-iPSC
A-iPSC
A-iPSC-Glut3
#15
#17
#18
PHLEO
p-ATM
β-ACTIN
E
Fold enrichment relative to IgG
50
45
40
35
30
25
20
15
10
5
0
ESC
ESC-IgG
Y-iPSC
Y-iPSC-IgG
A-iPSC
A-iPSC-IgG A
Background Distribution of ARE3-1
UUAUUUA(A/U)(A/U)
Fischers Exact test
p-value = 0.01224
Frequency per 100,000 Samples
Count of Observed ARE Containing 3' UTRs
B
Relative mRNA levels normalized to β-ACTIN
EXOSC1
EXOSC2
EXOSC5
FESC
Y-iPSC
A-iPSC-ZSCAN10
A-iPSC A
Relative GPX2 levels normalized to β-ACTIN
1.2
1
0.8
0.6
0.4
0.2
0
ESC
ESC shEXOSC2
ESC shEXOSC8
ESC shEXOSC2&8
AiPSC
B
Relative DNA fragmentation-% TMR-dUTP incorporated
1.6
1.4
1.2
1
0.8
0.6
0.4
0.2
0
P=0.0112
P=0.004
P=0.007
ESC
ESC-shEXOSC2
ESC-shEXOSC8
ESC-shEXOSC2&8

FIGURE 13 A-D
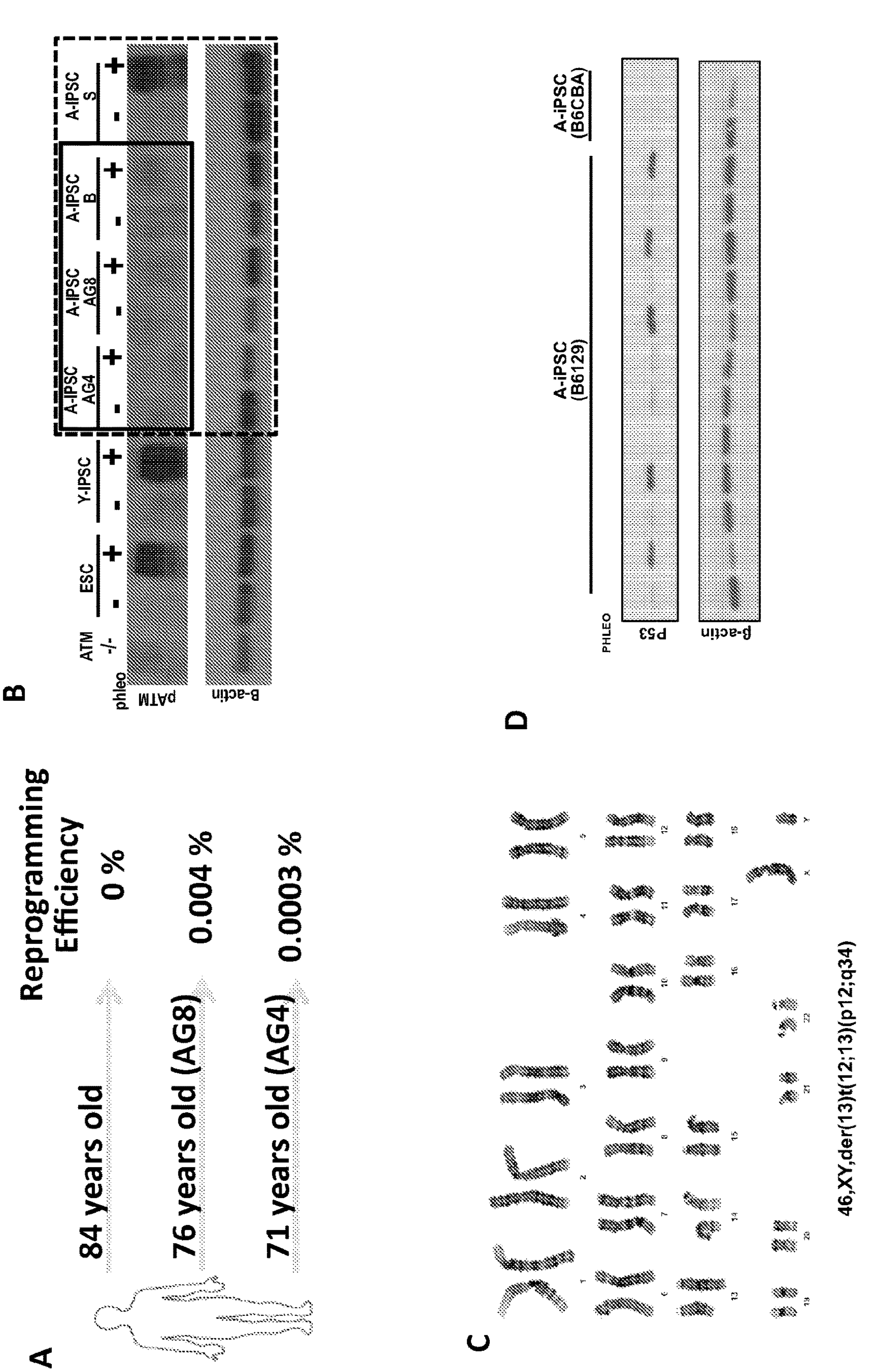

FIGURE 13 E-H
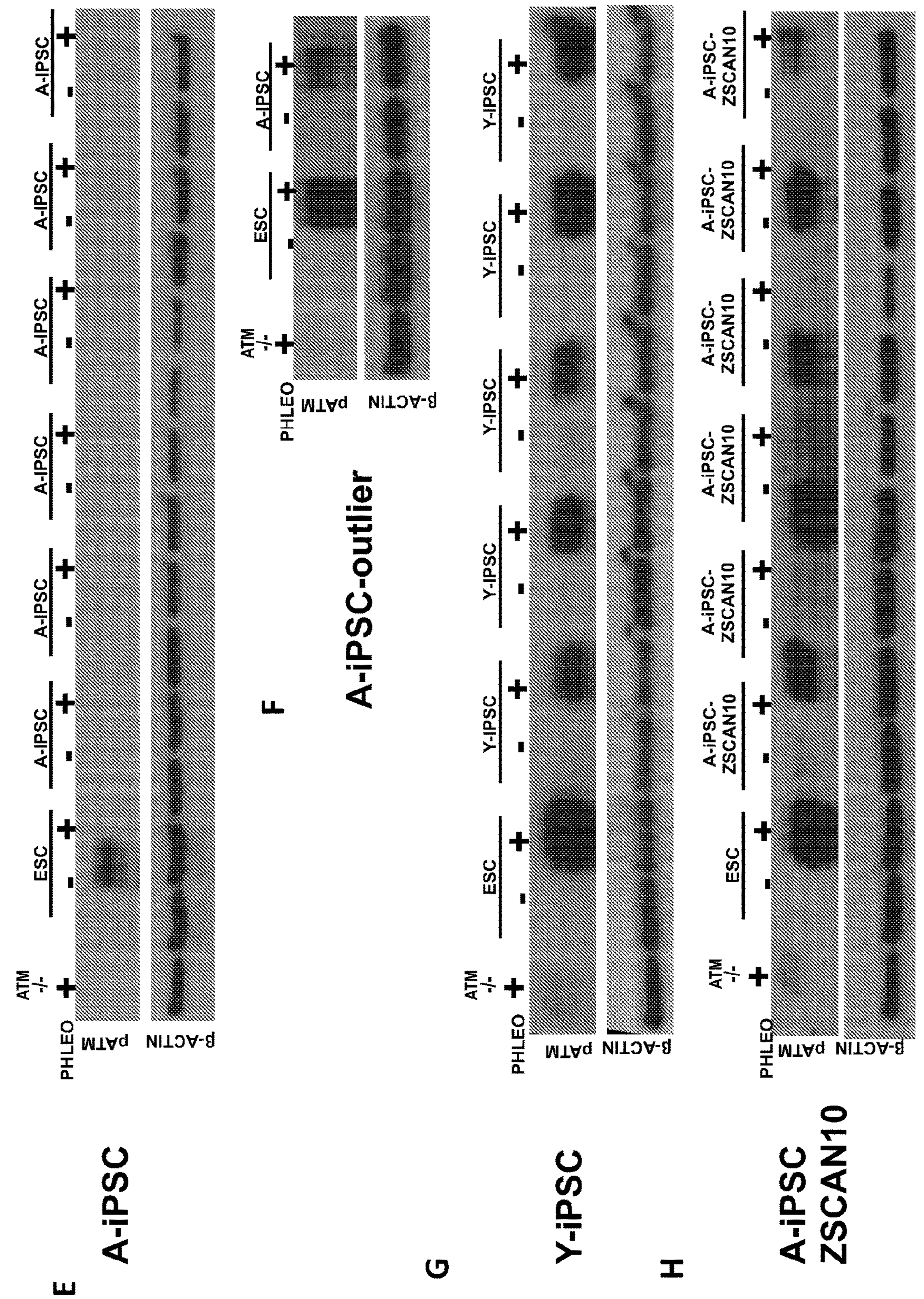

A
ZSCAN10
GSS PROMOTER
GSS GENE
B
Fold enrichment relative to IgG normalized by Input (Log2)
14
12
10
8
6
4
2
0
Y-iPSC
IgG control (Y-iPSC)
A-iPSC
IgG control (A-iPSC)
C
Relative GSS levels normalized to β-ACTIN
8
6
4
2
0
ESC
Y-iPSC
A-iPSC
A-iPSC ZSCAN10
Y-iPSC shZSCAN10
D
Relative fluorescence intensity
7
6
5
4
3
2
1
0
p=0.0186
p=0.037
ESC
Y-iPSC
Y-iPSC GSS
A-iPSC
A-iPSC ZSCAN10
A-iPSC shGSS

A

B

C

| | | 2 fold or more higher in ES cells | | | |
|---|---|---|---|---|---|
| Genes | Number of common targets | ESC over ESC | ESC over AiPSC-ZSCAN10 | ESC over Y-iPSC | ESC over A-iPSC |
| 40 | 7 | 0 | 5 | 5 | 10 |
| 89 | 6 | 0 | 12 | 13 | 16 |
| 103 | 5 | 0 | 13 | 9 | 16 |
| 198 | 4 | 0 | 18 | 13 | 29 |
| 376 | 3 | 0 | 21 | 17 | 33 |
| 767 | 2 | 0 | 39 | 41 | 68 |
| 2045 | 1 | 0 | 79 | 87 | 178 |
| 8252 | 0 | 0 | 179 | 207 | 470 |

SEQUENCE LISTING

<160> NUMBER OF SEQ ID NOS: 16

<210> SEQ ID NO 1
<211> LENGTH: 725
<212> TYPE: PRT
<213> ORGANISM: human

<400> SEQUENCE: 1

Met Gly Pro Arg Ala Ser Leu Ser Arg Leu Arg Glu Leu Cys Gly His
1               5                   10                  15

Trp Leu Arg Pro Ala Leu His Thr Lys Lys Gln Ile Leu Glu Leu Leu
            20                  25                  30

Val Leu Glu Gln Phe Leu Ser Val Leu Pro Pro His Leu Leu Gly Arg
        35                  40                  45

Leu Gln Gly Gln Pro Leu Arg Asp Gly Glu Glu Val Val Leu Leu Leu
    50                  55                  60

Glu Gly Ile His Arg Glu Pro Ser His Ala Gly Pro Leu Asp Phe Ser
65                  70                  75                  80

Cys Asn Ala Gly Lys Ser Cys Pro Arg Ala Asp Val Thr Leu Glu Glu
                85                  90                  95

Lys Gly Cys Ala Ser Gln Val Pro Ser His Ser Pro Lys Lys Glu Leu
            100                 105                 110

Pro Ala Glu Glu Pro Ser Val Leu Gly Pro Ser Asp Glu Pro Pro Arg
        115                 120                 125

Pro Gln Pro Arg Ala Ala Gln Pro Ala Glu Pro Gly Gln Trp Arg Leu
    130                 135                 140

Pro Pro Ser Ser Lys Gln Pro Leu Ser Pro Gly Pro Gln Lys Thr Phe
145                 150                 155                 160

Gln Ala Leu Gln Glu Ser Ser Pro Gln Gly Pro Ser Pro Trp Pro Glu
                165                 170                 175

Glu Ser Ser Arg Asp Gln Glu Leu Ala Ala Val Leu Glu Cys Leu Thr
            180                 185                 190

Phe Glu Asp Val Pro Glu Asn Lys Ala Trp Pro Ala His Pro Leu Gly
        195                 200                 205

Phe Gly Ser Arg Thr Pro Asp Lys Glu Glu Phe Lys Gln Glu Glu Pro
    210                 215                 220

Lys Gly Ala Ala Trp Pro Thr Pro Ile Leu Ala Glu Ser Gln Ala Asp
225                 230                 235                 240

Ser Pro Gly Val Pro Gly Glu Pro Cys Ala Gln Ser Leu Gly Arg Gly
                245                 250                 255

-continued

```
Ala Ala Ala Ser Gly Pro Gly Glu Asp Gly Ser Leu Leu Gly Ser Ser
            260                 265                 270

Glu Ile Leu Glu Val Lys Val Ala Glu Gly Val Pro Glu Pro Asn Pro
        275                 280                 285

Glu Leu Gln Phe Ile Cys Ala Asp Cys Gly Val Ser Phe Pro Gln Leu
    290                 295                 300

Ser Arg Leu Lys Ala His Gln Leu Arg Ser His Pro Ala Gly Arg Ser
305                 310                 315                 320

Phe Leu Cys Leu Cys Cys Gly Lys Ser Phe Gly Arg Ser Ser Ile Leu
                325                 330                 335

Lys Leu His Met Arg Thr His Thr Asp Glu Arg Pro His Ala Cys His
            340                 345                 350

Leu Cys Gly His Arg Phe Arg Gln Ser Ser His Leu Ser Lys His Leu
        355                 360                 365

Leu Thr His Ser Ser Glu Pro Ala Phe Leu Cys Ala Glu Cys Gly Arg
    370                 375                 380

Gly Phe Gln Arg Arg Ala Ser Leu Val Gln His Leu Leu Ala His Ala
385                 390                 395                 400

Gln Asp Gln Lys Pro Pro Cys Ala Pro Glu Ser Lys Ala Glu Ala Pro
                405                 410                 415

Pro Leu Thr Asp Val Leu Cys Ser His Cys Gly Gln Ser Phe Gln Arg
            420                 425                 430

Arg Ser Ser Leu Lys Arg His Leu Arg Ile His Ala Arg Asp Lys Asp
        435                 440                 445

Arg Arg Ser Ser Glu Gly Ser Gly Ser Arg Arg Arg Asp Ser Asp Arg
    450                 455                 460

Arg Pro Phe Val Cys Ser Asp Cys Gly Lys Ala Phe Arg Arg Ser Glu
465                 470                 475                 480

His Leu Val Ala His Arg Arg Val His Thr Gly Glu Arg Pro Phe Ser
                485                 490                 495

Cys Gln Ala Cys Gly Arg Ser Phe Thr Gln Ser Ser Gln Leu Val Ser
            500                 505                 510

His Gln Arg Val His Thr Gly Glu Lys Pro Tyr Ala Cys Pro Gln Cys
        515                 520                 525

Gly Lys Arg Phe Val Arg Arg Ala Ser Leu Ala Arg His Leu Leu Thr
    530                 535                 540

His Gly Gly Pro Arg Pro His His Cys Thr Gln Cys Gly Lys Ser Phe
545                 550                 555                 560

Gly Gln Thr Gln Asp Leu Ala Arg His Gln Arg Ser His Thr Gly Glu
                565                 570                 575

Lys Pro Cys Arg Cys Ser Glu Cys Gly Glu Gly Phe Ser Gln Ser Ala
            580                 585                 590

His Leu Ala Arg His Gln Arg Ile His Thr Gly Glu Lys Pro His Ala
        595                 600                 605

Cys Asp Thr Cys Gly His Arg Phe Arg Asn Ser Ser Asn Leu Ala Arg
    610                 615                 620

His Arg Arg Ser His Thr Gly Glu Arg Pro Tyr Ser Cys Gln Thr Cys
625                 630                 635                 640

Gly Arg Ser Phe Arg Arg Asn Ala His Leu Arg Arg His Leu Ala Thr
                645                 650                 655

His Ala Glu Pro Gly Gln Glu Gln Ala Glu Pro Pro Gln Glu Cys Val
            660                 665                 670
```

-continued

```
Glu Cys Gly Lys Ser Phe Ser Arg Ser Cys Asn Leu Leu Arg His Leu
        675                 680                 685

Leu Val His Thr Gly Ala Arg Pro Tyr Ser Cys Thr Gln Cys Gly Arg
    690                 695                 700

Ser Phe Ser Arg Asn Ser His Leu Leu Arg His Leu Arg Thr His Ala
705                 710                 715                 720

Arg Glu Thr Leu Tyr
                725


<210> SEQ ID NO 2
<211> LENGTH: 2239
<212> TYPE: DNA
<213> ORGANISM: human

<400> SEQUENCE: 2

gtacaaaaaa gcagaagggc cgtcaaggcc caccatgggg ccacgggcgt ccctgagccg      60

gctccgggag ctctgcggcc actggctgcg gccggctctg cacaccaaga aacagatcct     120

ggagctgctg gtgctggagc agttcctgag tgtgctgcct ccgcacctcc tgggccgcct     180

gcaggggcag ccgctcaggg atggggagga ggtggtgctg ctgctcgagg gcatccaccg     240

ggagcccagc cacgcggggc cgctggattt tagttgtaat gctggcaaga gttgtccccg     300

tgcagacgtc accttggagg aaaaggggtg tgcttcccag gtccccagcc acagccccaa     360

gaaggaattg cctgcggaag agccttcagt gctgggccca tcggatgagc ctccccgacc     420

ccagccaagg gctgcccagc ctgctgagcc gggacagtgg aggcttcccc caagttcaaa     480

gcagccgctg agcccggggc cccagaagac attccaggcc ctgcaagaaa gcagtcccca     540

gggcccctca ccatggccag aggagagttc ccgagatcag gagctggcgg ctgtgctgga     600

gtgcctgacc tttgaggatg tgccagagaa taaggcgtgg cctgcacacc ccctgggatt     660

cggaagcaga accccagaca aggaggaatt taaacaagaa gagcccaaag ggggctgcctg    720

gcccactccc atcttagcag agtcccaggc agatagtcct ggggtgccgg gagagccttg     780

cgcccagtcg ctcggacggg gcgctgcggc tagcggccct ggcgaagatg ggtcccttct     840

tggcagcagt gaaattttgg aggtcaaagt ggctgagggc gtccccgagc ccaatccgga     900

gttgcagttc atctgcgcgg actgcggggt gagcttcccg cagctgtctc gcctgaaggc     960

gcaccagctg cgctcgcacc cggctgggcg ctccttcctg tgcctttgct gcgggaagag    1020

cttcggccgc agctccattc tcaagctgca catgcgcact cacacggacg agcggccgca    1080

cgcctgccac ctgtgcggcc accgcttccg ccagagctcg cacctgagca agcacctgct    1140

gacccactcc tccgaacccg ccttcctgtg cgcagagtgc ggccgcggct tccagcgccg    1200

cgccagcctt gtgcagcacc tgctggcgca cgcccaggac cagaagccgc cctgcgctcc    1260

tgagagtaag gccgaagcgc cgccactgac cgatgtcctg tgctcccact gcggccagag    1320

cttccagcgc cgctccagcc tcaagcgcca cctgcggatc cacgccaggg acaaggaccg    1380

ccggtcctcc gaaggctccg gcagccgccg ccgggactcc gaccggaggc ccttcgtgtg    1440

cagcgactgc ggcaaggcct tccggcgcag cgagcacctg gtggcccacc ggagggtgca    1500

cacgggcgag cggcccttct cctgccaggc ttgcggccgc agcttcacgc agagctcgca    1560

gctggtcagc caccaacggg tgcacacggg cgagaagccc tacgcctgtc cgcagtgcgg    1620

gaagcgcttt gtgcgccggg ccagccttgc ccgccacctg ctgacccacg gtggccctcg    1680

gccccaccac tgcacccagt gcgggaagag tttcggccag acccaggatc tggcccgcca    1740

ccagcgcagc cacacgggcg agaagccctg ccgctgcagc gagtgcggtg agggcttcag    1800
```

-continued

```
ccagagcgcc cacctggcgc gccaccagcg catccacaca ggggagaagc cccacgcctg   1860

cgacacctgc ggccaccgtt tccgcaatag ctccaacctg gcccgccatc gccgcagcca   1920

cacgggcgag cggccctaca gctgtcagac gtgcggtcgc agcttccggc gcaacgcgca   1980

tctgcggcgg cacctggcta cccatgcgga gcccgggcag gagcaggccg agcccccgca   2040

ggagtgcgtg gagtgcggga agagcttcag ccgcagctgc aatctgctgc gacacctgct   2100

ggtgcacacg ggcgccaggc cctactcctg cacgcagtgt ggccgcagct tcagccgcaa   2160

ctcccacctg ctgcgccacc tgcgcaccca cgcccgcgag acgctgtact agggcctcat   2220

gggcccagct ttcttgtac                                                2239
```

<210> SEQ ID NO 3
<211> LENGTH: 2178
<212> TYPE: DNA
<213> ORGANISM: human

<400> SEQUENCE: 3

```
atggggccac gggcgtccct gagccggctc cgggagctct gcggccactg gctgcggccg     60

gctctgcaca ccaagaaaca gatcctggag ctgctggtgc tggagcagtt cctgagtgtg    120

ctgcctccgc acctcctggg ccgcctgcag gggcagccgc tcagggatgg ggaggaggtg    180

gtgctgctgc tcgagggcat ccaccgggag cccagccacg cggggccgct ggattttagt    240

tgtaatgctg gcaagagttg tccccgtgca gacgtcacct tggaggaaaa ggggtgtgct    300

tcccaggtcc ccagccacag ccccaagaag gaattgcctg cggaagagcc ttcagtgctg    360

ggcccatcgg atgagcctcc ccgaccccag ccaagggctg cccagcctgc tgagccggga    420

cagtggaggc ttcccccaag ttcaaagcag ccgctgagcc cggggcccca gaagacattc    480

caggccctgc aagaaagcag tccccagggc ccctcaccat ggccagagga gagttcccga    540

gatcaggagc tggcggctgt gctggagtgc ctgacctttg aggatgtgcc agagaataag    600

gcgtggcctg cacacccccct gggattcgga agcagaaccc cagacaagga ggaatttaaa    660

caagaagagc ccaaaggggc tgcctggccc actcccatct tagcagagtc ccaggcagat    720

agtcctgggg tgccgggaga gccttgcgcc cagtcgctcg gacggggcgc tgcggctagc    780

ggccctggcg aagatgggtc ccttcttggc agcagtgaaa ttttggaggt caaagtggct    840

gagggcgtcc ccgagcccaa tccggagttg cagttcatct gcgcggactg cggggtgagc    900

ttcccgcagc tgtctcgcct gaaggcgcac cagctgcgct cgcacccggc tgggcgctcc    960

ttcctgtgcc tttgctgcgg gaagagcttc ggccgcagct ccattctcaa gctgcacatg   1020

cgcactcaca cggacgagcg gccgcacgcc tgccacctgt gcggccaccg cttccgccag   1080

agctcgcacc tgagcaagca cctgctgacc cactcctccg aacccgcctt cctgtgcgca   1140

gagtgcggcc gcggcttcca gcgccgcgcc agccttgtgc agcacctgct ggcgcacgcc   1200

caggaccaga agccgccctg cgctcctgag agtaaggccg aagcgccgcc actgaccgat   1260

gtcctgtgct cccactgcgg ccagagcttc cagcgccgct ccagcctcaa gcgccacctg   1320

cggatccacg ccagggacaa ggaccgccgg tcctccgaag gctccggcag ccgccgccgg   1380

gactccgacc ggaggccctt cgtgtgcagc gactgcggca aggccttccg gcgcagcgag   1440

cacctggtgg cccaccggag ggtgcacacg ggcgagcggc ccttctcctg ccaggcttgc   1500

ggccgcagct tcacgcagag ctcgcagctg gtcagccacc aacgggtgca cacgggcgag   1560

aagccctacg cctgtccgca gtgcgggaag cgctttgtgc gccgggccag ccttgcccgc   1620
```

```
cacctgctga cccacggtgg ccctcggccc caccactgca cccagtgcgg gaagagtttc   1680

ggccagaccc aggatctggc ccgccaccag cgcagccaca cgggcgagaa gccctgccgc   1740

tgcagcgagt gcggtgaggg cttcagccag agcgcccacc tggcgcgcca ccagcgcatc   1800

cacacagggg agaagcccca cgcctgcgac acctgcggcc accgtttccg caatagctcc   1860

aacctggccc gccatcgccg cagccacacg ggcgagcggc cctacagctg tcagacgtgc   1920

ggtcgcagct tccggcgcaa cgcgcatctg cggcggcacc tggctaccca tgcggagccc   1980

gggcaggagc aggccgagcc cccgcaggag tgcgtggagt gcgggaagag cttcagccgc   2040

agctgcaatc tgctgcgaca cctgctggtg cacacgggcg ccaggcccta ctcctgcacg   2100

cagtgtggcc gcagcttcag ccgcaactcc cacctgctgc gccacctgcg cacccacgcc   2160

cgcgagacgc tgtactag                                                 2178
```

<210> SEQ ID NO 4
<211> LENGTH: 725
<212> TYPE: PRT
<213> ORGANISM: human

<400> SEQUENCE: 4

```
Met Gly Pro Arg Ala Ser Leu Ser Arg Leu Arg Glu Leu Cys Gly His
1               5                   10                  15

Trp Leu Arg Pro Ala Leu His Thr Lys Lys Gln Ile Leu Glu Leu Leu
            20                  25                  30

Val Leu Glu Gln Phe Leu Ser Val Leu Pro Pro His Leu Leu Gly Arg
        35                  40                  45

Leu Gln Gly Gln Pro Leu Arg Asp Gly Glu Glu Val Val Leu Leu Leu
    50                  55                  60

Glu Gly Ile His Arg Glu Pro Ser His Ala Gly Pro Leu Asp Phe Ser
65                  70                  75                  80

Cys Asn Ala Gly Lys Ser Cys Pro Arg Ala Asp Val Thr Leu Glu Glu
                85                  90                  95

Lys Gly Cys Ala Ser Gln Val Pro Ser His Ser Pro Lys Lys Glu Leu
            100                 105                 110

Pro Ala Glu Glu Pro Ser Val Leu Gly Pro Ser Asp Glu Pro Pro Arg
        115                 120                 125

Pro Gln Pro Arg Ala Ala Gln Pro Ala Glu Pro Gly Gln Trp Arg Leu
    130                 135                 140

Pro Pro Ser Ser Lys Gln Pro Leu Ser Pro Gly Pro Gln Lys Thr Phe
145                 150                 155                 160

Gln Ala Leu Gln Glu Ser Ser Pro Gln Gly Pro Ser Pro Trp Pro Glu
                165                 170                 175

Glu Ser Ser Arg Asp Gln Glu Leu Ala Ala Val Leu Glu Cys Leu Thr
            180                 185                 190

Phe Glu Asp Val Pro Glu Asn Lys Ala Trp Pro Ala His Pro Leu Gly
        195                 200                 205

Phe Gly Ser Arg Thr Pro Asp Lys Glu Glu Phe Lys Gln Glu Glu Pro
    210                 215                 220

Lys Gly Ala Ala Trp Pro Thr Pro Ile Leu Ala Glu Ser Gln Ala Asp
225                 230                 235                 240

Ser Pro Gly Val Pro Gly Glu Pro Cys Ala Gln Ser Leu Gly Arg Gly
                245                 250                 255

Ala Ala Ala Ser Gly Pro Gly Glu Asp Gly Ser Leu Leu Gly Ser Ser
            260                 265                 270
```

```
Glu Ile Leu Glu Val Lys Val Ala Glu Gly Val Pro Glu Pro Asn Pro
        275                 280                 285

Glu Leu Gln Phe Ile Cys Ala Asp Cys Gly Val Ser Phe Pro Gln Leu
    290                 295                 300

Ser Arg Leu Lys Ala His Gln Leu Arg Ser His Pro Ala Gly Arg Ser
305                 310                 315                 320

Phe Leu Cys Leu Cys Cys Gly Lys Ser Phe Gly Arg Ser Ser Ile Leu
                325                 330                 335

Lys Leu His Met Arg Thr His Thr Asp Glu Arg Pro His Ala Cys His
            340                 345                 350

Leu Cys Gly His Arg Phe Arg Gln Ser Ser His Leu Ser Lys His Leu
        355                 360                 365

Leu Thr His Ser Ser Glu Pro Ala Phe Leu Cys Ala Glu Cys Gly Arg
    370                 375                 380

Gly Phe Gln Arg Arg Ala Ser Leu Val Gln His Leu Leu Ala His Ala
385                 390                 395                 400

Gln Asp Gln Lys Pro Pro Cys Ala Pro Glu Ser Lys Ala Glu Ala Pro
                405                 410                 415

Pro Leu Thr Asp Val Leu Cys Ser His Cys Gly Gln Ser Phe Gln Arg
            420                 425                 430

Arg Ser Ser Leu Lys Arg His Leu Arg Ile His Ala Arg Asp Lys Asp
        435                 440                 445

Arg Arg Ser Ser Glu Gly Ser Gly Ser Arg Arg Arg Asp Ser Asp Arg
    450                 455                 460

Arg Pro Phe Val Cys Ser Asp Cys Gly Lys Ala Phe Arg Arg Ser Glu
465                 470                 475                 480

His Leu Val Ala His Arg Arg Val His Thr Gly Glu Arg Pro Phe Ser
                485                 490                 495

Cys Gln Ala Cys Gly Arg Ser Phe Thr Gln Ser Ser Gln Leu Val Ser
            500                 505                 510

His Gln Arg Val His Thr Gly Glu Lys Pro Tyr Ala Cys Pro Gln Cys
        515                 520                 525

Gly Lys Arg Phe Val Arg Arg Ala Ser Leu Ala Arg His Leu Leu Thr
    530                 535                 540

His Gly Gly Pro Arg Pro His His Cys Thr Gln Cys Gly Lys Ser Phe
545                 550                 555                 560

Gly Gln Thr Gln Asp Leu Ala Arg His Gln Arg Ser His Thr Gly Glu
                565                 570                 575

Lys Pro Cys Arg Cys Ser Glu Cys Gly Glu Gly Phe Ser Gln Ser Ala
            580                 585                 590

His Leu Ala Arg His Gln Arg Ile His Thr Gly Glu Lys Pro His Ala
        595                 600                 605

Cys Asp Thr Cys Gly His Arg Phe Arg Asn Ser Ser Asn Leu Ala Arg
    610                 615                 620

His Arg Arg Ser His Thr Gly Glu Arg Pro Tyr Ser Cys Gln Thr Cys
625                 630                 635                 640

Gly Arg Ser Phe Arg Arg Asn Ala His Leu Arg Arg His Leu Ala Thr
                645                 650                 655

His Ala Glu Pro Gly Gln Glu Gln Ala Glu Pro Pro Gln Glu Cys Val
            660                 665                 670

Glu Cys Gly Lys Ser Phe Ser Arg Ser Cys Asn Leu Leu Arg His Leu
        675                 680                 685

Leu Val His Thr Gly Ala Arg Pro Tyr Ser Cys Thr Gln Cys Gly Arg
```

```
    690                 695                 700

Ser Phe Ser Arg Asn Ser His Leu Leu Arg His Leu Arg Thr His Ala
705                 710                 715                 720

Arg Glu Thr Leu Tyr
                725


<210> SEQ ID NO 5
<211> LENGTH: 782
<212> TYPE: PRT
<213> ORGANISM: mouse

<400> SEQUENCE: 5

Met Leu Ala Glu Pro Val Pro Asp Ala Leu Glu Gln Glu His Pro Gly
1               5                   10                  15

Ala Val Lys Leu Glu Glu Asp Glu Val Gly Glu Glu Asp Pro Arg Leu
            20                  25                  30

Ala Glu Ser Arg Pro Arg Pro Glu Val Ala His Gln Leu Phe Arg Cys
        35                  40                  45

Phe Gln Tyr Gln Glu Asp Met Gly Pro Arg Ala Ser Leu Gly Arg Leu
    50                  55                  60

Arg Glu Leu Cys Asn His Trp Leu Arg Pro Ala Leu His Thr Lys Lys
65                  70                  75                  80

Gln Ile Leu Glu Leu Leu Val Leu Glu Gln Phe Leu Ser Val Leu Pro
                85                  90                  95

Pro His Val Leu Ser Arg Leu His Gly Gln Pro Leu Arg Asp Gly Glu
            100                 105                 110

Glu Val Val Gln Leu Leu Glu Gly Val Pro Arg Asp Ile Ser His Met
        115                 120                 125

Gly Pro Leu Asp Phe Ser Phe Ser Ala Gly Lys Asn Ala Pro Ala Asp
    130                 135                 140

Ile Ile Ser Glu Glu Gln Asn Ser Pro Ser Gln Val Pro Ser His Ser
145                 150                 155                 160

Pro Gln Thr Glu Leu Pro Ser Glu Glu Ile Pro Ala Leu His Pro Leu
                165                 170                 175

Asn Glu Leu Pro Pro Pro Gln Pro Ala Pro Ile Arg Pro Ala Glu Pro
            180                 185                 190

Glu Glu Trp Arg Leu Ala Pro Ser Ser Asn Trp Pro Met Ser Pro Glu
        195                 200                 205

Pro Gln Glu Ile Leu Gln Asp Pro Arg Glu Ser Asn Pro Ser Gln Gly
    210                 215                 220

Pro Ser Trp Leu Glu Glu Asn Ser Arg Asp Gln Glu Leu Ala Ala Val
225                 230                 235                 240

Leu Glu Ser Leu Thr Phe Glu Asp Thr Ser Glu Lys Arg Ala Trp Pro
                245                 250                 255

Ala Asn Pro Leu Gly Phe Gly Ser Arg Met Pro Asp Asn Glu Glu Leu
            260                 265                 270

Lys Val Glu Glu Pro Lys Val Thr Thr Trp Pro Val Val Ile Gly Ala
        275                 280                 285

Glu Ser Gln Thr Glu Lys Pro Glu Val Ala Gly Glu Pro Leu Thr Gln
    290                 295                 300

Thr Val Gly Gln Glu Thr Ser Ser Thr Gly Trp Gly Gly Thr Pro Ala
305                 310                 315                 320

Asp Gly Ser Glu Val Val Lys Val Arg Gly Ala Ser Asp Ala Pro Glu
                325                 330                 335
```

```
Pro Gln Gly Glu Met Gln Phe Ile Cys Thr Tyr Cys Gly Val Asn Phe
            340                 345                 350

Pro Glu Met Ser His Leu Gln Ala His Gln Leu Gln Ser His Pro Asn
        355                 360                 365

Leu Gln Pro His Pro Ser Ser Arg Ser Phe Arg Cys Leu Trp Cys Gly
    370                 375                 380

Lys Thr Phe Gly Arg Ser Ser Ile Leu Lys Leu His Met Arg Thr His
385                 390                 395                 400

Thr Asp Glu Arg Pro His Ala Cys His Leu Cys Asn Arg Arg Phe Arg
                405                 410                 415

Gln Ser Ser His Leu Thr Lys His Leu Leu Thr His Ser Ser Glu Pro
            420                 425                 430

Ala Phe Arg Cys Ala Glu Cys Asn Gln Gly Phe Gln Arg Arg Ser Ser
        435                 440                 445

Leu Met Gln His Leu Leu Ala His Ala Gln Gly Lys Asn Leu Thr Pro
    450                 455                 460

Asn Pro Glu Gly Lys Thr Lys Val Pro Glu Met Ala Ala Val Leu Cys
465                 470                 475                 480

Ser His Cys Gly Gln Thr Phe Lys Arg Arg Ser Ser Leu Lys Arg His
                485                 490                 495

Leu Arg Asn His Ala Lys Asp Lys Asp His Leu Ser Ser Glu Asp Pro
            500                 505                 510

Gly Ser Leu Ser Ser Ser Gln Glu Ser Asn Pro Tyr Val Cys Ser Asp
        515                 520                 525

Cys Gly Lys Ala Phe Arg Gln Ser Glu Gln Leu Met Ile His Thr Arg
    530                 535                 540

Arg Val His Thr Arg Glu Arg Pro Phe Ser Cys Gln Val Cys Gly Arg
545                 550                 555                 560

Cys Phe Thr Gln Asn Ser Gln Leu Ile Ser His Gln Gln Ile His Thr
                565                 570                 575

Gly Glu Lys Pro His Ala Cys Pro Gln Cys Ser Lys Arg Phe Val Arg
            580                 585                 590

Arg Ala Gly Leu Ala Arg His Leu Leu Thr His Gly Ser Leu Arg Pro
        595                 600                 605

Tyr His Cys Ala Gln Cys Gly Lys Ser Phe Arg Gln Met Arg Asp Leu
    610                 615                 620

Thr Arg His Val Arg Cys His Thr Gly Glu Lys Pro Cys Arg Cys Asn
625                 630                 635                 640

Glu Cys Gly Glu Gly Phe Thr Gln Asn Ala His Leu Ala Arg His Gln
                645                 650                 655

Arg Ile His Thr Gly Glu Lys Pro His Ala Cys Asp Ile Cys Gly His
            660                 665                 670

Arg Phe Arg Asn Ser Ser Asn Leu Ala Arg His Arg Arg Ser His Thr
        675                 680                 685

Gly Glu Arg Pro Tyr Ser Cys Pro Thr Cys Gly Arg Ser Phe Arg Arg
    690                 695                 700

Asn Ala His Leu Gln Arg His Leu Ile Thr His Thr Gly Ser Lys Gln
705                 710                 715                 720

Glu Lys Glu Val Pro Gln Glu Cys Pro Glu Cys Gly Lys Ser Phe Asn
                725                 730                 735

Arg Ser Cys Asn Leu Leu Arg His Leu Leu Val His Thr Gly Ala Arg
            740                 745                 750

Pro Tyr Ser Cys Ala Leu Cys Gly Arg Ser Phe Ser Arg Asn Ser His
```

```
        755                 760                 765

Leu Leu Arg His Leu Arg Thr His Ala Arg Glu Ser Leu Tyr
    770                 775                 780

<210> SEQ ID NO 6
<211> LENGTH: 2410
<212> TYPE: DNA
<213> ORGANISM: mouse

<400> SEQUENCE: 6

gtacaaaaaa gcagaagggc cgtcaaggcc caccatgctg gcggaaccag tccctgatgc      60

cctggaacaa gagcatcccg gagcagtgaa gttggaggag gatgaagttg gcgaggagga     120

tcccaggctc gcagagtcca ggcctaggcc tgaggtggcc caccagcttt tcagatgctt     180

ccagtatcag gaagatatgg ggccacgggc atccctgggc cggctccggg aactctgcaa     240

ccactggctg cgaccggctc tgcacaccaa gaagcagatc ctggagctgc tggtactgga     300

gcagttcctg agtgtcctgc ccccgcatgt gctgagccgg ctgcacggcc aaccgctccg     360

ggacggagag gaggtggtac agctattgga gggcgtgccc agagacatca gccacatggg     420

gccactggat tttagcttca gtgctggcaa gaatgcccct gcagacatca tctcagagga     480

acaaaatagc ccttcccagg tccccagcca cagcccccag acggagttgc cctcagaaga     540

gattccagcc ctacatccac tgaatgagtt acctccacct cagccagcac ccataaggcc     600

tgctgagcct gaggagtgga gactggcccc cagttcaaat tggccaatga gcccagagcc     660

ccaggagata ctccaggacc cacgagaaag caacccttcc cagggccctt catggcttga     720

ggaaaattcc agagaccaag agctggcggc tgtgttggag tccctcacct ttgaggatac     780

ctcagagaag agagcttggc ctgcaaaccc tcttggattt ggaagcagaa tgcctgacaa     840

tgaggaactt aaagttgaag agcctaaagt gactacttgg cctgtcgtca ttggagcaga     900

gtcccagaca gagaaacctg aagttgcagg agagcctctt acgcaaactg tagggcagga     960

gaccagcagc actggttggg gaggtactcc tgctgacggc agtgaagttg tgaaggttag    1020

aggagcttcc gatgccccag agccccaggg ggagatgcag ttcatatgta catattgtgg    1080

ggtaaacttc ccagagatgt ctcatctaca ggcccaccag ttacaatctc accccaactt    1140

gcaacctcac ccaagctctc gatccttccg atgtctgtgg tgtgggaaga cttttggacg    1200

cagctcgatc ctcaagctgc acatgcgcac tcacacagac gagcggccgc acgcctgtca    1260

tctctgcaac cgccgcttcc gccagagctc acacctgacg aagcacttgc taacgcattc    1320

ctctgagcct gccttccgat gcgccgagtg taaccagggt tttcagcgtc gctccagcct    1380

catgcagcac ctgctggcac atgcccaggg aaagaatctc acgccaaatc cagaaggcaa    1440

gacaaaagtg ccagagatgg cagctgtcct ctgttcccac tgcgggcaga ccttcaagcg    1500

gcgctctagc ttaaagcgtc acctgcgtaa ccatgccaag gacaaggacc atctgtcctc    1560

tgaagaccct ggcagcctta gctctagcca ggagagtaac ccctatgtgt gtagtgactg    1620

tggcaaggcc ttccgacaaa gcgagcaact aatgatccac actaggcgag tccatacccg    1680

tgaacgaccc ttctcctgcc aggtctgtgg ccgctgcttt acccaaaatt cccagctgat    1740

cagccaccag cagattcata cgggtgagaa gcctcacgcc tgtcctcagt gcagcaaacg    1800

ctttgtgaga cgagctggcc ttgctcggca tctgttgacc cacggtagcc tccggcctta    1860

ccactgtgcc caatgtggca aaagctttcg ccaaatgcga gacctaaccc gccacgtacg    1920

ctgccacacg ggggagaagc cctgccgatg caacgaatgt ggagaggggt tcacccagaa    1980
```

-continued tgcccacctg gcacgccacc aacgcatcca cacgggggag aagccccacg cctgtgacat 2040
ctgtggtcac cgctttcgta acagctccaa cttggcccgc caccgccgca gccacactgg 2100
cgaacggccc tatagctgtc caacctgtgg ccgcagtttc cggcgcaatg cgcacctgca 2160
gcgccacctg atcacacaca cagggtcaaa gcaagaaaag gaagttcctc aggagtgccc 2220
tgagtgtggc aagagcttca atcgcagctg caacttgctg cgccacctgc tggttcacac 2280
cggtgcaagg ccttactcct gtgcactgtg tggccgcagc ttcagccgta attcacacct 2340
gctgcgccac ctgcgaaccc atgcccggga atcgctgtac tagggcctca tgggcccagc 2400
tttcttgtac 2410

<210> SEQ ID NO 7
<211> LENGTH: 2349
<212> TYPE: DNA
<213> ORGANISM: mouse

<400> SEQUENCE: 7
atgctggcgg aaccagtccc tgatgccctg gaacaagagc atcccggagc agtgaagttg 60
gaggaggatg aagttggcga ggaggatccc aggctcgcag agtccaggcc taggcctgag 120
gtggcccacc agcttttcag atgcttccag tatcaggaag atatggggcc acgggcatcc 180
ctgggccggc tccgggaact ctgcaaccac tggctgcgac cggctctgca caccaagaag 240
cagatcctgg agctgctggt actggagcag ttcctgagtg tcctgccccc gcatgtgctg 300
agccggctgc acggccaacc gctccgggac ggagaggagg tggtacagct attggagggc 360
gtgcccagag acatcagcca catggggcca ctggatttta gcttcagtgc tggcaagaat 420
gcccctgcag acatcatctc agaggaacaa aatagccctt cccaggtccc cagccacagc 480
ccccagacgg agttgccctc agaagagatt ccagccctac atccactgaa tgagttacct 540
ccacctcagc cagcacccat aaggcctgct gagcctgagg agtggagact ggccccccagt 600 tcaaattggc caatgagccc agagccccag gagatactcc aggacccacg agaaagcaac 660
ccttcccagg gcccttcatg gcttgaggaa aattccagag accaagagct ggcggctgtg 720
ttggagtccc tcacctttga ggatacctca gagaagagag cttggcctgc aaaccctctt 780
ggatttggaa gcagaatgcc tgacaatgag gaacttaaag ttgaagagcc taaagtgact 840
acttggcctg tcgtcattgg agcagagtcc cagacagaga aacctgaagt tgcaggagag 900
cctcttacgc aaactgtagg gcaggagacc agcagcactg gttggggagg tactcctgct 960
gacggcagtg aagttgtgaa ggttagagga gcttccgatg ccccagagcc ccagggggag 1020
atgcagttca tatgtacata ttgtggggta aacttcccag agatgtctca tctacaggcc 1080
caccagttac aatctcaccc caacttgcaa cctcacccaa gctctcgatc cttccgatgt 1140
ctgtggtgtg ggaagacttt tggacgcagc tcgatcctca agctgcacat gcgcactcac 1200
acagacgagc ggccgcacgc ctgtcatctc tgcaaccgcc gcttccgcca gagctcacac 1260
ctgacgaagc acttgctaac gcattcctct gagcctgcct tccgatgcgc cgagtgtaac 1320
cagggttttc agcgtcgctc cagcctcatg cagcacctgc tggcacatgc ccagggaaag 1380
aatctcacgc caaatccaga aggcaagaca aaagtgccag agatggcagc tgtcctctgt 1440
tcccactgcg ggcagacctt caagcggcgc tctagcttaa agcgtcacct gcgtaaccat 1500
gccaaggaca aggaccatct gtcctctgaa gaccctggca gccttagctc tagccaggag 1560
agtaacccct atgtgtgtag tgactgtggc aaggccttcc gacaaagcga gcaactaatg 1620
atccacacta ggcgagtcca tacccgtgaa cgacccttct cctgccaggt ctgtggccgc 1680

```
tgctttaccc aaaattccca gctgatcagc caccagcaga ttcatacggg tgagaagcct   1740

cacgcctgtc ctcagtgcag caaacgcttt gtgagacgag ctggccttgc tcggcatctg   1800

ttgacccacg gtagcctccg gccttaccac tgtgcccaat gtggcaaaag ctttcgccaa   1860

atgcgagacc taacccgcca cgtacgctgc cacacggggg agaagccctg ccgatgcaac   1920

gaatgtggag aggggttcac ccagaatgcc cacctggcac gccaccaacg catccacacg   1980

ggggagaagc cccacgcctg tgacatctgt ggtcaccgct ttcgtaacag ctccaacttg   2040

gcccgccacc gccgcagcca cactggcgaa cggccctata gctgtccaac ctgtggccgc   2100

agtttccggc gcaatgcgca cctgcagcgc cacctgatca cacacacagg gtcaaagcaa   2160

gaaaaggaag ttcctcagga gtgccctgag tgtggcaaga gcttcaatcg cagctgcaac   2220

ttgctgcgcc acctgctggt tcacaccggt gcaaggcctt actcctgtgc actgtgtggc   2280

cgcagcttca gccgtaattc acacctgctg cgccacctgc gaacccatgc ccgggaatcg   2340

ctgtactag                                                           2349
```

<210> SEQ ID NO 8
<211> LENGTH: 782
<212> TYPE: PRT
<213> ORGANISM: mouse

<400> SEQUENCE: 8

```
Met Leu Ala Glu Pro Val Pro Asp Ala Leu Glu Gln Glu His Pro Gly
1               5                   10                  15

Ala Val Lys Leu Glu Glu Asp Glu Val Gly Glu Glu Asp Pro Arg Leu
            20                  25                  30

Ala Glu Ser Arg Pro Arg Pro Glu Val Ala His Gln Leu Phe Arg Cys
        35                  40                  45

Phe Gln Tyr Gln Glu Asp Met Gly Pro Arg Ala Ser Leu Gly Arg Leu
    50                  55                  60

Arg Glu Leu Cys Asn His Trp Leu Arg Pro Ala Leu His Thr Lys Lys
65                  70                  75                  80

Gln Ile Leu Glu Leu Leu Val Leu Glu Gln Phe Leu Ser Val Leu Pro
                85                  90                  95

Pro His Val Leu Ser Arg Leu His Gly Gln Pro Leu Arg Asp Gly Glu
            100                 105                 110

Glu Val Val Gln Leu Leu Glu Gly Val Pro Arg Asp Ile Ser His Met
        115                 120                 125

Gly Pro Leu Asp Phe Ser Phe Ser Ala Gly Lys Asn Ala Pro Ala Asp
    130                 135                 140

Ile Ile Ser Glu Glu Gln Asn Ser Pro Ser Gln Val Pro Ser His Ser
145                 150                 155                 160

Pro Gln Thr Glu Leu Pro Ser Glu Glu Ile Pro Ala Leu His Pro Leu
                165                 170                 175

Asn Glu Leu Pro Pro Pro Gln Pro Ala Pro Ile Arg Pro Ala Glu Pro
            180                 185                 190

Glu Glu Trp Arg Leu Ala Pro Ser Ser Asn Trp Pro Met Ser Pro Glu
        195                 200                 205

Pro Gln Glu Ile Leu Gln Asp Pro Arg Glu Ser Asn Pro Ser Gln Gly
    210                 215                 220

Pro Ser Trp Leu Glu Glu Asn Ser Arg Asp Gln Glu Leu Ala Ala Val
225                 230                 235                 240

Leu Glu Ser Leu Thr Phe Glu Asp Thr Ser Glu Lys Arg Ala Trp Pro
```

```
                245                 250                 255

Ala Asn Pro Leu Gly Phe Gly Ser Arg Met Pro Asp Asn Glu Glu Leu
            260                 265                 270

Lys Val Glu Glu Pro Lys Val Thr Thr Trp Pro Val Val Ile Gly Ala
        275                 280                 285

Glu Ser Gln Thr Glu Lys Pro Glu Val Ala Gly Glu Pro Leu Thr Gln
    290                 295                 300

Thr Val Gly Gln Glu Thr Ser Ser Thr Gly Trp Gly Gly Thr Pro Ala
305                 310                 315                 320

Asp Gly Ser Glu Val Val Lys Val Arg Gly Ala Ser Asp Ala Pro Glu
                325                 330                 335

Pro Gln Gly Glu Met Gln Phe Ile Cys Thr Tyr Cys Gly Val Asn Phe
            340                 345                 350

Pro Glu Met Ser His Leu Gln Ala His Gln Leu Gln Ser His Pro Asn
        355                 360                 365

Leu Gln Pro His Pro Ser Ser Arg Ser Phe Arg Cys Leu Trp Cys Gly
    370                 375                 380

Lys Thr Phe Gly Arg Ser Ser Ile Leu Lys Leu His Met Arg Thr His
385                 390                 395                 400

Thr Asp Glu Arg Pro His Ala Cys His Leu Cys Asn Arg Arg Phe Arg
                405                 410                 415

Gln Ser Ser His Leu Thr Lys His Leu Leu Thr His Ser Ser Glu Pro
            420                 425                 430

Ala Phe Arg Cys Ala Glu Cys Asn Gln Gly Phe Gln Arg Arg Ser Ser
        435                 440                 445

Leu Met Gln His Leu Leu Ala His Ala Gln Gly Lys Asn Leu Thr Pro
    450                 455                 460

Asn Pro Glu Gly Lys Thr Lys Val Pro Glu Met Ala Ala Val Leu Cys
465                 470                 475                 480

Ser His Cys Gly Gln Thr Phe Lys Arg Arg Ser Ser Leu Lys Arg His
                485                 490                 495

Leu Arg Asn His Ala Lys Asp Lys Asp His Leu Ser Ser Glu Asp Pro
            500                 505                 510

Gly Ser Leu Ser Ser Ser Gln Glu Ser Asn Pro Tyr Val Cys Ser Asp
        515                 520                 525

Cys Gly Lys Ala Phe Arg Gln Ser Glu Gln Leu Met Ile His Thr Arg
    530                 535                 540

Arg Val His Thr Arg Glu Arg Pro Phe Ser Cys Gln Val Cys Gly Arg
545                 550                 555                 560

Cys Phe Thr Gln Asn Ser Gln Leu Ile Ser His Gln Gln Ile His Thr
                565                 570                 575

Gly Glu Lys Pro His Ala Cys Pro Gln Cys Ser Lys Arg Phe Val Arg
            580                 585                 590

Arg Ala Gly Leu Ala Arg His Leu Leu Thr His Gly Ser Leu Arg Pro
        595                 600                 605

Tyr His Cys Ala Gln Cys Gly Lys Ser Phe Arg Gln Met Arg Asp Leu
    610                 615                 620

Thr Arg His Val Arg Cys His Thr Gly Glu Lys Pro Cys Arg Cys Asn
625                 630                 635                 640

Glu Cys Gly Glu Gly Phe Thr Gln Asn Ala His Leu Ala Arg His Gln
                645                 650                 655

Arg Ile His Thr Gly Glu Lys Pro His Ala Cys Asp Ile Cys Gly His
            660                 665                 670
```

```
Arg Phe Arg Asn Ser Ser Asn Leu Ala Arg His Arg Arg Ser His Thr
        675                 680                 685

Gly Glu Arg Pro Tyr Ser Cys Pro Thr Cys Gly Arg Ser Phe Arg Arg
    690                 695                 700

Asn Ala His Leu Gln Arg His Leu Ile Thr His Thr Gly Ser Lys Gln
705                 710                 715                 720

Glu Lys Glu Val Pro Gln Glu Cys Pro Glu Cys Gly Lys Ser Phe Asn
                725                 730                 735

Arg Ser Cys Asn Leu Leu Arg His Leu Leu Val His Thr Gly Ala Arg
            740                 745                 750

Pro Tyr Ser Cys Ala Leu Cys Gly Arg Ser Phe Ser Arg Asn Ser His
        755                 760                 765

Leu Leu Arg His Leu Arg Thr His Ala Arg Glu Ser Leu Tyr
    770                 775                 780


<210> SEQ ID NO 9
<211> LENGTH: 1105
<212> TYPE: DNA
<213> ORGANISM: human

<400> SEQUENCE: 9

cttgttcaaa cagcacttac aggtggggac ctgtttttgc taagtcatcc tggggatgct      60

caaagctcca ttgttagatc ctttctgtcc tccttcctgg ctcctccttc ctccccaccc     120

ctctaatagg ctcataagtg ggctcaggcc tctctgcggg gctcactctg cgcttcacca     180

tggctttcat tgccaagtcc ttctatgacc tcagtgccat cagcctggat ggggagaagg     240

tagatttcaa tacgttccgg ggcagggccg tgctgattga gaatgtggct tcgctctgag     300

gcacaaccac ccgggacttc acccagctca acgagctgca atgccgcttt cccaggcgcc     360

tggtggtcct tggcttccct tgcaaccaat ttggacatca ggagaactgt cagaatgagg     420

agatcctgaa cagtctcaag tatgtccgtc ctgggggtgg ataccagccc accttcaccc     480

ttgtccaaaa atgtgaggtg aatgggcaga acgagcatcc tgtcttcgcc tacctgaagg     540

acaagctccc ctacccttat gatgacccat tttccctcat gaccgatccc aagctcatca     600

tttggagccc tgtgcgccgc tcagatgtgg cctggaactt tgagaagttc ctcatagggc     660

cggagggaga gcccttccga cgctacagcc gcaccttccc aaccatcaac attgagcctg     720

acatcaagcg cctccttaaa gttgccatat agatgtgaac tgctcaacac acagatctcc     780

tactccatcc agtcctgagg agccttagga tgcagcatgc cttcaggaga cactgctgga     840

cctcagcatt cccttgatat cagtcccctt cactgcagag ccttgccttt cccctctgcc     900

tgtttccttt tcctctccca accctctggt tggtgattca acttgggctc caagacttgg     960

gtaagctctg ggccttcaca gaatgatggc accttcctaa accctcatgg gtggtgtctg    1020

agaggcgtga agggcctgga gccactctgc tagaagagac caataaaggg caggtgtgga    1080

aacggccaaa aaaaaaaaaa aaaaa                                          1105


<210> SEQ ID NO 10
<211> LENGTH: 1071
<212> TYPE: DNA
<213> ORGANISM: human

<400> SEQUENCE: 10

gctacagcct tgttcaaaca gttcacaggt gggtacctgt tttttgctaa gtcatcccgg      60

gaatgctcaa aggccctttg tgaagtcctt tcggtcttct ccggctcctc ctttcttccc     120
```

```
accggtctaa aggacttaag gaggctcaca gagcagggca gggctcactg ctcttcagca    180
tggcttacat tgccaagtcg ttctacgatc tcagtgccgt tggcctggat ggggagaaga    240
tagacttcaa tacgttcaga ggcagggctg tgctgattga gaatgtggcg tcactctgag    300
gaacaactac ccgggactac aaccagctca atgagctgca atgtcgcttt cccaggcgcc    360
tggtagttct cggcttccct tgcaaccagt tcggacatca ggagaactgt cagaacgagg    420
agatcctgaa cagcctcaag tatgtccgac ctgggggtgg gtaccagccc acctttagtc    480
ttacccaaaa gtgtgacgtc aatgggcaga acgagcatcc tgtctttgcc tacctgaaag    540
acaagctgcc ctacccttat gatgacccgt tctccctcat gaccgatccc aagctcatca    600
tatggagtcc cgtgcgccgc tcagacgtgt cctggaactt tgagaagttc ctcatagggc    660
cagaagggga gcccttccgt cgctacagcc gcagcttcca gaccatcaac atcgagcctg    720
acatcaaacg gctcctcaaa gttgccatct agatgagagc tgctcagccc aggaatctcc    780
cactgtttcc cctgagcagt cttcctcagg gctcagtgta ccctcgggag accctgggag    840
accaaggcat tccctgaata tcgtcccctt gccttcccta ccggccattt cctttagctc    900
cctcaaggct cttggggagt ttgcttgggg ctctaagtct ggggtaggtt ctgggccttc    960
acagaatgat ggcatcttcc taaacccttc tgggagatgt ctgagaagtt gtgaagggtc   1020
cagagccagt ctgctttaga gtccaataaa gtgtaggtgt ggcaatgaaa a            1071
```

```
<210> SEQ ID NO 11
<211> LENGTH: 1491
<212> TYPE: DNA
<213> ORGANISM: human

<400> SEQUENCE: 11
```

```
atggggacac agaaggtcac cccagctctg atatttgcca tcacagttgc tacaatcggc     60
tctttccaat ttggctacaa cactggggtc atcaatgctc ctgagaagat cataaaggaa    120
tttatcaata aaactttgac ggacaaggga aatgccccac cctctgaggt gctgctcacg    180
tctctctggt ccttgtctgt ggccatattt tccgtcgggg gtatgatcgg ctccttttcc    240
gtcggactct tcgtcaaccg ctttggcagg cgcaattcaa tgctgattgt caacctgttg    300
gctgtcactg gtggctgctt tatgggactg tgtaaagtag ctaagtcggt tgaaatgctg    360
atcctgggtc gcttggttat tggcctcttc tgcggactct gcacaggttt tgtgcccatg    420
tacattggag agatctcgcc tactgccctg cggggtgcct ttggcactct caaccagctg    480
ggcatcgttg ttggaattct ggtggcccag atctttggtc tggaattcat ccttgggtct    540
gaagagctat ggccgctgct actgggtttt accatccttc ctgctatcct acaaagtgca    600
gcccttccat tttgccctga aagtcccaga tttttgctca ttaacagaaa agaagaggag    660
aatgctaagc agatcctcca gcggttgtgg ggcacccagg atgtatccca agacatccag    720
gagatgaaag atgagagtgc aaggatgtca caagaaaagc aagtcaccgt gctagagctc    780
tttagagtgt ccagctaccg acagcccatc atcatttcca ttgtgctcca gctctctcag    840
cagctctctg ggatcaatgc tgtgttctat tactcaacag gaatcttcaa ggatgcaggt    900
gttcaagagc ccatctatgc caccatcggc gcgggtgtgg ttaatactat cttcactgta    960
gtttctctat ttctggtgga aagggcagga agaaggactc tgcatatgat aggccttgga   1020
gggatggctt tttgttccac gctcatgact gtttctttgt tattaaagga taactataat   1080
gggatgagct ttgtctgtat tggggctatc ttggtctttg tagccttctt tgaaattgga   1140
```

```
ccaggcccca ttccctggtt tattgtggcc gaactcttca gccagggccc ccgcccagct   1200

gcgatggcag tggccggctg ctccaactgg acctccaact tcctagtcgg attgctcttc   1260

ccctccgctg ctcactattt aggagcctac gtttttatta tcttcaccgg cttcctcatt   1320

accttcttgg cttttacctt cttcaaagtc cctgagaccc gtggcaggac ttttgaggat   1380

atcacacggg cctttgaagg gcaggcacac ggtgcagata gatctggaaa ggacggcgtc   1440

atggagatga acagcatcga gcctgctaag gagaccacca ccaatgtcta a            1491
```

<210> SEQ ID NO 12
<211> LENGTH: 1482
<212> TYPE: DNA
<213> ORGANISM: mouse

<400> SEQUENCE: 12

```
atggggacaa cgaaggtgac ccatctctg gtgttcgccg tgactgttgc cacgatcggc     60

tctttccagt ttggctacaa cactggagtc atcaatgcac ctgagacaat cctaaaggac    120

tttcttaact acactttgga agagcggtta gaagacctac caagtgaggg actgctgact    180

gccctctggt ccttatgtgt ggccatcttc tctgttggtg gcatgattgg ctctttttct    240

gttggactct ttgtcaaccg ctttggcaga cgcaactcta tgcttctagt caacttgctg    300

gccatcattg cgggctgcct tatgggattc gccaagatag cggagtctgt tgaaatgctg    360

atcctgggcc gcttactcat tggcattttc tgtggcctgt gcacgggctt tgtgcctatg    420

tacattggag aggtgtctcc cactgccctt cggggtgcat ttggcacact aaaccagctg    480

ggcatcgttg ttgggattct ggtagctcag atctttggtt tggactttat tctgggctct    540

gaagaactgt ggcctgggct ccttggctta accatcattc cagctatcct gcaaagcgca    600

gcccttccat tttgccctga gagtccaaga ttcttgctca ttaacaaaaa ggaggaagac    660

caagctacag agatcctgca gcgcttgtgg ggcacctcgg acgtggtcca ggagatccag    720

gagatgaagg atgagagtgt tcggatgtca caggagaagc aggtgactgt gctggagctc    780

ttcaggtcac ccaactacgt ccagccgctt ctcatctcca ttgtcctcca gctgtctcag    840

cagctctctg ggatcaatgc tgtgttctat tactcaacag gaatcttcaa ggacgcgggt    900

gtccaggaac cgatctatgc cacgattgga gcaggcgtgg tcaatactat cttcactgta    960

gtttctctgt tcctggtgga gagggcaggg aggagaaccc tgcatatgat aggcctggga   1020

ggcatggctg tttgctccgt tttcatgacg atttcgctgt tactaaagga tgactatgaa   1080

gccatgagct ttgtctgtat tgtggctatc ttgatctacg tagccttctt tgagattgga   1140

cctggcccca ttccctggtt tattgtggct gagctcttca gccagggccc ccgcccagct   1200

gccattgcgg tggctggctg ttgtaactgg acctccaact ttctggtcgg aatgctcttc   1260

ccctcagctg cagcctactt aggagcctac gtttttatca tcttcgctgc cttcctcatc   1320

ttcttcctaa tcttcacctt cttcaaagtc ccggagacca aaggcaggac tttcgaggac   1380

attgcccggg ccttcgaggg gcaggcgcac tctggaaaag gccctgccgg tgtggagttg   1440

aacagcatgc agccggtcaa ggagacccct ggcaacgcct ga                      1482
```

<210> SEQ ID NO 13
<211> LENGTH: 474
<212> TYPE: PRT
<213> ORGANISM: human

<400> SEQUENCE: 13

Met Ala Thr Asn Trp Gly Ser Leu Leu Gln Asp Lys Gln Gln Leu Glu

-continued 1 5 10 15

Glu Leu Ala Arg Gln Ala Val Asp Arg Ala Leu Ala Glu Gly Val Leu
20 25 30

Leu Arg Thr Ser Gln Glu Pro Thr Ser Ser Glu Val Val Ser Tyr Ala
35 40 45

Pro Phe Thr Leu Phe Pro Ser Leu Val Pro Ser Ala Leu Leu Glu Gln
50 55 60

Ala Tyr Ala Val Gln Met Asp Phe Asn Leu Leu Val Asp Ala Val Ser
65 70 75 80

Gln Asn Ala Ala Phe Leu Glu Gln Thr Leu Ser Ser Thr Ile Lys Gln
85 90 95

Asp Asp Phe Thr Ala Arg Leu Phe Asp Ile His Lys Gln Val Leu Lys
100 105 110

Glu Gly Ile Ala Gln Thr Val Phe Leu Gly Leu Asn Arg Ser Asp Tyr
115 120 125

Met Phe Gln Arg Ser Ala Asp Gly Ser Pro Ala Leu Lys Gln Ile Glu
130 135 140

Ile Asn Thr Ile Ser Ala Ser Phe Gly Gly Leu Ala Ser Arg Thr Pro
145 150 155 160

Ala Val His Arg His Val Leu Ser Val Leu Ser Lys Thr Lys Glu Ala
165 170 175

Gly Lys Ile Leu Ser Asn Asn Pro Ser Lys Gly Leu Ala Leu Gly Ile
180 185 190

Ala Lys Ala Trp Glu Leu Tyr Gly Ser Pro Asn Ala Leu Val Leu Leu
195 200 205

Ile Ala Gln Glu Lys Glu Arg Asn Ile Phe Asp Gln Arg Ala Ile Glu
210 215 220

Asn Glu Leu Leu Ala Arg Asn Ile His Val Ile Arg Arg Thr Phe Glu
225 230 235 240

Asp Ile Ser Glu Lys Gly Ser Leu Asp Gln Asp Arg Arg Leu Phe Val
245 250 255

Asp Gly Gln Glu Ile Ala Val Val Tyr Phe Arg Asp Gly Tyr Met Pro
260 265 270

Arg Gln Tyr Ser Leu Gln Asn Trp Glu Ala Arg Leu Leu Leu Glu Arg
275 280 285

Ser His Ala Ala Lys Cys Pro Asp Ile Ala Thr Gln Leu Ala Gly Thr
290 295 300

Lys Lys Val Gln Gln Glu Leu Ser Arg Pro Gly Met Leu Glu Met Leu
305 310 315 320

Leu Pro Gly Gln Pro Glu Ala Val Ala Arg Leu Arg Ala Thr Phe Ala
325 330 335

Gly Leu Tyr Ser Leu Asp Val Gly Glu Glu Gly Asp Gln Ala Ile Ala
340 345 350

Glu Ala Leu Ala Ala Pro Ser Arg Phe Val Leu Lys Pro Gln Arg Glu
355 360 365

Gly Gly Gly Asn Asn Leu Tyr Gly Glu Glu Met Val Gln Ala Leu Lys
370 375 380

Gln Leu Lys Asp Ser Glu Glu Arg Ala Ser Tyr Ile Leu Met Glu Lys
385 390 395 400

Ile Glu Pro Glu Pro Phe Glu Asn Cys Leu Leu Arg Pro Gly Ser Pro
405 410 415

Ala Arg Val Val Gln Cys Ile Ser Glu Leu Gly Ile Phe Gly Val Tyr
420 425 430

```
Val Arg Gln Glu Lys Thr Leu Val Met Asn Lys His Val Gly His Leu
        435                 440                 445

Leu Arg Thr Lys Ala Ile Glu His Ala Asp Gly Gly Val Ala Ala Gly
    450                 455                 460

Val Ala Val Leu Asp Asn Pro Tyr Pro Val
465                 470


<210> SEQ ID NO 14
<211> LENGTH: 34366
<212> TYPE: DNA
<213> ORGANISM: human

<400> SEQUENCE: 14

tcctcacttt gattccacag gcatttcctg agcagcaatg ctggcccagg cctgtgctag     60

gggctggaag acagaggaat tccactctga atggccaaag cagtggcccc cagccaggtg    120

gggagatggc ctcataaaca acagtatgag gcagggtgat atcactgcta aaaagagaca    180

gtagccatgt gcacagatgc agaccatgtg tgatgcagac cctggggctg acagagatgt    240

tccaatcaaa aggcacagtc cagtggctgg gtgcggtggc tcccgcctgt aatcccagca    300

ctttgggagg ctgaggcggg tggatcacaa ggtcaggaga tcgagaccat cctggctaac    360

acggtgaaac cccatctcta ctaaaaatag aaaaaattag gcgggcgtgg tggcaggcgc    420

ctgtagtccc agctactcgg gaggctgagg taggagaatg gcatgaacac gggaggcgga    480

gcttgcagtg agccaagatg gcgccactgc actctagcct gggctacaaa gcaagactcc    540

atctcaaaaa aacaaaaaca aaaaaaaccc acagtccaga cttggagaga ggccctcgca    600

gggagaaagg caagacacaa aattaaggga ttggcctcca ttcacagtga agtacatccc    660

tgcatacctt ttttcaccta attcagaccc aaatgttccc acaaacccca agaacagagg    720

atgaaattga ttcaacagtt agctttggga agtctgagcc catggcatgt cccaaggtac    780

atatgtggga acaccatggc tgacactgct gctgtgatct ttggcaagtc aggatacctc    840

ttcaagcctt cctttccccg gctgtaaaat ggaggctata aagatactga tgtgataggg    900

aggtaaggga aagtgagata acgactgtaa agtcattagc caagtacctg acacttagcg    960

accagatcaa taaagggtag ttattgttag gaaaaaacag atttcacttt gaaagtgagg   1020

aaagccaggc gcggtggctc acacctgtaa tcccagcact ttgggaggct gaggcaggca   1080

gatcacgagg tcaggagttc gagaccagcc tggacagcaa ggtgaaaccc tgtctccact   1140

aaaaatacaa aaaattagct gggcatggtg gcatgtgcct gtaatcccag ctactcggga   1200

gactgaggca ggagaattgc ctgaacccgg gaggcagagg ttgcagtgag ccaagatcgt   1260

gccactgcac tccagcctgg gtgacagaga gagactccat ctcaaaaaaa aaaaaaagaa   1320

agaaagaaaa aaaataaaat gaggaaagtg ggattcggag aggtgagatg acttctgcac   1380

agtcaggatt caaactcagg tctgagacac cagaggctca gggcaaatca tctccctctg   1440

ctccggaatc ttcagcaggt tccctacagt ccactacatg gactccatcc ttgccaggga   1500

gtgaggatcc agcaaaggcc tggggccaaa aagaccctgg gcaagttccc caatcctatg   1560

tgtcttgatc tgagatcccc aagtgagcct gagaaggtct gtgaattcct ccacgtagct   1620

gatgcaaaat tttatactaa tggatctcag acgagtctat agcctcaaaa gtaacaaacc   1680

acagacttga cctgacttag catggtttct tattcaccca atggagatac gatttctacc   1740

ttgaaaggct gtgaagggat taaatgaggt aatttgtgag aagtacttga aacatcctca   1800

gctttcatta aatgttggtt tccttctctt tctctctccc caaactattt ccatcagtta   1860
```

-continued

```
gcaaatatta ttgagcatct gccacgtggc aggcaccagt caggtcctgg gggtaaagtg   1920
gtgaacaaga cagacatggc ccattttcat ggggctcaca ttctagcaga gggaaacagc   1980
aaacaaataa aagcaacaat ttcagatatg aataactgct atgaagaaaa tacaaggccg   2040
ggcacggtgg ctcacgcctg taatcccagc actttgagag gcagaggcgg acggatcaca   2100
aggtcaggag tttgagacca gcctgatcaa catggtgaaa ccctgtctct cctaaaaata   2160
caaaaattag ccgggcatgg tggcacgtgc ctgtaatccc agctactcag gagactgagg   2220
caggagaatt gtttgaaccc aggagacaga ggttgcagtg agccaagatc gcaccactgc   2280
actccagcct gggcaacaga gtgagactcc atctcaaaaa aaagaaaagg ataacgtgat   2340
agacttatag ggtggggcag cctccaggga tgaaacatct gaatgaccaa aggagccagt   2400
catgccagga ttttggagga aagcacccag gcagagagtg cagaaagggc aaacgctccc   2460
tggaaagatt cttagtcaag agtccttcac tcccagtcct accacaaact gggtcacctt   2520
gaacaagtca cgtaacttct gaggctcagc tgccacatct acaaaatggg aataaagaca   2580
tcttacctgc cacattgtga gaggtttcaa ccaaagggct gttaaggtct gggatcctcc   2640
ccaaatctca ccatagacac ctgatactca tcacttggca cccgtcttgg aagaggggaa   2700
cctgcacaga gaaccctggg tcatgctttt gatttttaat ttcatgctgc actagaaata   2760
gcttcttttg ttcctggttg acccaggagc ctcttcctgc cacctggggc ctattctagt   2820
taacagctgc ttatcccctc aggtacaaaa gccaacgagg aaaggacatc aggaaacatt   2880
gttctgggaa taaccagaca cctatctgcc accatctccc cccatcccgt gaccacacac   2940
gggagactgg aggactcagc ctgtcctgta gtcagataat gtacatggtt tatttaaaga   3000
gtcaaaaggg gccgggcgca gtggctaacg cctgtaatcc tagcactctg ggaggctggg   3060
gcgggtggat cacctgagct caagagtttc agaccaatct ggccaacatg gtgaaaccct   3120
gtctctacca aaaatacaaa aattagccgg gtgtggtggt ggacgcctgt aatcccagct   3180
acttgggagg ctgaggcagg agaattgctt gaacctggga agtggaggtt gcagtgagct   3240
gagatcgtgc cactgcactc cagcctgggc aacaacaacg aaaactccgt ctcaaaaaaa   3300
aaaaaaaaaa aaaagagtca aaaggatctt ggtccctggg ttgggccact gatttacgat   3360
cactaggagt tctcactcct aaatttcttt gatctgttcg cttcgctcca tctccacagc   3420
tgctgcactg gctacagcct catgatctca catcttaact ctctctgctt tctctggccc   3480
atctccccac ttccaaacca tttgtcacgc tgtaaccagt gcctaacaca caaaactaac   3540
catgtccttc ccctgcttaa agcccttagc tcctgttgct cagtggaact ggcgtctgag   3600
gctacctctc caagcctaag cgcctaagtc ctgttgcaac cctcaggccc ttcctcatta   3660
tccacaccaa actcctcagt gtctgtaaaa caagccgagc aaccctcaga attatatgcc   3720
ttcgctgctc gtttgttttg tttttaggac agggtctcac gctgtcaccc aggcaggagt   3780
gctgcagcgt gatctcagct cacagcagcc tccgtctccg ggctcaaga attctcacgc   3840
cgcagcctcc cgagtagctg ggattacagg cacgggccaa cacacccggc taattcttgt   3900
atttctagta gagacggggt ttcgccatgt tgcccagcct ggtctccaac tcctgagctc   3960
aagtaatcca cctgcctcgg cctctcaaag tgctgggatt acaggtctga gccactgcac   4020
ccagccagcc tttgctgctt ttgttcctgc aatttggaac actgtcccca tcccagcctc   4080
tcacctctac ccctacctcc ttcactacct ataccttcct atccatcctt caagacccca   4140
aaaaccatcc ctgattcctt cagaaaggca gtttattgcc tatcttatca gactgaaagc   4200
```

-continued

```
agtggctgtg tcttatttat ggttaattcc ctagaagctg gactgataca ttccatttaa   4260
ctaaaattcg tatcaggtgc ttcggactgc agacaagcct atcacaaccc agaaggaaga   4320
aacagggaag gcacctgggg gctgccaagc aatgaggtgg ggggtaggaa tcatgaatcc   4380
gcatattttt aaaaactgcc ccagatcctg atgtaaacgg tacaagagag tctgagaaac   4440
acagggctcc cctcaaacag tcctgacttc agcattcctg gaaaaatgaa aatcctttcc   4500
ttttgcctct aatgctttcc ctgctggtat cccaggttaa aaaaaaatag ataaaatcag   4560
ggggattttt ctgggacttg gctgggctgg gaaacaagcc tgggttctaa tacaggctca   4620
gcccctgacg tactatgggc ccctgcccct ccttggggcc tccattacca cggccacccc   4680
caccccttatc aattgtgtgc ccctgaggta gtgactgtcc cgctctgagc attagtttcc   4740
ccatcttcca ctagtcgtcg tcagctctga cgctctatga gctatgcata cccgtagctc   4800
cccgccgacc ccgatggtcc cctcccctcc ttcccaaggt ccatccgcca gggtgcagcc   4860
gacgcactcc taatgctaag gccgccctct catcgaccgc cccttcctgg cctcgactca   4920
gcgccaaagg tatgggtctc tgccccgcct gctctttaag cctagccggg gcggtcagcg   4980
caagcgcact gggtcgcatc gaggccccgc cccctgagcc tgggtagcgg cgcgagggcc   5040
gggagaaccg ttcgcggagg aaaggcgaac tagtaggttg gggcggccac ggcggccggc   5100
atgggtcacg tttcctcggg aggaacgatg tgagggaggg gtctggcaag agattggaat   5160
tccggaggcc gggagacctt gtggctgaaa cccttcgtag gagcggggca actagtgtct   5220
agtgaggggg ttgggctggc gcgcactgat cccagacttt ccggatcttc tgcctttaga   5280
tcgggccggt gtcggggcat gtaggccagt gagactggag ccagttagag ctacaacggg   5340
gagcgattag ggccaaactt tgtccagggt ggaagcgagc gggcccgtga agtggggcca   5400
gcctgggcag ccgaccgtgt cgttgcctcg gggcctttcc aggcactggc ctaagtcctg   5460
gcgataaagt gcgaccgatt tccttgtggg cgttttgagg ctttcggtga tctgacccgt   5520
ctgtcattca ttcttcattc attcatgtga tgaatgaata cagtactaag cgcggctaat   5580
tactaggtag agaagtgatc aagacaaaca ctgttcctac ggtacaggga aaagtgatgg   5640
gctgtagaat gtagaagccc ggggcggaga acagggacag cttccggaac gaaatcgcga   5700
gcccagatca ggagtggtgg cgagagttcc aaagagaaga cagcacgtgc caagtcctgg   5760
aagggggaca gaggccaaca tatcctggtc actgaagaca cctgactctg aatctgtttc   5820
acgcccaggg aagagatgac agtggccggg gctaggctac aaactctgga aatggagata   5880
aataaaggaa ttcaaagtac tatatactta ggcagcaaaa tccataggat ttggggagag   5940
tgagatgtag gaaacaagta ctcaaggctt gggtacctgg gtggggttca tcagagaaga   6000
agcagatttg tgggagacaa caacaaattc tattctggtt gtatggagac tcgcaggaaa   6060
aaattggata ttctagtttg aaggtaggaa agtattgctg tgaagatgta gatttgaatg   6120
tcatcagcaa aacataaata aagccaaggg agggttgagg ctgtagaatg agaaaaacaa   6180
agggcccact tagcaccttc atctgatttc ttttctttct ttcttttttt cttttttttt   6240
ttttttgaca gagctttgct cttgttgccc aggctggagt gcaatggcac gatctcggct   6300
cactacaacc tccacctcct gggttcaagc tattctcctg cctcagcctc ccaagtagct   6360
cggattacag gcatgcgcca ccaggcccgg ctaattttgt atttttagta gagatggggt   6420
ttctccatgt tggtgaggct ggtctcgaac tcccgacctc gggtgatccg cctgcctcgg   6480
cctcacaaag tgctgggatt acacgagtga gccaccacac ctggcccatg gtgattatct   6540
ttatgtctta tcctcctcca tatccccagt acctagtcaa gggagtggca ttaaatgcaa   6600
```

-continued

```
atcagtgttt gccaactaaa taaaagccca acagcaaaca gatgttggaa tttcagagtt   6660
gtggaacgat gggggctcat ggagggtttc attactctaa tgtcaaggta atgggttctt   6720
gtcctggctc tgccactagg cttctgtgtg acctctgaca agtctcctcc tacctataaa   6780
gagagtacag ccaaaaaatg gtctcatgta tagagcttca aacactgctg ataaatttca   6840
cactgatttt tctcttttaa tccacacagc aatcttactt gaaagggaag tcggctgggc   6900
ggggtggctc acgcctgtaa tcccagcact ttgggaggcc gagagtgggg gatcacgaga   6960
tcgagaccat cctggctaac acggtgaaac cccgtctcta ctaaaaatac aaaaaattag   7020
ccgggcatgg tggcaggtgc ctgtagtccc agctactcgg gaggctgagg caggagaatg   7080
gcatgaaccc aggaggcgga gcttgcagtg agccgagatc gtgcggctgc actccagcct   7140
gggcgacaga gccagactcc gtcaaaaaaa aaaaaaaaga aagaaagagg gagggagaga   7200
gagagaaaga aagaaaaaga aggaaggaag gaaggaaaga aggagggaag ggaaagggaa   7260
agggaaaagg aaggaaggaa agaagggaaa gggagaagtc gtattattat ggactcaaac   7320
ccaggtctgt ctgtctgtct gacttgaacc ttgttcttta ctatgattgc cctcatgtat   7380
gtctcactca acagggatat tatcaggacc ctcttgagat cacatgcgca ttctttcaaa   7440
gcattgtgct gaggctggca gactttcata attggcctgg cactggctct gtcatgggga   7500
caggggggaca gagctgaatg tgatggaggt ttcctattat tctctaactc ccttcctggg   7560
gaccactgag ttgggcaacc atgttctgtt aaatggcaac agggcagaac aaaattagtg   7620
actgtgtttc cagattttta cccagatctt aaactcctga ggcctgctga aaaatgaatg   7680
agtatcaggg tgtgagtttg tacacctctg tatgtctctg ggcaaccaat cagacaactt   7740
ctcctattac attggacact tgggtttcag caatttccat cttgctaatg tgatttctca   7800
aaaatatttt ctgtcttttg gtgctttgat gataaatgtc catatatgga atgtagtcat   7860
ttcctgctac taagattcct tctggtttgt ataagggagg agttcacctt attcgcattt   7920
catggtattc cacaaagagc tccctccccc ttcccatgta atttatttga gatctgctga   7980
catgagttgt tggagcttga agggaattaa taatgtactg cagtgactcc tatcccagga   8040
aaacttgtta aaaatacaaa gcctcggctg ggtgtgatgg ctcacgcctg taatcccagt   8100
actttgggag gtcgaggcgt gtggatcaca aggtcagaag atcaagatca tcctggctaa   8160
cacggtgaaa ccccgtctct actaaaatac aaaaaattag ccaggcgtgg tggtgtgtgc   8220
ctgtaatccc agctactcag ggaggctgag gcgggagaat tacttgaacc caggaggcgg   8280
aggttgcagt gagccaagat cgagccactg aactccagcc taggcgactg agtgagactc   8340
catatcaaaa aaaaaaaaat acaaagcctc aacccctcct tcccatcagg cctcttgcat   8400
cagagtctct gggatggggc ccaggaatct gtattctttc ccagctcccc agaatgttca   8460
gccaggtttg gaaactgatc tatccgattc ttcttgtttc acagttaggg aatctgtagc   8520
tctgggaagg gaaggaactt gccccagtca catctgatat tagtgcttct ttctccaatg   8580
aagagccttt aggctgggag tccagagaca tgggttcaag tccaggctat accagtcatc   8640
acctcgggca agtcatttca cctctccaag cctctgcttc cttactgtga gaataatgcc   8700
attgtgttgg gaatcaaaag agagagtggc aatggaaatg ctttgtcaag ctttctattt   8760
tgtgcacatg gaagttgtta agagctagaa ccagccagtg ttcactcctg tataccacgc   8820
tgttcccttc caacagaggt cagggtcctg ctgtgttggg ggtggccgcc agccagtttc   8880
ggtggttgct gggcttcagg ccatctgtta ccaactctct tctctccatc ttttgcaggt   8940
```

-continued

```
gttgggatgg ccaccaactg ggggagcctc ttgcaggata aacagcagct agaggagctg   9000
gcacggcagg ccgtggaccg ggccctggct gagggagtat tgctgaggac ctcacaggag   9060
cccacttcct cggaggtaag cccctagctc ctccccacag cattcaccat ggcccactgt   9120
ctggccccgg ccaggctgag ggtcactcct ttgcatcagg gaccatatct cttttgcctt   9180
attttttcca gtaactaaaa ttgatctcta gaagtagaaa ataaaaaggc agtgtcctgg   9240
agtaatcaaa tttaaatatg ggtttgaag tgtgacttag gcaaattact taaccgctct   9300
cagctgcagt ttcttcaggt gtaaaaatgg gataataata ggacctacct cactggtttg   9360
gtaagagaat tacaggatga ttcatgtgaa gcactttgcc cagtgagcta ttactgaaaa   9420
ccccataatc actctacctt ctctgtaact ggtttgtgat atatgctttc aagcctttct   9480
ctgtgcattt atatacatag ataggtatat atagaaatac gtcttttta aaaaacaaat   9540
tgtatcatat atattattct atgatatgtt tttggttttt tatttgtctg tcttagaact   9600
ttctaatgcc ttctattagg gtcatcttca ttctgaggca tagtattcca gatgtgggtg   9660
tatcacagtt tagcttccct ctactcatgt ctatttaggt gatttctcat tattttatga   9720
ccataaatag cattataggg aacatccatg catatgtctg ttggggcacc tatgtgagtg   9780
tttctccagg ttcaatacgt aaaagtagaa ctgctgagtc caaaccacac ctttttaaaa   9840
cctcatcctt agggaagaaa aaaaaataaa aaaataaaat ctttttaat ttggtgacta   9900
ggtaagacat tttcatggtt caaattcaaa tggtacaaga gtttacccta atgcagcttg   9960
tgttttggtt tcttgttgat cctttcagat ggcttattca taacaagtaa ctaataacaa  10020
gtaaatatat tccttggggc ctcgctctgt tgcccaggct ggagtgtagt ggcacaatct  10080
tggctcactg caacctccgc ctcctgggtt caagcaattc tcccacctca gcctcccaag  10140
tagctgggac tacaggcatg tgccactacg cctggctaat tttttttttt tttttggtag  10200
ggacagggtt tcaccatgtt gtccaggctg gtctcaaact cctgacttca agtgatccac  10260
tggcctctgc cccccaaaat tgctgggatt acaggtgtga accaccgtgc ccagcctcct  10320
tttgcccact tttttttctt taacttaaca gtacacctta agaccatatt ggtgactaaa  10380
gagctgccaa catctcttct ttttttagcc agacccattc ttttttgtct ctgtgtgccc  10440
agaacctaca caggcctgat ggagtccaca ctcagtaatt gtttgctaag gcccaagtaa  10500
atgacaatgt ctgtcaccta aggcaggctg atggtatgga atagaattgc ttgggctgtg  10560
aacctagatt ttgtgaatta cttgtatgaa tctaaaatga agcattttct cttccacgct  10620
tttgtttctt ctgttaatca ataggtacca tgtgaagatc caacacttgg tctttctggg  10680
aggttatgga gcctagaaaa ggcgtaatcc acaatgagat ttctaatcca gaaaaaaagt  10740
cagaaagtgt acgtgtgtgt gtatgtgtgt gtgtgtgtgt gtgtgagaga gagagagaga  10800
gaatgatttt actccaaatc tttaccaaat gcctgctcta tgccgggcca ttgtaggcac  10860
tgaggacaga gaggtgagtc agccagagcc ctagcctctg gggctcctgg tctagttaga  10920
gaacatacca caaaacaaaa ttaaataaca tcagctctat gaggaaacac aggcagtctg  10980
ctacacaaag ttaactatca tttattgagt atttagtatg tgccaggcat tattctaaac  11040
actttggaat cactgactcc tcaccacaac agagataagg aaaccgaagc ccagagaggc  11100
taagtaacct acctgaggtt atttaaatgg taaaataatt ggcagagcca ggatgtgaac  11160
ccaaggaatt tggctcctga gtccatgctc tgaacatcca tgcttttttt cctctcccaa  11220
gatactatat aggacagctg gaagaaagag tagttcatta tgattagatg attgagatgg  11280
ggggtggtat ttgaactaga ccttaaaaga caaataggga aaaggaacag catagcaagg  11340
```

-continued

```
acccaaaagt aggaaaaggc aaaaaaaaaa aaaaatgttc aagagaatgc agctgaaatg  11400
cagggcgcat aagtggatat agtgggaaag aaggcaggcc agcgtcagac agccgcgggg  11460
ccttagctac tgggtggagg aggagtatga actttatcct gtagatcaga gctgcaaact  11520
agccatatct aggctgagta tttggctcct gcagtgtttg gggagttaat ttgtttttta  11580
caataagtaa tacgttcaaa tacatttgaa cagggcgcaa aattcaaaag ggtattcagt  11640
acagagtaag tccccttcct ccagccactg tttccctgac caggggcaag cattgttaac  11700
agttgttttc accagagtat ttttaaaaag tcagagccaa catttaaaaa aaaaaatcat  11760
gaaattaaaa caaaaaatct agcaacccaa cttgtcttga aaaattatat catctggcaa  11820
ctctggccta ctttcctgca tggcaacaat tggctagagc agagttctgg ctgcccccct  11880
tagagaagat gcaagtactt ctttttgcca caattcctat cactccctgt tgcttcctgg  11940
ctacaaagca gaattttgtc atgcacgtgc tataggtttt tttaaatagt agaaaaatgt  12000
ttcttttttt ttttttgaga cagagtctca ctctgtcgcc aggctggagt gcagtggcac  12060
gatctcagct cactgcaacc tctgcctcct gggttcaagc gattctcctg cctcagcctc  12120
cagagcagct gggactacgg gtgtgtgcca ccacgcccag ctaatttttg tatttttagt  12180
agagatgggg tttcaccatg ttggccagga tggtctcgat ctcttgatct tgtgatctgc  12240
ccgcctcggc ctcccaaagt gctgggatta caggcatgag ccaccgtgcc cggccagtaa  12300
tgtcatttta tgttaatgtc tctatcaaaa gtgagaagac tgtgtgtttc agcctttagc  12360
ctgtagatag cagagaacag ctataaacta ttgatcctaa attcaggagg gcataatgag  12420
ccctgggaca gaggcagagg gatgtcttag cagaaaaact ctgagttttt gaggccaaga  12480
tgagacttgt tgggggcagc agagctctat gtgttcaagc caaggaaatg ctcctgtagt  12540
catcacatag ctactcaggg tattaggtca ccccttatgt aatctgcagt cattcccatt  12600
ctaactcata aaggcttcag actgaataaa ccttattctc acaaatagcc ttcctcagtt  12660
ttatcttaga tgctgaggcc agggcagtgg tacacacctg cagtctcagc tactggggag  12720
gctgagacag gaggattgct tgagcccagg aatttgaggc tatagtgcac tatgatggca  12780
cctatgaata gccactgtat tccagtctgg gcaacatagt aagaccccac tccaaaaaaa  12840
aaaaaaaaag atgctgagaa gggtaattta gaaattatct accaaaattt aaaatagatt  12900
tacctgaatt acttgatatt tttactttta gaaatttaga atgtatggac tttctcatat  12960
atgaaaatat ctagaatgta tattctagga tacccattga aacattaatg gtaataggaa  13020
aataaagaaa ccacctatat actagattca ataaattatg gtatatccta agagtagaat  13080
aatatacagc aattaaaaat aatgaaaatg ctctatttga acatataagg aaatatttaa  13140
aaagcacaat gtagtatagt ttgctatggg ggtgaaaaaa agagaaaata tatgtgtata  13200
catatatatc aatacaaaga tgactggaag gatgtgtgag acactagtct gtcatttgcc  13260
tctggggagg agaactgggt ggctggggcc cagtcttttc cccaggagac tggaatgaga  13320
gtgagacata cttctcacta tatattctta tgtctctttt gaattttgta tcatgtattt  13380
gtattacctg ttaaaaaaat aataatattt tggctgggca tggtggctca tgcctgtaat  13440
cccaacactt tgggaggctg aggcaggcag atcacttgag gccaggtgtt tgagaccagc  13500
ctggacaaca cagtgaaacc ccatctctac taaaaataca aaaattacct gggtgtggtg  13560
gcacacacct gtagtctcag ctacttggga ggctgaggca ggagaattgc ttgaacccag  13620
gagatggagg ttgcagtgag ccgagattgt accactgcac tccagcctgg gcaacagagt  13680
```

-continued

```
gagactctac ctcaaaaaaa aaaatagtac tttaaaaata aatatctaaa taccaagttc  13740
taacaccgta aacttatacc accataatga caaactgata ttaactcaaa ggttaaactc  13800
aggaatgctt tataatacaa gtcacaagat tttcttttca tctcttaccc aagttctagt  13860
tcagttgttg gcagggatct cagaatgcac ttttcccttc tagaatcagt gtccttgatg  13920
gtatttgggt ttctcgtcta tgataaagtc caaagaatgc ggaatgcagc tgaactctag  13980
gcctgttaac ctgagtcacc atcactaaca ttggtggaaa aaacactcct ggcttctact  14040
aagggaacca gagttcactt gtcctaccca gtaaccaaat caaaatcaaa aggcaaggaa  14100
actggagtgt gagctcctga tgcatggaag ggcctgggct tgaacatcaa ccagcaagga  14160
gcaggcttcc atgtatgtat gtgtgtgttg tgtttagtaa ccatcctggt tcaaatccca  14220
gcaccccgtt actagctgaa tataattttg gatctgttaa ctgttctggt tcaaatccca  14280
gcaccagttc ctagctgaat ataattttgg atctgttaac ctctctttct caggtcccgt  14340
ctctgttaag tgtggataat aatagtatct tcctcacagg gctgaatgat gaatctatgt  14400
aaagtattta aaatagtacc ttgcacatag taagtgctca ataacttgtg ggtttctttt  14460
tgttatttgc attttgcttt tttgcttctc tctcttcaat acgtagagat aaactatcac  14520
agaatctgga agctctctgg gttccactct ccccccttcca ctctcccaag gtaaccacta  14580
atctacagtt ggtgtgtcct cagtaaatat aggccagact ttccatggga ttccatttgc  14640
aggaagacaa cccgttcaca ggtgccctac ccctgtccca ttctctcttc ttgatcacag  14700
gtggtgagct atgccccatt cacgctcttc ccctcactgg tccccagtgc cctgctggag  14760
caagcctatg ctgtgcagat ggacttcaac ctgctagtgg atgctgtcag ccagaacgct  14820
gccttcctgg agcaaactct ttccaggtag gggacagtga agcattgggg ggccaggagc  14880
tgccagagcc aaggaactgg aagattgcag agccgtgagg tgttactgtg tcagctgact  14940
tggtgggata gaggaaaggt acctccaaag aacaaaaagt cataggagtc aggaaagctg  15000
gcttctaatc ctggctcgac cagttattta tatggcctca agccactccc tttccttctc  15060
tgggcctaag gtttcttcat ctgaaaaatg aagagactgg cttaaatcca agatcccttt  15120
attgttgaca ttctgtaatc cgtgacaccc tactttgaag actgatattt ccatttggaa  15180
ttaggggaag tcagcctggt tttggaggaa aacagaggta gggaaggtta ttgggttaaa  15240
gtcagatttt ctacttctcc taagcagcga cactttcttg tcacctcagg cctctcatct  15300
ttggatggga tggggtacag actgggccac actcagggca tgaggaagca acctctgaaa  15360
tggttcagcc catccgccct tctctgtctc tttcccttga tctttttttt tttttcttca  15420
gattctgggg caatttctta aaatttcttt atttatttta gaattaaata tatataggct  15480
gggcgcggtg gctcaggcct gtaatcccag cactttggga ggccgaggtg ggtggatcac  15540
ttaaggtcag gagtttgaga ccagcctggc caacatggtg aaaccccgtc tctactaaaa  15600
atataaaaaa attagctggg tgtggtggcg ggtgcctata atcccagcta cttgggaggc  15660
tgaggcagga gaatcgcttg aacccaggag gcagaggctg cagtaagcca agatcacgac  15720
actgtactcc agcctgggcg acagagcgag actccatctc aaaaaaaaag aaataataat  15780
acatatatat atgtatatat attcattgta gaattaaata tctagaaata ttatgtattt  15840
acatatacat gctagatgtg tatatactgt acaggttgag catccctaat ccaaaaatcc  15900
aaaagctgaa atgctccaaa attcaaaact tgttgaacac cacatgactc taccagtgga  15960
aaacgccacg cctgatgtca tgtgacaggt gcagtcaaaa cacagtcaaa agtttgtttc  16020
atgcacaaaa ttaattaaaa tattgtataa aataatcttc aggctatgag tataaggtgt  16080
```

atatgaaaca aatgaatttt gtgtttagac ttgagtccca tccccaagat gtctcattac 16140
gtatatgcaa atcttccaaa atccgaaaga cttctggtcc caagcatttc ggataaggga 16200
tatccaacct gtaattgcat gtctttgatt aatttttcaa cagaaattag acttttgttg 16260
gagacaaaat cttttaaaaa tgtgtgggtg aatatgagaa ggggtcataa tggtaagaag 16320
cttggaaacc attgacttgt agccaaaaac ccaatgagtc atgaatgtat gaatctgccc 16380
accaccttgc ccctgagctg tttcttggaa tgggcccagc tttgtacctg caatcctgga 16440
ttgtgggaaa catgagcagc ctggcttata accctaatga tgcaattatg aaggagactt 16500
gcagctcatc tttgcaaccc ctgccttctc tgttcctctc tcctctcata cacatataaa 16560
ccctagttcc taagggagaa gagcccccta caaaacatga aggggagcac ctcttcagaa 16620
aaaggaaagt gtgtctcaac ttccttggag gctgaagccc agctgggact ctcctcctaa 16680
ccaagggctg gcatgagaga gctcaccctt gggagagagc tggctgagga gcagaggaac 16740
ttcagggcag gcctgggcta cttggcttcc ccccactggt ctgctgtgac gtttctgtaa 16800
caaggtgatt caggcttgag caggtgtgca gaatccaccc tgaatctcaa agggcagtaa 16860
gtgtgatgtt aatcacctgt ggattccttc ttactgtggc tcttgttgag acttcagaaa 16920
accatactgg ataggcccct aacacatgtc acatgtcatg gcagtacact gagctgtgac 16980
gatgagcctg catagacaca gccattacct tcatgaggtt tatagtcaaa caggagagat 17040
gacactaatc atcacacaaa gaaaatgtaa aattgcaact gcagtcagtg ctgtaaagga 17100
gtggttctta gttctatgag aacacatagt agggggatct gactcagata gggaaggctt 17160
ccctgaggaa atcacatcat atgaggacta gttgaagaag aaacaaacaa acaaaaaaaa 17220
cccaggatat ttagcttggg tcagaaaaat cttattggtg cacagggcat aactgctgtc 17280
ttctaatctc caagggctgc tgtggaggag gaggagaagg ctcaccctgg gaggtcgcag 17340
agggtaggaa aagctatgga gagttagtat taggtcaacc agaaggcttg ccaaccatca 17400
gagctattca agtagaatag atacatcatg tcattttcta gctcttcttc ggtgcagtat 17460
gttcaattct ttgaatgtaa tatcttattg gctttttacc acaactctat gatataaata 17520
taattatatt ctccatttta aagatcagca aactgagaca cagagaggtg aaatgattcc 17580
ctgaggttgc ctactagtga gtggtagagc taggatttga acccaggtct agagttggat 17640
tcttagccac tgttctctac cacattgggg cggacattca agttttggcc agtagactca 17700
gagaggattc aggagtcaat gactgaggat gggactcctt gaaattttag gtccaattaa 17760
gcctgcaaaa tgttctctgt ttcttcctcc agcaccatca aacaggatga ctttaccgct 17820
cgtctctttg acatccacaa gcaagtccta aaagagggca ttgcccaggt aaccattccc 17880
agccctactc cagtctgtaa cctgtccctc ccatctctgt ttgttttctg ttttgcttga 17940
agaatttggt ccaggccctc agctcatggg aatctgcctc tcactggtcc tcactgggtt 18000
tatcccagtg accaattcta ggatgaccag aagaatgatt ccactgggct tgggagtgtt 18060
tgctggtacc tctaatctct gtgtagagtt catggtacct gtgtgctctg tggctaggtc 18120
ctcagagtca gtccctgggc aggtactgtc agccttcagt tttccccaca gactgtgttc 18180
ctgggcctga atcgctcaga ctacatgttc cagcgcagcg cagatggctc cccagccctg 18240
aaacagatcg aaatcaacac catctctgcc agctttgggg gcctggcctc ccggacccca 18300
gctgtgcacc ggtgggtccc ctgggcagcc cccggcatac ctgtggggtg acatgctgat 18360
gggtgtacag tcactggcta ggccagggaa ctccagctat gattgtgctt tcctgggccc 18420

-continued

```
cgggtcacat gttgcccctg gccaccccga cagcagtttc cacttgtaat gagatccttg  18480
gtatgtcagg gagaaaaagg acctcatagc tcatctagtc ctgtccctcc attgtacagg  18540
cagagggaac aatatcttga gagccccaga gagaggaatg cagggacttc tgtctggggg  18600
ctgggcctgg tagcatccat ttctagccag cagtgatgct ccaggttgca atgattttag  18660
atggtctgca gcaggattcc agacagcacc tggaggccca gagtaagggg ctccagctca  18720
ctgggacact agggtaggtt ggggtgggga cagaggctct caggtctcct ccaggcatat  18780
acaccagggg ccaaggttag ggcagcccag catattccaa cctgaagtgg atcttacagg  18840
aatgtgatgg gaggatgctt tttagtgctc agctgattct cagagtcatg ttgctgtata  18900
tatgaggtca tgggcagagg ggtcttccag gtccatccaa ttactgaaca gccatctctc  18960
ttccaacaga catgttctca gtgtcctgag taagaccaaa gaagctggca agatcctctc  19020
taataatccc agcaagggac tggccctggg aattgccaaa gcctgggagc tctacggctc  19080
acccaagtaa gggtgtgaaa aggtagcagg aggatcctgc tttagtttca gcattcatgg  19140
gtttagcaac ttcttttctt gccagccatc attagagaat aaggggattt ttctaggaat  19200
agaaacttat acctttacat gccaaaatta ttttaaggtt tccttcttaa ataacagatg  19260
ctgactatga tttaactttt tcttattgag tggaggtcat cattatgact gtcaacaatt  19320
gcagcttgct gtaatacagt agtgctacct agggttagag aggcacgcaa ggctgtttgc  19380
ctgcgctaat agctctgact gctaggcttt aagttcttag tcatttcctt tttttttttt  19440
ttttgagaca gagtctcact ctctcaccca ggctggagtg cagtggtaca atcttggctt  19500
acttcaacct ccacctcccg ggttcaagca attcttctgc ctcagcctcc tgagtagctg  19560
ggatttcagg cgcatgctgc cacacctggc taatttttgt atttttagta gagacggggt  19620
ttcaccatgt tggtcatgct ggtctcgaac tcctgacctc gtgatccgcc caccttggcc  19680
tcccaaagtg ctgggattac aggcatgagc cactgcaccc ggcctctcat tcattttctt  19740
catagttttc ttgtctgttt cccaattctc agctcttact tttgactgct gttggtatgc  19800
ttgaatttgg aatcctccac cccccatgcc catgcctccc ttctgatttg ctgtggtttg  19860
ggaaaacaaa tgatccagat tgttatgatt gggtctgaag agtgtgaggg cctcttggat  19920
gagtaaatgc ataagctttg actacgaaat tttatggtat ccttttttaac tgcttagagg  19980
catttttgc tttcttccta tttctcaagt gaagatgtta ggtaagtgat tttcagatca  20040
tcgaggggcc gctatactaa cagttattgc aatgttaata tagcattaat agtccttaat  20100
gtacacttac tagtgctaca ccttgtgcta agctctgtac atacaggatc tcattgaatt  20160
ctcataataa gctctctgag gtcaatactg ttcaactccc tcattttaca gatgaggaaa  20220
ctgaggttct gagaaacgaa gtgaattgtt aaggctaagt gatgagttgg tggcagatcc  20280
caaagtctac ctccctctaa aacctccact cttaatcatg ctcttacctc caagggagcc  20340
tctctgtcct tgctaagcct cactaagccc aaagaaacct cagactgtaa gcatttagaa  20400
gtcatcagac aaatattctt tcaagtatat tggctaggtt gtattttaag agagtgaagc  20460
caggggatgg gtcagctggg gaactgctga cagacaaatg ctgcagaggg ttttgcctgc  20520
cagcctgtca gtaacgtgga cagaaaatac ttgtgtgtcc aaaattaggc actggtaggt  20580
aggagttatg tggcacctga gccagaactg gcttccccca ttgtgagagt gagataggtt  20640
cttctgctga catagcacat gaccttggca agttagttct tctctgagct tcagtttcct  20700
catttgtaaa ataggagtaa taataatacc taaaggggtg ttagtgagaa ttaaatgaga  20760
tcatggatct gaaaaatgtt tttaaaaatc tgtgtggatc attatgtggt actttcaata  20820
```

ataataatag gccgggtgca gtggctcaca cctctaatcc cagcactttg ggagaccgag 20880
gcgggtggat catcagaggt caggagttca aggccagcct ggccaacatg gtgaaacctt 20940
gtctctacta aaaaatacaa aaattagcca ggcatggtgg caggcacctg tagtcccagc 21000
tacttgggat gctgaggcag gagaatcact tgaacccggg aggtggaagt tgcagtggcc 21060
aagatcaccc cactgcactc cagcctgggc gacagagcga gactccatct caaaaaaaaa 21120
aaaaacaaaa aacaaaccca aataataata ataatagcta tcatttgaca agtattagtt 21180
ttaattcata caacagcaaa ctgaggctaa gagagtttga ataacttgcc caaagttaca 21240
caaccggtaa gtatagaatt catctgcctc taaagcctat gttctctcta cttccctatt 21300
ctgcctttaa gagatatggt tccacagtat tgactgaaaa actgcattgg tagagcagat 21360
taattttcgt caattatctc atgattttta aaatttctta aaaatggaag cctgcaaaat 21420
gacttacaat ttcaatttag acaaactctc aaagcatagg gcctgtggtt agaatgagta 21480
gaataagaaa aggggactac tggtgataaa agtttgggaa ctgtgatctt tttaacacca 21540
atttttttct ttttttttga gacagagttt cgtttttgtt gcccaggctg gagtgcaatg 21600
gcacgatctc ggctcactac atcctccacc ttccaggttc aagggatttt cctgccttag 21660
cctcccaagt aactgggatt acaggtgccc accaccacgc ctggctaatt ttgtattttt 21720
agtagaaacg gggtttctcc atgttggtca ggctggtctc aaactcccga cctcaggcaa 21780
tccgcccgcc tcggcctctt aaagtgctgg gactataggc gtgagctacc atgcccagcc 21840
ataacactct tattttatag atgggaaaac cagggcccaa ggaacgaaat tgccttaccc 21900
aagtcaatta ccaagacaca ctacaagtca ctggcagagc ctggactacc tacgactcag 21960
gggtcctcac ccccagcccg catgcgtcct tagctgacaa ctttcctact aggaaacaga 22020
ctgctgagaa ctgctcagaa ctgaaggcag gagaggtcaa atatgttttc tgagcccagc 22080
tctgattgtt tagcagttgg caggctgact taattagctg gggcgtgcag ttcctcttta 22140
acctccagct gccagccttc ctcctccgcc tctttttgga ggtgggccag cctgggccaa 22200
ctgcctccct cccacacaca ccctcaccca tgagcgggac agtttaggct gcaaagtgaa 22260
gagcaaagcc attggccctt aggactctct cagggcaaga tgacttgtga gagcaccact 22320
tttagtttgt ctctcaggca cccaactcaa agccaagact cagcttaaca tcacatctga 22380
cctcatgaga tttcaggcaa accaggagag gggacttact aagacctata ttttggctaa 22440
gcagaaagga gtcaggcaaa cagagtttag actaagaggt tcagccaagg tcaggagaag 22500
cagagataga caagagaggc taagcagagg aggtcaggga atacacactt agaatcctaa 22560
gccaaagcct agggttccat gggtctcagg aagaagccac agacacaaag cagtacagtc 22620
acagcaaaaa tggagtttgg aggctgagcg cagtggctca cacctgtaat gctaacactt 22680
tgggaggccg aggcgggcag atcacctgag gtcaggagtt cgagcccagc ctggccaaca 22740
tggtgaaacc ccatctctac tcaaactaca aaaattagcc ggcgggggtg gtgcacacct 22800
gaaatcccag ctacccggga ggctgaagca ggagaatcgc tggaacccag ggggtggagg 22860
ttgcagtgag cctagattgt gccactgcac tccagcctgg gcaacagggg gagactccgt 22920
ctcaaaaaaa taaataaaat aaaatgtaaa agaaaaaaaa tgcagtttgg tactgctgag 22980
cattagccct aggaatctct taggggactg gacctatctt tgacaacgga aatatgttag 23040
ctggcagcca aacagatagt tccctggcat aagcttttcc ctgagccctc aagcccctgc 23100
ctctttaaga aatacatgaa taatcagaga ggaagaagcc acataagccc tagtgatctc 23160

```
attaatacta tgagatcaaa tgtggccctg tgtacattat aggaatcttg ggagggccca  23220
ggagataatg tcgttgtttg tagttggccc tgtgggtttc tgtagggttc catcttgtgt  23280
aagaaccaca ttcctttatt gtatccttta caatctagta atagagccat tagccccgga  23340
ccccctgcat tgttctttta caaaatgttc ctcaatactc ccacttgttt attcttccag  23400
aaagatttta gaattatgtt aagttctaag aaaaagtcct cttgggtttt tgagatggtt  23460
ttaaatctaa attttaattt gcacagaaat tcatcaaccc atgacatcat tacaatattt  23520
catctgccca ctggagaagg gtcagaggca tcttcatttt tgaagttttc tattttcagg  23580
aaatcatatg tgatagcatc aggtgtctat gcctgaggta atctcaaggt tcctgagaga  23640
gggaacatct gttctttcag ggaagcggtg ttcttattct tattccagga ggtggggcgg  23700
tatgggggtt gaggggagaa acaaaagaag aacaagttct atagtagcct cgggccacct  23760
gtgctctttc cccagtgctc tggtgctact gattgctcaa gagaaggaaa gaaacatatt  23820
tgaccagcgt gccatagaga atgagctact ggccaggtaa gtaaaggaag ggggacttct  23880
aggtgtggct ccaggattag gggtggggca ctcagaacat agcatccatt ccctctggct  23940
cttgcccatt tttcccagga acatccatgt gatccgacga acatttgaag atatctctga  24000
aaaggggtct ctggaccaag accgaaggct gtttgtgtaa gcattcccaa gaatccagtg  24060
gaaggctggt ttatgaaact catcctgcca ccctcttccc caaaatgatt ctttcttctg  24120
ggagatgtga tggcttgctt ccttctctca taattcctga aatatctcat cctcccagga  24180
aattttggag aaagccagcc acgctgtgct tctatcagag ctgttgacat tctggatcag  24240
ggtctcctta gagatcatct tagttttcat atgccctaag ttcccaaaag ttttcttgcc  24300
tctcctagta aggtgaggtc aggcctgaga agctgagctg ggcagtcagg gaggaagagg  24360
agcagctggc tcatgctgtg attggtctgg atgccactgt ctgagctcga gcctggattt  24420
gtgttccaag ccaagcctta tccttttctc taggggccac caccaggtag atttggtgct  24480
acatatttgg gtagcattgc agcacatata tttagaccta gacctttgtg attgttaaaa  24540
ttaaaactgt ccatggaatt tcacaatacc actcactgtt tttcaaaatg tgcttttatc  24600
ataactaaac aaagtagtta atttactttt cagataaact agacaatatc aaataggtca  24660
aagaaaagga aaagacattt aaaaagcctg tgtcttaatc agactcatca ttttacatgt  24720
ttgcgttttc accttcaccc ctgccattaa aaatttttc attctggttt cagctgcttt  24780
aagcagtgga aatataaagt gtgttttact acacatggca gtatgattct gctgctcggt  24840
aatttcgagc caacatttgt atgcatttac caaatttgat tctagtgacc ttcttgttcc  24900
ttctggcctt cttagaatga ctctaaatct ggcatattct aaagtattct gtatggcaca  24960
cctccctgtt ttcagtggaa gccctggtag tgtggatatc tactttcact ggttccagtg  25020
aacccctgac caggctccca ctgtgggctg aattttgaaa aagccaaatt catcttgatg  25080
caccctgaaa tagattgaac cactgaacaa atcagttata atttaacaca gcagccttct  25140
ccatcctgtg ttccagggat ggccaggaaa ttgctgtggt ttacttccgg gatggctaca  25200
tgcctcgtca gtacagtcta caggttggta ttttctgtga gaccattctt tgcctcctgg  25260
gacccacaag agctccacag agacccaatt caggcttata acaacctggg ttttccgagt  25320
cctcacttca cttctttctc agggagcttg ctgctagaac ctcctatcct ccctcaagcc  25380
ttttgctacc tatcactcta cacagtcttc tagaatttga atcctcagga atccacagag  25440
cttcagccat ttacactgtt tccagagatg tgctggcaaa tgtttaacaa caatcagctc  25500
tcactggttg atataagcca gttccagcat actgctgacc atttttttc ctgccaactc  25560
```

ttacctttcc tttatctgaa tcagaaagtt ttatcatctc ctcattcatg ttaatgacag 25620
ttatatcacc tcattttgct atcctaccat gtagtttcat tagtttccac atccattatt 25680
tcatttaacc ctcacaacca ctcggtgagg catataatta tccccattat acagatggag 25740
aaactaacgt ttagagagat ggagaggctt ctctaaggcc ctacaggaag ttcccaggtt 25800
ttctgacttt caggccgatg gtattcccat tcttctcctc tgctcctaac atccacatca 25860
tggagaggct aagaagctct gctctcagct gggagatgat aaaggaggaa ataagtttag 25920
aaataccatg ggcagtgagc tggaggtcat gagcttgact gcctctgtgt gatgatgggc 25980
aagttcctga ccctttctag gtctgtttct atgagcgggg ggagctacac tagaaaactg 26040
agggggctcc ttctaggtct gtaattcatc taggactccc cccgagggtt gagctccaca 26100
tgaggaggct ctatagaggt ggtatctcga tagaacatcc ttttctttag ataggtggtt 26160
agcagtggtg gcaacttgct gactacagga gagataaact gtctattaga aaaataggtc 26220
taggccgggc acggtggttc acgcctataa tcccagcact ttgggaggcc aaggcaggtg 26280
gattacctga ggtcaggagt tcaagaccag cctggccaac atggtgaaac cccgtctcta 26340
ctaaaaatac aaaaattagc cgggcgtggt ggcatacccc tgtaatccca gctactcagg 26400
acgctgaggc aggagaattg cttgagcccg ggaggcagag gttgcagtaa gttgagatca 26460
tgccactgca ctccagcctg gctgacagag cgagactctg tctcaaaaaa aaaaaaaaga 26520
aatgggtcta gatttcaaaa cacgacaaag aaaacttaga agagtttgag ataacaagga 26580
aggaaagtag tgtttaaaga ggtagacttt tttttttttt tgagacagag ttttgctctt 26640
gttgaccagg ctggagtaca gtggtgcgat ctcggctcac tgcaaccttt gacttccagt 26700
ttcaagcgat tctcctgcct cggcctcctg agtagctggg attacaggca cccaccacca 26760
cacccagcta atttttgtat ttttaataga gacagggttt caccatgttg gccaggctgg 26820
tctcgaactc ctgaccttac gatccaccca ccttggcctc ccaaagtgct gggattacag 26880
gtgttagcca ccacacctgg ccaagaggta gacattttta gggaactgag cagctcagag 26940
caggtttaga catggagaga gatctagaag gcttagtgac ttactagatg accctgggca 27000
agtccttgct tatctttggt tttgctttcc tgcttctacc ataatggggt atttctctgg 27060
gtttatttct gatgttctgg tcacgtgtga ttctgcgtgg aatgccagac tagtagttgg 27120
gttcctgggg ttattgatga agatcaggtc aaggtgctac aggtggacca gtagtatcaa 27180
aggaaggaca gcattgggtg ggggtcacag gagagacctg atcctgctgt gtgcagtttg 27240
cagtggtctg gagccaagga cagactgtct ccccattgca tgagaatggg aaccagagtt 27300
gggaggcatg atcccctgct gtttccttgc cttttatacc ctcagctctt gtggtaataa 27360
accattcatc ctgtgatcat ccacttgaga cctgtgttca tattattctc ttagcctgag 27420
tatcccttcc ctattgagtc tcacttgtca ggctctacct gtccttcaga accccactca 27480
aatttcaact tattcagcaa caacaacaaa tatttattga gcaactacaa agtgccagga 27540
actgtgttag acactggaga tacaacagaa aatgaggaaa atgataagag ccctgtgcta 27600
tggagctcac agtctggtca gagaaatggg catcagaaag taaacaaaaa tatggccatt 27660
tactgtggct cgtacctgta atcccagcac tttgggaggc ctaggtaggt ggattgcatg 27720
agctcaggag ttcaagacca gcctgggcaa catggcaaaa ccccatctct acaaataata 27780
caaaaattag ctgggtgtgg tggcgtgcac ctgtagtccc agctacttgg gaggctgagg 27840
agggaggatc acttgagccc aggaggtaga agttgcagtg agccaagatt gcgctgttgc 27900

```
actccagtct gggtgacaga gcaagaccca cgtctcaaaa gaaaaaaaaa gtaaacaaaa  27960
ataggaaaaa aaaattggga tttgtgtgtg tatgtttgtg tgcgtgtgcg tgtatgtgtg  28020
catgtgtgtg ttttagtctc aggtaactgc tttcaatgaa acaactgggt aaaaagagaa  28080
ttatgggaaa tccacattaa atagagtgga cagggaagcc ttctctgaaa aggtgacatt  28140
gagctgagat gtaaggatgg taaggatcca gctatgcatg ggaaaagccg aaaggaaggg  28200
ggtttcaggt tgagggaaaa gcagtgcagg ccctgaggag ggaaagagct ttgtgatttg  28260
aggaatgaca ggcctgtgtg agtagaatgg cagagactag gagtcaggga tggtacaagg  28320
ttgaaaaagt agacaggagc cagctcctga aggatcttga aggccatggt agggagtatg  28380
gaacacagtg ggaagctgag cacgtagaca aatgttctac ccttacacct tctattgttt  28440
cccacagatt gggggattct tgcctttgca ggggctcaca gtctggcaca atgatacata  28500
actacaacat atcacacctg gctcacaagg atgttagaat gatcctgggt gataatgagg  28560
gtgaagatac aaatcatgat acctggcacc taatggatgg atgttcagta aacgtcagct  28620
gaagtaaaat aaagtcgaat tccttttgtc ttcttccctc tgcagaattg ggaagcacgt  28680
ctactgctgg agaggtcaca tgctgccaag tgcccagaca ttgccaccca gctggctggg  28740
actaagaagg tgcagcagga gctaagcagg ccgggcatgc tggagatgtt gctccctggc  28800
cagcctgagg ctgtggcccg cctccgcgcc acctttgctg gcctctactc actggatgtg  28860
gtacgtgggc agcctgtttc tcctaccaca ggcctcctag gtggcagaga cctacagccc  28920
aatgtgttgg ggagggtgga gctggcattg tgacaagggg aaggtggagc tggcaaggtt  28980
ggtgatgctc tggagaaccc ctagaactct gagcagaagg gcagcctcat aatggaagga  29040
tgggggctgg aatccattgt aagctccctc agcaaaggta gagatgagga tggcaaccag  29100
agggaaggga ctaaggcagg tggcaagaat tgagaagtgt atcaggctgc ctgctgcaga  29160
gccctgagct gttgctaaag aaaggcctgt tctcattgca tcggctgctg caggggggttt  29220
gttgggagtg tcatccagat agtagcatcc tgcctgaagg aatttgtggc tgttctccct  29280
cctgctcttc ctctgatgct gctctgcata accagctgga cctaagcttc ttgcctcttt  29340
agcctttaaa cttttgataa ctgctttctg cctcctgcca gggtgaagaa ggggaccagg  29400
ccatcgccga ggcccttgct gcccctagcc ggtttgtgct aaagccccag agagagggtg  29460
gaggtaggtg gatctccctt tgcagggctc ctcaatgaga gggactagca ggctgtggcc  29520
agtgctcatt ggcacttact ctgggcacag tcccgggcat gggggaaact attggaactg  29580
acacaggcca catgttggac agtgtcccct aagaccctgt gaccaagtcc gggagcacag  29640
gggaatctga ttaaccagca ttgaagggtt tggacaagtt ttacctgagg tgcctgtggg  29700
tagattgttg ggaagtagag tagggtcata ttaggagact ggagagaata catgtctgtt  29760
ttcctttcta gtttgaaact ccttgaggtc aggggtcatg tctgcctctc cagaggagag  29820
gatttttta atctttgtct taagaggtgg gtaggaattt cccaggtgga aaggaggaag  29880
agtgttccat acaaaaggga caacctcaag ccaaggcacc gggccatgaa agtgtgagat  29940
gtttggaggt taatgagaaa ctggtgaggc tggaggggga gctgggaggg gacagggatt  30000
taggctggaa aaatggtttg catcctgatt ataaagggcc ttgaatatat actgagaaat  30060
tggattttat cttaagggca gtgggaagcc attagggagt tttaagccag gaagggacac  30120
attgatccag gactcaagtg gttagcagtg gtgggaactt gcaaaactta cagtttctgc  30180
attgtagaag atgtcctgga atgaggggag acactggaag cagaaagacc gtggaagagg  30240
ctgatacagt tgttcagaag agcaacgtag aggcctgggc tagggctatg actatggggc  30300
```

-continued

```
caactggaga gacatgtcct agatagtgag agggtagtgg aagggaggag ttaaatatga  30360
ctcaggggta ccttttgcct gattgggagt aggaaggtcc aggaggggca ggttcaggca  30420
gaagtaataa gttctgcttg gacaagttga gtttgtttgg gggccagtca tatgatgtct  30480
aagcagggag cctgcattaa atatttggaa gttaacaatt tttttttttt ttttgagacg  30540
gattctcgct ctgtcaccag gctggagtgc agtggcatga tcttggctca ctgcaaccac  30600
tgcctcccag gttcaagcga ttctcctgcc tcagcctcct gagtagctgg gactacaggt  30660
gtgcgccacc acacccagct aatttttgta tttttagtag agatggggtt tcatcatatt  30720
ggccaggatg gtctcaatct cttgacctca tgatctgcct gcctcggcct cccaaagtgc  30780
tgggattaca ggcgtgagcc accatgcccg gccggaagtt aacaattttt agggtataga  30840
tggagactca ggaataggag agatctcctt gggaaaatgt acatggggga gagagcaagc  30900
gtggaggacc aattcccctg ggaccccagc atttaagaga aggagccagc aatggagctt  30960
gagaaggaac agctgtaggt aggaggagaa ccagggcaga acagtgtagt ggaagatgtg  31020
ttcactgcat gagtaagggc tctcctgtca aagtgagctt ccctcctgag aagccagata  31080
tgccctggct tcactgagcg ggtgccagga actgaggctg ctgacttgcc catgtggccc  31140
caaaagtgag ggcatgggat ggaggaggta ggcagagggt ccagggtgac tggccagttt  31200
cattgcaggt aacaacctat atggggagga aatggtacag gccctgaaac agctgaagga  31260
cagtgaggag agggcctcct acatcctcat ggagaagatc gaacctgagc cttttgagaa  31320
ttgcctgcta cggcctggca gccctgcccg agtggtccag tgcatttcag agctgggcat  31380
ctttggggtc tatgtcaggt gagccaatca ggagaagctc tttccactac ctgcttgcaa  31440
gagtgccagc caagtgagcc agcctagagg ggaacactgg aaagagtcag gaatcctggg  31500
cttcggtgcc agctctgcca atcactagct ttattacctg tttctttatc tattaaatga  31560
ggccaaggac ccaagacctg cccaccttac cagggtatca gatgaagccc tgatgagaag  31620
tcctttgcaa ccgtgaagga aactccaaat agcaccaaga ggactcagaa cacatggttt  31680
gacaacctag gactagaagg agactccaga gaggcataga gactctaaaa tcctagcact  31740
ttcttggtat agacagttac ccaggtactg ctcagctggg tccagggaag gtcctgggtt  31800
tggggctgag tccaggtgat gtgtgtcccc tgcctccatt tctataggca ggaaaagaca  31860
ctcgtgatga acaagcacgt ggggcatcta cttcgaacca aagccatcga gcatgcagat  31920
ggtggtgtgg cagcgggagt ggcagtcctg gacaacccat accctgtgtg agggcacaac  31980
caggccacgg gaccttctat cctctgtatt tgtcattcct ctcctagccc tcctgagggg  32040
tatcctccta aagacctcca aagtttttat ggaagggtaa atactggtac cttcccccag  32100
ctttccatct gaggaccaga aaagttgtgt ctcccttaga tgagatctag acgcccccaa  32160
atccttgaga tgtgggtata gctcagggta agctgctctg aggtaaaggt ccatgaaccc  32220
tgccccactc ctgtcagccc ctcatcagcc ttttcagcag gttccagtgc ctgacttggg  32280
ataggactga gtggtaggag gagggggagt ggaggggcat agcctttccc taattctgcc  32340
ttaaataaaa ctgcattgct gattcagtga tgattcctta cttcgtgcat agaggggagg  32400
cgggagctgt aatctacgtt agcccactta agatgtatta gagcagggaa gtgactggtc  32460
tgtaatcagg gtccccctag accagtctct acaggtggaa ccctgaagtt tcaatcctta  32520
gccacccact aatgctctta ctggatcaca gggaggaatg agagtccctg gcaggagccc  32580
aggagggaag gcaaccaaga tgggacatac ataacagttg tgaactggct tcagtcactt  32640
```

```
tcctgcttag ctcaggggct tgtcaaaggc cctgtcagtg aagcctcctt cgctctgccc  32700
aaaccaaaag ttctagaagg aagatattgg ggatagtcct aggaaatacc cctcccttcc  32760
catctgccac acaaatcaga gccactaatg aatatacagc ctcagggcac agatacctaa  32820
gaaaacaagt caccacttct tgagatcaca ggctttattc ctacaaccac agggcttgag  32880
cctgactggg gcaagaaaac agagtttcat ctgagaatgt ctcttatggg ctgggttctg  32940
ttcaggggag ggtgggaaca gaggacaagg aagacaagct cctctggccc taggaacaaa  33000
acacatttac tccttcaaag aagcagatga tctgaatacc ctctggagac tgaatctgcc  33060
catacagccc ctggagccaa tgggcagaca gtactggcat ctggcacaaa agggaattca  33120
gacccagaac agaagcagca aaatatttta aaaatagtaa attgttcctg gactcacaaa  33180
tcattgtttt taagggcaag tgcatgccca atataagtac tggggcttcc taagagagct  33240
gacataggat tacacagctg cctccctgct tcagtggagg ccctcacatc ccctttgaac  33300
acttaacttg ggtaggagag gtagcctttt cgtctctgtt ctgggttctg agagctctgc  33360
agtctggagg cacagcagac tgaggctgac ctgggccctg tcctttctgc ctggcagtca  33420
caggatgttg tctctacctg gagacaaagc tggtttccgg tcccagacag ctggtcaagg  33480
gagggtagtg tgggtcaaca ctggccctca gcactcctga gggggcaaag aggatgggca  33540
aagtttggag caggaggaat cctaggtaaa ggtcaggatc atgttcactg gatggtcagg  33600
cagcggtggc tgaagaggtg actgatgaca gatgggtcag ccacagtaga catgtccccg  33660
aggtcatggt cattctgagc aatcttccga agcactcgcc tcatgatttt ccctggggaa  33720
ccacagacct ctagttactt ggtgaaagca ctgacccacc ctagccctgc caaaggcttt  33780
catccacgca caccccacca ccaccaggcc tcagcccatc ccaatccatg gaggcctctg  33840
aacatacctg agcgggtttt aggcaagcca ggtgcattct ggatgtagtc tggtgtggca  33900
atggggccaa tcttttctct aactgtaacc aacaaatcat caagcatttc ttcagcaccc  33960
ttagccagac ttttcaaaaa tcaaagtaga gatggctttg ttccccacct gtttcctcct  34020
caagtccctg cccacagaga cagcctcagg ttcactgctt ctcttgctct caacacactt  34080
gtctctttac tctctcattt tatcttatgg aactcaggct gtagaatgag cctgctagag  34140
tttaaatgcc acctttctag cagtgtggcc ttgggcaagt gatttaactt ccatgagtct  34200
cagtttcatc atctttagca tgaaggtaac aataagatct gtttcatgga ggtgactcta  34260
gggattaagt ggggtaattc atttaaagca cttagcctag cggtggcaca aagtattcta  34320
gaaatgttgg ctattattat tatcctagtg ggagactagt ggagac                34366
```

<210> SEQ ID NO 15
<211> LENGTH: 1889
<212> TYPE: DNA
<213> ORGANISM: mouse

<400> SEQUENCE: 15

```
cccacgcgtc cgcagctgga caacgagcga gttgggatgg ctaccagctg ggcagcatc     60
ttgcaggatg agaagcagct ggaagaactg gcaaagcagg ccatagaccg ggccctggcc    120
gagggcgtgt tgctgaggtc cgcacagcat cccagctcct ccgacgtggt gacatatgcc    180
ccattcacgc ttttcccctc gccagtaccc agtgctctgc tggagcaggc ctatgctgtg    240
cagatggact tcaacatact ggtggatgct gtcagccaga acccagcctt cctggagcaa    300
acactgtcta gcaccatcaa aaaggacgac tatactgccc gtctctttga tatctacaaa    360
caagtcctga aagagggcat tgcccagacc gtgttcctgg gcctgaatcg ctcagattac    420
```

-continued

```
atgttccagt gcggcgcaga cggctccaaa gccctgaaac agatcgagat caacactatc    480

tctgccagct ttgggggcct ggcctcccgg actccagctg tgcaccgaca cgttctcaat    540

gtcctgaata agaccaaaga agcttccaag atcctgtcca ataaccccag caagggactg    600

gccctgggga tcgccaaagc ctgggagctc tatggctcag ctaatgcggt ggtgctactg    660

attgctcaag agaaggaaag gaacatattt gaccagcgtg ccgtagagaa cgagctgcta    720

gacaggaaga tccatgtcat ccgtggaaga tttgaagatg tctctgaaag ggttctctg    780

gaccaaaacc gaaggctgtt tatggatgac caggaagttg ctgtggtgta cttccgagat    840

ggctacatgc ccagtcagta taattcacag aactgggaag cacgcctgat gctagagaga    900

tctcgtgctg ccaagtgtcc agacattgcc atacagctgg ctgggactaa gaaggtgcag    960

caggaactga gcagggtggg tctgctggaa gcactgctcc cgggccagcc cgaggctgtg   1020

gcccgcctcc gagccacctt tgctggcctc tattcactgg acatgggtga agaaggggac   1080

caggccattg ctgaggccct tgctgctcct agccactttg tgctgaagcc ccagagagag   1140

ggtggaggta acaacttata cggggaagaa atggtacaag ctctggagca gctgaaggac   1200

agtgaggaga gagcctccta catcctcatg gagaagattg aacctgagcc ttttaggaat   1260

tgcttgctac ggcctggcag ccctgcccaa gtggtccagt gtatctcgga gctgggtatt   1320

tttggagtct atgtcagaca gggaacaaca ctggtgatga acaagcatgt ggggcacctg   1380

cttcgaacca aagccgtgga gcatgcagac ggaggtgtgg cggcaggagt ggcagtcctg   1440

gacaacccct accctgtgtg aaggcgccat ctggacttca ctcaggaggc cttctatccc   1500

ctgtacttgg cactcctctt ctgaggggtt gcccctgtcc ctatcttagg ggagcttgtc   1560

tcttccatag acctccaaaa cttcagggaa gggaaaaccc agggtatctt ccctcagcag   1620

ccttccagcc gaggaccaga aaagctatga ttccattaga agacttctgg aggtccccag   1680

atctttggag tgtgggaatg gaagctgctt tgaggcaaag gctcataaac cctgcaagtc   1740

ttcatggtct tctcaccagc ctttccagca ggttctagtg ccttgacctg gggtaggacc   1800

gagtgaagga ggaagagggt aaaagggcac agacttcccc agctctgccc taaataaaat   1860

aacaatgctg attcaaaaaa aaaaaaaaa                                       1889
```

<210> SEQ ID NO 16
<211> LENGTH: 474
<212> TYPE: PRT
<213> ORGANISM: mouse

<400> SEQUENCE: 16

```
Met Ala Thr Ser Trp Gly Ser Ile Leu Gln Asp Glu Lys Gln Leu Glu
1               5                   10                  15

Glu Leu Ala Lys Gln Ala Ile Asp Arg Ala Leu Ala Glu Gly Val Leu
            20                  25                  30

Leu Arg Ser Ala Gln His Pro Ser Ser Ser Asp Val Val Thr Tyr Ala
        35                  40                  45

Pro Phe Thr Leu Phe Pro Ser Pro Val Pro Ser Ala Leu Leu Glu Gln
    50                  55                  60

Ala Tyr Ala Val Gln Met Asp Phe Asn Ile Leu Val Asp Ala Val Ser
65                  70                  75                  80

Gln Asn Pro Ala Phe Leu Glu Gln Thr Leu Ser Ser Thr Ile Lys Lys
                85                  90                  95

Asp Asp Tyr Thr Ala Arg Leu Phe Asp Ile Tyr Lys Gln Val Leu Lys
            100                 105                 110
```

-continued

```
Glu Gly Ile Ala Gln Thr Val Phe Leu Gly Leu Asn Arg Ser Asp Tyr
        115                 120                 125

Met Phe Gln Cys Gly Ala Asp Gly Ser Lys Ala Leu Lys Gln Ile Glu
    130                 135                 140

Ile Asn Thr Ile Ser Ala Ser Phe Gly Gly Leu Ala Ser Arg Thr Pro
145                 150                 155                 160

Ala Val His Arg His Val Leu Asn Val Leu Asn Lys Thr Lys Glu Ala
                165                 170                 175

Ser Lys Ile Leu Ser Asn Asn Pro Ser Lys Gly Leu Ala Leu Gly Ile
            180                 185                 190

Ala Lys Ala Trp Glu Leu Tyr Gly Ser Ala Asn Ala Val Val Leu Leu
        195                 200                 205

Ile Ala Gln Glu Lys Glu Arg Asn Ile Phe Asp Gln Arg Ala Val Glu
    210                 215                 220

Asn Glu Leu Leu Asp Arg Lys Ile His Val Ile Arg Gly Arg Phe Glu
225                 230                 235                 240

Asp Val Ser Glu Arg Gly Ser Leu Asp Gln Asn Arg Arg Leu Phe Met
                245                 250                 255

Asp Asp Gln Glu Val Ala Val Val Tyr Phe Arg Asp Gly Tyr Met Pro
            260                 265                 270

Ser Gln Tyr Asn Ser Gln Asn Trp Glu Ala Arg Leu Met Leu Glu Arg
        275                 280                 285

Ser Arg Ala Ala Lys Cys Pro Asp Ile Ala Ile Gln Leu Ala Gly Thr
    290                 295                 300

Lys Lys Val Gln Gln Glu Leu Ser Arg Val Gly Leu Leu Glu Ala Leu
305                 310                 315                 320

Leu Pro Gly Gln Pro Glu Ala Val Ala Arg Leu Arg Ala Thr Phe Ala
                325                 330                 335

Gly Leu Tyr Ser Leu Asp Met Gly Glu Glu Gly Asp Gln Ala Ile Ala
            340                 345                 350

Glu Ala Leu Ala Ala Pro Ser His Phe Val Leu Lys Pro Gln Arg Glu
        355                 360                 365

Gly Gly Gly Asn Asn Leu Tyr Gly Glu Glu Met Val Gln Ala Leu Glu
    370                 375                 380

Gln Leu Lys Asp Ser Glu Glu Arg Ala Ser Tyr Ile Leu Met Glu Lys
385                 390                 395                 400

Ile Glu Pro Glu Pro Phe Arg Asn Cys Leu Leu Arg Pro Gly Ser Pro
                405                 410                 415

Ala Gln Val Val Gln Cys Ile Ser Glu Leu Gly Ile Phe Gly Val Tyr
            420                 425                 430

Val Arg Gln Gly Thr Thr Leu Val Met Asn Lys His Val Gly His Leu
        435                 440                 445

Leu Arg Thr Lys Ala Val Glu His Ala Asp Gly Gly Val Ala Ala Gly
    450                 455                 460

Val Ala Val Leu Asp Asn Pro Tyr Pro Val
465                 470
```

METHOD TO REDUCE ONCOGENIC POTENTIAL OF INDUCED PLURIPOTENT STEM CELLS FROM AGED DONORS

CROSS REFERENCE TO RELATED APPLICATIONS

This application is a U.S. National Phase Application under 35 U.S.C. § 371 of International Patent Application No. PCT/US2015/054319, filed Oct. 6, 2015, which claims priority to the following three U.S. Provisional Patent Applications: No. 62/060,532 filed Oct. 6, 2014; No. 62/121,460 and No. 62/121,463 both filed Feb. 26, 2015. The contents of each application are incorporated by reference herein.

GOVERNMENT SPONSORED RESEARCH OR DEVELOPMENT

This invention was made with government support under HL093212, AG043531 and CA008748 awarded by the National Institutes of Health. The government has certain rights in the invention.

SEQUENCE LISTING

The present application includes a sequence listing in electronic form as a txt file in ascii format titled "7704-0021-PCT_ST25[3]_.txt" and having a size of 133.7_kb. The contents of this txt file are incorporated by reference herein.

BACKGROUND OF THE DISCLOSURE

Field of the Disclosure

This disclosure relates to improvements in induced pluripotent stem cells and more specifically to induced pluripotent stem cells having reduced oncogenic potential and/or improved apoptosis response, and/or improved DNA damage response and/or improved genomic stability.

Description of the Related Art

Direct reprogramming of somatic cells, for example with the transcription factors Oct4, Sox2, Klf4, and c-Myc1 (also known as the Yamanaka protocol), yields induced pluripotent stem cells (iPSC) with remarkable similarity to embryonic stem cells (Takahashi et al. *Cell* 126: 663-676, 2006). Other protocols for making iPSC are known, as described for example in González, F. et al. *Nature Reviews Genetics* 12: 231-242 (Apr. 1, 2011). Analogous to ES cells, iPSC form teratomas, differentiated tumors with tissues from all three embryonic germ layers, and contribute to all tissues when injected into murine blastocysts.

Derivation of patient-specific iPSC for several disorders has been reported (Part et al. *Cell* 134:877-86, 2008; Dimos et al. *Science* 321: 1218-21, 2008). Development of iPSC provides opportunities for disease modeling using patient derived iPSC and directed differentiation methods. Additional areas that can greatly benefit from iPSC are drug development and drug screening. Finally, considering that iPSC resemble ESC in the pluripotency potential, but circumvent the histo-incompatibility issues associated with ESC-based therapies, iPSC hold enormous potential for generating histo-compatible transplantable tissue using a patient's own somatic cells.

According to the United Network for Organ Sharing (UNOS), approximately 120,000 Americans are currently waiting to receive organ transplants, but only 24,000 transplants were performed between January and October of 2013. UNOS estimates that 18 patients die each day while waiting for an immune-matched organ from a small number of donors.

iPSC are useful in many different ways: first, as research tools, they enable otherwise inaccessible experiments to link gene function to tissue formation; second, they offer a new approach to drug discovery and development including both screening and toxicity testing as iPCS can be differentiated into human cells of different tissues and organs. But the most important utility of iPCS is in organ and tissue generation for engraftment, to replace missing or nonfunctioning organs and tissues and to treat degenerative diseases, including without limitation those associated with an aging population.

While iPSC offer great opportunities, there are still many unexplored questions and hindrances related to their application in clinical setting. For example, different tissues show variable susceptibility to reprogramming (Maherali et al. *Cell Stem Cell* 3:340-345, 2008; Aoi et al. *Science* 321: 699-702, 2009). Additionally, recent studies have shown that iPSC contain a residual epigenetic signature depending on the tissue type of the donor tissue used (Kim et al, *Nat Biotechnol* 29(12): 1117-1119, 2011) and that iPSC from aged donors (A-iPSC) retain an aging-specific epigenetic memory (Kim et al. *Nature* 467(7313):285-290, 2010). Furthermore, while Yamanaka and others identified four iPSC reprogramming factors required for generating iPSC using young donor tissue (Y-iPSC), it is not clear whether the same four factors would be sufficient for reprogramming iPSC from aged donor tissue (A-iPSC).

Prigione, A. et al *PLoS One.* 2011; 6(11):e27352. doi: 10.1371/journal.pone.0027352 also reported the presence of karyotype aberrations in aged-iPSC from humans although in their experiment they did not find resistance to apoptosis. These investigators measured micro-nuclei formation which is an indicator of a cell under apoptotic process as opposed to the fact of cell death (apoptosis) itself. Also lactate dehydrogenase was used for normalization which would not permit detection of already dead cells. Lastly, the time interval between DNA damage infliction and measurement may have been too long. Nevertheless, these authors also stressed the importance of developing reprogramming protocols that preserve the genomic stability of aged somatic cells.

As older patients are more likely to benefit from the clinical application of iPSC in tissue regeneration and both heterologous and autologous transplantation, and because iPSC are already being studied in clinical trials of a number of aging-related degenerative diseases, such as macular degeneration and Parkinson's disease, there is a significant need to comprehensively evaluate A-iPSC and determine how to reverse the negative effects of aging in these cells in order to improve their quality and consequently their function upon differentiation and transplantation.

One of the recognized drawbacks of iPSC has been their potential oncogenicity. This has been variously putatively ascribed to the use of oncogenes to generate them and possibly to the use of integrating viral-based vectors. As a result, efforts have been devoted to avoiding the use or integration of oncogenes and to avoiding the use of viral vectors. See, for example Nakagawa, M. et al *Nat Biotechnol.* 2008 January; 26(1):101-6 for reprogramming without MYC. Other researchers have turned to nonintegrative viruses such as Sendai virus to generate iPSC: Chen I P et al (2013) Induced Pluripotent Stem Cell Reprogramming by Integration-free Sendai Virus Vectors from Peripheral Blood of Patients with craniometaphyseal dysplasia, Cell Reprogram. 2013 December; 15(6):503-13; and Lieu P T et al (2013) Generation of Induced Pluripotent Stem Cells with CytoTune, a Non-Integrating Sendai Virus, *Methods Mol. Biol.* 2013; 997:45-56 (from blood cells or fibroblasts). Yet others use RNA-based (vector-free) methods and tools for this purpose (such as B18R protein) are commercially available: see, e.g., Affymetrix eBioscience http://www.ebioscience.com/knowledge-center/cell-type/induced-pluripotent-stem-cells.htm#benefits%20of%20rna; or Warren, L. et al Feeder-Free Derivation of Human Induced Pluripotent Stem Cells with Messenger RNA, Nature Scientific reports, 2:#657 (Sep. 14, 2012). Yet others have used protein: Kim, D. et al, Generation of human induced pluripotent stem cells by direct delivery of reprogramming proteins, *Cell Stem Cell.* 2009 Jun. 5; 4(6):472-6. However, these methods may suffer from low reprogramming efficiency while oncogenicity can persist. Moreover, prior reprogramming efforts did not take into account age of donor cells in considering oncogenicity. Nor have there been proposals to use any additional factor as an adjunct to the reprogramming protocol.

SUMMARY OF THE DISCLOSURE

In one aspect, the disclosure provides a method for improving at least one of DNA damage response, apoptosis response, genomic stability and glucose metabolism of A-iPSC, the method comprising supplementing A-iPSC with at least one of (i) pluripotency factor ZSCAN10; (ii) pluripotent stem cell-specific glucose transporter GLUT3; and (iii) an exosome subunit, each as an adjunct to reprogramming of the A-iPSC to substantially restore said at least one of DNA damage response, apoptosis response, glucose metabolism and genomic stability to levels approximating those of Y-iPSC.

In some embodiments, excessive expression of GSS or GPX2 is inhibited by at least one of the following:

- supplementing A-iPSC with pluripotency factor ZSCAN10; and/or
- supplementing A-iPSC with pluripotent stem cell-specific glucose transporter 3 GLUT3; and
- supplementing A-iPSC with an exosome subunit.

wherein the supplementation is an adjunct to reprogramming pluripotency factors and is in an amount effective to accomplish total or partial rescue in one or more of DNA damage response, apoptosis, and genomic stability in said A-iPSC.

In another aspect, the disclosure provides a method for reducing the oncogenic potential of induced pluripotent stem cells (iPSC) said cells having one or more of genomic instability, a defect in apoptosis, a defect in DNA damage response and a defect in glucose metabolism and exhibiting excessive glutathione-mediated $H_2O_2$ scavenging activity compared to embryonic stem cells or induced pluripotent stem cells from young donors (Y-iPSC), the method comprising:

- inhibiting glutathione-mediated $H_2O_2$ scavenging activity in said iPSC to partially or totally restore homeostasis in said iPSC by directly and/or indirectly inhibiting excessive expression of glutathione peroxidase 2 (GPX2) in said iPSC.

In yet another aspect, the disclosure provides a method for reducing the oncogenic potential of induced pluripotent stem cells derived from aged donors (A-iPSC) said A-iPSC exhibiting excessive glutathione-mediated $H_2O_2$ scavenging activity compared to induced pluripotent stem cells derived from young donors (Y-iPSC), the method comprising:

- inhibiting glutathione-mediated $H_2O_2$ scavenging activity in said A-iPSC to partially or completely restore glutathione/$H_2O_2$ homeostasis in said A-iPSC by directly and/or indirectly inhibiting excessive expression of glutathione peroxidase 2 (GPX2) in said A-iPSC.

In still another aspect, the disclosure provides a method for reducing the oncogenic potential of induced pluripotent stem cells (iPSC) said cells having one or more of genomic instability, a defect in apoptosis, a defect in DNA damage response and a defect in glucose metabolism, and exhibiting excessive glutathione-mediated $H_2O_2$ scavenging activity compared to embryonic stem cells or induced pluripotent stem cells from young donors (Y-iPSC), the method comprising supplementing A-iPSC with at least one of (i) pluripotency factor ZSCAN10; (ii) pluripotent stem cell-specific glucose transporter GLUT3; and (iii) an exosome subunit, each as an adjunct to reprogramming to substantially restore said at least one of DNA damage response, apoptosis response, glucose metabolism and genomic stability to levels substantially the same as those of Y-iPSC or ESC.

In some embodiments, the supplementation is carried out by adding ZSCAN 10 and/or GLUT3 and/or an exosome subunit to a culture medium in which said A-iPSC are maintained.

In some embodiments, the supplementation is carried out by increasing the expression of ZSCAN10 and/or GLUT3 and/or an exosome subunit in said cells.

In some embodiments, the supplementation is sufficient to restore ZSCAN 10 and/or GLUT3 and/or exosome subunit levels in said A-iPSC to about 50% or more of the respective levels of embryonic stem cells (ESC).

In some embodiments, the supplementation is sufficient to reduce oxidation capacity of glutathione in said A-iPSC to within the range from about 80% to about 120% of that of ESC.

In some embodiments, the supplementation is sufficient to restore genomic stability of said A-iPSC to approximately that of Y-iPSC.

In some embodiments, genomic stability is measured by incidence of aneuploid clones.

In some embodiments, the apoptosis rate is measured by DNA fragmentation assay in response to a DNA damaging agent.

In some embodiments, DNA damage response is measured by ATM or H2AX phosphorylation in response to a DNA damaging agent.

In some embodiments, the supplementation is sufficient to reduce oxidation capacity of glutathione in said A-iPSC to approximately that of Y-iPSC.

In some embodiments the supplementation is sufficient to reduce GSS or GPX2 levels in said A-iPSC to approximately those of Y-iPSC.

In some embodiments the expression of ZSCAN10 and/or GLUT3 and/or an exosome subunit in said cells is increased by transfecting said cells with a vector harboring nucleic acid for said ZSCAN10 and/or GLUT3 and/or an exosome subunit.

In some embodiments, expression of said vector harbored nucleic acid encoding ZSCAN10 is transient.

In some embodiments, the reprogramming factors are the Yamanaka factors OCT4, SOX2, KLF4 and MYC.

In some embodiments, the reprogramming pluripotency factors are selected from the group of those of Yamanaka wherein one or more of OCT4, SOX2, KLF4 and MYC are replaced as follows:

Factors(LIN28+Nanog,Esrrb,Pax5shRNA,C/EBPa, p53.siRNA,UTF1,DNMTshRNA,Wnt3a, SV40LT(T), hTERT) or chemicals(BIX-01294,BayK8644,RG108, AZA,dexamethasone, VPA,TSA,SAHA,PD025901+ CHIR99021(2i), A-83-01).

In some embodiments the reprogramming pluripotency factors are selected from the group of those of Yamanaka wherein one or more of OCT4, SOX2, KLF4 and MYC are replaced as follows: Nanog and Lin28 replace Klf4 and MYC; esrb replaces Klf4; SV40 LT (T) replaces Klf4, MYC, lin28 and Nanog; BIX-01294 replaces SOX2, and OCT4; VPA replaces Klf4 and MYC.

In some embodiments, the supplementation is with an exosome subunit, the exosome subunit being one or more of the following EXOSC1, EXOSC2, EXOSC3, EXOSC4, EXOSC5, EXOSC6, EXOSC7, EXOSC8, EXOSC9, EXOSC10 and hDis3.

In some embodiments, the supplementation is by DNA gene transfer or by RNA delivery or by delivery of proteins into the A-iPSC.

In another aspect, the present disclosure provides an iPSC derived from a somatic cell of an aged donor where the iPSC has been engineered to express ZSCAN10 at levels comparable to an iPSC derived from a young healthy donor.

In another aspect, the present invention comprises one or more vectors comprising nucleic acid encoding (i) stem cell reprogramming factors and (ii) ZSCAN10.

Thus, as a result of the work described herein, ZSCAN10 has emerged as a major co-regulatory factor of reprogramming protocols to make induced pluripotent stem cells from somatic cells, especially but not exclusively from somatic cells of aged donors, which upon reprogramming using the existing protocols would be deficient in ZSCAN 10, GLUT3 or an exosome subunit.

Accordingly, in another aspect, the present disclosure provides an iPSC derived from a somatic cell where the iPSC in the absence of ZSCAN10 supplementation would be deficient in ZSCAN10 expression, expressing either no ZSCAN10 or a level of ZSCAN 10 substantially lower than that of a control iPSC derived from a healthy young donor, wherein the iPSC has been engineered to express ZSCAN10 levels comparable to those of an iPSC derived from a healthy young donor.

In a related aspect, the present disclosure is directed to an iPSC derived from a somatic cell said iPSC originally displaying one or more of (i) reduced ZSCAN10 expression level, (ii) increased oncogenic potential (as measured for example by reduced DNA damage response, reduced apoptosis response, genomic instability and reduced glucose metabolism), (iii) reduced GLUT3 expression level; (iv) reduced exosome subunit level; and (v) increased GPX2 or increased GSS expression level, compared to a Y-iPSC or ESC control, wherein the iPSC has been supplemented with ZSCAN10 to restore said one or more reduced or increased levels to levels substantially closer to those encountered in said control.

In another aspect the present disclosure is directed to a vector or set of vectors comprising nucleic acid encoding (i) reprogramming pluripotency factors and (ii) ZSCAN10. In a more specific embodiment, the disclosure relates to a set of vectors according to claim 38 wherein the vector comprising ZSCAN10 nucleic acid is a separate vector from the vector or vectors comprising the reprogramming factors nucleic acid.

In some embodiments, the present disclosure is directed to a method for assessing the quality of an iPSC comprising measuring or testing the expression level of one or more proteins selected from the group of ZSCAN10, GLUT3, an exosome subunit (such as a core exosome subunit), GPX2 and GSS and comparing it to a control expression level of the same protein in Y-iPSC or ESC; and determining said quality on the basis of whether the measured or tested expression level is substantially similar to the control expression level. In more specific embodiments the quality assessed is one or more of oncogenic potential or glutathione/hydrogen peroxide homeostasis.

BRIEF DESCRIPTION OF THE DRAWINGS

FIG. 1F is a bar graph showing a higher frequency of polyploidy in multiple independent clones of A-iPSC, and rescue of polyploidy defect with ZSCAN10 expression. DNA content was estimated by Propidium Iodide (PI) staining followed by flow cytometry analysis of multiple independent clones. The number of clones analyzed is indicated in each group. Statistical significance was determined by chi-squared test. FIG. 1G is a dot plot of a number of chromosomal structural abnormalities observed by cytogenetic analysis in each A-iPSC clone, and rescue with ZSCAN10 expression. Error bars indicate standard error of the mean of four independent clones analyzed per group. The total number of metaphases analyzed is indicated in each group. Statistical significance was determined by t-test.

FIG. 6 are immunoblots showing impaired DNA damage response in A-iPSC compared with Y-iPSC and ESC, and permanent restoration following transient expression of ZSCAN10. Reduced ATM phosphorylation was observed in A-iPSC after phleomycin treatment (2 h, 30 μg/ml), and recovery of ATM activation upon ZSCAN10 expression (FIG. 6A). FIG. 6F is a scanned image of an immunoblot indicating phospho-ATM, pH2AX, and p53 levels in ESC, Y-iPSC, A-iPSC and A-iPSC-ZSCAN10 following radiation treatment. FIG. 6G is a scanned image of an immunoblot of pATM and beta-actin in ESC, Y-iPSC, A-iPSC and A-iPSC-ZSCAN10 following the treatment with $H_2O_2$.

FIG. 7 is a scatter plot showing higher DNA methylation of ZSCAN promoter in A-iPSC compared to ESC and Y-iPSC.

285-90. doi: 10.1038/nature09342. Epigenetic memory in induced pluripotent stem cells.

Figure 11:
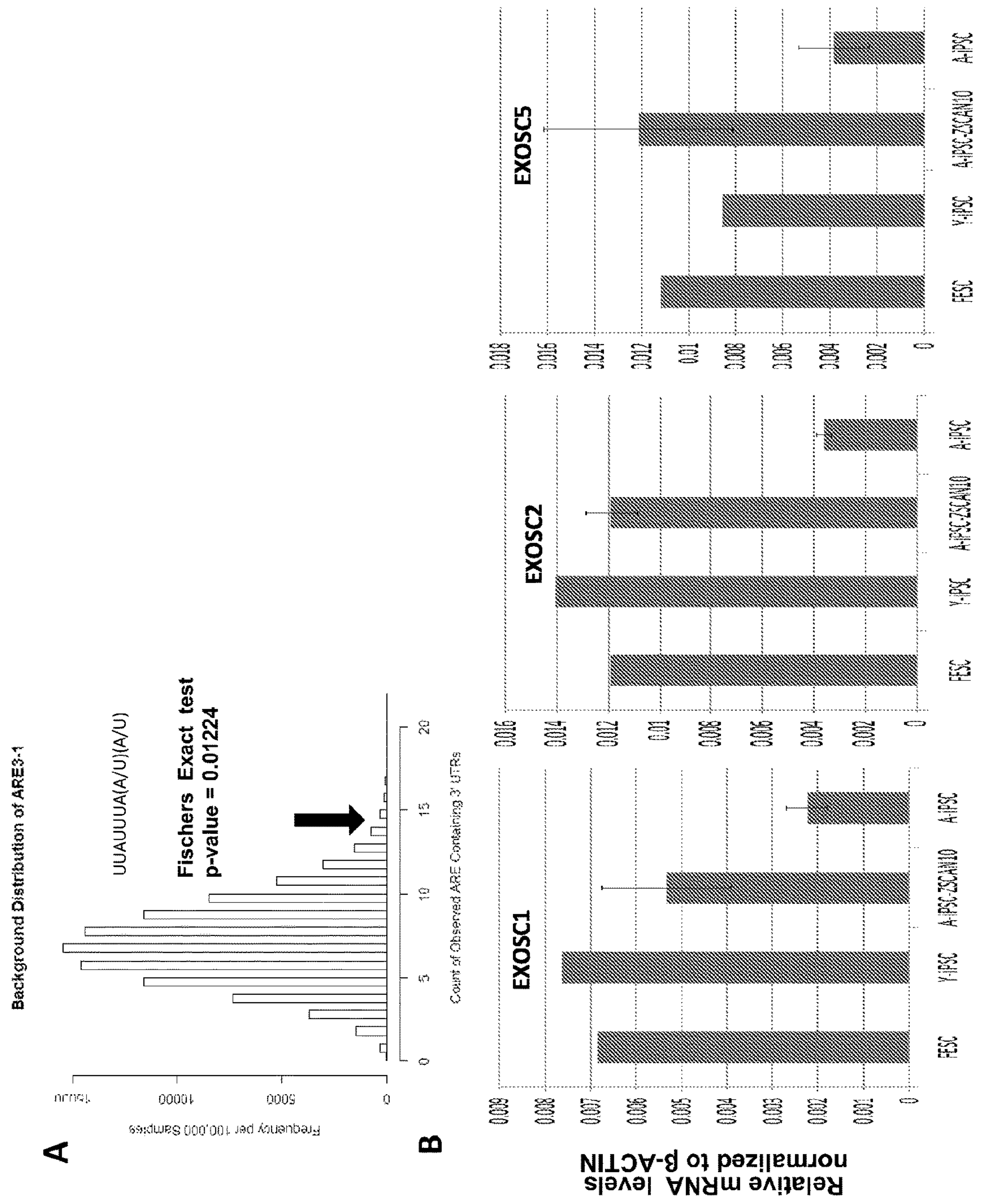
FIG. 11 A is a histogram showing statistical probability to find 14 genes with ARE-sequences by random resampling as disclosed in Kim, K. et al *Nature.* 2010 Sep. 16; 467(7313)

FIG. 11B is a series of bar graphs showing relative mRNA levels (normalized to β-actin) of exosome subunits EXOSC1, EXOSC2, and EXOSC5 in FESC, Y-iPSC, A-iPSC-ZSCAN10 (A-iPSC supplemented with ZSCAN10, and A-iPSC. The histogram indicates that the likelihood of any given transcript to have the UUAUUUA(A/U)(A/U) ARE sequence is 7, so the odds of finding 14 in a sample based on just random chance are very low (p=0.01224).

Figure 12:
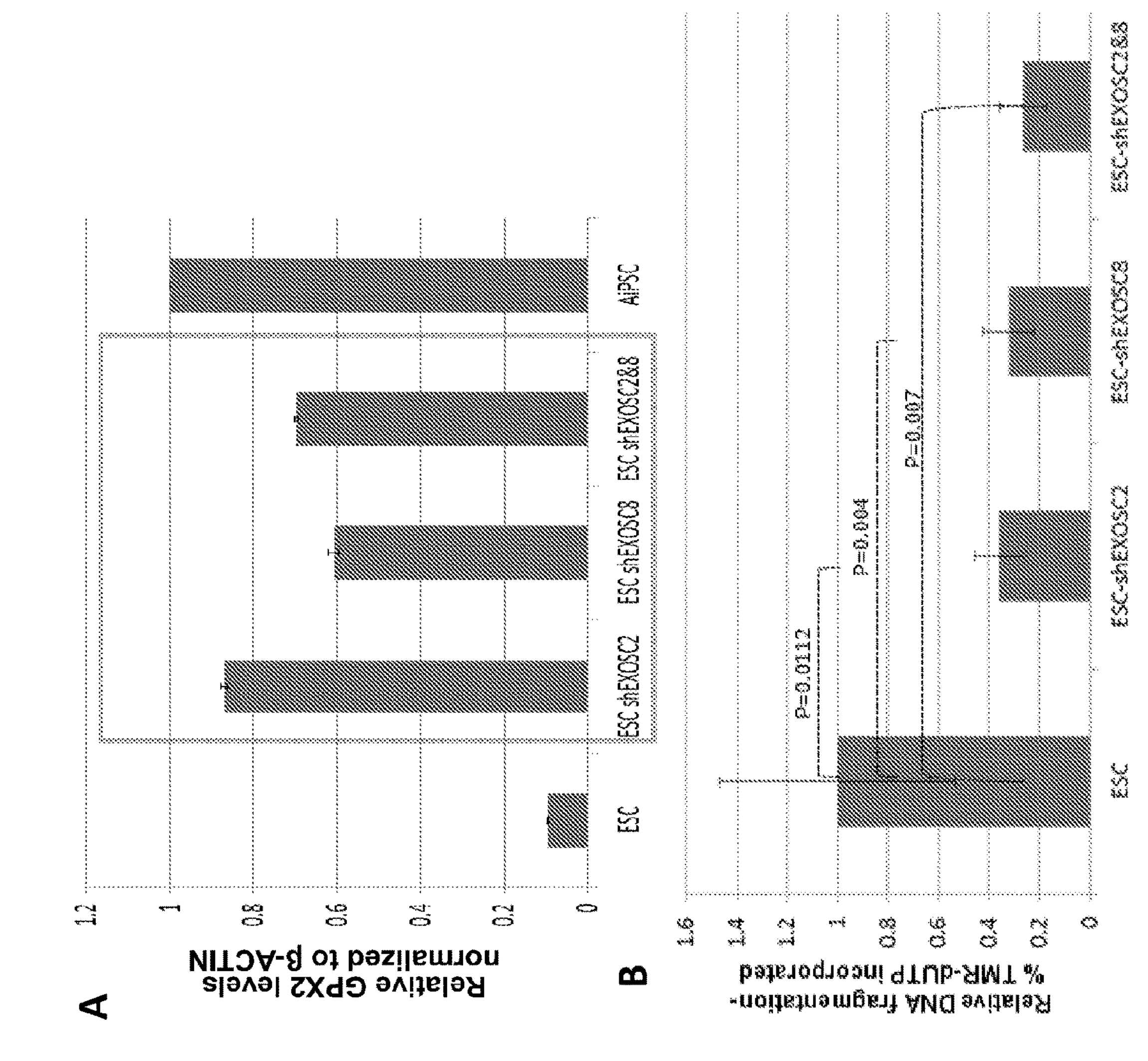

FIG. 12A is a bar graph of relative GPX2 mRNA expression (normalized to β-actin) in ESC, ESCshEXOSC2, ESCshEXOSC8, ESCshEXOSC2&8, and A-iPSC. Error bars indicate standard error of the mean. FIG. 12B is a quantification of apoptotic response by DNA fragmentation assay after phleomycin treatment of ESC, ESCshEXOSC2, ESCshEXOSC8, and ESCshEXOSC2&8. Error bars indicate standard error of the mean of technical and biological replicates.

FIG. 13A is a schematic representation of reprogramming in different individuals. FIG. 13B is a scanned image of an immunoblot showing the levels of pATM and beta-actin proteins. ESC, Y-iPSC and A-iPSC were generated from different individuals (A-iPSC AG8-76 years old, A-iPSC AG4-71 years old, A-iPSCB, and A-iPSCS) and treated with phleomycin. FIG. 13C is karyogram of A-iPSC generated from AG4 individual. FIG. 13D is a scanned image of an immunoblot of p53−/− iPSC (negative control), A-iPSC generated from B6129 mouse genetic background, and A-iPSC generated from B6CBA mouse genetic background and treated with phleomycin. Levels of p53 and β-actin are shown. FIGS. 13E-13H show scanned images of immunoblots showing the levels of pATM and beta-actin proteins in six different clones of human A-iPSC (FIG. 13E), one clone of human A-iPSC-outlier (FIG. 13F), five different clones of Y-iPSC (FIG. 13G), and six clones of A-iPSC overexpressing ZSCAN10. FIG. 13I is a bar graph of relative mRNA levels of ZSCAN10 normalized to beta-actin in human ESC, human A-iPSC that exhibit no DNA damage response, and in A-iPSC that exhibit normal DNA damage response.

Figures 14A, 14B, 14C, 14D:
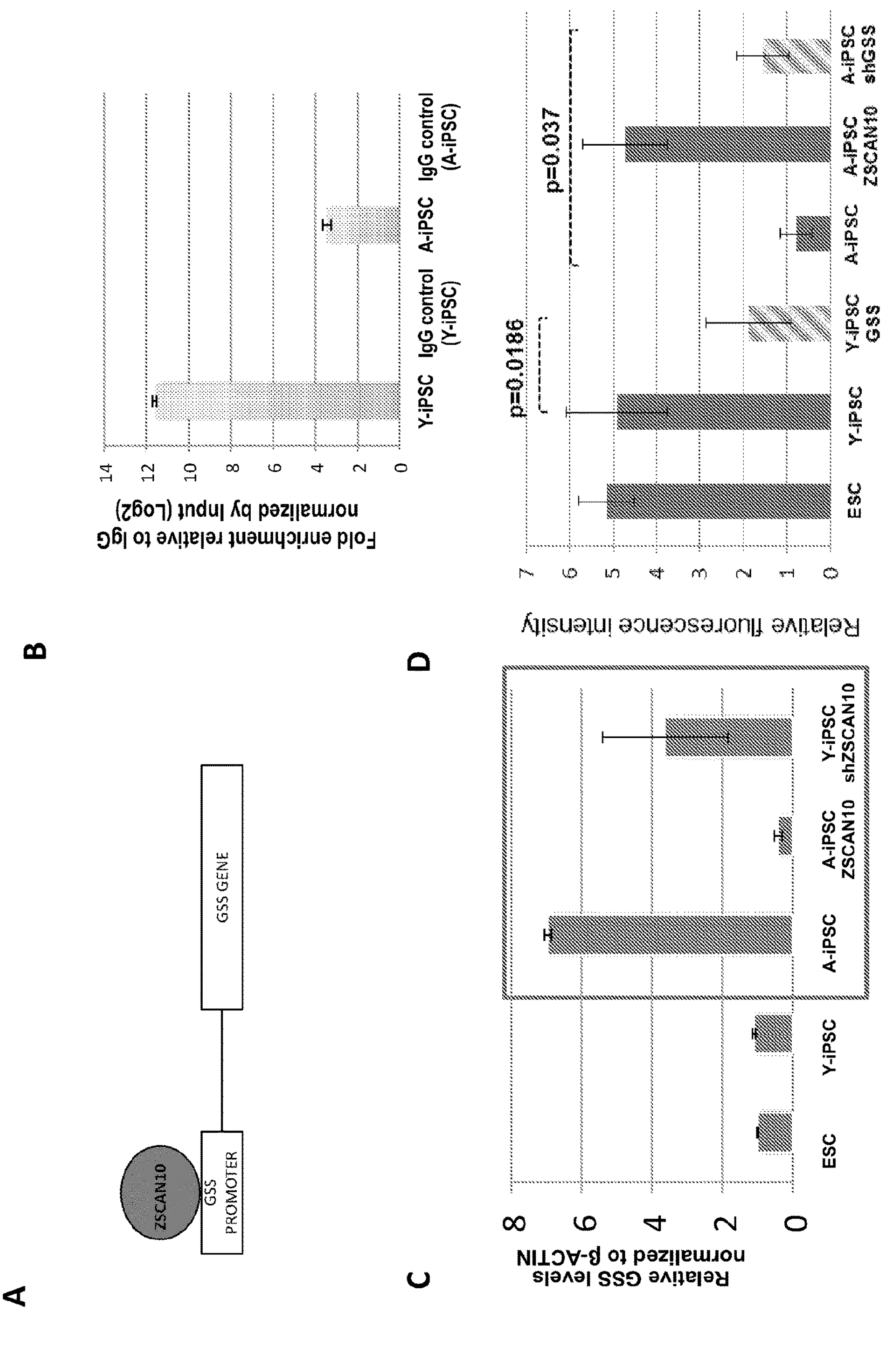
Figures 14E, 14F:
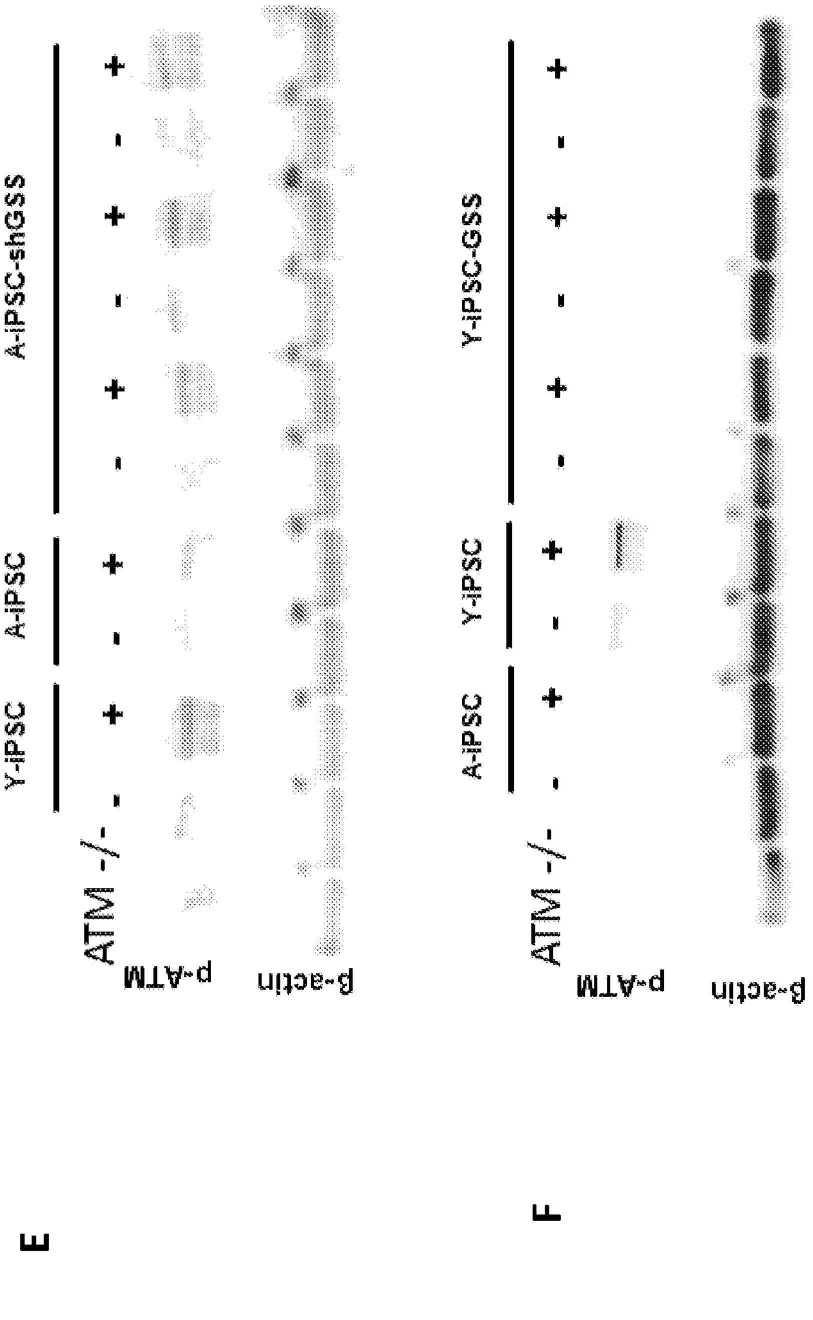
Figure 14G:
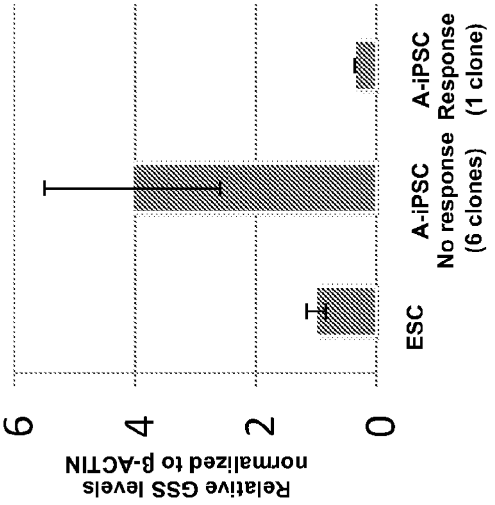

FIG. 14A is a schematic diagram showing ZSCAN10 binding to the glutathione synthetase (GSS) promoter. FIG. 14B is a bar graph of ChIP-quantitative PCR analysis of ZSCAN10 binding to the GSS promoter in Y-iPSC and A-iPSC. Values are given as percent enrichment compared with the input. FIG. 14C is a bar graph showing mRNA levels (determined by Q-PCR) of GSS in ESC, Y-iPSC, A-iPSC-ZSCAN10, and A-iPSC. Error bars indicate standard error of the mean. FIG. 14D is a quantification of apoptotic response by DNA fragmentation assay (obtained by image quantification) after phleomycin treatment of ESC, Y-iPSC, Y-iPSCGSS, A-iPSC, A-iPSC-ZSCAN10, and A-iPSCshGSS. Error bars indicate standard error of the mean of technical and biological replicates. FIGS. 14E and 14D are immunoblots of phospho-ATM showing recovery of the DNA damage response (p-ATM) after phleomycin treatment in three independent clones of A-iPSC with GSS shRNA expression (FIG. 14E), or in three independent clones of Y-iPSC after lentiviral expression of GSS (FIG. 14F). β-actin levels are used as a loading control. FIG. 14G is a bar graph showing mRNA levels of GSS normalized to beta-actin in human ESC, A-iPSC (no DNA damage response) and A-iPSC (with normal DNA damage response).

Figure 15A:
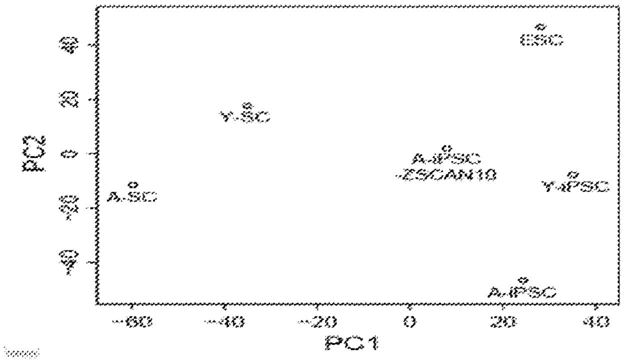
Figure 15B:
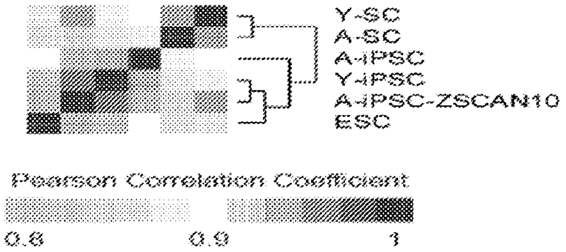
Figure 15C:
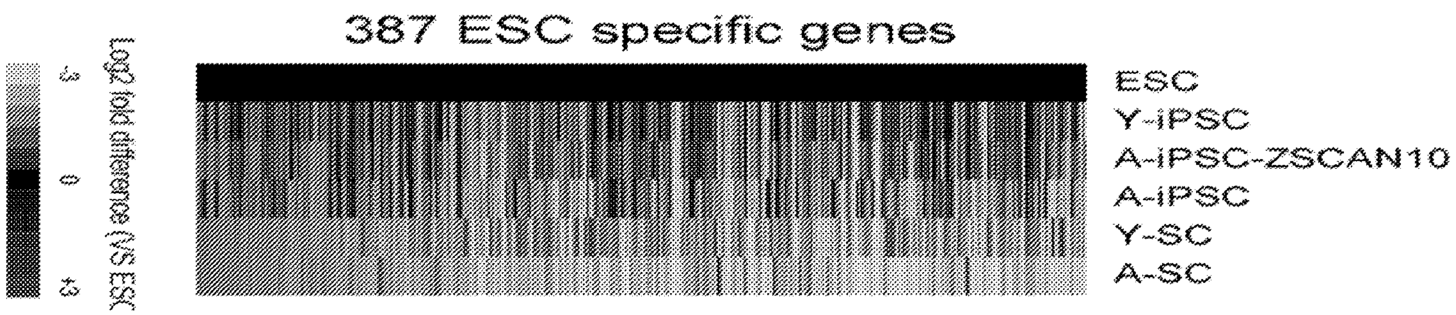

FIG. 15A is a plot of data from Principal Component Analysis (PCA) using whole gene expression profiles of fibroblast cells (A-SC, Y-SC), iPS cells (A-iPSC, Y-iPSC, A-iPSC-ZSCAN10) and ES cells (ESC). FIG. 15B is a heat map of unsupervised clustering analysis of whole gene expression profiles. The heat maps shows pairwise gene expression similarities measured by Pearson Correlation Coefficient. FIG. 15C is a microarray heat map of relative expression levels of ES cell specific genes in fibroblast (A-SC, Y-SC), iPS cells (A-iPSC, Y-iPSC, A-iPSC-ZSCAN10) and ES cells (ESC). ES cell specific genes were defined as those with 3 fold or higher expression levels in ES cells than average expression in adult and young fibroblast cells. The heat map shows relative expression fold differences over ES cells.

DETAILED DESCRIPTION

Definitions

As used herein, the following terms shall have the meanings ascribed to them below unless the context clearly indicates otherwise:

The term "DNA damage response" refers to any process that results in a change in state or activity of a cell (in terms of movement, secretion, enzyme production, gene expression, etc.) as a result of a stimulus, indicating damage to its DNA from environmental insults or errors during metabolism.

The term "apoptosis response" refers to a process that results in apoptosis of a cell, for example in response to DNA damage. A lower apoptotic rate or a failure of a cell to apoptose at all (collectively referred to a reduced apoptosis response) is associated with uncontrolled cell proliferation and more specifically with malignancy.

The term "polyploidy" refers to the condition in which a normally diploid cell or organism exhibits more than two sets of chromosomes; the term "aneuploidy" means any ploidy (more or less than the normal two sets of chromosomes).

The term "chromosomal structural abnormalities" refers to any change in the normal structure of a chromosome. Chromosomal structural abnormalities include, but are not limited to: duplications, deletions, translocations, inversions, and insertions.

The term "genomic instability" (also "genome instability or "genetic instability) refers to an increase in structural chromosomal alterations (deletions, amplifications, and translocations), numerical chromosomal aneuploidy, or mutations on DNA sequence within the genome of a cellular lineage.

The term "oncogenic potential" means the likelihood that a cell after its transplantation into a host will generate malignant tumors in the host. The term is applied for example to induced pluripotent stem cells, and to their propensity to generate malignant tumors upon differentiation and transplantation to an animal or human. Phenotypic traits such as genomic instability, impaired DNA damage response, reduced apoptosis response and reduced glucose metabolism indicate elevated oncogenic potential whether the iPSC has been derived from an aged donor or not.

The term "effective amount" of a factor or other active molecule means an amount effective to bring about a particular result. For example, in the case of ZSCAN10 or GLUT3 or exosome subunit supplementation (or GPX2 or GSS inhibition), an effective amount is that which brings about substantial restoration of apoptosis response, and/or DNA damage response and/or glucose metabolism defect or preserves genomic stability.

The term "reprogramming factors" refers to transcription factors i.e., proteins that alone, or in combination with other reprogramming factors, have the ability to reprogram differentiated somatic cells to cells to a pluripotent state.

The term "transcriptional pluripotency network" refers to a network of transcription factors involved in the transcriptional control of pluripotency in embryonic stem cells (ESC). The present inventors have shown that ZSCAN10 is part of the "transcriptional pluripotency network" and should be supplemented in stem cells deficient in ZSCAN10 by comparison to Y-IPSC or ESC.

The term "mutagenic potential" refers to the potential or capacity of a substance to induce a change in the regulatory, protein-coding or other portions of a DNA sequence, increasing the frequency of mutations above a normal (background) level.

The term "young" used in connection with iPSC means iPSC derived from young donors, in case of mice up to 5 days old, in case of humans up to 16 years old and more generally to iPSC derived from donors that exhibit a "young" signature, e.g., slowing active growth stage to initiate the entry into fully grown adult stage.

The term "old" used in connection with iPSC means iPSC derived from aged donors, in case of mice older than 1.4 years old, in case of humans later than 50 years old, which begin to show age related degenerative diseases or states.

The term "substantial" used in the context of restoration, preservation recovery or rescue of glucose metabolism or DNA damage response, or apoptosis response, or genomic stability of A-iPSC denotes achievement of a state approximately or exactly the same as that of Y-iPSC and ESC. See for example FIGS. 1F-G, where A-iPSC with ZSCAN10 supplement have about the same ploidy and structural chromosomal abnormalities as Y-iPSC. See also FIGS. 2, 5*a* and 6. Additionally, levels of ZSCAN 10 and/or GLUT3 and/or exosome subunit in A-iPSC of about 50% or more of the respective levels of embryonic stem cells are considered substantially restored. Finally, if the oxidation capacity of glutathione in A-iPSC is reduced (for example by supplementation of ZSCAN10 or by inhibition of GSS or GPX2) to be within the range from about 80% to about 120% of that of ESC or Y-iPSC, it is considered substantially restored.

The term "exosome" refers to the multi-protein exosome complex (or PM/Scl complex, often just called the exosome) capable of degrading various types of RNA (ribonucleic acid) molecules. Substrates of the exosome include messenger RNA, ribosomal RNA, and many species of small RNAs. Exosome comprises nine core subunits and two exonuclease co-factors listed in Table 3.

The term "exosome subunit" refers to eleven components (listed in Table 3) of the exosome, comprising nine core subunits and two co-factors: EXOS1, EXOS2, EXOS3, EXOS4, EXOS5, EXOS6 EXOS7, EXOS8, EXOS9, EXOS10, and DIS3.

Unless otherwise required by context, singular terms shall include the plural. For example, "an exosome subunit" shall mean one or more exosome subunits.

General Description of this Disclosure

The present disclosure is based on the following discoveries:

1. Induced pluripotent stem cells derived from aged donors (A-iPSC), which have been previously shown to have a higher oncogenic potential, show increased genomic instability, a defect in apoptosis, and a blunted DNA damage response compared to those derived from young donors (Y-iPSC).

2. A-iPSC are also shown to exhibit excessive glutathione-mediated $H_2O_2$ scavenging activity (glutathione/$H_2O_2$), which in turn inhibits DNA damage response and apoptosis.

3. Inhibition of this pathway substantially rescues these defects and consequently reduces the oncogenic potential of A-iPSC.

4. A-iPSC are shown to be deficient in a pluripotency factor ZSCAN10 which is poorly activated in A-iPSC. ZSCAN10 acts to inhibit GPX2, a glutathione-mediated $H_2O_2$ scavenger protein. ZSCAN10 expression shows a strong relationship with induction of the glucose transporter GLUT3 such that GLUT3 endogenous expression is increased when ZSCAN10 expression is increased. ZSCAN10 regulates GLUT3 directly by binding to its promoter.

5. It was further found that supplementation of ZSCAN10, e.g., by expression (even transient expression) in A-iPSC as an adjunct to reprogramming, leads to substantial or even complete recovery of genomic stability, DNA damage response, apoptosis response and glucose metabolism in A-iPSC, to render them similar to those of Y-iPSC. This is shown to be accomplished through normalizing homeostasis of glutathione/$H_2O_2$. Significantly, adequate or even complete recovery of these Y-iPSC attributes has been shown not to require supplementation of ZSCAN10 to exactly the levels present in ESC or even in Y-iPSC. Moreover, because ZSCAN10 is not expressed in A-iPSC, it is anticipated that this finding transcends induction protocols. In other words, ZSCAN10 supplementation can be added to any stem cell induction protocol to be used in the event of deficiency in this factor. This a vector comprising nucleic acid encoding ZSCAN10 can be added to a set of vectors comprising nucleic acid for other reprogramming factors. Alternatively, a single vector comprising nucleic acid for reprogramming factors and ZSCAN10 can be utilized for example in the event of reprogramming of cells that would otherwise yield iPSC deficient in ZSCAN10.

6. GLUT3 (a pluripotent stem cell-specific glucose transporter) is also poorly activated in A-iPSC. Poor activation of GLUT3 in A-iPSC inhibits the pluripotent stem cell specific transition from oxidative phosphorylation to glycolysis in glucose metabolism due to lack of sufficient intracellular glucose. Thus, A-iPSC use energy efficient oxidative phosphorylation (FIG. 10) to generate enough energy source with less glucose. However, oxidative phosphorylation generates higher $H_2O_2$, and consequently increases GPX2/glutathione mediated $H_2O_2$ scavenging activity (FIG. 8). Excessive GPX2/glutathione mediated $H_2O_2$ scavenging activity blocks $H_2O_2$- and ATM-mediated DNA damage response (FIG. 6). Direct or indirect supplementation of GLUT3, e.g., through increased expression in A-iPSC or addition to culture media or ZSCAN10-mediated increase in GLUT3, has similar effects in that it also normalizes DNA damage response and apoptosis in A-iPSC (FIG. 10D) as well as glucose metabolism.

7. These results indicate that inhibition of glutathione/$H_2O_2$ notably through delivery of ZSCAN 10 and/or GLUT3, will be clinically useful, resulting in A-iPSC of reduced oncogenic potential. Thus, the present results indicate that supplementation (including without limitation any upregulation) of ZSCAN10 and by extension modulation of any factor, such as GSS or GPX2 that contributes to inhibition of excessive glutathione/$H_2O_2$ activity (or its effects) in A-iPSC, will be clinically useful in substantially restoring DNA damage response, apoptosis response, glucose metabolism and genomic stability (integrity) in A-iPSC and consequently reduce their oncogenic potential. Assessment of one or more such factors would be useful in ascertaining the quality of iPSC.

8. Intervention in reducing excessive glutathione/$H_2O_2$ activity is preferably practiced simultaneously with reprogramming somatic cells from aged donors into iPSC. Thus ZSCAN10 can be introduced into somatic cells at the same time or shortly following reprogramming whether through use of the Yamanaka factors OCT4, SOX2, KLF4, and c-MYC or through any other induction protocol, such as those discussed and/or cited in the Background section. ZSCAN10 supplementation can take place during or shortly following reprogramming and in any event prior to inducing differentiation. Increased GLUT3 expression can be introduced at the same times as ZSCAN10. Alternatively, GSS and/or GPX2 can be inhibited either by curbing their expression or by introducing effective amounts of inhibitors of the corresponding proteins.

Figures 1A, 1B:
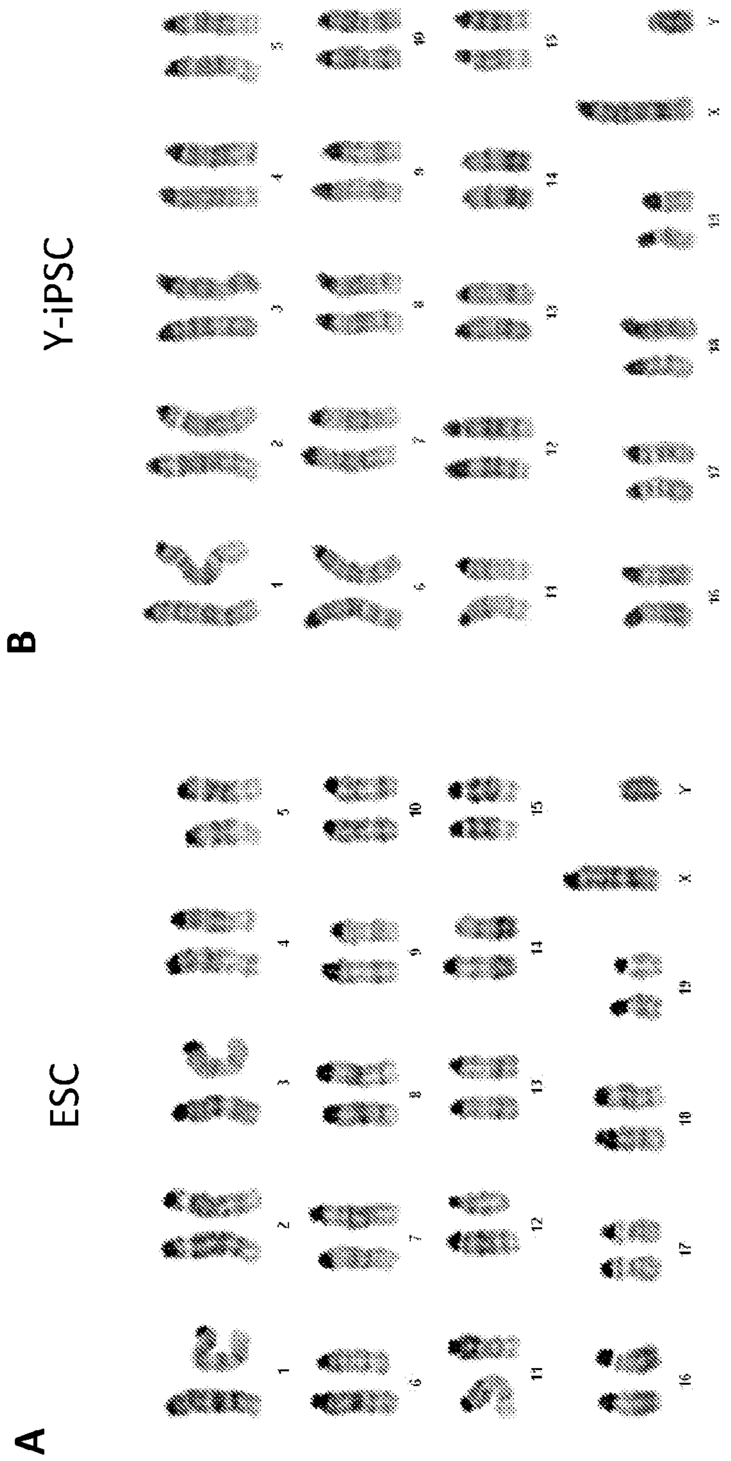
FIGS. 1A-1G show karyograms of ESC (FIG. 1A), Y-iPSC (FIG. 1B), A-iPSC-ZSCAN10 (FIG. 1C), and A-iPSC (FIGS. 1D and 1E).
Figures 1C, 1D:
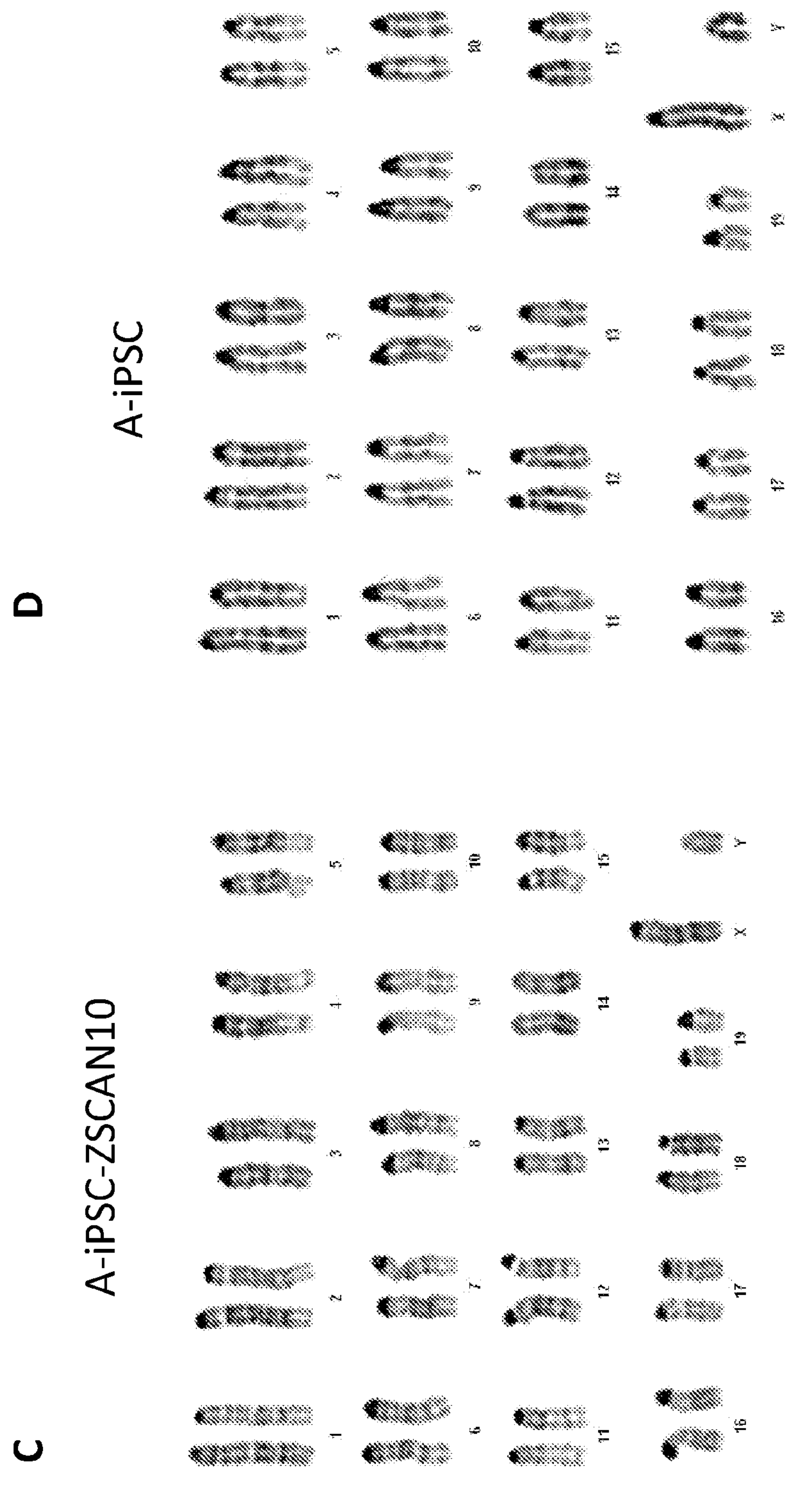
Figure 1E:
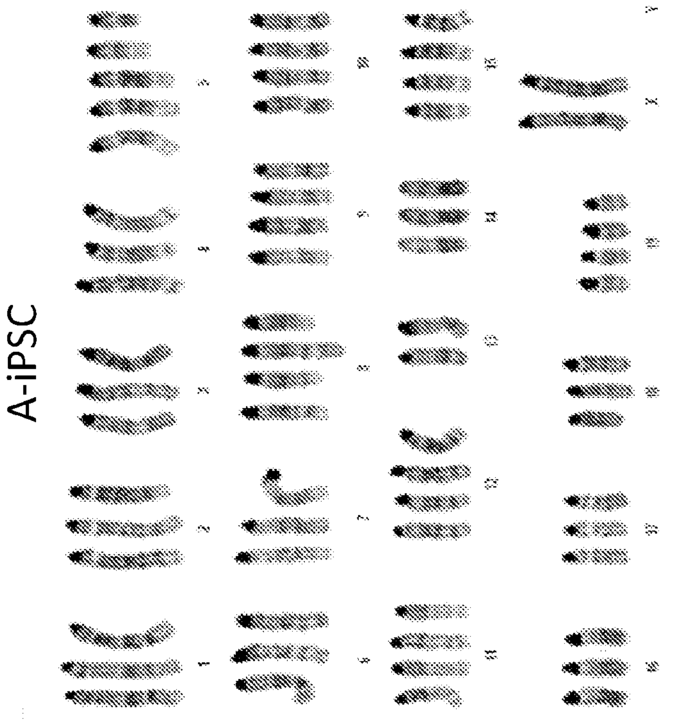
Figure 1F:
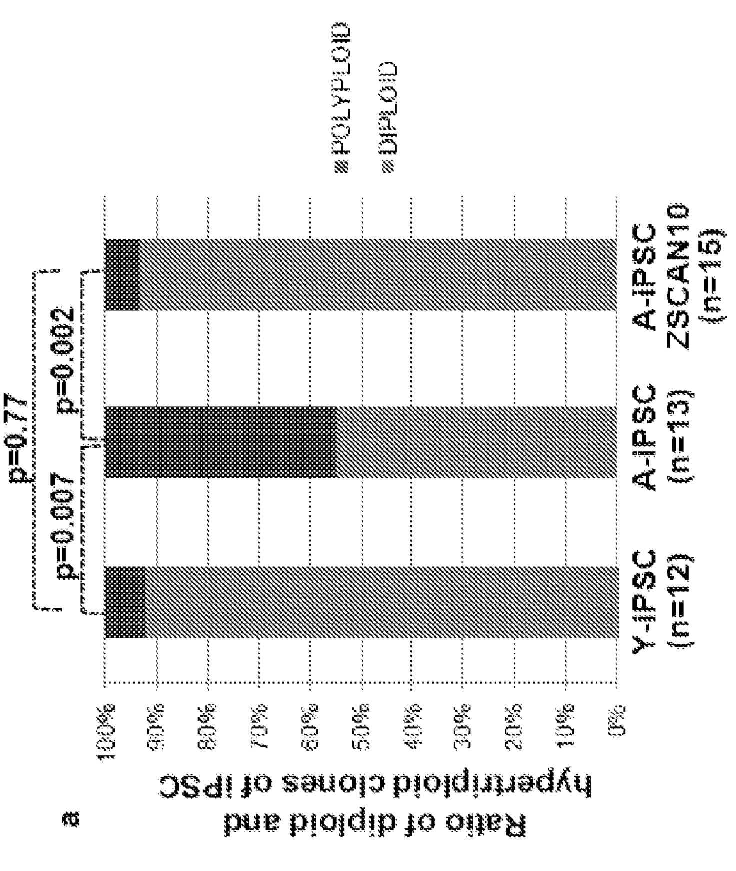
Figure 1G:
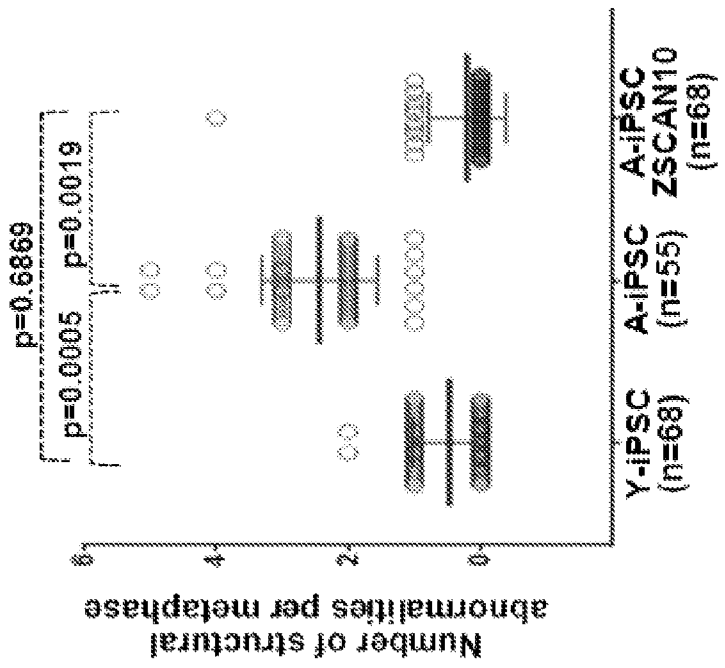

The present inventors discovered genes associated with A-iPSC by comparing expression of genes in Y-iPSC, A-iPSC and ESC. Very few genes were differentially expressed and even fewer affected the oncogenicity potential as assessed by DNA damage response, apoptosis response and genomic stability. To arrive at the significant genes, the inventors first generated Y-iPSC (using mouse skin fibroblasts from E15.5 embryos to 5-day-old neonates) and A-iPSC (using mouse skin fibroblast from donors 1.4 years old) using standard Yamanaka iPSC reprogramming methods as described in Kim, K. et al, 2010 supra (as discussed elsewhere herein, alternative iPSC induction protocols could have been used instead). A large number of clones were selected based on morphology and groups of at least 12 clones of each type. Each Y-iPSC and A-iPSC clone was put through a series of pluripotency tests and compared to ESC as the gold standard, e.g., multi-lineage contribution to three germ layers in teratoma analysis and pluripotent gene expression analysis (AP/OCT4/SSEA1/NANOG)(data not shown). Silencing of the four reprogramming factors (OCT4, SOX2, KLF4, MYC) in each clone was confirmed by quantitative PCR (Q-PCR) (data not shown). DNA ploidy was tested in multiple iPSC clones, and Y-iPSC and A-iPSC clones with normal ploidy (data not shown) were identified. However, a higher frequency of polyploidy was observed in A-iPSC compared to Y-iPSC (FIG. 1F). A-iPSC also displayed more chromosomal structural abnormalities than Y-iPSC (FIG. 1G).

The inventors hypothesized that the poor genomic stability of A-iPSC was due to poor induction of apoptosis response as in iPSC it is direct apoptosis that eliminates severely damaged cells from the population. They found that both Y-iPSC and ESC controls showed a significant level of apoptosis after treatment with phleomycin (a drug inducing DNA breakage which would normally mobilize DNA damage response such as apoptosis). In contrast, A-iPSC showed a poorer apoptotic response to phleomycin. They then set about to develop methods to correct the apoptotic response and therefor improve genomic stability in A-iPSC. They reasoned that additional pluripotency factors would be necessary to yield iPSC with the genomic stability of ESC or Y-iPSC. Screening of a number of previously identified pluripotency network genes yielded ZSCAN10 a transcription factor specifically expressed in ESC (and not expressed in somatic cells) and forming part of the transcriptional pluripotency regulatory network including SOX2, OCT4, and NANOG. ZSCAN10 also binds to the promoters of DNA damage response genes, such as ATM, PLK1 and JNK2.

The inventors further found that the ZSCAN10 promoter is hypomethylated/activated in Y-iPSC and ESC, and hypermethylated/inactive in A-iPSC. When added to the pluripotency induction protocol, ZSCAN 10, when transiently expressed during reprogramming of A-iPSC, led to hypomethylation/activation of the endogenous ZSCAN10 promoter to levels closer to that seen in Y-iPSC. A-iPSC with the foregoing ZSCAN10 supplementation exhibited reduced abnormalities in chromosomal ploidy and structure to levels comparable to Y-iPSC and ESC. ZSCAN10 also reduce the mutagenicity of A-iPSC to levels comparable to Y-iPSC and ESC. ZSCAN10 also recovered responsiveness of A-iPSC to DNA damaging agents (ATM phosphorylation, H2AX phosphorylation and p53 expression) confirming that ZSCAN10 recovers the DNA damage response of A-iPSC bringing it closer to that of Y-iPSC.

They inventors also investigated the mechanism by which the oxidative capacity of glutathione is elevated in A-iPSC and found that in mice it is driven by glutathione peroxidase 2 (GPX2) elevated expression in A-iPSC but not in Y-iPSC or ESC. Reduction of GPX2 expression in A-iPSC recovered glutathione/$H_2O_2$ homeostasis to levels comparable to Y-iPSC and ESC. Conversely overexpression of GPX2 in Y-iPSC induced an imbalance in glutathione/$H_2O_2$ homeostasis. In humans however, the elevation of the oxidative capacity of glutathione in A-iPCS is driven by elevated levels of glutathione synthetase (GSS). Downregulation of GSS results in recovery of glutathione/$H_2O_2$ homeostasis.

Oncogenic Potential

It is known that aging and oncogenicity are known to be strongly correlated. See, e.g., Stoll E A, Horner P J, Rostomily R C. The impact of age on oncogenic potential: tumor-initiating cells and the brain microenvironment. Aging Cell. 2013; 12(5):733-41. PMID: 23711239. Furthermore, it is also known that oncogenicity in general is increased by events such as DNA hypermethylation, defective apoptosis mechanisms (whereby apoptosis occurs less frequently) and blunting of DNA damage response. Liu, J. C. et al. High mitochondrial priming sensitizes hESCs to DNA-damage-induced apoptosis. Cell stem cell 13, 483-491, doi:10.1016/j.stem.2013.07.018 (2013). In addition, excessive glutathione and/or excessive glutathione activity is associated with certain cancers such as pancreatic cancer and colorectal cancer. Furthermore, the inventors found that excessive glutathione activity is triggered by excessive expression of GPX2 in A-iPSC in mice and excessive expression of GSS in humans. Accordingly, one or more of such phenotypic defects have been used in the present disclosure to assess oncogenic potential and can be used for this purpose as well as more generally to assess the quality of iPCS in methods of the present disclosure. Furthermore, amelioration in these phenotypic defects is considered to reduce oncogenic potential. Donnerstag, B. et al Cancer Lett. 1996 Dec. 20; 110(1-2):63-70.

Both DNA damage response and apoptosis play a critical role in tumorigenesis. Certain DNA damage response proteins such as ATM. H2AX, and p53 link DNA damage pathway to apoptosis. Thus, apoptosis is a secondary response to DNA damage. However, induction of DNA damage response can occur without the trigger of programmed cell death. For example, activation of the tumor suppressor p53 by DNA damage induces either cell cycle arrest or apoptosis, and the outcome of this is highly contextual. Thus, a defect in the activation of any of the proteins that mediate DNA damage response, and/or apoptosis, such as H2AX, ATM, and p53, may indicate a defect in A-iPSC and can be used to assess quality of such stem cells.

ZSCAN10 is an embryonic stem (ES) cell-specific transcription factor required to maintain ES cell pluripotency. See http://www.genecards.org/cgi-bin/carddisp.pl?gene=ZSCAN10 (last visited Feb. 24, 2015). It and nucleic acid encoding it (see, e.g., NCBI Genbank Reference Sequence: NC 000016.10) are publicly available. Human, mouse and rat ZSCAN10 cDNA is available from GE Dharmacon Life Sciences (http://dharmacon.gelifesciences.com/mammalian-cdna/mgc-cdnas/?term=ZSCAN10&sourceId=EG/84891&productId=416CB003-5022-4263-B1C6-293625B70CE1) (last visited Feb. 24, 2015). Human cDNA is also available as plasmid pENTR223.1 e.g., from DNASU plasmid Repository at Tempe Ariz. (http://dnasu.org/DNASU/GetCloneDetail.do?cloneid=295134; last visited Feb. 24, 2015) The human cDNA insert for ZSCAN10 has SEQ ID NO:1.

The methods of this disclosure relate to the exposure of iPSC to ZSCAN10 to accomplish improved reprogramming of iPSC. In some embodiments, the present disclosure relates to iPSC cells generated from aged donors (A-iPSC). In some embodiments, the iPSC cells are characterized by genomic instability, reflected by polyploidy or increased chromosomal structural abnormalities. In some embodiments, iPSC cells exhibit poor DNA damage response. In some embodiments, iPSC cells exhibit a defect in induction of apoptosis. In some embodiments, iPSC cells exhibit a defect in glucose metabolism. iPSC exhibiting one or more of these defects (genomic instability, poor DNA damage response, decreased apoptotic response and lower glucose metabolism) can be improved to levels comparable to those of Y-iPSC or ESC by increasing the levels of ZSCAN10. (As disclosed elsewhere herein, the levels of ZSCAN 10 may but need not reach levels of Y-iPSC as long as the phenotypic defect is adequately restored.) This process can be achieved by introduction of an mRNA encoding ZSCAN10 into the iPSC-derived somatic cell and subsequent translation into a functional ZSCAN protein. Additional methods for increasing the levels of ZSCAN10 include, but are not limited to transfection with numerous vectors, such as adeno-associated virus, lentivirus, retrovirus, Sendai virus, DNA plasmids such that ZSCAN10 expression is effected at the DNA, RNA, and/or protein level in either a transient or long-term manner. Additionally, ZSCAN10 protein levels can be increased by contacting the cell with an agent that leads to increased ZSCAN10 protein levels (expressed in a transient or long-term manner), or by contacting the cell directly with recombinant ZSCAN10 protein. As disclosed herein, the present method provides increasing the levels of ZSCAN10 in iPSC at a dosage sufficient to substantially: (a) restore genomic instability, (b) improve poor DNA damage response, or (c) restore apoptotic response in human or animal (e.g., mouse) iPSC.

When used as an adjunct to reprogramming, ZSCAN10 supplementation can be added to one or more vectors harboring nucleic acid encoding reprogramming factors or can be included in a separate vector (such that it will be used only if needed) in a set of such vectors. Vectors useful for reprogramming are commercially available. Any of these can be modified to include nucleic acid encoding ZSCAN10 (and optionally any other elements useful for its expression as one of ordinary skill in this field would appreciate).

Figure 4:
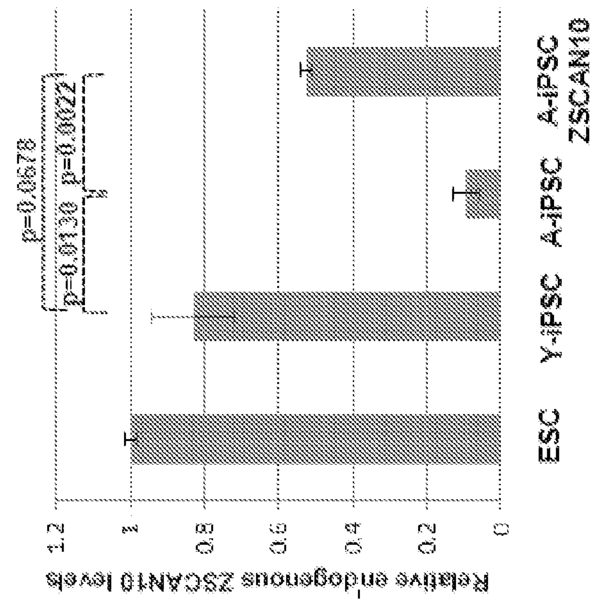
FIG. 4 is a bar graph showing poor activation of ZSCAN10 expression in A-iPSC and complete reactivation with transient expression of ZSCAN10. Endogenous ZSCAN10 mRNA levels were determined by Q-PCR in ESC, Y-iPSC, A-iPSC, and A-iPSC-ZSCAN10. Endogenous ZSCAN10 levels were normalized to β-ACTIN. Error bars indicate standard error of the mean. Statistical significance was determined by t-test.

ZSCAN10 supplementation in amounts effective to substantially restore one or more of DNA damage response, apoptosis response, glucose metabolism and genomic stability should be in an amount related to the deficiency in ZSCAN10 exhibited by the particular A-iPSC (reprogrammed in the absence of such intervention) compared to ZSCAN10 levels of Y-iPSC. In this regard, FIG. 4 is informative because it shows that increased expression of ZSCAN10 in A-iPSC to a level about 5 times that of the untreated cells to a level of about 50% of the ESC level (and about 60% of the Y-iPSC level) was effective to restore the assessed phenotypic responses. In general, the more meaningful comparison of appropriate ZSCAN10 is to be closer or even identical to the level of ESC and Y-iPSC (although identical level is not required for restoration of defects). Supplementation of ZSCAN10 to reach a level from about 40% up to about 90 or 95% of ESC ZSCAN10 level or from about 50% to 100% of Y-iPSC ZSCAN10 level is an effective range. In some embodiments, supplementation sufficient to substantially restore the assessed phenotypic parameters (DNA damage response, apoptosis response, genomic stability or glucose metabolism) is sufficient even though higher levels are possible and indeed encountered in Y-iPSC and ESC.

In the event sufficient endogenous amounts ZSCAN10 are expressed but ZSCAN10 is not effective, the amount of supplementation should be adjusted upwards as appropriate and in such instances can reach amounts higher than 100% of the amount of Y-iPSC.

Methods of supplementation of ZSCAN10 or any other factor proposed to be supplemented herein include addition to the culture medium or transfection with a delivery vector or any other system that facilitates expression of these factors or in any event exposure of a cell to these factors. For methods of vector-free delivery, see, e.g., Zhou H, et al. (2009), Generation of induced pluripotent stem cells using recombinant proteins. *Cell Stem Cell* 4: 381-384. Any type of DNA gene transfer (retroviral, lentiviral, adenoviral, Talen, CrispR etc.) can be used to effect supplementation. Alternatively, RNA delivery or delivery into the cells in form of proteins can also be used. These techniques are well-known in the art. The time of delivery can be before, during or after adding the reprogramming factors and before differentiation and transplantation. Accordingly combinations of reagents (vector or vector-free) for reprogramming cells including reagents for supplementation of ZSCAN10 are envisioned for producing induced pluripotent stem cells of higher quality and phenotypic traits resembling those of Y-iPSC and ESC. These are commercially available or can be readily constructed given that both nucleic acid and amino acid sequences for ZSCAN10 are known. For example, vectors and viral particles that can be used to introduce Yamanaka reprogramming pluripotency factors into the cells can be obtained from such sources as Applied Biological Materials, Richmond BC, Canada; Clontech Laboratories, Mountain View, Calif.; and Addgene, Cambridge, Mass.

While the present examples provide for transient expression of ZSCAN10, the methods of the present invention are not limited by whether ZSCAN10 expression is inducible or not. Nor are they limited to supplementation of ZSCAN10 in A-iPSC induced by a particular protocol. Indeed, there are many known protocols for iPSC induction and any one of them can be used with the present methods. See, Singh, V K et al, Front. In Dev. Biol. 3(2):1-18, February 2015; Yu, J., Vodyanik, M. A., Smuga-Otto, K., Antosiewicz-Bourget, J., Frane, J. L., Tian, S., et al., (2007). Induced pluripotent stem cell lines derived from human somatic cells. Science 318, 1917-1920. doi:10.126/science.151526. Dimos, J. T., Rodolfa, K. T., Niakan, K. K., Weisenthal, L. M., Mitsumoto, H., Chung, W., et al. (2008). Induced pluripotent stem cells generated from patients with ALS can be differentiated into motor neurons. *Science* 321, 1218-1221. doi:10.1126/science.1158799. Hanna, J., Markoulaki, S., Schorderet, P., Carey, B. W., Beard, C., Wernig, M., et al. (2008) Direct reprogramming of terminally differentiated mature B Lymphocytes to pluripotency. *Cell* 133, 250-264. doi: 10.1016/J.cell2008.03.028. Huangfu, D., Macht, R., Guo, W., Eijkelenboom, A., Snitow, M., Chen, A. E., et al. (2008a). Induction of pluripotent stem cells by defined factors is greatly improved by small-molecule compounds. *Nat. Biotechnol.* 26, 795-1797. doi:10.1038/nbt1418 Mali, P., Ye, Z., Hommond, H. H., Yu, X., Lin, J., Chen, G., et al. (2008) Improved efficiency and pace of generating induced pluripotent stem cells from human adult and fetal fibroblasts. *Stem Cells* 26, 1998-2005. doi:10.11634/stemcells.2008-0346; Marson, A., Foreman, R., Chevalier, B., Bilodeau, S., Kahn, M., Young, R. A., et al. (2008). Wnt signaling promotes reprogramming of somatic cells to pluripotency. *Cell Stem Cell* 3, 132-135. doi:10.1016/j.stem.2008.06.019; Mikkelsen, T. S., Hanna, J., Zhang, X., Ku, M., Wernig., M., Schorderet, P., et al. (2008). Dissecting direct reprogramming through integrative genomic analysis. *Nature* 454, 49-55. doi:10.1038/nature 07056; Park, I. H. Zhao, R., West, J. A., Yabuchi, A., Huo, H., Ince, T. A., et al. (2008a). Reprogramming of human somatic cells to pluripotency with defined factors. *Nature* 451, 141-146. doi:10.1038/nature 06534; Shi, Y., Desponts, C., Do, J. T. Hahm, H. S., Scholer, H. R., and Ding, S. (2008a). Induction of pluripotent stem cells from mouse embryonic fibroblasts by Oct4 and Klf4 with small-molecule compounds. Cell Stem Cell 3, 568-574. doi:10.1016/J.stem.2008.10.004; Shi, Y., Do, J. T. Desponts, C., Hahm, H. S., Scholer, H. R., and Ding, S. (2008b). A combined chemical and genetic approach for the generation of induced pluripotent stem cells. *Cell Stem Cell* 2, 525-528. doi:10.1016j.stem.2008.05.011.

Vectors for Increasing ZSCAN10 Expression

Suitable vectors include without limitation viral gene delivery vectors (lentivirus-based vectors such as those derived from HIV1, HIV2, FIC and EIAV, which may be pseudotyped, AAV-based vectors etc.), plasmids, etc. In the experiments described herein delivery of ZSCAN10 and GLUT3 was made by using a commercially available lentiviral vector harboring OCT4 gene (Plasmid 19778: FU-tet-o-hOct4 from Addgene), excising the same and replacing it by ZSCAN10 or GLUT3. See http://www.addgene.org/19778/ (last visited Feb. 25, 2015).

Examples of additional vectors that can be used include excisable vectors such as STEMCCA available from EMD Millipore. However, ZSCAN10 supplementation is not limited to any particular expression vector and any method suitable for induction of pluripotent stem cell (whether using a vector or not) can be readily adapted for supplementing ZSCAN10. The same holds true for GLUT3, GPX2 and any other nucleotide inserted into stem cells in accordance with the present disclosure.

Vector free methods can also be used following and adapting known protocols as exemplified herein.

Provenance of iPSC

In principle, any somatic cell can be reprogrammed into iPSC. The basic Yamanaka protocol (Takahasji, K. et al, Cell. 2006 Aug. 25; 126(4):663-76; Takahashi, K. et al Cell. 2007 Nov. 30; 131(5):861-72) can be used with such modifications as described for example in the references cited in the Background section for alternative protocols of iPSC induction. Additionally, there are other protocols for reprogramming known in the art. See for example WO2013177228 Generation of Integration/Transgene-Free Stem Cells.

The cells most often used for reprogramming include fibroblasts, such as embryonic, neonatal, young and adult fibroblasts as needed.

It should be noted that according to Kim, K. et al, Nature, 2010, supra, and Kim, K. et al, Nature Biotechnology 2011, supra, there is some tissue specificity in the properties of iPSC depending on the tissue from which the somatic cells were chosen from prior to reprogramming. The present disclosure is directed to A-iPSC (and more broadly to any iPSC) exhibiting defects in genomic stability and/or apoptosis response and/or DNA damage response and to an increase in oncogenic potential associated with dysregulation of the glutathione/$H_2O_2$ pathway and in more specific embodiments with deficiency in ZSCAN10 and/or in glucose metabolism, for example those associated with insufficient endogenous expression of GLUT3. Accordingly, when it is not known whether iPSC exhibit such defects, testing should be performed following for example the procedure of Example 1. If determination of ZSCAN10 deficiency is needed, the procedure of assessing ZSCAN10 levels in Example 2 can for example be followed. If GLUT3 levels need to be assessed, the procedure of Example 8 for assessing GLUT3 levels of expression can for example be used.

GLUT3

Cellular uptake of glucose occurs through facilitated diffusion mediated by a family of glucose transporter proteins, where GLUT3 (also known as SLC2A3) is one of the major isoforms. With the exception of neurons and a few hematopoietic cell types, GLUT3 is generally not expressed in adult tissues. However, GLUT3 expression has been detected in various cancer types. While the expression of GLUT3 in different cancer types has been observed, its functional role remains unknown.

Within the context of brain tumor initiating cells (also often referred to as brain cancer stem cells), GLUT3 expression has been found to correlate with the induced pluripotency and to predict poor survival in multiple tumor types (Flavahan, W A, *Nature Neuroscience* 16: 1373-1382 (2013).

Figures 10A, 10B:
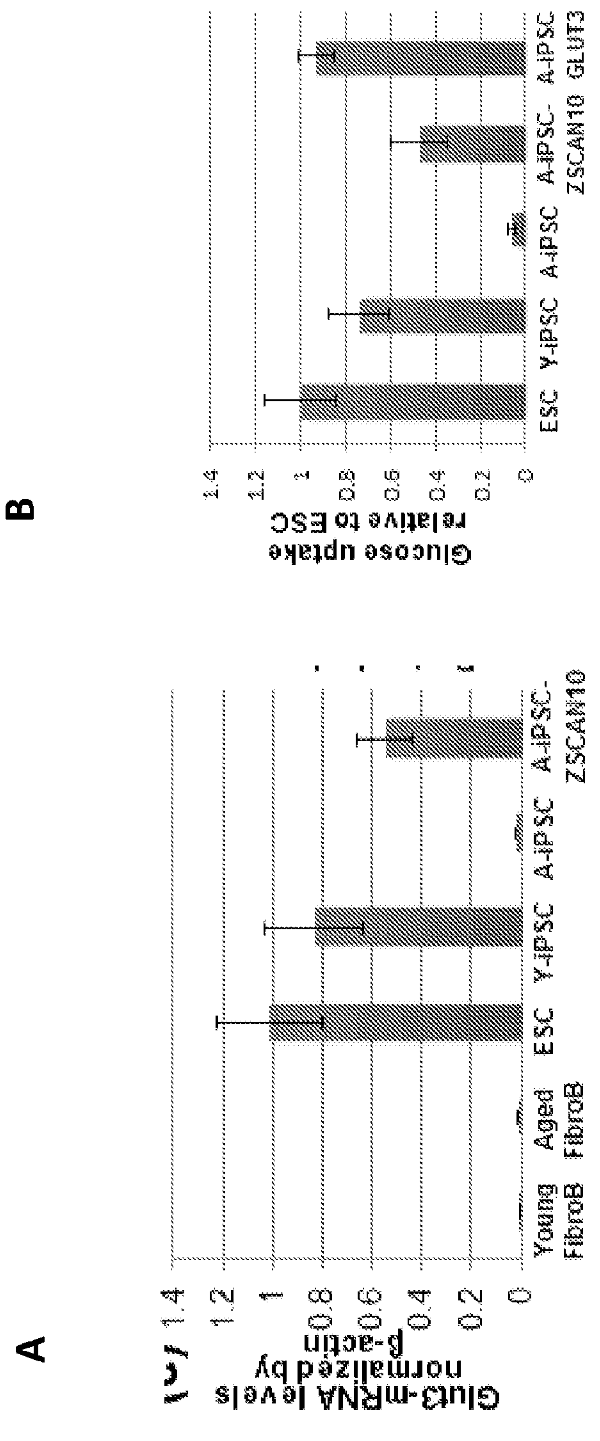
FIG. 10A is a bar graph showing real time qPCR for mRNA of GLUT3 in somatic cells (fibroblast samples from young and aged donors), ESC, Y-iPSC, A-iPSC, and A-iPSC-ZSCAN10.
FIG. 10B is a bar graph showing intracellular glucose uptake rate in ESC, Y-iPSC, A-iPSC, A-iPSC-ZSCAN10, and A-iPSC-GLUT3. Glucose uptake rate was measured by a glucose uptake analysis kit (cat #K606-100, Biovision Inc., Milpitas, Calif., USA).
Figures 10C, 10D, 10E:
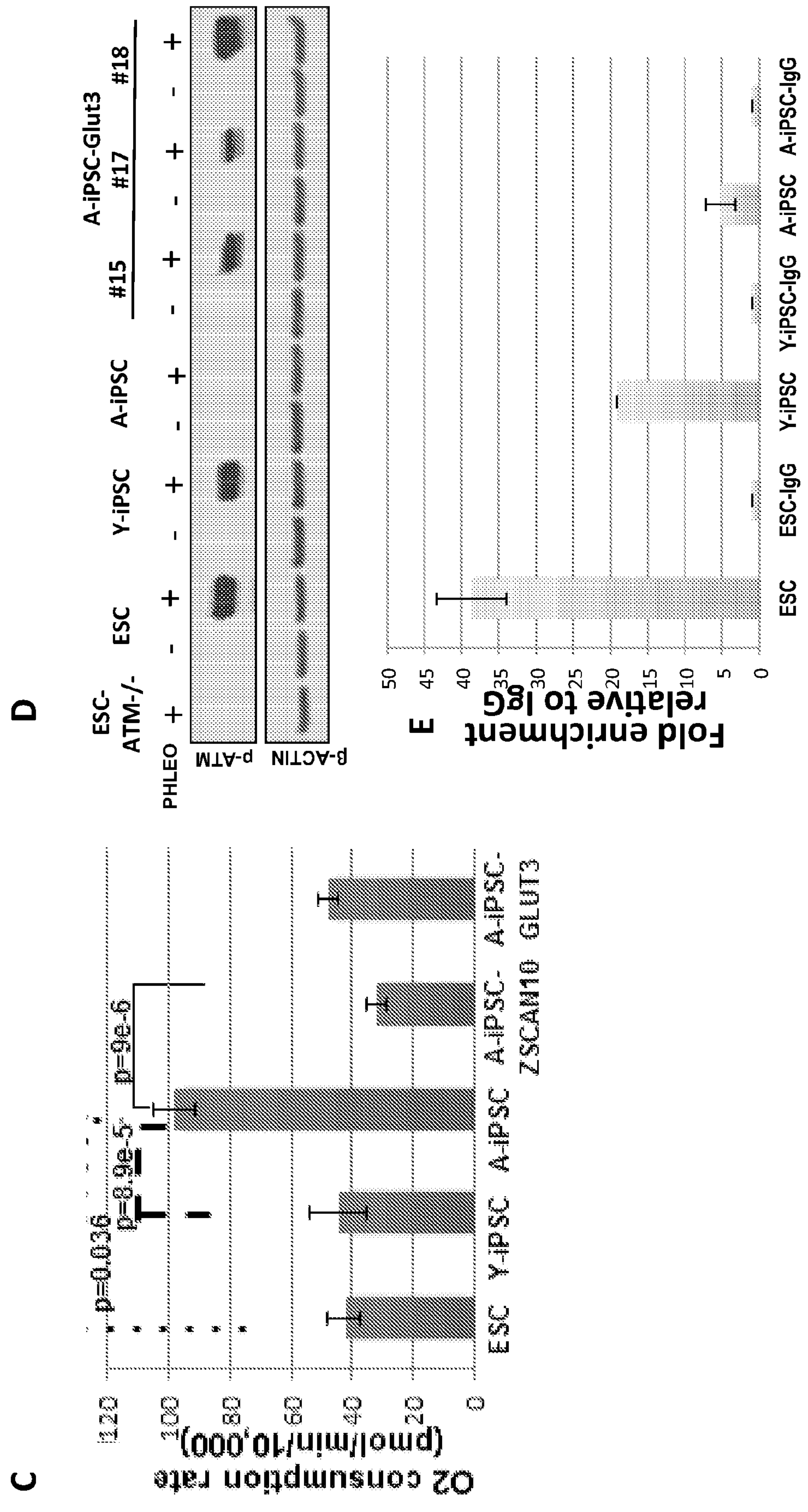
FIG. 10C is a bar graph of activation of the oxidative phosphorylation by glutamine A-ntESC (ES cells generated using nuclear transfer method), ESC, Y-iPSC, A-iPSC, A-iPSC-ZSCAN10, and A-iPSC-GLUT3. Oxygen consumption rate was determined after adding glutamine to a final concentration of 4 mM.
FIG. 10D is an immunoblot of ATM showing recovery of the DNA damage response after phleomycin treatment in three independent clones of A-iPSC with increased GLUT3 expression compared to controls (ESC, ATM knockdown in ESC, Y-iPSC and A-iPSC).
FIG. 10E is a graph showing Chromatin IP analysis of ZSCAN10 binding to the GLUT3 promoter. ESC, Y-iPSC, or A-iPSC were incubated with Igg control or ZSCAN10 antibody, followed by the qPCR using primers specific for the GLUT3 promoter.

The inventors discovered that GLUT3 levels are significantly lower in iPSC cells that exhibit defect in chromosome number and/or structure, induction of DNA damage response, or in apoptosis compared to cells characterized by normal chromosome number and/or structure, induction of DNA damage response, or apoptosis. In one instance, cells expressing lower or non-detectable levels of GLUT3 are A-iPSC cells. As illustrated in Example 8, increased expression of GLUT3 in A-iPSC led to substantial restoration of DNA damage response, similarly to the effects of ZSCAN10 expression in A-iPSC (FIG. 10D). Moreover, data presented in this disclosure show that ZSCAN10 leads to the induction of GLUT3, implying that ZSCAN10 and GLUT3 are interlinked in iPSC. ChIP-seq and immunoprecipitation analysis revealed that ZSCAN10 binds to the GLUT3 promoter, indicating direct regulation of GLUT3 by ZCAN10. The following materials are commercially available and can be procured online using websites such as those exemplified below (all last visited on Feb. 25, 2015).

cDNA sequence encoding human, murine, and rat GLUT3 can be found here (SEQ ID NO:2): http://www.ncbi.nlm-.nih.gov/gene/6515. (Kayano T. *J. Biol. Chem.,* 263 (30): 15245-15248 (1988))

http://www.ncbi.nlm.nih.gov/gene/20527 (Nagamatsu S. *J Biol Chem.,* 267 (1): 467-72 (1992)).

http://www.ncbi.nlm.nih.gov/gene/25551 (Krishnan S N. *Life Sci.* 56 (14): 1193-7 (1995).

Plasmids carrying human GLUT3 are commercially available from Genecopoeia, and can be found here: http://www.genecopoeia.com/product/search/detail.php?prt=1&cid=&key=C0200 (visited on Oct. 6, 2014, at 12:30 pm).

Additionally, recombinant GLUT3 protein is commercially available from mybiosource.com and can be found here: http://www.mybiosource.com/datasheet.php?products_id=1214582 (last visited Feb. 25, 2015).

GLUT3 supplementation in the amounts effective to substantially restore one or more of glucose metabolism, genomic stability, DNA damage, and/or apoptotic defects in iPSC, or more specifically, in A-iPSC, should be in an amount related to GLUT3 levels in iPSC cells that do not exhibit the above-mentioned defects. Alternatively, GLUT3 supplementation in A-iPSC can be related to the amount of GLUT3 detected in Y-iPSC and ESC. It is expected that the supplementation amounts effective in restoring the defects observed in iPSC due to reduced levels of GLUT3, will be in the range qualitatively similar to the range determined for ZSCAN10. Methods of supplementation of GLUT3 are diverse and the protocols described for the supplementation of ZSCAN10 apply to the supplementation of GLUT3.

The supplementation of GLUT3 can be achieved by introduction of an mRNA encoding GLUT3 into the iPSC-derived somatic cell and subsequent translation into a functional GLUT3 protein. Additional methods for increasing the levels of GLUT3 include, but are not limited to transfection with numerous vectors, such as adeno-associated virus, lentivirus, retrovirus, Sendai virus, DNA plasmids such that GLUT3 expression is effected at the DNA, RNA, and/or protein level in either a transient or long-term manner.

Alternatively, protein levels of GLUT3 can be increased by contacting the cell with an agent that leads to increased GLUT3 protein levels (in a transient or long-term manner). As shown in Example 8, ZSCAN10 expression leads to increased levels of GLUT3. Thus, it is expected that increasing the cellular levels of ZSCAN10 will result in the upregulation of GLUT3. Additionally, GLUT3 levels can be increased by contacting the cell with recombinant GLUT3 protein. As disclosed herein, the present method provides increasing the levels of ZSCAN10 in iPSC at a dosage sufficient to substantially or completely: (a) restore genomic stability, (b) improve poor DNA damage response, or (c) restore apoptotic response in human or animal (e.g., mouse) iPSC, or (d) restore glucose metabolism to levels similar to ESC or Y-iPSC.

GPX2

Figures 8A, 8B:
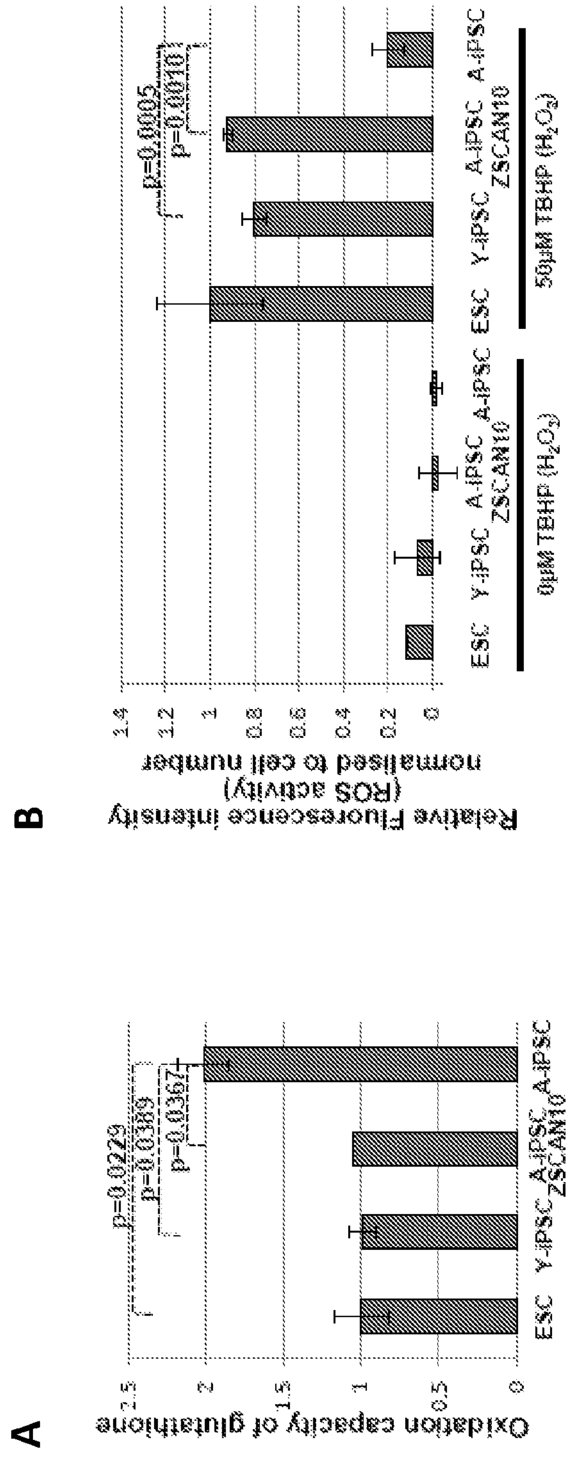
FIG. 8A is a bar graph showing excessive oxidation capacity of glutathione in A-iPSC, and recovery by ZSCAN10. Quantification of reduced glutathione (GSH) and oxidized glutathione (GSSG) was used to determine the total glutathione level (maximum oxidation capacity) in ESC, Y-iPSC, A-iPSC, and A-iPSC-ZSCAN10. Mean±standard deviation is plotted for three replicates from each condition.
FIG. 8B is a bar graph indicating $H_2O_2$ scavenging activity of ESC, Y-iPSC, A-iPSC-ZSCAN10, and A-iPSC expressed as reactive oxygen species ROS activity. A cellular reactive oxygen species assay kit (Abcam, ab113851) was used to measure the $H_2O_2$ scavenging activity after the treatment with TBHP (tert-butyl hydrogen peroxide; stable chemical form of $H_2O_2$) for 3 hours at 50 μM. Mean±standard deviation is plotted for four replicates from each condition.

Glutathione peroxidases catalyze the reduction of $H_2O_2$ using reduced glutathione. GPX2 is a member of the glutathione peroxidase family encoding one of two isoenzymes responsible for the majority of the glutathione-dependent hydrogen peroxide-reducing activity in the epithelium of the gastrointestinal tract. Published literature suggests that stem cells reside in redox niches with low ROS levels, where the balance of redox homeostasis governs stem cell self-renewal by an intricate network. In the work described herein, it was found that A-iPSC show perturbed glutathione-$H_2O_2$ homeostasis, with the oxidation capacity of glutathione elevated compared to ESC and Y-iPSC (FIG. 8A).

Figures 9A, 9B:
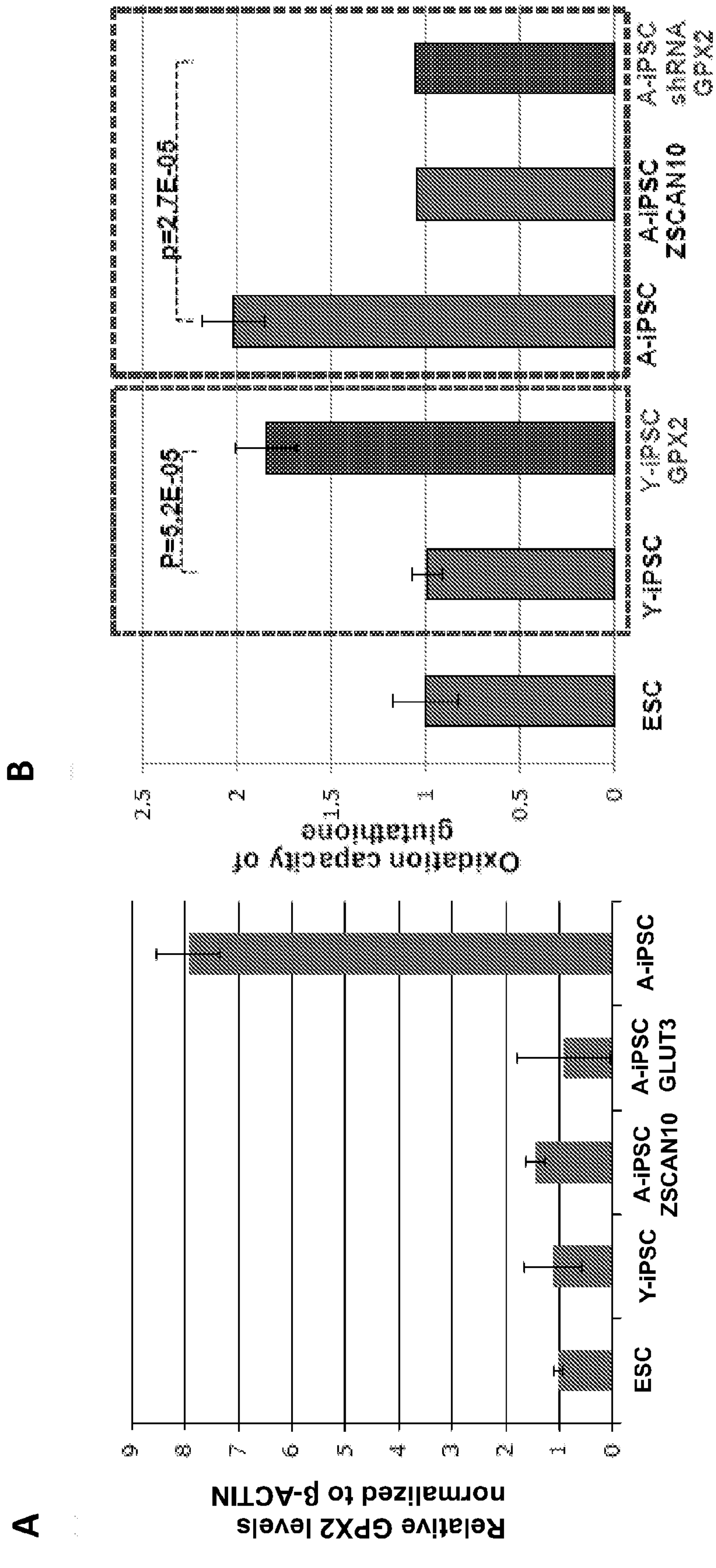
FIG. 9A is a bar graph showing mRNA levels (determined by Q-PCR) of GPX2 in ESC, Y-iPSC, A-iPSC-ZSCAN10, A-iPSC-GLUT3, and A-iPSC. Error bars indicate standard error of the mean.
FIG. 9B is a bar graph of oxidation capacity of glutathione in ESC, Y-iPSC, Y-iPSC-GPX2, A-iPSC, A-iPSC-ZSCAN10, and A-iPSC-shRNA-GPX2. Quantification of reduced glutathione (GSH) and oxidized glutathione (GSSG) was measured to determine the total glutathione level (maximum oxidation capacity). Mean±standard deviation is plotted for three replicates from each condition. Glutathione analysis was conducted using Glutathione Fluorometric Assay (Biovision, K264-100).
Figures 9C, 9D:
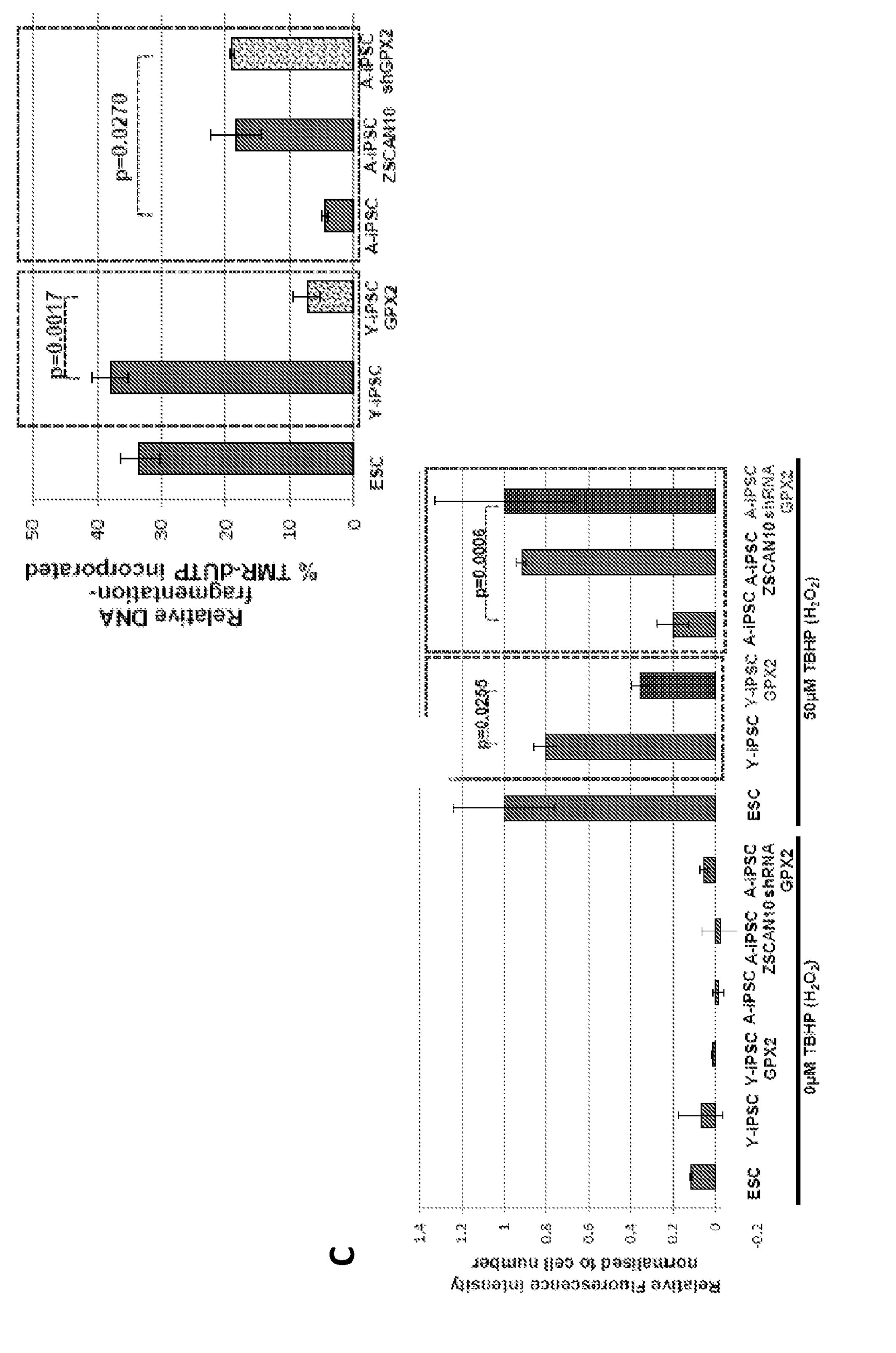
FIG. 9C is a bar graph showing $H_2O_2$ scavenging activity in ESC, Y-iPSC, Y-iPSC-GPX2, A-iPSC, A-iPSC-ZSCAN10, and A-iPSC-shRNA-GPX2 after the treatment with TBHP (tert-butyl hydrogen peroxide; stable chemical form of $H_2O_2$) for 3 hours at 50 μM. Mean±standard deviation is plotted for four replicates from each condition.
FIG. 9D is bar graph showing TUNEL-positive apoptotic cells (TMR-dUTO) in ESC, Y-iPSC, Y-iPSC-GPX2, A-iPSC, A-iPSC-ZSCAN10, and A-iPSC-shRNA 15 hours after the end of phleomycin treatment (2 hours, 30 μg/ml).
Figure 9E:
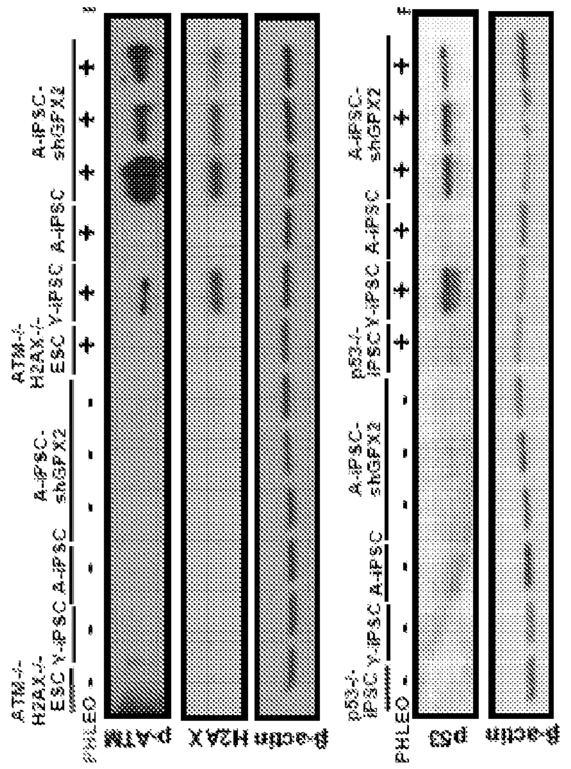
FIG. 9E is an immunoblot of pATM/pH2AX/p53 showing recovery of the DNA damage response (p-ATM, pH2AX and p53) after phleomycin treatment in three independent clones of A-iPSC with GPX2 shRNA and in controls (ATM and H2AX knockdown ESC as well as Y-iPSC and A-iPSC with and without phleomycin).

Prior analysis of GPX2 expression in the intestine suggested a role for GPX2 in the stem cell compartment of the gut, however, a role for GPX2 in ESC or iPSC has not been described so far. As shown in Example 7, in mouse A-iPSC, excessive glutathione activity scavenges hydrogen peroxide generated by genotoxic insult (abnormal glutathione-hydrogen peroxide homeostasis), thus blocking the normal apoptosis and DNA damage response. As a result, cells that are damaged are not eliminated. The enhanced glutathione activity is due to excessive elevation of GPX2. As indicated in FIGS. 9B and 9C, knockdown of GPX2 in A-iPSC resulted in the normalization of gluthathione-$H_2O_2$ homeostasis. Moreover, downregulation of GPX2 restored the defects in DNA damage and apoptosis in mouse A-iPSC (FIGS. 9E and 9D). Mechanistically, the inventors discovered that GPX2 expression in the mouse is regulated by ZSCAN10 in A-iPSC, as overexpression of ZSCAN10 in A-iPSC led to a decrease of GPX2 mRNA.

As further proof that high levels of GPX2 are indeed responsible for the abnormal reprogramming of A-iPSC, the inventors overexpressed GPX2 in mouse Y-iPSC. High levels of GPX2 in Y-iPSC shifted the behavior of Y-iPSC towards that of A-iPSC. Overexpression of GPX2 in Y-iPSC decreased apoptosis, reduced the DNA damage response, decreased glucose metabolism and induced an imbalance in glutathione-$H_2O_2$ homeostasis (increased oxidative metabolism).

Thus, in one aspect of the present disclosure, reduction of GPX2 levels in cells exhibiting abnormal chromosome number and/or structure, induction of DNA damage, or apoptosis can lead to substantial restoration of the mentioned defects to substantially those of ESC and Y-iPSC. In one aspect, the iPSC cell can be A-iPSC. Reduction of GPX2 levels in A-iPSC can cause the molecular and phenotypic changes within the iPSC in a way that will make it closely resemble ESC or Y-iPSC. Levels of GPX2 in A-iPSC or more generally in iPSC and their proximity or difference to those of Y-iPSC from healthy young donors or ESC can also be used as a surrogate marker for assessing quality of iPSC.

Reduction in levels of GPX2 can be achieved through numerous methods. For example, a small molecule inhibitor known to directly or indirectly reduce protein levels of GPX2 can be used. Additionally, various RNA interference (such as siRNA, shRNA) technologies can be used to inhibit GPX2 at the RNA level. Thus, any agent that leads to reduction of protein, RNA, or DNA levels of GPX2 can be used to restore the chromosomal stability, DNA damage, and/or apoptotic defects observed in A-iPSC, or any iPSC that are characterized by one or more of those defects. Human GPX2 ORF cDNA is available commercially for example from GeneCopoeia, Rockville Md. (http://www.genecopoeia.com); mouse GPX2 ORF cDNA is also available commercially for example from Origene, Rockville Md. http://www.origene.com/cdna.

DNA Methylation

Although somatic cells within an organism share the same genomic sequence, they can differ significantly in gene expression patterns due to chromatin modifications as well as DNA methylation. The conversion of somatic cells into pluripotent stem cells via overexpression of reprogramming factors involves epigenetic remodelling. However, recent studies have revealed that the process of reversal is not fully completed at all times. For example, although mice have been successfully generated from iPSC, not all pluripotent stem cell-derived mice are epigenetically stable, and instability has been linked to overweight and sudden-death syndrome in mice. Furthermore, iPSC contain a residual epigenetic signature depending on the tissue type of the donor tissue used (Kim et al, *Nat Biotechnol* 29(12): 1117-1119, 2011). Finally, iPSC from aged donors (A-iPSC) have been shown to preserve an aging-specific epigenetic memory (Kim et al. *Nature* 467(7313):285-290, 2010).

In normal cells, DNA methylation assures accurate regulation of gene expression and stable gene silencing. DNA methylation is linked to histone modifications and the interplay between these modifications is critical for the functioning of the genome by changing chromatin architecture. The covalent addition of a methyl group occurs generally in cytosine within CpG dinucleotides which are concentrated in large clusters known as CpG islands. The aberrant DNA methylation landscape is a characteristic feature of cancer. It has been established that inactivation of specific tumor-suppressor genes arises as a consequence of hypermethylation (inactivation) within the promoter regions and numerous studies have shown a broad range of genes silenced by DNA methylation in various types of cancer. Furthermore, hypomethylation (activation), which can induce genomic instability, also contributes to cell transformation.

Figures 7A, 7B:
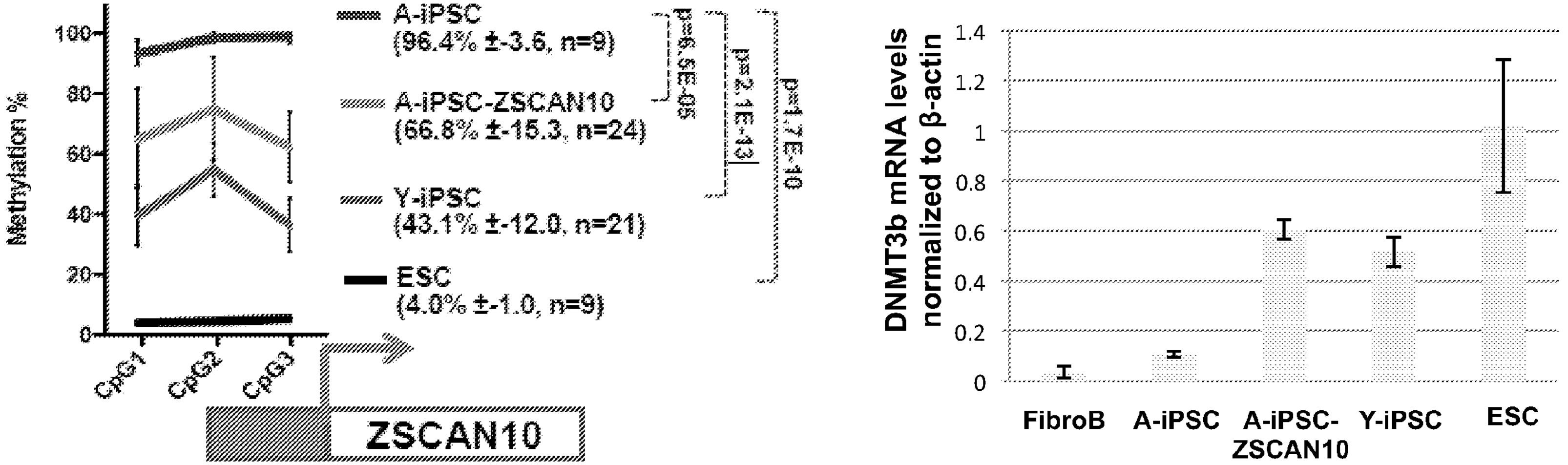
FIG. 7A is a plot of pyrosequencing data of ZSCAN10 promoter, indicating relatively higher DNA methylation in A-iPSC. Transient expression of ZSCAN10 led to lower DNA methylation of ZSCAN promoter (A-iPSC-ZSCAN10). Error bars indicate standard error of the mean of four independent clones analyzed per group. Statistical significance was determined by t-test.
FIG. 7B is a bar graph showing mRNA levels of DNMT3b normalized to beta-actin in fibroblasts, A-iPSC, A-iPSC-ZSCAN10, Y-iPSC, and ESC.

In the present disclosure, the ZSCAN10 promoter is activated in Y-iPSC and ESC, and inactive in A-iPSC. This modification resulted in poor levels of ZSCAN10, but was restored with the transient expression of ZSCAN10 in A-iPSC which led to hypomethylation (activation) of the endogenous ZSCAN10 promoter to levels similar to those detected in Y-iPSC (FIG. 7). Furthermore, DNA methylation analysis of mouse Y-iPSC and A-iPSC compared with mouse ESC showed that A-iPSC contain a higher number of differentially methylated regions (DMRs) than Y-iPSC. In addition, the number of hypermethylated DMRs is higher in mouse A-iPSC than in Y-iPSC. Moreover, depending on the genetic background of the donor, human A-iPSC show greater DNA methylation, similar to that observed in mouse A-iPSC. Moreover, recent studies have revealed that poor DNA demethylation in human cells is associated with inefficient reprogramming (Bagci, H. et al, *Cell Stem Cell* 3:265-269 (2013)), further establishing comparable patterns of DNA methylation between mouse and human cells. Thus, in one aspect, the present disclosure provides a method where distinct epigenetic differences such as the number of hypermethylated DMRs or the methylation status of ZSCAN10 in iPSC can serve as a marker or indicator of the specific iPSC properties. In another aspect, the present disclosure provides a method for substantially or completely restoring DNA methylation patterns in A-iPSC to be similar to those observed in Y-iPSC.

Genes affecting oncogenic potential of A-iPSC were identified by performing microarray analysis on ESC/Y-iPSC/A-iPSC/ZSCAN10/A-iPSC to detect differential expression of genes in A-iPSC. Both GPX2 and GLUT3 were identified thus.

ZSCAN Regulates Exosome, which in Turn Regulates GPX2

In the present disclosure, ChIP-Seq analysis revealed that ZSCAN10 binds to and upregulates subunits of the exosome complex. A-iPSC displayed lower mRNA levels of exosome subunits compared to FESC and Y-iPSC (FIG. 11A). Furthermore, overexpression of ZCAN10 led to restoration of exosome subunit mRNA, demonstrating a direct interaction between ZSCAN10 and exosome.

The multisubunit exosome complex is a major ribonuclease of eukaryotic cells that participates in the processing, quality control and degradation of nearly all classes of RNA (Schmid et al. *Trends Biochem Sci.* (10):501-10, (2008)). Previous studies have demonstrated that the interaction between the exosome and AU-rich elements (ARE) plays a key role in regulating the efficiency of ARE-containing mRNA turnover. The GPX2 gene contains highly conserved ARE sequences (Singh et al. *Am J Respir Cell Mol Biol.* 35(6):639-50 (2006)), making the ZSCAN10→EXOSOME→GPX2 axis a potential mechanism of GPX2 regulation. To test this hypothesis, different exosome subunits were knocked-down in ESC and the levels of GPX2 mRNA determined (FIG. 12A). Knock-down of EXOSC2 or EXOSC8 led to dramatic increase in GPX2 expression in ESC, which was accompanied by lower apoptotic response (FIG. 12B). Thus, these findings indicate that ZSCAN10 regulates GPX2 via mechanism that involves exosome complex including various subunits. Consequently, supplementing A-iPSC in the mouse with an exosome subunit would lead to amelioration of phenotypic defects and oncogenic potential associated with aging iPSC.

iPS Cells Derived from Aged Human Donors Exhibit Different Reprogramming Efficiencies and Phenotypic Defects A-iPSC cells generated from aged human donors confirm the findings observed in A-iPSC generated from aged animals regarding low reprogramming efficiency (FIG. 13A). Interestingly, a significant difference in reprogramming efficiency is observed between two different donors of similar age, which was also reflected in their DNA damage response (FIG. 13B). A-iPSC generated from the donor that exhibited significant defect in DNA damage response also displayed structural chromosome abnormality (FIG. 13C). These results suggest that genetic background of an individual plays a significant role in reprogramming efficiency and DNA damage response of A-iPSC. It is anticipated that this defect can be rescued by supplementation as described herein.

Multiple laboratory mouse strains of various genetic backgrounds are available. To test the hypothesis that genetic background is crucial for A-iPSC, A-iPSC were generated from distinct mouse strains, B6129 and B6CBA. As shown in FIG. 13D, A-iPSC derived from the B6129 background mice exhibit normal DNA damage response (indicated by activation of p53), while A-iPSC from the B6CBA background mice showed blunted DNA damage response. Collectively, these findings indicate that reprogramming efficiency, chromosomal stability, as well as a DNA damage response associated with A-iPSC are all highly dependent on genetic background of the individual or animal from which they are derived as well as on epigenetic factors and aging.

GSS

De novo synthesis of glutathione (GSH) is catalyzed by two enzymes, γ-glutamylcysteine synthetase (γ-GCS) and glutathione synthetase (GSS). The rate-limiting step of GSH synthesis is the formation of the amide linkage between the gamma-carboxyl moiety of glutamic acid and the amino moiety of cysteine. The rate at which GSH is synthesized is based on both the activity of the enzyme (GCS) and the availability of cysteine. GSS completes the GSH synthesis by catalyzing the conversion of the γ-GluCys dipeptide to GSH via the addition of glycine (Johnson et al. *Nutrients.* 4(10): 1399-440 (2012)).

The enzymes involved in GSH synthesis are controlled by multiple mechanisms both pre and post transcriptionally. Previous studies focused on genome-wide mapping of ZSCAN10-binding sites in ESC identified ~3500 target genes, including GSS (Yu et al. *J Biol Chem.* 284(45): 31327-31335 (2009)). In the present disclosure, the inventors have shown that in humans ZSCAN10 binds directly to the GSS promoter (Example 12, FIG. 14B). Additionally, they have shown that the levels of GSS mRNA are significantly upregulated in A-iPSC compared with Y-iPSC and ESC and that this upregulation is diminished upon ZSCAN10 overexpression in A-iPSC (Example 12, FIG. 14C).

Additional experiments disclosed herein provide further proof that GSS is indeed involved in regulating oncogenic potential of A-iPSC in humans. As described in Example 13 and FIGS. 14D-F, GSS plays a role in both apoptosis, as well as in the regulation of the DNA damage response. Downregulation of GSS in A-iPSC using shRNA led to increased apoptotic response (Example 13, FIG. 14D) as well as in the rescue of the DNA damage response (Example 13, FIGS. 14E-14F). On the contrary, overexpression of GSS in Y-iPSC caused lower apoptotic response compared to control Y-iPSC cells (FIG. 14D) and loss of DNA damage response (FIGS. 14E and 14F).

Thus, in one aspect of the present disclosure, reduction of GSS levels in cells exhibiting abnormal chromosome number and/or structure, induction of DNA damage, or apoptosis can lead to substantial restoration of the aforementioned defects in these phenotypic traits and their restoration to substantially those of ESC and Y-iPSC. In one aspect, the iPSC cell can be A-iPSC. Reduction of GSS levels in A-iPSC can cause the molecular and phenotypic changes within the iPSC in a way that will make it closely resemble ESC or Y-iPSC.

Reduction in levels of GSS can be achieved through numerous methods. For example, various RNA interference (such as siRNA, shRNA) technologies can be used to inhibit GSS at the RNA level. Thus, any agent that leads to reduction of protein, RNA, or DNA levels of GSS can be used to restore the chromosomal stability, DNA damage, and/or apoptotic defects observed in A-iPSC, or any iPSC that are characterized by one or more of those defects. Both human and mouse GSS ORF cDNA is available commercially for example from OriGene Technologies, Rockville, Md. (http://www.origene.com/cdna). To target GSS at the DNA level, clustered regularly interspaced short palindromic repeats (CRISPR)-Cas genome editing tool can be used (Sander and Joung, *Nature Biotechnology* 32, 347-355 (2014). Additionally, GSS levels or activity can be reduced using inhibitors known to directly or indirectly reduce protein levels and/or activity of GSS. For example, buthionine sulfoximine (Drew and Miners, *Biochem Pharmacol.* 33(19):2989-94 (1984)), 6-Diazo-5-oxo-L-norleucine (Vanoni M A and Curti B, *IUBMB Life.* 60(5):287-300 (2008)), and azaserine (Hensley et al. *J Clin Invest.* 123(9): 3678-84 (2013)) have been shown to inhibit GSS. Thus, in one embodiment of the present disclosure, GSS levels are reduced or activity inhibited using buthionine sulfoximine, 6-Diazo-5-oxo-L-norleucine (Vanoni M A and Curti B, *IUBMB* and/or azaserine, or any inhibitor shown to reduce the activity and/or levels of GSS. In addition to using each inhibitor individually, the reduction of GSS activity and/or levels can be achieved by combination of two or more known inhibitors. In inhibiting GSS it is important that the inhibition not be complete. Some amount of glutathione is important to the cell.

Alternatively, ZSCAN10 can be upregulated as described herein to suppress upregulation of GSS since the present inventors have shown that GSS is directly regulated by ZSCAN10 through binding to the promoter of GSS. Through the work described herein ZSCAN 10 has emerged as an important coregulatory of somatic cell reprogramming to produce iPSC especially iPSC from aged donors.

GSS can also be used as a surrogate marker for assessing oncogenic potential and glutathione/$H_2O_2$ homeostasis and more generally quality of iPSC especially A-iPSC by measuring levels of GSS in A-iPSC and more generally iPSC and comparing them to those of Y-iPSC or ESC from healthy donors. If the levels of GSS are low, i.e., comparable to those of Y-iPSC and ESC then the stem cells have low oncogenic potential, have robust glutathione homeostasis and are generally of good quality.

Experimental Procedures

Cell Culture

ESC and iPSC were cultured in ESC media containing 10% FBS and 1,000 U/ml of LIF (ESGRO® Leukemia Inhibitory Factor [LIF], 1 million units/1 mL). For generation of ESC, established methods previously reported were used (Kim et al. *Nature* 467: 285-290, 2010). For iPSC reprogramming of somatic cells, retrovirus expressing OCT4, SOX2, KLF4, and MYC were introduced. For the somatic cells containing inducible reprogramming factors, the media was supplemented with 2 μg/ml doxycycline (MP Biomedicals, doxycycline hyclate). For DNA and RNA isolation, ESC or iPSC were trypsinized and re-plated onto new tissue culture dishes for 30 min to remove feeder cells, and nucleic acids were extracted from the non-adherent cell suspension.

Generation of Mouse Y-iPSC, A-iPSC, A-iPSC-ZSCAN10, A-iPSC-shGPX2, A-iPSC-shGSS, A-iPSC-GLUT, ESC-shEXOSC2, ESC-shEXOSC8, ESC shEXOSC2&8, Human Y-iPSC, and Human A-iPSC $10^6$ skin fibroblast cells were collected from B6CBAF1 mouse E15.5 embryonic skin, 5-day-old tail tip skin, and 1.4-year-old tail tip skin; infected with retrovirus generated from pMX-mOCT4, pMX-mSOX2, pMX-mKLF4,2 and pEYK-mMYC3 in 6-well dishes with 0.5 ml of each viral supernatant (total 2 ml per well); and spun at 2500 rpm at RT for 90 min (BenchTop Centrifuge, BeckmanCoulter, Allegra-6R). For the generation of A-iPSC-ZSCAN10, the procedure was identical but in addition to the four reprogramming factors, a doxycycline inducible system was added to overexpress ZSCAN10. This system consisted of two lentiviruses generated from a plentiRZ-ZSCAN10 and a plenti-RTTA vector (Kim et al. *Nat Biotechnol* 29: 1117-1119, 2011). The vector was generated by replacing the insert of a commercially available vector with ZSCAN10 (or GLUT3 or other insert described herein). All cells infected with the reprogramming factors and those with additional ZSCAN10, shGPX2, shGSS and GLUT3 were plated on irradiated CF-1 mouse embryonic feeder cells in a 10-cm tissue culture dish in ESC media containing 20% FBS and 1,000 U/ml of LIF. Media were changed on day 2 and doxycycline addition started on day 3 for ZSCAN10 overexpression. Floating cells were collected by media centrifugation and returned to culture during media changes. On day 4, cultured cells were trypsinized and replated onto four 10-cm dishes pre-coated with gelatin (0.1%) and irradiated mouse embryonic fibroblasts in ESC maintenance media. Media were changed daily until ESC-like colonies were observed. The reprogrammed colonies were tested for pluripotency by teratoma assay formation, alkaline phosphatase staining, SSEA-1 and NANOG staining, and OCT4 expression levels.

For the generation of A-iPSC-shGPX2, A-iPSC were infected post-reprogramming with a set of shRNA viral vectors for GPX2 (6 GIPZ Lentiviral shRNA vectors from Thermo Scientific: RMM4532-EG14776). Clones were selected with puromycin, and the levels of down-regulation were measured by Q-PCR. For the generation of A-iPSC-shGSS, A-iPSC were infected post-reprogramming with a set of shRNA viral vectors for GSS (GE DHARMACON, RMM4532-EG14854).

For the generation of A-iPSC-shZSCAN10, mouse A-iPSC were infected post-reprogramming with a set of shRNA lentiviral vectors designed to target NM_001033425.3. A set of ZSCAN10 set shRNAs is commercially available from Abmgood.com (last visited on Oct. 6, 2015).

For the generation of Y-iPSC-GPX2, mouse Y-iPSC were infected with a lentivirus carrying the GPX2 cDNA post-reprogramming (Harvard Plasmid Core (http://plasmid.med-.harvard.edu/PLASMID/Home.jsp). The infected clones were assessed for GPX2 expression levels by Q-PCR. For the generation of Y-iPSC-GSS, mouse Y-iPSC were infected with a lentivirus carrying the GSS cDNA (Harvard Plasmid Core (http://plasmid.med.harvard.edu/PLASMID/) post-reprogramming. The infected clones were sorted for a red fluorescent marker and the GSS expression levels were assessed by Q-PCR.

For the generation of human A-iPSC, $10^5$ skin fibroblasts from 84 years old, 76 years old, and 81 years old subjects were infected with retrovirus generated from the tetracistronic SFG-SV2A vector encoding for hOCT4, hSOX2, hKLF4 and hMYC in 6-well dishes with 0.5 ml of each viral supernatant (total 2 ml per well); and spun at 2500 rpm at RT for 90 min (BenchTop Centrifuge, BeckmanCoulter, Allegra-6R).

For the generation of ESC-shEXOSC2, ESC-shEXOSC8 and ESC shEXOSC2&8, ESC were infected with a set of shRNA viruses for EXOSC2 and/or EXOSC8 (2 GIPZ Lentiviral shRNA vectors for EXOSC2 from GE DHARMACON: RMM4431-200370629, RMM4431-200332733 and 3 GIPZ Lentiviral shRNA vectors for EXOSC8 from GE DHARMACON: RMM4532-EG69639). Clones were selected with puromycin treatment.

Retrovirus Generation 293T cells were seeded overnight at $5\times10^6$ cells per 150-mm dish with DMEM supplemented with 10% FBS and penicillin/streptomycin. Retrovirus was generated using pMX-mOCT4, pMX-mSOX2, pMX-mKLF4, and pEYK-mMYC constructs as described previously (Koh et al. *Nucleic Acids Res.* 30: e142, 200; Takahashi et al. *Cell* 126: 663-676, 2006). The cells were transfected with standard calcium phosphate method as previously described. Media were replaced with fresh DMEM two times, 18 hours after transfection. Approximately 48 hours after transfection, medium containing the lentivirus was collected and the cellular debris was removed with centrifugation. The supernatant was filtered through a 0.45-μm filter, and the retrovirus was pelleted with ultracentrifugation at 33,000 rpm in 45 Ti rotors (Beckman) for 90 min at 4° C. The retroviral particles were resuspended in the ESC medium and stored at −80° C.

Lentivirus Production 293T cells were seeded overnight at 5×106 cells per 150-mm dish with DMEM supplemented with 10% FBS and penicillin/streptomycin. The cells were transfected with plentiRZ-ZSCAN10 and plenti-RTTA using calcium phosphate cell transfection, as previously described (Kim et al. *Nat Biotechnol* 29: 1117-1119, 2011). The ZSCAN10 cDNA was clone MmCD00295052 in the pENTR223.1 backbone. The cDNA for mZSCAN10 was subcloned into a plentiRZ vector and the cDNA for GPX2 into a plenti-puro vector using the Gateway® system. See https://tools.lifetechnologies.com/content/sfs/manuals/gatewayman.pdf. At 48 hours after transfection, the medium containing the lentivirus was collected and the cellular debris was removed with centrifugation. The supernatant was filtered through a 0.45-μm filter, and the lentivirus was pelleted with ultracentrifugation at 33,000 rpm in 45Ti rotors (Beckman) for 90 min at 4° C. The lentivirus particles were resuspended in DMEM medium and stored at −80° C.

Teratoma analysis was carried out for ESC, Y-iPSC, A-iPSC, and A-iPSC-ZSCAN10 cells. The results revealed decreased incidence of malignant tumors for A-iPSC-ZSCAN10 cells compared to A-iPSC without insert. Teratoma analysis for A-iPSC-GLUT3 will be performed in analogous manner and it is anticipated that the results will be qualitatively the same.

Quantitative Real Time-PCR (Q-PCR) Analysis

The expression levels of genes (ZSCAN10, OCT4, GPX2, GLUT3, and β-ACTIN) were quantified by Q-PCR with Power SYBR Green PCR mastermix (Applied Biosystems). Total RNAs (1 μg) were reverse-transcribed in a volume of 20 μl using the M-MuLV Reverse Transcriptase system (New England Biolabs), and the resulting cDNA was diluted into a total volume of 200 μl. 10 μl of this synthesized cDNA solution was used for analysis. For pluripotent genes, each reaction was performed in a 25-μl volume using the Power SYBR Green PCR mastermix (Applied Biosystems). The conditions were programmed as follows: initial denaturation at 95° C. for 10 min followed by 40 cycles of 30 sec at 95° C., 1 min at 55° C., and 1 min at 72° C.; then 1 min at 95° C., 30 s at 55° C., and 30 sec at 95° C. All of the samples were duplicated, and the PCR reaction was performed using an Mx3005P reader (Stratagene), which can detect the amount of synthesized signals during each PCR cycle. The relative amounts of the mRNAs were determined using the MxPro program (Stratagene). The amount of PCR product was normalized to a percentage of the expression level of β-ACTIN. The PCR products of OCT4, ZSCAN10, GPX2 and β-ACTIN were also evaluated on 1.2% agarose gels after staining with ethidium bromide. The primers used to amplify the cDNA were the following: OCT4-For 5'-GGCTCTCCCATGCATTCAA-3' and OCT4-Rev 5'-TTTAACCCCAAAGCTCCAGG-3', ZSCAN10-For 5'-GGCTCAGAGGAATGCGTTAG-3' and ZSCAN10-Rev 5'-CATCTACAGGCCCACCAGTT-3', GPX2-For 5'-GTGCTGATTGAGAATGTGGC-3' and GPX2-Rev 5'-AGGATGCTCGTTCTGCCCA-3', β-ACTIN-For 5'-TCGTGGGTGACATCAAAGAGA-3' and β-ACTIN-Rev 5'-GAACCGCTCGTTGCCAATAGT-3', and HPRT-For 5'-CTCCTCAGACCGCTTTTTGC-3' and HPRT-Rev 5'-TCGAGAGCTTCAGACTCGT-3', EXOSC2-For CCCCAAGGAGCATCTGACAA and EXOSC2-Rev CCAACCCACCATTACCTCCC, EXOSC1-For ATGGGTTGGTGATGGGCATAG and EXOSC1-Rev CCCATGCTGTCACTATTGGGT, EXOSC5-For CCGATTCTACCGGGAATCACT and EXOSC5-Rev CTACATGGGCACAGACAGAGG. Transgene silencing (OCT4, SOX2, KLF4, and MYC) was confirmed using the following primers, which span the 5' region of the viral vector and the 5' end of the structural genes. Uninfected fibroblasts were used as a negative control and day 3 fibroblasts transfected with Yamanaka factors were used as a positive control. The primer sequences to detect the transgene flanked the pMX vector and the transgene: pMX-51811-For 5'-GACGGCATCGCAGCTTGGATACAC-3', and OCT4-Rev 5'-CAGTCCAACCTGAGGTCCAC-3', KLF4 Rev 5'-GACAACGGTGGGGGACAC-3', SOX2 Rev 5'-CTGGAGTGGGAGGAAGAGGT-3', and MYC Rev 5'-CCAGATATCCTCACTGGGCG-3'. the primers for GLUT3 were mGlut3-xba-F atttctagaATGGGGACAACGAAGGTGACC and mGlut3-xba-R atggatccTCAGGCGTTGCCAGGGGTC.

Drug Treatments and Irradiation

Phleomycin (Sigma) was added at 30 μg/ml for 2 hours. Cells were processed for analysis 30 min after phleomycin treatment unless indicated otherwise. After the 30-min recovery in ESC media, the cells were collected and processed for following experiments. For the detection of the DNA damage response in the extended period, the cells were given 6 hours to recover after phleomycin treatment and were processed for H2AX immunostaining. In the DNA fragmentation assay, the cells were given 15 hours to recover. To check the mutagenesis potential, the cells were treated with phleomycin 30 μg/ml for 2 hours and cultured for one passage after each treatment. This process was repeated three times and then the cells were processed for 6TG selection. Cells were irradiated at 10 Gy, allowed to recover for 2 hours, and then lysates were collected for immunoblot analysis.

Teratoma Analysis iPSC were collected by trypsin collagenase treatment, resuspended in Matrigel mix (DMEM:Matrigel:collagen at 2:1:1 ratio), and $10^6$ undifferentiated cells were injected into the subcutaneous tissue above the rear haunch of Rag2/γC immunodeficient mice (Taconic). Teratoma formation was monitored for 3 months post-injection. Collected tumors were fixed in 10% formalin solution and processed for hematoxylin and eosin (H/E) staining by the Molecular Cytology facility of Memorial Sloan Kettering Cancer Center and by Histowiz, Inc. Protocols for H/E staining are provided at http://protocolsonline.com/histology/dyes-and-stains/haematoxylin-eosin-he-staining/ and http://www.nsh.org/sites/default/files/Guidelines_For_Hematoxylin_and_Eosin_Staining.pdf.

Immunoblot Analysis

Treated and untreated cells (1×105 cells) were collected 30 min after the 2-hour phleomycin treatment (30 μg/ml). To harvest protein, 100-200 mL RIPA buffer (50 mM Tris-HCl [pH 7.4], 150 mM NaCl, 1% NP40, 0.25% Na-deoxycholate, 1 mM PMSF, protease inhibitor cocktail, and phosphatase inhibitor cocktail) was added to floating cell pellets and the remaining adherent cells. The samples were incubated on ice (10 min) and centrifuged (14,000 g, 10 min, 4° C.). Protein concentrations were determined using a BCA protein assay kit (Pierce). Samples were adjusted to the same concentration with RIPA buffer (3000 μg/ml) and were combined with Laemmli Sample Buffer (Biorad) and β-Mercaptoethanol (Sigma) then heated at 95° C. for 5 min and loaded onto a 4-15% Mini Protean TGX SDS-PAGE gel (BioRad). Samples on the SDS-PAGE gel were transferred to a 0.2-mm PVDF membrane at 100 V for 1 h, using a wet electro-transfer method (0.2 M glycine, 25 mM Tris, and 20% methanol). The membrane was blocked with 5% BSA in PBS-T (1 h at 4° C.), followed by incubation with primary antibodies anti-H2AX (Millipore, 05-636) (1:1000), anti-p53 (Leica Biosystems, P53-CM5P) (1:1000), anti phospho-ATM (Pierce, MA1-2020), or anti-beta actin (Cell Signaling, #4967) (1:5000) in blocking solution (5% BSA in phosphate-buffered saline containing Tween-20 [1:1000] PBS-T, overnight at 4° C.). After primary antibody incubation, membranes were washed three times in PBS-T) prior to addition of secondary antibody labelled with peroxidase. Secondary antibodies were from Cell Signaling (1:10,000).

Bisulfite Pyrosequencing Analysis 500 ng of genomic DNA was bisulfite-treated using the EZ DNA Methylation-Gold Kit (Zymo Research) according to the manufacturer's specifications. Bisulfite-treated genomic DNA was PCR-amplified using ZSCAN10 specific primers. The position of interest of ZSCAN10 promoter was based on Ensembl Genome assembly: GRCm38 (GCA000001635.4) on Chr17:23599958-23600647. The assay (PCR and Pyrosequencing) covered three CpG sites immediately upstream of the transcription start site on 23600600 (CpG 3), 23600645 (CpG 2), and 23600647 (CpG 1). The pyrosequencing was designed and performed by Epigendx (Hopkinton, Mass., USA).

Cytogenetic Analysis

Cytogenetic analysis was performed by metaphase chromosome preparation, G-band karyotyping, and flow cytometry analysis with PI staining. Metaphase chromosome preparation and the G-band karyotyping were performed by the Molecular Cytogenetics Core Facility of Memorial Sloan Kettering Cancer Center. For PI staining, the cells were harvested and washed in PBS and then fixed in cold 70% ethanol (added drop-wise to the pellet while vortexing to minimize clumping) for 30 min at 4° C. The cells were washed in PBS twice, treated with ribonuclease, and stained with PI (Propidium Iodide Staining Solution: 3.8 mM sodium citrate, 40 μg/ml PI [Sigma, P 4170] in PBS).

Immunohistochemistry Staining

Cells were fixed in 3.7% formaldehyde for 20 min at room temperature and washed with PBS. Samples were then permeabilized with 0.1 Triton X-100 in PBS for 20 min and blocked for 1 h with 3% BSA in PBS-T, and primary antibodies were incubated for 2 h at room temperature or overnight at 4° C. Anti-H2AX was purchased from Millipore (05-636), anti-SSEA-1 phycoerythrin conjugated was purchased from R&D systems (FAB2155P), and anti-NANOG from BETHYL Laboratories (A300-397A). Primary antibodies were used at 1:500 dilution. Alexa 568-conjugated goat anti-mouse IgM (A-21124) and Alexa 633-conjugated goat anti rabbit IgG (A-21072) were from Molecular Probes. Secondary antibodies were used at 1:1000 dilution. The nuclei were stained with 4',6-diamidino-2-phenylindole (DAPI, Sigma). Alkaline phosphatase (AP) staining was performed using the Alkaline Phosphatase Detection Kit (Millipore) according to the manufacturer's instructions. Fluorescence images were obtained using an AxioImager Z1 microscopy system (Zeiss).

DNA Fragmentation Analysis

DNA fragmentation was measured using an in situ cell death assay kit (Roche) for visualization of DNA strand breaks by labelling the free 3'-OH termini with modified nucleotides (e.g., biotin-dUTP, DIG-dUTP, fluorescein-dUTP) in an enzymatic reaction. iPSC cells (1×105 cells) were treated with phleomycin (30 μg/ml) for 2 hours. Samples were collected as control or treated for analysis 15 hours after phleomycin treatment. Additionally, cells were treated with DNAase I recombinant (Roche) (10 min, 3 U/ml, at 15° C. to 25° C.) to induce DNA strand breaks, as a positive control for apoptosis. Medium containing floating cells and attached cells was centrifuged (1000 g, 5 min) and collected. Cells were processed for flow cytometry analysis.

$H_2O_2$ Reactive Oxygen Species (ROS) Assay $H_2O_2$ scavenging activity was measured using a cellular reactive oxygen species assay kit (Abcam, ab113851). ESC/iPSC were labelled with 20 μM DCFDA (2',7'-dichlorofluorescein diacetate; a fluorogenic dye that measures hydroxyl, peroxyl, and other ROS activity within the cell), and cultured for 3 h with 50 μM TBHP (tert-butyl hydrogen peroxide; stable chemical form of $H_2O_2$). Cells were then analyzed on a fluorescent plate reader. Mean±standard deviation is plotted for four replicates from each condition.

TBHP Treatment

Cells were treated with 350 μM TBHP solution (Luperox® TBH70X, tert-Butyl hydroperoxide solution 70 wt.

% in H2O, 458139) for 30 min in PBS. Lysates were collected for immunoblot analysis. The control untreated cell lines were cultured in either ESC media or PBS, and DNA damage response was not induced in both media without TBHP treatment (data not shown).

HPRT Assay

HPRT assay was performed according to the previously published protocol (Tsuda et al., *AATEX* 11 (2), 118-128, 2005). After ESC, Y-iPSC, A-iPSC, and A-iPSC-ZSCAN10 were cultured with three rounds of phleomycin treatment, $10^6$ ESC and iPSC were plated onto 10-cm tissue culture dishes containing feeder cells (CF-1 MEF) and added 5 μg/ml of 6-TG (2-amino-6-mercaptopurine; Sigma) for negative selection. The mutation frequency was estimated by the inactivation of HPRT promoter activity. Individual colonies were counted/picked at day 12, and the number of colonies was normalized to the percentage of colonies that did not express HPRT in each group by Q-PCR analysis.

Glutathione Detection Assay

Feeder-free cells were cultured on Matrigel-coated tissue culture plates in MEF-conditioned ESC-media. On day 3, the cells were washed in PBS and scraped and pelleted by centrifugation. Subsequent steps were performed using a Glutathione Fluorometric Assay Kit (cat #K264-100, Bio-vision Inc., Milpitas, Calif., USA) according to the manufacturer's manual. Briefly, cell pellets were homogenized in ice cold glutathione assay buffer, preserved in perchloric acid, and centrifuged. Supernatants were neutralized with potassium hydroxide. After centrifugation, the supernatant was either used to detect reduced glutathione (GSH), or total glutathione was measured by reducing oxidized glutathione (GSSG) to GSH before measurement. For measuring GSSG concentrations specifically, existing GSH was quenched before reducing agent was applied. OPA (o-phtalaldehyde) probe, which reacts with GSH and emits fluorescence, was added to samples, and signal was acquired at Ex/Em=340 nm/420 nm on a Varioscan Flash by Thermo Scientific. Oxidation capacity of glutathione was determined by the quantity of total glutathione (GSH+GSSG).

EXAMPLES

Example 1 iPS Cells Derived from Aged Mice Exhibit Higher Genomic Instability and Lower Apoptotic Activity Yamanaka and others (Takahashi et al., Cell, 126, 663-676, 2006) identified the four epigenetic reprogramming factors for generating iPSC using young donor tissue, but never tested whether or not the same four factors were sufficient for iPSC reprogramming of aged donor tissue.

Here, iPSC cells were generated using mouse skin fibroblasts from E15.5 embryos to 5-day-old neonates (Y-iPSC) or using mouse skin fibroblast from donors 1.4 years of age (A-iPSC) according to the standard Yamanaka iPSC reprogramming protocol.

12 clones of each cell type were randomly picked based on the morphology, and analyzed for pluripotency compared to ECS as the gold standard. Multi-lineage contribution to three germ layers in teratoma analysis and pluripotent gene expression analysis (AP/OCT4/SSEA1/NANOG) showed successful reprogramming of mouse skin fibroblasts isolated from both young and aged donors. Silencing of the four reprogramming factors (OCT4, SOX2, KLF4, MYC) in each clone was confirmed by quantitative PCR (Q-PCR). Initially, when DNA ploidy was tested in multiple iPSC clones, both Y-iPSC and A-iPSC clones with normal ploidy were observed (FIGS. 1A, 1B, and 1D); however, a higher frequency of polyploidy was observed in A-iPSC compared to Y-iPSC (FIGS. 1B, 1E, and 1F). Additionally, A-iPSC displayed more chromosomal structural abnormalities than Y-iPSC (FIG. 1G).

Pluripotent stem cells are known to have a unique DNA damage response that is different from the canonical DNA damage response of somatic cells and cancer cells. The maintenance of genomic stability in pluripotent stem cells is achieved by directly inducing apoptosis to eliminate severely damaged cells from the population (Liu, J, Trends in Cell Biology, 24, 268-274, 2014; Liu, J, Cell Stem Cell, 13, 483-491, 2013). Thus, it was postulated that the poor genetic stability observed in A-iPSC was due to defects in apoptosis. In order to test this hypothesis, activation of apoptosis in response to DNA damage was evaluated in all independent clones.

Figure 2:
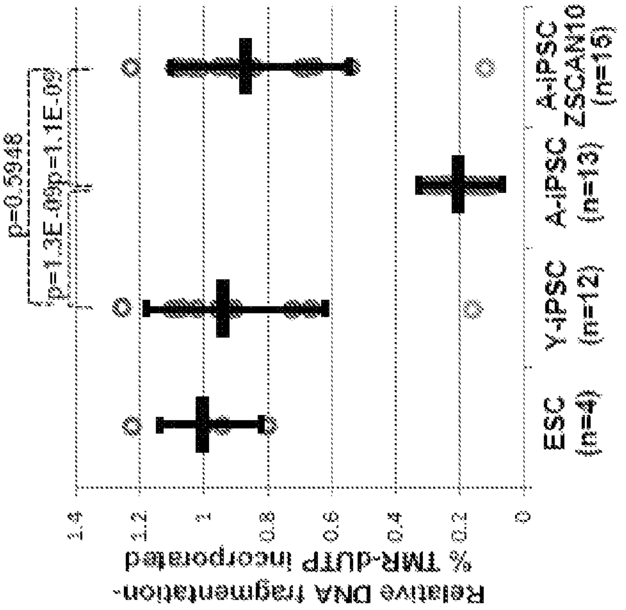
FIG. 2 is a dot plot showing image-quantification of lower apoptotic response by DNA fragmentation assay after phleomycin treatment (30 μg/ml for 2 hours) in ESC, Y-iPSC, A-iPSC, and recovery with ZSCAN10 expression (A-iPSC-ZSCAN10). Error bars indicate standard error of the mean of technical and biological replicates. The exact number of biological replicates is indicated below each group.

In situ cell death assays of ESC, Y-iPSC, and A-iPSC were performed 15 hours after the end of treatment with a DNA damage inducing agent, phleomycin (2 hours, 30 μg/ml). A-iPSC show fewer cells staining for cell death compared to ESC and Y-iPSC. Y-iPSC group treated with dye in the absence of enzymatic reaction was used as a negative control. Nuclei were stained with DAPI. As shown in FIG. 2, lower apoptotic response was observed by DNA fragmentation assay after phleomycin treatment of A-iPSC, while ESC and Y-iPSC displayed comparable DNA fragmentation under same conditions. Collectively, the data presented here suggest that A-iPSC are characterized by higher genomic instability and lower apoptotic activity compared to ESC and Y-iPSC.

Example 2

Figure 3:
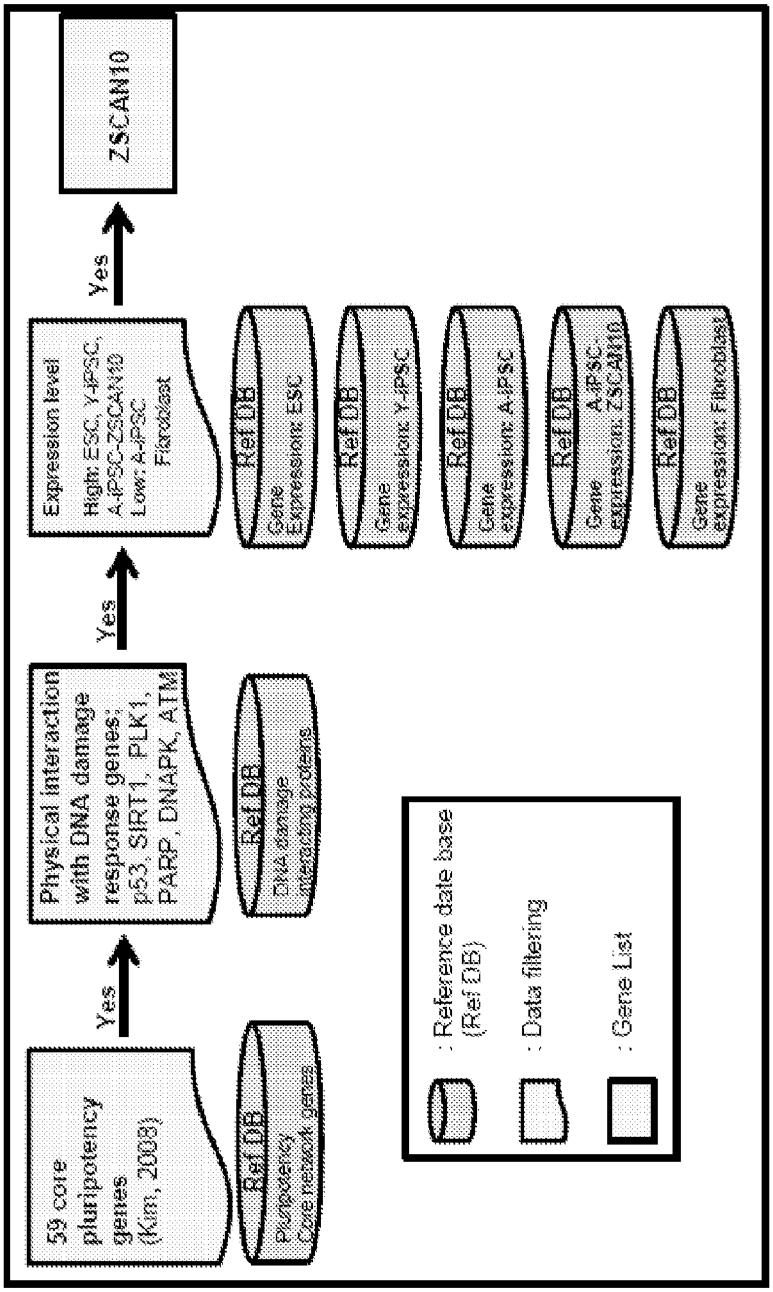
FIG. 3 is a schematic representation of a method used to identify ZSCAN10. Initially, 59 core pluripotency genes derived from the pluripotency network analysis were filtered against genes that are known to be associated with DNA damage response, such as p53, SIRT1, PLK1, and genes upstream of p53 (ATM, PARP, and DNAPK). The gene list was then filtered based on differential expression in A-iPSC vs. Y-iPSC/ESC, which narrowed down the candidates to a single gene, ZSCAN10.

ZSCAN10 is a Pluripotency Factor Poorly Activated in A-iPSC Compared to ESC and Y-iPSC In order to identify ESC-specific pluripotency factors that are poorly activated in A-iPSC compared to ESC and Y-iPSC, and are most likely responsible for the defects observed in A-iPSC, a strategy was developed starting from a known network of 59 pluripotency genes. Kim et al. (Kim, J., *Cell* 132, 1049-1061) previously reported 59 core pluripotency genes derived from the pluripotency network analysis (FIG. 3). Initially, these 59 core genes were filtered against the genes known to be associated with DNA damage response, such as p53, SIRT1, PLK1, and genes upstream of p53 (ATM, PARP, and DNAPK). From there, the gene list was further filtered based on differential expression in A-iPSC vs. Y-iPS and A-iPSC vs. ESC, which narrowed down the candidates to a single gene, ZSCAN10. ZSCAN10 is a known zinc finger transcription factor specifically expressed in ESC, and is an integrated part of the transcriptional regulatory network with SOX2, OCT4, NANOG, and ZSCAN4.

To further evaluate the role of ZSCAN in reprogramming, the levels of ZSCAN were determined in ESC, Y-iPSC, and A-iPSC by quantative real-time-PCR (Q-PCR). As expected, ZSCAN10 mRNA levels were significantly lower in A-iPSC compared to ESC and Y-iPSC (FIG. 4). Thus, it was concluded that ZSCAN10 expression is low in somatic cells, higher in Y-iPSC and ESC, but restricted in A-iPSC.

The data presented here suggests that ZSCAN10 is a potential factor responsible for the genomic instability observed in A-iPSC cells.

Example 3

ZSCAN10 Expression Restores Genetic Stability and Apoptosis in A-iPSC

To explore the function of ZSCAN10 in reprogramming, iPSC were generated from aged donor fibroblasts using the four Yamanaka factors (OCT4, SOX2, KLF4, and MYC) plus ZSCAN10 within a doxycycline (Dox)-inducible lentiviral expression vector. A-iPSC-ZSCAN10 cells were grown in media supplemented with 2 μg/ml of doxycycline for two days. Following doxycycline withdrawal, reprogrammed colonies were tested for pluripotency by teratoma assay formation, alkaline phosphatase staining, SSEA-1 and NANOG staining, and OCT4 expression levels, which confirmed that A-iPS-ZSCAN10 have undergone successful reprogramming. Next, A-iPSC-ZSCAN10 were tested for their ability to rescue genomic stability and apoptotic defects observed in A-iPSC containing low levels of ZSCAN10.

Using a doxycyline system, transient expression of ZSCAN10 in A-iPSC permanently increased endogenous ZSCAN10 expression to levels similar to those in Y-iPSC and ESC (FIG. 4). Moreover, transient expression of ZSCAN10 during reprogramming in A-iPSC reduced the abnormal chromosomal ploidy and structural abnormalities to levels comparable to Y-iPSC and ESC (FIGS. 1C, 1F, and 1G). In order to test the effect of ZSCAN10 on apoptosis in A-iPSC, A-iPSC-ZSCAN10 were treated with DNA damage inducing agent, phleomycin (2 hours, 30 μg/ml), and the apoptotic response was evaluated by DNA fragmentation assay. ZSCAN10 expression in A-iPSC restored the defect in induction of apoptosis following DNA damage induction (FIG. 2).

These results indicate that ZSCAN expression in A-iPSC rescues the genomic stability and apoptosis defects detected in iPS cells generated from aged donors.

Example 4

A-iPSC Display Higher Mutagenic Potential Compared to ESC and Y-iPSC, which is Restored by ZSCAN10 Expression As discussed in Example 3, transient expression of ZSCAN10 in A-iPSC during reprogramming restored genomic stability and apoptosis to levels comparable to ESC and Y-iPSC. To define the mechanism by which ZSCAN10 expression restores genomic stability and apoptosis in A-iPSC, a comprehensive molecular analysis of a minimum of three independent clones (each of ESC, Y-iPSC, A-iPSC-ZSCAN10, and A-iPSC) was performed. Since A-iPSC showed a defect in induction of apoptosis, it was hypothesized that A-iPSC failed to eliminate damaged cells and would accumulate more genomic mutations than Y-iPSC or ESC.

The mutagenic potential in ESC, Y-iPSC, A-iPSC, and A-iPSC-ZSCAN10 was determined using the mutagenic destruction of HPRT promoter activity (Tsuda et al., AATEX 11 (2), 118-128, 2005. The hypoxanthine phosphorybosyl transferase (HPRT), gene located on the X chromosome of mammalian cells, is widely used as a model gene to investigate gene mutations in mammalian cell lines. The HPRT methodology detects mutations that destroy the functionality of the HPRT gene and or/protein, where the detection of mutations is achieved by selection using a toxic analogue 6-thioguanine (6-TG). Various types of mutations in the HPRT gene lead to cells resistant against lethal 6-TG incorporated into their DNA. Thus, only cells with HPRT mutations can grow in 6-TG containing media. This method detects a broad range of mutagens, since any mutation resulting in the ablation of proper gene function produces an HPRT mutant.

Following three rounds of phleomycin treatment (2 hours each, at 30 μg/ml), ESC, Y-iPSC, and A-iPSC were cultured in media containing 6-TG (5 μg/ml). The mutation frequency was estimated by the inactivation of HPRT promoter activity. Individual colonies were counted/picked at day 12, and the number of colonies was normalized to the percentage of colonies that did not express HPRT in each group by Q-PCR analysis.

Figures 5A, 5B, 5C, 5D, 5E:
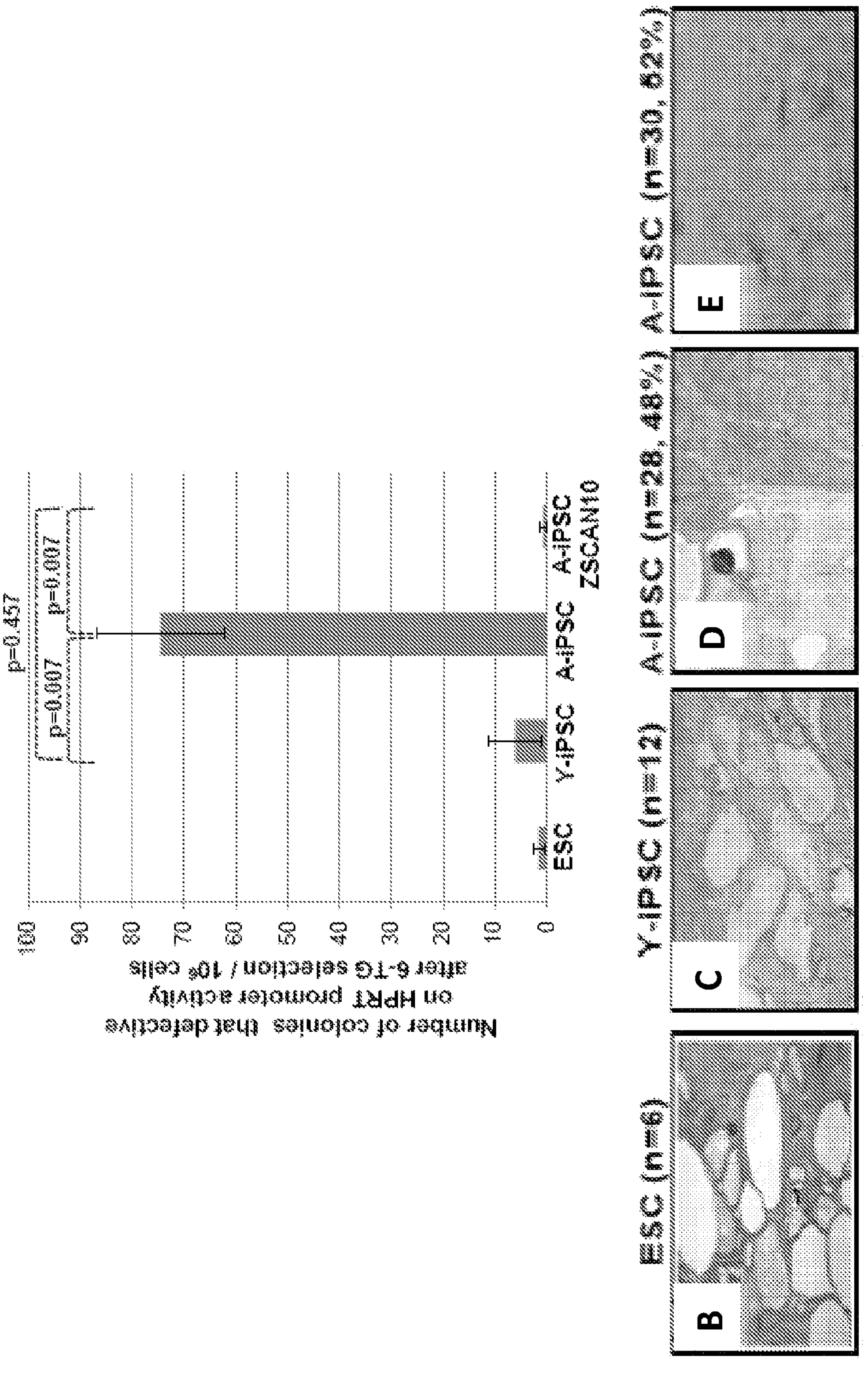
FIG. 5A is a bar graph showing increased mutagenic frequency in A-iPSC compared to ESC and Y-iPSC. The mutation frequency was estimated by the inactivation of HPRT promoter activity in the presence of 6-thioguanine-mediated negative selection, and confirmed by Q-PCR. Higher mutation frequency observed in A-iPSC was decreased to normal levels following ZSCAN expression. Error bars indicate standard error of the mean of three replicates. Statistical significance was determined by t-test.
FIG. 5B-5E show hematoxylin and eosin (H&E) staining of teratomas indicating higher in vivo oncogenicity of A-iPSC compared to ESC and Y-iPSC. Teratoma analysis was carried out by injecting $10^6$ undifferentiated cells into the subcutaneous tissue above the rear haunch of Rag2/γC immunodeficient mice (Taconic), and teratoma formation was monitored for 3 months post-injection. Collected tumors were fixed in 10% formalin solution and processed for hematoxylin and eosin (H/E) staining. ESC (FIG. 5B) and Y-iPSC (FIG. 5C) form Y-iPSC form benign teratoma containing various tissue types that develop into cystic structures, with no signs of carcinoma. In contrast, 48% (n=28) (FIG. 5D) of individual A-iPSC clones generated a mixture of malignant carcinoma and benign teratoma tissues, and 52% (n=30) (FIG. 5E) of A-iPSC clones contained only teratocarcinoma.

A-iPSC displayed significantly higher mutation rate compared to ESC and Y-iPSC (FIG. 5A). Consistent with the findings that ZSCAN10 can restore genomic stability and apoptosis defects in A-iPSC, transient expression of ZSCAN10 reduced the mutagenic potential in these cells (FIG. 5A).

Mutagenic potential of ESC, Y-iPSC, and A-iPSC was further tested in vivo. Teratoma formation is an established assay that determines the capacity of differentiation in vivo and is considered to be the essential method for evaluating human ES and iPS cell lines. Teratoma analysis revealed that while ESC and Y-iPSC form benign teratoma, significant percentage of A-iPSC clones (48%) form a mixture of malignant carcinoma and benign teratoma (FIGS. 5B-5E).

Taken together, these results show that A-iPSC exhibit higher mutagenic potential, both in vitro and in vivo, than ESC and Y-iPSC.

Example 5

ZSCAN10 Corrects the Blunted DNA Damage Response in A-iPSC Via ATM, p53, and H2AX The aging process gradually alters DNA repair mechanisms through a chronic activation of the DNA damage response. To evaluate the DNA damage response in more detail in A-iPSC and the role of ZSCAN10 in this process, activation of known DNA damage effector proteins was assessed.

The cellular response to DNA damage involves a series of events that lead to apoptosis. One of the early events is the phosphorylation of Ataxia telangiectasia mutated (ATM), a serine/threonine kinase that plays a central role in the repair of DNA double-strand breaks. ATM further phosphorylates several key proteins that initiate activation of the DNA damage checkpoint, leading to cell cycle arrest and apoptosis. ATM activation leads to phosphorylation of tumor suppressors p53 and histone 2AX (H2AX). With the goal of gaining a better understanding of the events affected by ZSCAN10, phosphorylation of ATM, H2AX, and p53 was examined in A-iPSC following the induction of DNA damage.

Figures 6A, 6B, 6C:
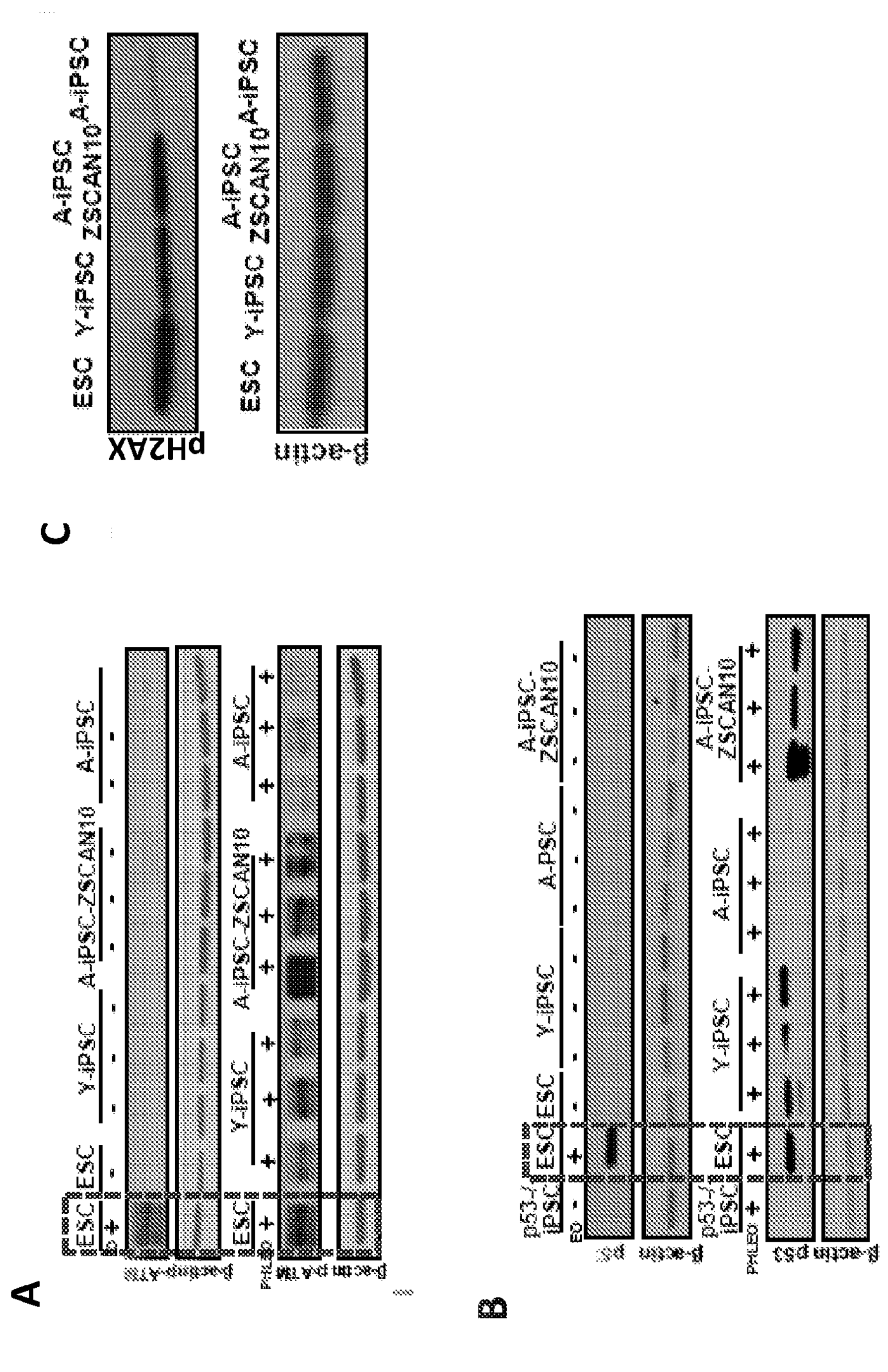
FIG. 6B shows impaired p53 DNA damage response in A-iPSC and recovery with transient expression of ZSCAN10 in three independent clones after phleomycin treatment (2 h, 30 μg/ml). The red line indicates the same ESC sample loaded in both immunoblots as an internal control.
FIG. 6C indicates low H2AX phosphorylation in A-iPSC after phleomycin treatment (2 h, 30 μg/ml) and recovery of H2AX signal with ZSCAN10 expression.

ESC, Y-iPSC, and A-iPSC were treated with 30 μg/ml of DNA damage inducing agent phleomycin for 2 hours. Protein levels of ATM, H2AX, and p53 were determined by immunoblot analysis. As shown in FIGS. 6A, 6B, and 6C, A-iPSC exhibit either low, or undetectable levels of phosphorylated ATM, p53, and H2AX following the treatment with phleomycin compared to ESC and Y-iPSC. These defects are, in part, mediated by ZSCAN10 since expression of ZSCAN10 in A-iPSC restores the phosphorylation of DNA damage pathway proteins to levels comparable to those detected in ESC and Y-iPSC (FIGS. 6A, 6B, and 6C). In order to confirm that the defect in DNA damage response was universal and not dependent on phleomycin, experiments were conducted using the same experimental design, but changing the DNA damage inducing agent. Similarly to data observed with phleomycin, ESC and Y-iPSC, but not A-iPSC, show an increase in ATM/H2AX/p53 levels after irradiation and hydrogen peroxide $H_2O_2$ treatment. For radiation experiments, cells were irradiated with 10 Gy, allowed to recover for 2 hours, and the lysates were collected for immunoblot analysis. Both radiation and $H_2O_2$ are known inducers of DNA damage response. Importantly, the ATM/H2AX/p53 response to irradiation and $H_2O_2$ in A-iPSC was recovered by transient expression of ZSCAN10 (FIGS. 6F and 6G).

Figures 6D, 6E:
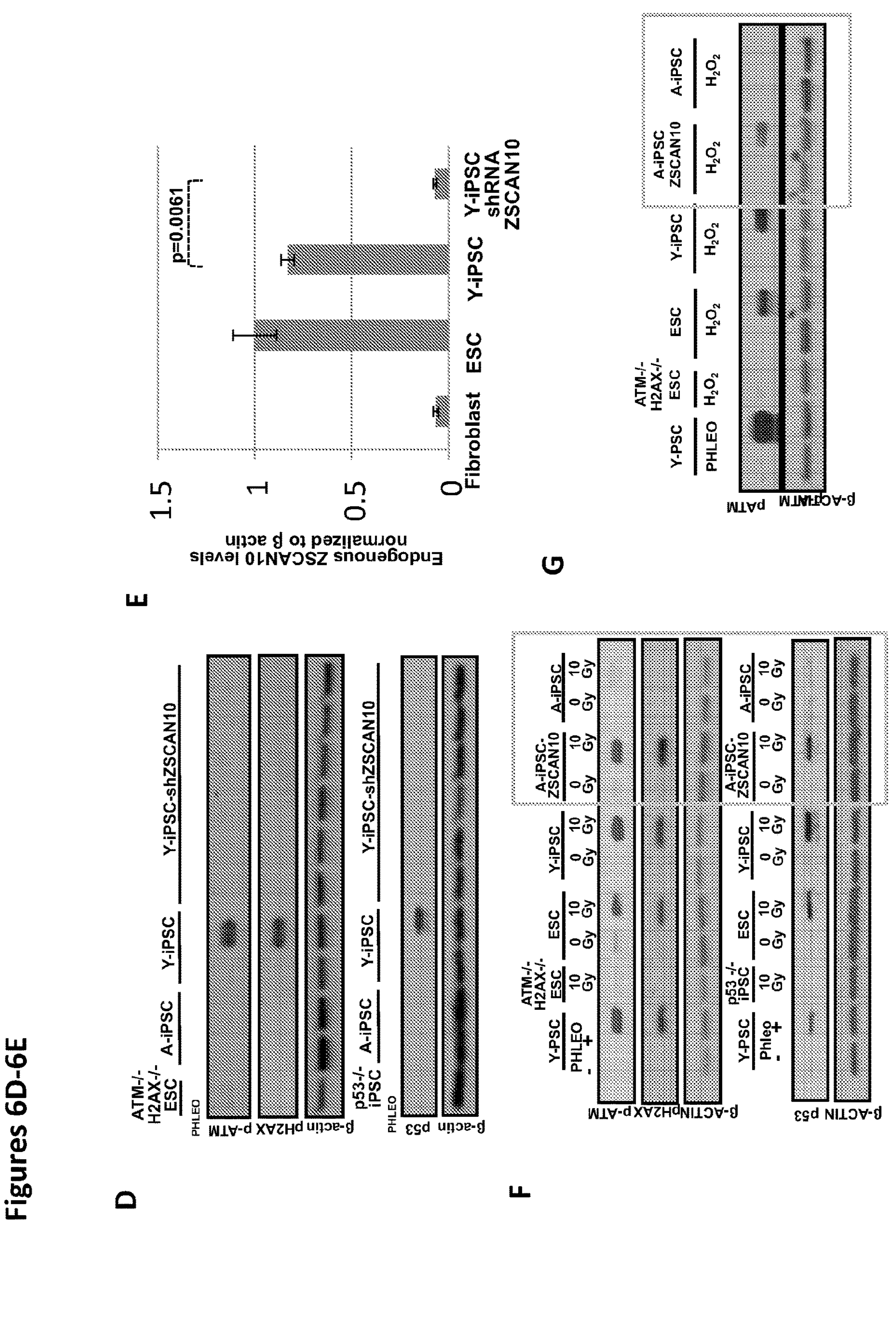
FIG. 6D are scanned images of immunoblots showing phosphorylated levels of ATM and H2AX proteins, and levels of p53 in ATM−/−H2AX−/− ESC, A-iPSC, Y-iPSC, and in Y-iPSC transduced with shRNA against ZSCAN10 (Y-iPSC-shZSCAN10). Beta-actin was used as a loading control.
FIG. 6E is a bar graph of mRNA ZSCAN10 levels in fibroblasts, ESC, Y-iPSC and Y-iPSC-shZSCAN10.

In addition to overexpression experiments, the inventors reduced ZSCAN10 levels using shRNA targeting ZSCAN10 in Y-iPSC (FIGS. 6D and 6E). Further providing support for the role of ZSCAN10 in the regulation of DNA damage response, Y-iPSC with reduced ZSCAN10 expression exhibited lower apoptotic response compared to those that had normal ZSCAN10 levels (FIG. 6D).

Collectively, these results indicate that impaired DNA damage response in A-iPSC is recovered with the transient expression of ZSCAN10.

Example 6

Endogenous ZSCAN10 is Hypermethylated in A-iPSC and Hypomethylated in ESC and Y-iPSC Induction of pluripotency in somatic cells is considered an epigenetic process that among other things entails changes in DNA methylation patterns. With the aim of further elucidating the changes that occur in A-iPSC compared to ESC and Y-iPSC, and the role of ZSCAN10, DNA methylation analysis was performed. Bisulfite pyrosequencing analysis of the ZSCAN10 promoter regions showed that the ZSCAN10 promoter is hypomethylated/activated in Y-iPSC and ESC, and hypermethylated/inactive in A-iPSC (FIG. 7). To test whether transient ZSCAN10 expression can restore the methylation pattern of A-iPSC, A-iPSC-ZSCAN10 cells generated using a Dox-inducible expression system were analyzed. Similar to the ability of ZSCAN10 to restore other defects in A-iPSC, transient expression of ZSCAN10 in A-iPSC led to hypomethylation/activation of the endogenous ZSCAN10 promoter to levels closer in Y-iPSC.

Microarray analysis of mouse ESC versus aged and young mouse fibroblasts (Y-SC and A-SC—wherein "SC" here stands for "somatic cells") as well as Y-iPSC, A-iPSC, revealed differential regulation of DNA (cytosine-5-)-methyltransferase 3 beta (DNMT3b) gene (a gene reviewed in (Kim et al. *Cell Mol Life Sci.* 66(4): 596-612 (2009)). Contrary to DNMT3b, the levels of DNMT3a were similar among various cell types. This finding was further corroborated by q-PCR (FIG. 7B), where DNMT3b mRNA levels were lowest in fibroblasts, and highest in ESC. Given the role of DNMT3b in DNA methylation, the inventors postulate that poor activation of DNMT3b may be responsible for differential methylation of ZSCAN promoter in A-iPSC. In addition DNMT3b can be overexpressed in A-iPSC cells and achieve the same result as ZSCAN10 overexpression. Thus, the exogenous introduction of DNMT3b into the A-iPS cells may result in diminished oncogenic potential of these cells or any stem/iPS cells associated with reduced ZSCAN10 expression.

Example 7

Imbalance of H2O2/Glutathione Homeostasis in A-iPSC, and Recovery by ZSCAN10 Via Reduction of Excessively Activated GPX2 in A-iPSC As described in Example 5, the defective DNA damage response of A-iPSC and its restoration by ZSCAN10 were also confirmed in response to various DNA damaging agents such as radiation and $H_2O_2$. DNA damaging agents can induce $H_2O_2$ and result in genomic damage. A normal cellular response against $H_2O_2$ involves two distinct mechanisms: (1) $H_2O_2$ can be scavenged by glutathione to maintain genomic stability, and (2) $H_2O_2$ itself acts as a signal transducer to activate DNA damage response pathways, such as ATM. An imbalance in glutathione-$H_2O_2$ homeostasis, with lower glutathione and higher $H_2O_2$ activity, induces genomic damage to trigger the DNA damage response. Conversely, higher glutathione activity that favors $H_2O_2$ scavenging and lowers $H_2O_2$ activity blunts the DNA damage response and damaged cells fail to be eliminated, leading to genomic instability. Therefore, homeostasis of glutathione-$H_2O_2$ regulation plays a critical role in maintaining overall genomic stability.

To determine the status of glutathione-$H_2O_2$, oxidation capacity of glutathione as well as $H_2O_2$ scavenging activity (maximum oxidation capacity) were evaluated in various iPSC lines. The ratio of intracellular reduced and oxidized forms of glutathione (GSH/GSSG) is often used as an indicator of cellular redox state, the degree of oxidative stress and the antioxidant capacity of cells. Glutathione analysis was conducted using Glutathione Fluorometric Assay (Biovision, K264-100). As shown in FIG. 8A, A-iPSC exhibit excessive oxidation capacity, which was normalized to the level of ESC and Y-iPSC by transient expression of ZSCAN10. $H_2O_2$ scavenging activity was measured using reactive oxygen species (ROS) assay kit (Abcam, ab113851). A-iPSC show strong $H_2O_2$ scavenging activity (FIG. 8B), with a reduced response against the treatment of TBHP (tert-butyl hydrogen peroxide; stable chemical form of $H_2O_2$, 3 h). Upon ZSCAN10 expression, the elevated glutathione activity was reduced to levels equivalent to those seen in Y-iPSC/ESC (FIGS. 8A and 8B).

The mechanism by which the oxidation capacity of glutathione to scavenge $H_2O_2$ is elevated in A-iPSC compared to Y-iPSC and ESC was further evaluated. A comparative gene expression analysis among the different cell lines led to the identification of candidate genes that were up- or down-regulated in A-iPSC compared to A-iPSC-ZSCAN10, and that were expressed at similar levels in A-iPSC-ZSCAN10, ESC, and Y-iPSC. Glutathione peroxidase 2 (GPX2) gene was excessively expressed in A-iPSC and its expression was normalized by ZSCAN10 expression (FIG. 9A).

GPX2 is a $H_2O_2$ scavenger protein that regulates glutathione-mediated scavenging activity. In order to test whether excess levels of GPX2 are responsible for imbalance in glutathione-$H_2O_2$ homeostasis in A-iPSC, GPX2 was inhibited in A-iPSC using shRNA. Knockdown of GPX2 in A-iPSC normalized glutathione-$H_2O_2$ homeostasis (FIGS. 9B and 9C), increased apoptosis (FIG. 9D), and recovered the DNA damage response (FIG. 9E).

Example 8

GLUT3 Gene Expression is Significantly Increased in Y-iPSC, but not in A-iPSC

In order to gain a deeper understanding of biological processes that occur during cellular reprogramming, an innovative approach was taken to reveal additional factors important for the reprogramming of aged somatic cells. Comparative genomic analysis of ESC, Y-iPSC, A-iPSC, and A-iPSC-ZSCAN10 in the presence or absence of phleomycin treatment (30 μg/ml for 2 hours) led to identification of GLUT3, a pluripotent stem cell-specific glucose transporter. FIG. 10A shows poorly activated GLUT3 in A-iPSC compared to ESC and Y-iPSC.

Glucose metabolism is essential to maintain cell homeostasis within the microenvironment of various tissues. Most somatic cells generate 36 ATP from each glucose molecule through oxidative phosphorylation in the presence of oxygen; by contrast, ESC use glycolysis to generate 2 ATP from each glucose in the absence of oxygen. During iPSC reprogramming, glucose metabolism shifts from somatic cell-specific oxidative phosphorylation to ESC-specific glycolysis. Although ESC-specific glycolysis consumes 18-fold more glucose than oxidative phosphorylation to generate the same amount of ATP, the benefit of glycolysis is that it generates ATP while producing fewer $H_2O_2$ which can cause genomic mutation.

To investigate a role of GLUT3 in glucose metabolism within the context of mouse A-iPSC, intracellular glucose uptake was monitored in mouse ES and iPS cell lines. A-iPSC take up 18-fold less glucose than Y-iPSC and ESC (FIG. 10B) and have a higher oxygen consumption rate as measured by oxidative phosphorylation (FIG. 10C). These results suggest that A-iPSC continue to generate ATP via somatic cell-specific oxidative phosphorylation, rather than switching to ESC-specific glycolysis.

During the transition from somatic cells to iPSC, GLUT3 gene expression is significantly increased in Y-iPSC, but not in A-iPSC (FIG. 10A). Interestingly, GLUT3 expression is induced by ZSCAN10 (FIG. 10A), suggesting that the loss of ZSCAN10 and GLUT3 activity are mechanistically connected in A-iPSC. Indeed, increased expression of GLUT3 also shows the recovery of DNA damage response (FIG. 10D) as increased expression of ZSCAN10 had, confirming the hypothesis of mechanistic connection. To test the ability of ZSCAN10 to target GLUT3, the inventors tested the ability of ZSCAN10 to bind to the promoter of GLUT3 using Chromatin IP analysis. As demonstrated in FIG. 10E, ZSCAN10 binds to the GLUT3 promoter in ESC, Y-iPSC, and A-iPSC.

Figures 10F, 10G:
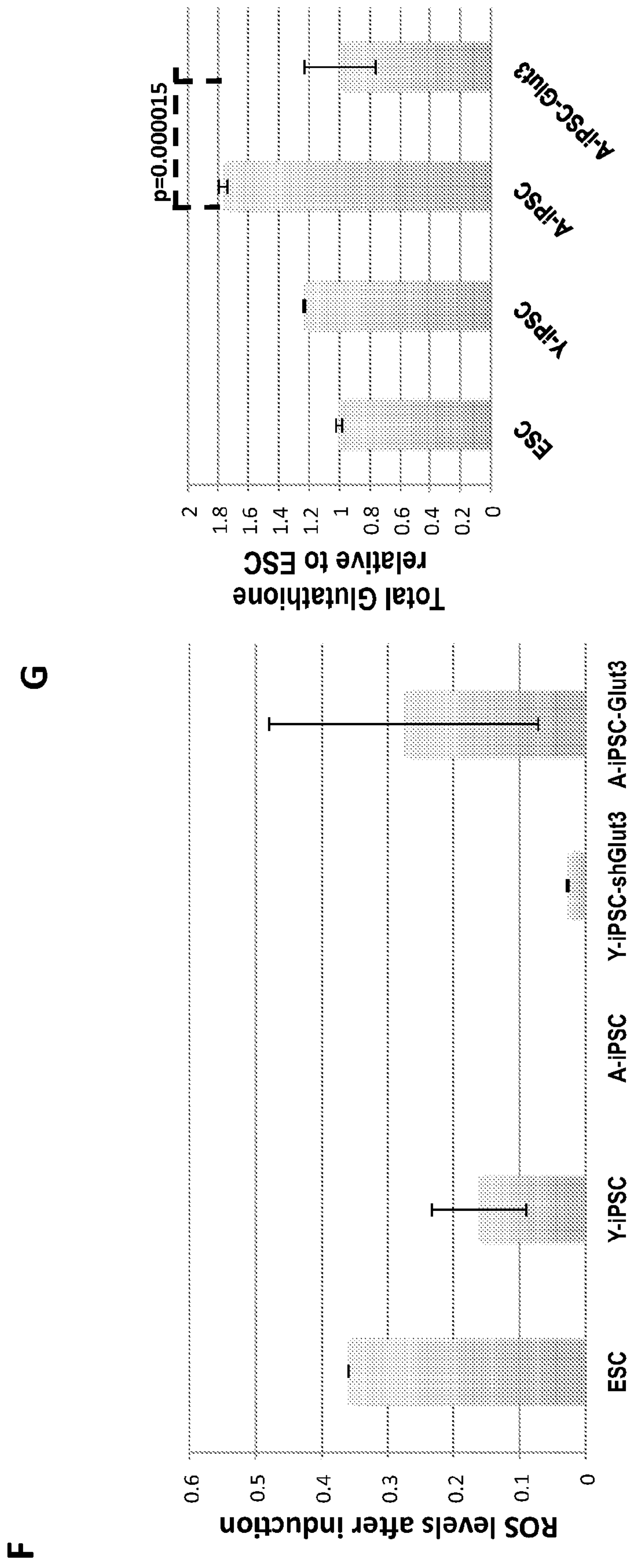
FIG. 10F is a bar graph of ROS levels in ESC, Y-iPSC, A-iPSC, Y-iPSC expressing shRNA against GLUT3 (Y-iPSC-shGLUT3), and A-iPSC expressing shRNA against GLUT3 (A-iPSC-shGLUT3).
FIG. 10G is a bar graph of total glutathione levels relative to ESC in ESC, Y-iPSC, A-iPSC, and A-iPSC overexpressing GLUT3 (A-iPSC-GLUT3).

Given that GLUT3 expression is induced by ZSCAN10, and that oxidative phosphorylation induces production of $H_2O_2$, which is known to trigger the DNA damage response, it is likely that the loss of this response in A-iPSC contributes to increased oncogenicity. Indeed, overexpression of GLUT3 in A-iPSC recovered the normal ROS levels, wherein the downregulation of GLUT3 in Y-iPSC decreased the ROS levels (FIG. 10F). Furthermore, glutathione levels were reduced to normal (similar to those observed for ESC and Y-iPSC) in A-iPSC upon overexpression of GLUT3 (FIG. 10G).

Collectively, the data presented here suggest a model where poor GLUT3 activation in A-iPSC, as a consequence of low ZSCAN10 expression (or even independently), leads to hyperactivation of oxidative phosphorylation and an increase in $H_2O_2$ production, which induces glutathione.

Prophetic Example 1

As a part of preliminary analysis, the inventors sought to determine what are the major differences between the various types of iPSC (Y-iPSC, A-iPSC, A-iPSC-ZSCAN10) and ESC. Microarray analysis of ESC versus Y-iPSC, A-iPSC, and A-iPSC-ZSCAN10 reveled sets of the differentially expressed genes. Table 1. indicates the number of differentially regulated genes among the specific groups. Using the mean Z-score analysis, it was determined the genes were grouped based on the fold change of differential expression. A higher score in the table means a more pronounced difference in expression from ESC.

The data summarized in Table 1. show that a smaller number of genes are differentially expressed in A-iPSC-ZSCAN10 compared to ESC, than the number of genes differentially expressed between Y-iPSC and ESC. These results suggest that at least on the level of overall gene expression, A-iPSC-ZSCAN10 share more similarities with ESC not only compared to A-iPSC, but also compared to Y-iPSC. In order to confirm that this observation is also reflected in the analysis of the core pluripotency network genes, expression of core pluripotency network genes among different iPSC lines and ESC was performed. As shown in Table 2. Similarly to what was observed in Table 1, number of genes differentially expressed between A-iPSC-ZSCAN1 and ESC was fewer than the number of genes differentially expressed between the Y-iPSC and ESC. Collectively, this data suggests unique features Future experiments will include further investigation into why ZSCAN10-supplemented A-iPSC are closer to ESC than to Y-iPSC when it comes to gene expression. This will be part of a deeper level analysis of epigenetic alterations that affect aged somatic cells and also A-iPSC in a negative manner (e.g., block differentiation of A-iPSC, favor oncogenicity upon transplantation of cells derived from A-IPSC). For example, the ability of ZSCAN10 to recover poor tissue differentiation potential of A-iPSC will be assessed. It is anticipated that after ZSCAN10 supplementation, A-iPSC will display substantially improved tissue differentiation compared to untreated A-iPSC. Thus, tissue differentiation potential will be another aspect of the quality of A-iPSC that will be improved by ZSCAN10 supplementation (and can be assessed by measuring ZSCAN10 levels or measuring levels of another surrogate marker described herein and comparing the level to that of a Y-iPSC or ESC control).

TABLE 1

| | Differentially expressed gene between ESC vs. | | |
|---|---|---|---|
| | Y-iPSC | A-iPSC-ZCAN10 | A-iPSC |
| 1.2 fold change | 3304 | 2115 | 4212 |
| 1.5 fold change | 2036 | 11195 | 3361 |
| 2.0 fold change | 775 | 507 | 2010 |
| 3.0 fold change | 141 | 127 | 386 |

TABLE 2

| 2.0 Fold Change Number of common target | Genes | Differentially expressed gene between ESC vs. Y-iPSC | A-iPSC-ZSCAN10 | A-iPSC |
|---|---|---|---|---|
| 7 Core factor | 47 | 6 | 6 | 12 |
| 6 Core factor | 100 | 24 | 18 | 35 |
| 5 Core factor | 124 | 36 | 30 | 57 |
| 4 Core factor | 227 | 53 | 47 | 94 |
| 3 Core factor | 427 | 76 | 68 | 148 |
| 2 Core factor | 901 | 129 | 106 | 251 |
| 1 Core factor | 2350 | 252 | 186 | 543 |
| 0 Core factor | 9686 | 292 | 168 | 770 |
| Total Target Genes | 13862 | 868 | 629 | 1910 |

Furthermore, DNA methylation status of the genes most prominently differentially expressed between ESC and Y-iPSC, A-iPSC, or A-iPSC-ZSCAN10 will be assessed. One of the aims of this analysis is to test whether already observed difference in DNA methylation (comparing ESC to A-iPSC and Y-iPSC in the absence of ZSCAN10 supplementation) follows the same pattern as the gene expression pattern outlined in Table 1 and Table 2. It is anticipated that the methylation pattern of ZSCAN10-supplemented A-iPSC, similarly to gene expression pattern, will be closer to that of ESC than that of Y-iPSC.

The same experiment may be repeated with GLUT3 supplementation instead of ZSCAN10 supplementation in A-iPSC. The results are anticipated to be qualitatively the same.

TABLE 3

Exosome components and co-factors

| | Domains | Human[c] | Loc[d] |
|---|---|---|---|
| Exosome core | RNasePH | hRrp41 (hSki6; EXOS4) | n + c |
| | | hRrp42 (EXOS7) | n + c |
| | | hRrp46 (EXOS5) | n + c |
| | | hRrp43 (OIP2; EXOS8) | n + c |
| | | hMtr3 (EXOS6) | n + c |
| | | hRrp45 (Pm/Scl-75; EXOS9) | n + c |
| | Si and KH domains | hRrp4 (EXOS2) | n + c |
| | | hRrp40 (EXOS3) | n + c |
| | | hCs14 (EXOS1) | n + c |
| Exonuclease | RNase II | hRrp44 (hDis3) | n + c |
| | RNase D | hRrp6 (PM/Scl-100; EXOS10) | n + c |

Example 9

ZSCAN10 Binds and Up-Regulates Exosomes

In further study, the inventors sought to gain a better understanding of the mechanism by which ZSCAN10 inhibits the expression of GPX2 in A-iPSC. Analysis of GPX2 sequence revealed that GPX2 gene contains highly conserved ARE sequences (Singh et al. *Am J Respir Cell Mol Biol.* 35(6):639-50 (2006)). Interestingly, it is known that exosome, which mediates the degradation of mRNA, targets ARE sequences to induce mRNA decay. (Mukherjee et al. *EMBO J.* 21(1-2):165-174 (2002); Schmid et al. *Trends Biochem Sci.* 2008 October; 33(10):501-10.).

mRNA turnover is a highly regulated process that plays a role in regulating the levels of transcripts that encode an array of proteins (Schoenberg et al. *Nat Rev Genet.* 13 (4): 246-259 (2012)). Given the presence of ARE sequences in GPX2, the inventors performed enrichment analysis of ARE sequences in 60 upregulated genes in A-iPSC (upregulated compared to Y-iPSC/ESC and A-iPSC-zscan10)". Gene enrichment analysis (FIG. 11A histogram) showed that the likelihood of any given transcript to have the UUAUUUA (A/U)(A/U) ARE sequence is 7, so the odds of finding 14 genes containing ARE sequences in a sample of 60 genes based on just random chance is very low (p=0.01224)." The control group was 18,299 non-duplicated longest ensemble transcripts based on the microarray ILLUMINA platform Mouseref-8 v2.0. Thus, the enrichment analysis of A-iPSC demonstrates a significant up-regulation of genes with ARE sequences, which is highly likely a result of non-functional exosomes.

In order to gain a deeper understating of the type of interactions that relate to ZSCAN10, Chromatin Immunoprecipitation sequencing (ChIP-Seq), which combines chromatin IP with DNA sequencing, was performed. ChIP-Seq detects DNA-protein interactions and as such could provide knowledge regarding the network of proteins regulated by ZSCAN10, The exosome constitutes a complex of 11 exonucleases. In order to test the hypothesis that ZSCAN10 regulates GPX2 via exosomes in A-iPSC, ChIP-Seq was performed, and the results showed that indeed, ZSCAN binds to exosome subunits. ESC and Y-iPSC were used as the comparison in the study. Furthermore, as shown in FIG. 11B, ZCSAN10 up-regulates exosomes. A-iPSC contained lower mRNA levels of exosome core subunits EXOSC1, EXOSC2, and EXOSC5 than ESC and Y-iPSC. Importantly, overexpression of ZSCAN10 in A-iPSCs resulted in the restoration of EXOSC1, EXOSC2, and EXOSC5 levels comparable to those observed in ESC and Y-iPSC, confirming that ZSCAN10 regulates the expression of various exosome subunits. Endogenous mRNA levels were normalized to β-ACTIN. Error bars indicate standard error of the mean.

Example 10

Regulation of GPX2 by ZSCAN10 Via ARE Sequences is Mediated by Exosomes

To expand on functional relevance of findings described in Example 9, ESC containing high level of exosomes (FIG. 11B) were depleted of EXOSC2, EXOSC8, or both. Following knockdown of exosomes using shRNA, GPX2 mRNA was determined by Q-PCR. While ESC contain low expression levels of GPX2, depletion of exosomes resulted in dramatic increase of GPX2 mRNA (FIG. 12A). This increase was similar to the levels observed in A-iPSCs. DNA fragmentation assay demonstrated that cells deficient in exosomes contained lower apoptotic response after phleomycin treatment (2 h, 30 μg/ml) of A-iPSC (FIG. 12B), further confirming the functional significance of exosomes in the maintenance of DNA damage response, apoptosis response, glucose metabolism and genomic stability to levels approximating those of Y-iPSC or ESC (FIG. 12B).

Example 11

Depending on the Donor, iPS Cells Derived from Aged Human Donors Exhibit Different Reprogramming Efficiencies, DNA Damage Response, and Structural Chromosomal Abnormality Findings disclosed in Example 1 showed that iPS cells derived from aged mice exhibit higher genomic instability and lower apoptotic activity than iPSC generated from young mice. To determine whether results observed in animal cells are comparable to human cells, i-PSC derived from young and aged individuals were generated and their reprogramming efficiency evaluated. As shown in FIG. 13A, aging phenotype observed in mice was also present in human A-iPSC. However, there was a significant difference in programming efficiency among individuals of similar age. In order to analyze DNA damage response in human iPSC and test whether it parallels the findings regarding reprogramming efficiency, cells were treated with double-strand break inducing drug phleomycin for 4 h (30 μg/ml).

Immunoblot analysis revealed blunted DNA damage response in A-iPSC from certain donors (See FIG. 13B, donors AG4, AG8, "B" and "S"). Furthermore, karyotype examination of A-iPSC from the donor AG4 showed structural chromosome abnormality (FIG. 13C). In respect to A-iPSC derived from donor AG8, the results are not final and are subject to further confirmation regarding whether or not A-iPSC derived from this patient display normal or defected DNA damage response. Finally, similar results were obtained for A-iPSC generated from different mouse strains. To determine whether genetic background affects DNA damage response, A-iPSC were generated from two distinct mouse strains and treated with phleomycin for 4 h (30 μg/ml). p53 protein levels were used as an indicator of DNA damage response. As demonstrated in FIG. 13D, A-iPSC derived from the mice of B6129 background exhibit normal DNA damage response (indicated by activation of p53) in higher frequency, while A-iPSC from the mice of B6CBA background contained blunted DNA damage response. These findings indicate that reprogramming efficiency, chromosomal stability, as well as a DNA damage response associated with A-iPSC are in substantial part dependent on genetic background of the individual or animal from which they are derived. Nevertheless, use of the materials and reagents of the present disclosure would ameliorate the quality of A-iPSC regardless of whether they work on genetic or epigenetic traits or both.

Analysis of 6 additional human A-iPSC clones revealed poor DNA damage response (FIG. 13E), whereas one A-iPSC clone referred to as "A-iPSC-outlier" displayed proper activation of DNA damage response as indicated by the phosphorylation of ATM. Overexpression of ZSCAN10 in human A-iPSC that exhibited poor DNA damage response rescued that defect (FIG. 13H). Comparison of FIGS. 13G and 13H illustrates that overexpression of ZSCAN10 in human A-iPSC leads to the restoration of the DNA damage response similar to the one observed in human Y-iPSC (FIG. 13G).

Figure 13:
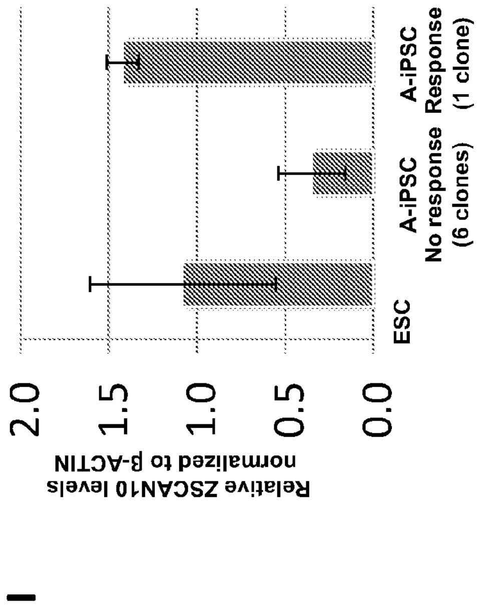

It was postulated that the "A-iPSC outlier" maintains a proper DNA damage response due to the normal expression levels of ZSCAN10. Indeed the inventors observed that ZSCAN10 mRNA expression in the "A-iPSC outlier" is similar to the levels observed in the ESC, while the ZSCAN10 expression in a clone that exhibited poor DNA damage response was low (FIG. 13 I). Since ZSCAN10 mRNA levels correlate with the ability of A-iPSC to elicit a proper DNA damage response, ZSCAN10 can serve as a suitable biomarker of genomic integrity, where higher ZSCAN10 levels correlate with improved genomic integrity.

Example 12

ZSCAN10 Binds to GSS and Downregulates its Expression

As discussed in Example 8, glucose metabolism is essential for both tissue homeostasis as well as in reprogramming. Glutathione synthetase (GSS) is an enzyme that catalyzes the second and final step in the synthesis of GSH from gamma-glutamylcysteine (c-GC) and glycine. Genome-wide mapping of ZSCAN10-binding sites in ESC identified more than 3500 target genes, including GSS (Yu et al. *J Biol Chem.* 284(45): 31327-31335 (2009)). Thus, given the importance of glutathione activity in apoptosis and DNA damage response, it was postulated that ZSCAN10 might exert its function, at least in part, through GSS especially in humans.

To test this hypothesis, the ability of ZSCAN10 to bind directly to the GSS promoter was initially tested in mouse cells. Chromatin IP (ChIP) qPCR was performed using general steps of the ChIP, which include: (1) crosslinking the protein to the DNA; (2) isolating the chromatin; (3) chromatin fragmentation; (4) immunoprecipitation with antibodies against the protein of interest; (5) DNA recovery; and (6) PCR identification of factor associated DNA sequences. In the present example, IgG isotype was used as a negative control, while ZSCAN10-specific antibody was used to pull down the ZSCAN10-DNA complexes. Following the recovery of DNA, GSS specific primers were used for the detection of GSS promoter sequences. The experiment was performed both in Y-iPSC and A-iPSC. As shown in FIG. 14B, ZSCAN10 binding to the GSS promoter was detected in both mouse Y-iPS and A-iPS cells, while IgG control did not result in the detection of GSS promoter by qPCR.

To further confirm the role for ZSCAN10 in the regulation of GSS expression, mRNA levels of GSS were evaluated in ESC, Y-iPSC, A-iPSC, and A-iPSC-ZSCAN10 cells. As illustrated in FIG. 14C, human A-iPSC express significantly higher levels of GSS compared to Y-iPSC and ESC. Importantly, overexpression of ZSCAN10 in A-iPSC lead to downregulation of GSS to the levels comparable to or below those observed in ESC and Y-iPSC.

Taken together, the results described in FIGS. 14B-14D demonstrate that ZSCAN10 regulates GSS expression via direct binding to the GSS promoter (FIG. 14A). These findings imply that inhibition of GSS in A-iPSC would lead to the reduction in oncogenic potential of iPS cells with decreased ZSCAN10 expression, such as A-iPSC. This was confirmed in the experiment described below.

Example 13

Recovery of Apoptotic and DNA Damage Defects in A-iPSC by ZSCAN10 Via Reduction of Excessively Activated GSS Considering the findings described in Example 12, the inventors further postulated that GSS may play a role in processes associated with oncogenic potential of human cells, including, but not limited to apoptosis and DNA damage response. To evaluate the role of GSS in apoptosis, a DNA fragmentation assay was performed. Briefly, a DNA fragmentation assay was carried out in mouse ESC, Y-iPSC, Y-iPSC-GSS, A-iPSC, A-iPSCZSCAN10, and A-iPSC with GSS shRNA expression (FIG. 14D). Briefly, cells were treated with phleomycin for 2 hours at 30 μg/ml, and samples were collected for analysis 15 hours after phleomycin treatment. Fluorescence was determined by image quantification analysis. Similar to the observation seen in Example 1 (FIG. 2), lower apoptotic response was detected in A-iPSC, which was recovered by ZSCAN10 overexpression (A-iPSC-ZSCAN10) (FIG. 14D). Additionally, knockdown of GSS in A-iPSC using shRNA (A-iPSC-shGSS) rescued the apoptotic defect in these cells (FIG. 14D). Further demonstrating a role for GSS in mediating oncogenic potential, such as apoptotic response, overexpression of GSS in Y-iPSC resulted in lower apoptotic response compared with Y-iPSC (FIG. 14D). Together, these observations indicate that GSS inhibition restores the lower apoptotic response associated with A-iPSC.

Example 5 demonstrated that impaired DNA damage response in A-iPSC is recovered with the transient expression of ZSCAN10. In order to further delineate the role for GSS in A-iPSC, phleomycin treatment (2 hours, 30 μg/ml) was performed in Y-iPSC, A-iPSC, A-iPSC-shGSS (FIG. 14E), and Y-iPSC-GSS (FIG. 14F). Cells were collected and Western blot performed using p-ATM antibody. β-actin was used as a loading control. As shown in FIG. 14E, inhibition of GSS in A-iPSC using shRNA restored the ATM phosphorylation. Furthermore, overexpression of GSS in Y-iPSC resulted in no ATM phosphorylation (FIG. 14F). Thus, GSS expression leads to a defect in DNA damage response, whereas GSS inhibition rescues the defect.

The inventors next sought to evaluate GSS levels in human cells. In accordance with mouse data, GSS levels were significantly higher in A-iPSC that exhibited poor DNA damage response compared with the levels observed in human ESC (FIG. 14G). Furthermore, A-iPSC cells that exhibited normal DNA damage response displayed low levels of GSS (FIG. 14G), supporting the notion that similar to ZSCAN10, GSS can also serve as a good biomarker of genomic integrity.

Collectively, these results indicate that excessively activated GSS mediates both impaired apoptosis and impaired DNA damage response observed in A-iPSC, while the inhibition of GSS leads to the restoration of those deficiencies.

Example 14

Reprogramming and Pluripotency Improvement of A-iPSC by Addition of ZSCAN10

Next, the inventors sought to determine the significant differences between distinct types of mouse cells: fibroblast cells (A-SC, Y-SC), iPSC (A-iPSC, Y-iPSC, A-iPSC-ZSCAN10) and ES cells (ESC). FIG. 15A shows Principal Component Analysis (PCA) using whole gene expression profiles of each cell type. FIG. 15B illustrates unsupervised clustering analysis of whole gene expression profiles. The heat map in FIG. 15B shows pairwise gene expression similarities measured by Pearson Correlation Coefficient. Finally, FIG. 15C presents a heat map of relative expression levels of ES cell specific genes in fibroblast and various iPS cells. ES cell specific genes were defined as those with 3 fold or higher expression levels in ES cells than average expression in adult and young fibroblast cells. The heat map shows fold differences in relative expression over ES cells. The results are summarized in Table 4, where reprogramming and pluripotency network genes are defined by core factor co-occupancy. Correlation between seven core factor co-occupancy (Kim et al. Cell 132(6) 1049-61 (2008)) and number of ESC specific genes (2 fold or higher in ESC over indicated sample) were tested to define the functional link between pluripotency networks and reprogramming. Core factors tested in this analysis are Nanog, Sox2, Oct4, Klf4, Dax1, Nac1, and Zfp281. The number of ESC enriched genes and their core factor co-occupancies (by 7 TFs to 0 TF) are shown.

TABLE 4

| | | 2 fold or more higher in ES cells | | | |
|---|---|---|---|---|---|
| Genes | Number of common targets | ESC over ESC | ESC over AIPSC-ZSCAN10 | ESC over Y-iPSC | ESC over A-iPSC |
| 40 | 7 | 0 | 5 | 5 | 10 |
| 89 | 6 | 0 | 12 | 13 | 16 |
| 103 | 5 | 0 | 13 | 9 | 16 |
| 198 | 4 | 0 | 18 | 13 | 29 |
| 376 | 3 | 0 | 21 | 17 | 33 |
| 767 | 2 | 0 | 39 | 41 | 68 |
| 2045 | 1 | 0 | 79 | 87 | 178 |
| 8252 | 0 | 0 | 179 | 207 | 470 |

The results shown in Table 4 indicate that a greater number of genes is differentially expressed in A-iPSC compared to ESC, than the number of genes differentially expressed between Y-iPSC and ESC. However, overexpression of ZSCAN10 in A-iPSC cells resulted in a decreased number of differentially expressed genes. Furthermore, ZCSAN10 overexpression lead to differences in gene expression (between A-iPSC-ZSCAN10 and ESC) similar to those observed between Y-iPSC and ESC. Therefore, ZSCAN10 expression in A-iPSC influences the global gene expression of reprogramming and pluripotency network, by making A-iPSC resemble Y-iPSC in reprogramming and pluripotency properties.

From the work described in this disclosure, ZSCAN10 emerges as an important co-regulatory factor in induced pluripotent stem cells.

The breadth of the present disclosure is not limited to specific embodiments described herein.

All references cited herein, whether patents, patent applications or nonpatent literature are incorporated by reference in their entirety.

EMBODIMENTS

A. Use for improving for improving at least one of DNA damage response, apoptosis response, genomic stability and glucose metabolism of A-iPSC, the use comprising supplementing A-iPSC with at least one of (i) pluripotency factor ZSCAN10; (ii) pluripotent stem cell-specific glucose transporter GLUT3; and (iii) an exosome subunit, each as an adjunct to reprogramming of the A-iPSC to substantially restore said at least one of DNA damage response, apoptosis response, glucose metabolism and genomic stability to levels approximating those of Y-iPSC.

B. The use of Embodiment A, wherein excessive expression of GPX2 or GSS is inhibited by at least one of the following:

supplementing A-iPSC with pluripotency factor ZSCAN10; and/or supplementing A-iPSC with pluripotent stem cell-specific glucose transporter 3 GLUT3; and supplementing A-iPSC with an exosome subunit wherein the supplementation is an adjunct to reprogramming pluripotency factors and is in an amount effective to accomplish substantial rescue in one or more of DNA damage response, apoptosis and genomic stability in said A-iPSC.

C. The use of Embodiment A or B wherein the supplementation is carried out by adding ZSCAN 10 and/or GLUT3 and/or an exosome subunit to a culture medium in which said A-iPSC are maintained.

D. The use of one of Embodiments A through C wherein the supplementation is carried out by increasing the expression of ZSCAN10 and/or GLUT3 and/or an exosome subunit in said cells.

E. The use of one of Embodiments A through D wherein the supplementation is sufficient to restore ZSCAN 10 and/or GLUT3 and/or an exosome subunit levels in said A-iPSC to about 50% or more of the respective levels of embryonic stem cells (ESC).

F. The use of one of Embodiments A through E wherein the supplementation is sufficient to reduce oxidation capacity of glutathione in said A-iPSC to within the range from about 80% to about 120% of that of ESC.

G. The use of one of Embodiments A through F wherein the supplementation is sufficient to restore genomic stability of said A-iPSC to approximately that of Y-iPSC.

H. The use of one of Embodiments A through G wherein genomic stability is measured by incidence of hypertriploid clones.

I. The use of one of Embodiments A through H wherein the supplementation is sufficient to restore apoptosis rate of said A-iPSC to approximately that of Y-iPSC.

J. The use of Embodiment I wherein said apoptosis rate is measured by DNA fragmentation assay in response to a DNA damaging agent.

K. The use of one of Embodiments A through J wherein the supplementation is sufficient to restore DNA damage response of said A-iPSC to approximately that of Y-iPSC.

L. The use of Embodiment K wherein DNA damage response is measured by ATM or H2AX phosphorylation in response to a DNA damaging agent.

M. The use of one of Embodiments A through K wherein the supplementation is sufficient to reduce oxidation capacity of glutathione in said A-iPSC to approximately that of Y-iPSC.

N. The use of Embodiment N wherein the supplementation is sufficient to reduce GPX2 levels in said A-iPSC to approximately those of Y-iPSC.

O. The use of one of Embodiments A through N wherein the expression of ZSCAN10 and/or GLUT3 and/or an exosome subunit in said cells is increased by transfecting said cells with a vector harboring nucleic acid for said ZSCAN10 and/or GLUT3.

P. The use of Embodiments O wherein expression of said vector harbored nucleic acid encoding ZSCAN10 is transient.

Q. Use for reducing the oncogenic potential of induced pluripotent stem cells derived from aged donors (A-iPSC) said A-iPSC exhibiting excessive glutathione-mediated $H_2O_2$ scavenging activity compared to induced pluripotent stem cells derived from young donors (Y-iPSC), the method comprising:

inhibiting glutathione-mediated $H_2O_2$ scavenging activity in said A-iPSC to substantially restore glutathione/$H_2O_2$ homeostasis in said A-iPSC by directly and/or indirectly inhibiting excessive expression of glutathione peroxidase 2 (GPX2) in said A-iPSC.

R. A method for improving at least one of DNA damage response, apoptosis response and genomic stability of A-iPSC the method comprising supplementing A-iPSC with at least one of (i) pluripotency factor ZSCAN10; (ii) pluripotent stem cell-specific glucose transporter GLUT3 and/(iii) an exosome subunit, each as an adjunct to reprogramming to partially or completely restore said at least one of DNA damage response and genomic stability to levels approximating those of 4-iPSC.

AA. The use of Embodiment Q or R wherein the supplementation is carried out by adding ZSCAN 10 and/or GLUT3 and/or an exosome subunit to a culture medium in which said A-iPSC are maintained.

BB. The use of one of Embodiment Q or R wherein the supplementation is carried out by increasing the expression of ZSCAN10 and/or GLUT3 and/or an exosome subunit in said cells.

CC. The use of one of Embodiment Q or R wherein the supplementation is sufficient to restore ZSCAN 10 and/or GLUT3 levels in said A-iPSC to about 50% or more of the respective levels of embryonic stem cells (ESC).

DD. The use of one of preceding Embodiments O wherein the supplementation is sufficient to reduce oxidation capacity of glutathione in said A-iPSC to within the range from about 80% to about 120% of that of ESC.

EE. The use of one of preceding Embodiments wherein the supplementation is sufficient to restore genomic stability of said A-iPSC to approximately that of Y-iPSC.

FF. The use of one of preceding Embodiments wherein genomic stability is measured by as measured by incidence of hypertriploid clones.

GG. The use of one of preceding Embodiments wherein the supplementation is sufficient to restore apoptosis rate of said A-iPSC to approximately that of Y-iPSC.

HH. The use of Embodiment GG wherein said apoptosis rate is measured by DNA fragmentation assay in response to a DNA damaging agent.

II. The use of one of preceding Embodiments wherein the supplementation is sufficient to restore DNA damage response of said A-iPSC to approximately that of Y-iPSC.

JJ. The use of Embodiment II wherein DNA damage response is measured by ATM or H2AX phosphorylation in response to a DNA damaging agent.

KK. The use of one of preceding Embodiments wherein the supplementation is sufficient to reduce oxidation capacity of glutathione in said A-iPSC to approximately that of Y-iPSC.

LL. The use of preceding Embodiment KK wherein the supplementation is sufficient to reduce GPX2 levels in said A-iPSC to approximately those of Y-iPSC.

MM. The use of one of preceding Embodiments wherein the expression of ZSCAN10 and/or GLUT3 in said cells is increased by transfecting said cells with a vector harboring nucleic acid for said ZSCAN10 and/or GLUT3 and/or an exosome subunit.

NN. The use of Embodiments MM wherein expression of said vector harbored nucleic acid encoding ZSCAN10 or an exosome subunit is transient.

OO. A use for reducing the oncogenic potential of induced pluripotent stem cells (iPSC) said cells having one or more of genomic instability, a defect in apoptosis, a defect in DNA damage response and a defect in glucose metabolism and exhibiting excessive glutathione-mediated $H_2O_2$ scavenging activity compared to embryonic stem cells or induced pluripotent stem cells from young donors (Y-iPSC), the method comprising:

inhibiting glutathione-mediated $H_2O_2$ scavenging activity in said to partially or totally restore homeostasis in said iPSC by directly and/or indirectly inhibiting excessive expression of glutathione peroxidase 2 (GPX2) in said iPSC.

PP. A use for reducing the oncogenic potential of induced pluripotent stem cells derived from aged donors (A-iPSC) said A-iPSC exhibiting excessive glutathione-mediated $H_2O_2$ scavenging activity compared to induced pluripotent stem cells derived from young donors (Y-iPSC), the method comprising:

inhibiting glutathione-mediated $H_2O_2$ scavenging activity in said A-iPSC to partially or completely restore glutathione/$H_2O_2$ homeostasis in said A-iPSC by directly and/or indirectly inhibiting excessive expression of glutathione peroxidase 2 (GPX2) in said A-iPSC QQ. A use for reducing the oncogenic potential of induced pluripotent stem cells (iPSC) said cells having one or more of genomic instability, a defect in apoptosis, a defect in DNA damage response and a defect in glucose metabolism, and exhibiting excessive glutathione-mediated $H_2O_2$ scavenging activity compared to embryonic stem cells or induced pluripotent stem cells from young donors (Y-iPSC), the method comprising supplementing A-iPSC with at least one of (i) pluripotency factor ZSCAN10; (ii) pluripotent stem cell-specific glucose transporter GLUT3; and (iii) an exosome subunit, each as an adjunct to reprogramming to substantially restore said at least one of DNA damage response, apoptosis response, glucose metabolism and genomic stability to levels substantially the same as those of Y-iPSC or ESC.

RR. The use of Embodiment PP or QQ wherein the supplementation is carried out by adding ZSCAN 10 and/or GLUT3 and/or an exosome subunit to a culture medium in which said A-iPSC are maintained.

SS. The use of Embodiment PP or QQ wherein the supplementation is carried out by increasing the expression of ZSCAN10 and/or GLUT3 and/or in said cells.

TT. The use of Embodiment SS wherein the supplementation is sufficient to restore ZSCAN 10 and/or GLUT3 and/or exosome subunit levels in said A-iPSC to about 50% or more of the respective levels of embryonic stem cells (ESC).

UU. The use of Embodiment PP or QQ wherein the supplementation is sufficient to reduce oxidation capacity of glutathione in said A-iPSC to within the range from about 80% to about 120% of that of ESC.

VV. The use of Embodiment PP or QQ wherein the supplementation is sufficient to restore genomic stability of said A-iPSC to approximately that of Y-iPSC.

WW. The use of embodiment VV wherein genomic stability is measured by incidence of aneuploid clones.

XX. The use of claim PP or QQ wherein the supplementation is sufficient to restore apoptosis rate of said A-iPSC to approximately that of Y-iPSC.

YY. The use of claim 26 wherein said apoptosis rate is measured by DNA fragmentation assay in response to a DNA damaging agent.

ZZ. The use of Embodiment PP or QQ wherein the supplementation is sufficient to restore DNA damage response of said A-iPSC to approximately that of Y-iPSC.

AAA. The use of Embodiment B wherein the reprogramming factors are the Yamanaka factors OCT4, SOX2, KLF4 and MYC.

BBB. The method of Embodiment B wherein the reprogramming pluripotency factors are selected from the group of those of Yamanaka wherein one or more of OCT4, SOX2, KLF4 and MYC are replaced as follows:

Factors(LIN28+Nanog,Esrrb,Pax5 shRNA,C/EBPa, p53.siRNA,UTF1,DNMTshRNA,Wnt3a, SV40LT(T), hTERT) or chemicals(BIX-01294,BayK8644,RG108, AZA,dexamethasone, VPA,TSA,SAHA,PD025901+ CHIR99021(2i), A-83-01)

CCC. The use of embodiment B wherein the reprogramming pluripotency factors are selected from the group of those of Yamanaka wherein one or more of OCT4, SOX2, KLF4 and MYC are replaced as follows: Nanog and Lin28 replace Klf4 and MYC; esrb replaces Klf4; SV40 LT (T) replaces Klf4, MYC lin28 and Nanog; BIX-01294 replaces SOX2, OCT4; VPA replaces Klf4 and MYC DDD. The Use of Embodiment A wherein the supplementation is with an exosome subunit, the exosome subunit being one or more of the following EXOSC1, EXOSC2, EXOSC3, EXOSC4, EXOSC5, EXOSC6, EXOSC7, EXOSC8, EXOSC9, EXOSC10 and hDis3.

EEE. The use of Embodiment B wherein the supplementation is by DNA gene transfer or by RNA delivery or by delivery of proteins into the A-iPSC.

Key to the Sequence Listing (SEQ ID NO's):

SEQ ID NO 1: Human ZSCAN10 Protein Sequence
SEQ ID NO 2: Human ZSCAN10 DNA Sequence
SEQ ID NO 3: Human ZSCAN10 transcript variant 1, DNA Sequence
SEQ ID NO 4: Human Zscan10 transcript variant 1 Protein Sequence
SEQ ID NO 5: Mouse ZSCAN10 Protein Sequence
SEQ ID NO 6: Mouse ZSCAN10 DNA Sequence
SEQ ID NO 7: Mouse ZSCAN10 transcript variant 1 DNA Sequence
SEQ ID NO 8: Mouse ZSCAN10 transcript variant 1 Protein Sequence
SEQ ID NO 9: Human GPX2 DNA Sequence
SEQ ID NO 10: Mouse GPX DNA Sequence
SEQ ID NO 11: Human GLUT3 DNA Sequence
SEQ ID NO 12: Mouse GLUT DNA Sequence
SEQ ID NO 13: Human GSS Protein Sequence
SEQ ID NO 14: Human GSS Genomic DNA Sequence
SEQ ID NO 15: Mouse GSS DNA Sequence
SEQ ID NO 16: Mouse GSS Protein Sequence Human Zscan10

```
FEATURES    Location/Qualifiers
source      1 . . . 2239
            /organism = "synthetic construct"
            /mol_type = "other DNA"
            /db_xref = "taxon: 32630"
            /clone = "MGC: 195844 IMAGE: 100068227"
            /clone_lib = "NIH_MGC_435"
            /lab_host = "DH10B"
            /focus
            /note = "Vector: pENTR223.1 with stop codon"
source      35 . . . 2212
            /organism = "Homo sapiens"
            /
ORIGIN
   1 gtacaaaaaa gcagaagggc cgtcaaggcc caccatgggg ccacgggcgt ccctgagccg

  61 gctccgggag ctctgcggcc actggctgcg gccggctctg cacaccaaga aacagatcct

 121 ggagctgctg gtgctggagc agttcctgag tgtgctgcct ccgcacctcc tgggccgcct

 181 gcaggggcag ccgctcaggg atggggagga ggtggtgctg ctgctcgagg gcatccaccg

 241 ggagcccagc cacgcggggc cgctggattt tagttgtaat gctggcaaga gttgtccccg

 301 tgcagacgtc accttggagg aaaaggggtg tgcttcccag gtccccagcc acagccccaa

 361 gaaggaattg cctgcggaag agccttcagt gctgggccca tcggatgagc ctccccgacc

 421 ccagccaagg gctgcccagc ctgctgagcc gggacagtgg aggcttcccc caagttcaaa

 481 gcagccgctg agcccggggc cccagaagac attccaggcc ctgcaagaaa gcagtcccca

 541 gggcccctca ccatggccag aggagagttc ccgagatcag gagctggcgg ctgtgctgga
```

-continued

```
 601 gtgcctgacc tttgaggatg tgccagagaa taaggcgtgg cctgcacacc ccctgggatt
 661 cggaagcaga accccagaca aggaggaatt taaacaagaa gagcccaaag gggctgcctg
 721 gcccactccc atcttagcag agtcccaggc agatagtcct ggggtgccgg gagagccttg
 781 cgcccagtcg ctcggacggg gcgctgcggc tagcggccct ggcgaagatg ggtcccttct
 841 tggcagcagt gaaattttgg aggtcaaagt ggctgagggc gtccccgagc ccaatccgga
 901 gttgcagttc atctgcgcgg actgcggggt gagcttcccg cagctgtctc gcctgaaggc
 961 gcaccagctg cgctcgcacc cggctgggcg ctccttcctg tgcctttgct gcgggaagag
1021 cttcggccgc agctccattc tcaagctgca catgcgcact cacacggacg agcggccgca
1081 cgcctgccac ctgtgcggcc accgcttccg ccagagctcg cacctgagca agcacctgct
1141 gacccactcc tccgaacccg ccttcctgtg cgcagagtgc ggccgcggct tccagcgccg
1201 cgccagcctt gtgcagcacc tgctggcgca cgcccaggac cagaagccgc cctgcgctcc
1261 tgagagtaag gccgaagcgc cgccactgac cgatgtcctg tgctcccact gcggccagag
1321 cttccagcgc cgctccagcc tcaagcgcca cctgcggatc cacgccaggg acaaggaccg
1381 ccggtcctcc gaaggctccg gcagccgccg ccgggactcc gaccggaggc ccttcgtgtg
1441 cagcgactgc ggcaaggcct tccggcgcag cgagcacctg gtggcccacc ggagggtgca
1501 cacgggcgag cggcccttct cctgccaggc ttgcggccgc agcttcacgc agagctcgca
1561 gctggtcagc caccaacggg tgcacacggg cgagaagccc tacgcctgtc cgcagtgcgg
1621 gaagcgcttt gtgcgccggg ccagccttgc ccgccacctg ctgacccacg gtggccctcg
1681 gccccaccac tgcacccagt gcgggaagag tttcggccag acccaggatc tggcccgcca
1741 ccagcgcagc cacacgggcg agaagccctg ccgctgcagc gagtgcggtg agggcttcag
1801 ccagagcgcc cacctggcgc gccaccagcg catccacaca ggggagaagc cccacgcctg
1861 cgacacctgc ggccaccgtt tccgcaatag ctccaacctg gcccgccatc gccgcagcca
1921 cacgggcgag cggccctaca gctgtcagac gtgcggtcgc agcttccggc gcaacgcgca
1981 tctgcggcgg cacctggcta cccatgcgga gcccgggcag gagcaggccg agcccccgca
2041 ggagtgcgtg gagtgcggga agagcttcag ccgcagctgc aatctgctgc gacacctgct
2101 ggtgcacacg ggcgccaggc cctactcctg cacgcagtgt ggccgcagct tcagccgcaa
2161 ctcccacctg ctgcgccacc tgcgcaccca cgcccgcgag acgctgtact agggcctcat
2221 gggcccagct ttcttgtac

   1 atggggccacgggcgtccctgagccggctccgggagctctgcggc
     M  G  P  R  A  S  L  S  R  L  R  E  L  C  G

  46 cactggctgcggccggctctgcacaccaagaaacagatcctggag
     H  W  L  R  P  A  L  H  T  K  K  Q  I  L  E

  91 ctgctggtgctggagcagttcctgagtgtgctgcctccgcacctc
     L  L  V  L  E  Q  F  L  S  V  L  P  P  H  L

 136 ctgggccgcctgcaggggcagccgctcagggatggggaggaggtg
     L  G  R  L  Q  G  Q  P  L  R  D  G  E  E  V

 181 gtgctgctgctcgagggcatccaccgggagcccagccacgcgggg
     V  L  L  L  E  G  I  H  R  E  P  S  H  A  G

 226 ccgctggattttagttgtaatgctggcaagagttgtccccgtgca
     P  L  D  F  S  C  N  A  G  K  S  C  P  R  A

 271 gacgtcaccttggaggaaaaggggtgtgcttcccaggtccccagc
     D  V  T  L  E  E  K  G  C  A  S  Q  V  P  S

 316 cacagccccaagaaggaattgcctgcggaagagccttcagtgctg
     H  S  P  K  K  E  L  P  A  E  E  P  S  V  L
```

-continued

```
 361 ggcccatcggatgagcctccccgaccccagccaagggctgcccag
     G  P  S  D  E  P  P  R  P  Q  P  R  A  A  Q

 406 cctgctgagccgggacagtggaggcttcccccaagttcaaagcag
     P  A  E  P  G  Q  W  R  L  P  P  S  S  K  Q

 451 ccgctgagcccggggccccagaagacattccaggccctgcaagaa
     P  L  S  P  G  P  Q  K  T  F  Q  A  L  Q  E

 496 agcagtccccagggcccctcaccatggccagaggagagttcccga
     S  S  P  Q  G  P  S  P  W  P  E  E  S  S  R

 541 gatcaggagctggcggctgtgctggagtgcctgacctttgaggat
     D  Q  E  L  A  A  V  L  E  C  L  T  F  E  D

 586 gtgccagagaataaggcgtggcctgcacacccccctgggattcgga
     V  P  E  N  K  A  W  P  A  H  P  L  G  F  G

 631 agcagaaccccagacaaggaggaatttaaacaagaagagcccaaa
     S  R  T  P  D  K  E  E  F  K  Q  E  E  P  K

 676 ggggctgcctggcccactcccatcttagcagagtcccaggcagat
     G  A  A  W  P  T  P  I  L  A  E  S  Q  A  D

 721 agtcctggggtgccgggagagccttgcgcccagtcgctcggacgg
     S  P  G  V  P  G  E  P  C  A  Q  S  L  G  R

 766 ggcgctgcggctagcggccctggcgaagatgggtcccttcttggc
     G  A  A  A  S  G  P  G  E  D  G  S  L  L  G

 811 agcagtgaaattttggaggtcaaagtggctgagggcgtccccgag
     S  S  E  I  L  E  V  K  V  A  E  G  V  P  E

 856 cccaatccggagttgcagttcatctgcgcggactgcggggtgagc
     P  N  P  E  L  Q  F  I  C  A  D  C  G  V  S

 901 ttcccgcagctgtctcgcctgaaggcgcaccagctgcgctcgcac
     F  P  Q  L  S  R  L  K  A  H  Q  L  R  S  H

 946 ccggctgggcgctccttcctgtgcctttgctgcgggaagagcttc
     P  A  G  R  S  F  L  C  L  C  C  G  K  S  F

 991 ggccgcagctccattctcaagctgcacatgcgcactcacacggac
     G  R  S  S  I  L  K  L  H  M  R  T  H  T  D

1036 gagcggccgcacgcctgccacctgtgcggccaccgcttccgccag
     E  R  P  H  A  C  H  L  C  G  H  R  F  R  Q

1081 agctcgcacctgagcaagcacctgctgacccactcctccgaaccc
     S  S  H  L  S  K  H  L  L  T  H  S  S  E  P

1126 gccttcctgtgcgcagagtgcggccgcggcttccagcgccgcgcc
     A  F  L  C  A  E  C  G  R  G  F  Q  R  R  A

1171 agccttgtgcagcacctgctggcgcacgcccaggaccagaagccg
     S  L  V  Q  H  L  L  A  H  A  Q  D  Q  K  P

1216 ccctgcgctcctgagagtaaggccgaagcgccgccactgaccgat
     P  C  A  P  E  S  K  A  E  A  P  P  L  T  D

1261 gtcctgtgctcccactgcggccagagcttccagcgccgctccagc
     V  L  C  S  H  C  G  Q  S  F  Q  R  R  S  S

1306 ctcaagcgccacctgcggatccacgccagggacaaggaccgccgg
     L  K  R  H  L  R  I  H  A  R  D  K  D  R  R

1351 tcctccgaaggctccggcagccgccgccgggactccgaccggagg
     S  S  E  G  S  G  S  R  R  R  D  S  D  R  R

1396 cccttcgtgtgcagcgactgcggcaaggccttccggcgcagcgag
     P  F  V  C  S  D  C  G  K  A  F  R  R  S  E

1441 cacctggtggcccaccggagggtgcacacgggcgagcggcccttc
     H  L  V  A  H  R  R  V  H  T  G  E  R  P  F

1486 tcctgccaggcttgcggccgcagcttcacgcagagctcgcagctg
     S  C  Q  A  C  G  R  S  F  T  Q  S  S  Q  L

1531 gtcagccaccaacgggtgcacacgggcgagaagccctacgcctgt
     V  S  H  Q  R  V  H  T  G  E  K  P  Y  A  C
```

-continued

```
1576 ccgcagtgcgggaagcgctttgtgcgccgggccagccttgcccgc
     P  Q  C  G  K  R  F  V  R  R  A  S  L  A  R

1621 cacctgctgacccacggtggccctcggccccaccactgcacccag
     H  L  L  T  H  G  G  P  R  P  H  H  C  T  Q

1666 tgcgggaagagtttcggccagacccaggatctggcccgccaccag
     C  G  K  S  F  G  Q  T  Q  D  L  A  R  H  Q

1711 cgcagccacacgggcgagaagccctgccgctgcagcgagtgcggt
     R  S  H  T  G  E  K  P  C  R  C  S  E  C  G

1756 gagggcttcagccagagcgcccacctggcgcgccaccagcgcatc
     E  G  F  S  Q  S  A  H  L  A  R  H  Q  R  I

1801 cacacaggggagaagccccacgcctgcgacacctgcggccaccgt
     H  T  G  E  K  P  H  A  C  D  T  C  G  H  R

1846 ttccgcaatagctccaacctggcccgccatcgccgcagccacacg
     F  R  N  S  S  N  L  A  R  H  R  R  S  H  T

1891 ggcgagcggccctacagctgtcagacgtgcggtcgcagcttccgg
     G  E  R  P  Y  S  C  Q  T  C  G  R  S  F  R

1936 cgcaacgcgcatctgcggcggcacctggctacccatgcggagccc
     R  N  A  H  L  R  R  H  L  A  T  H  A  E  P

1981 gggcaggagcaggccgagcccccgcaggagtgcgtggagtgcggg
     G  Q  E  Q  A  E  P  P  Q  E  C  V  E  C  G

2026 aagagcttcagccgcagctgcaatctgctgcgacacctgctggtg
     K  S  F  S  R  S  C  N  L  L  R  H  L  L  V

2071 cacacgggcgccaggccctactcctgcacgcagtgtggccgcagc
     H  T  G  A  R  P  Y  S  C  T  Q  C  G  R  S

2116 ttcagccgcaactcccacctgctgcgccacctgcgcacccacgcc
     F  S  R  N  S  H  L  L  R  H  L  R  T  H  A

2161 cgcgagacgctgtactag 2178
     R  E  T  L  Y  *
```

Mouse Zscan10

```
FEATURES    Location/Qualifiers
source      1 . . . 2410
            /organism = "synthetic construct"
            /mol_type = "other DNA"
            /db_xref = "taxon: 32630"
            /clone = "MGC: 195458 IMAGE: 100066321"
            /clone_lib = "NIH_MGC_436"
            /lab_host = "DH10B
            /focus
            /note = "Vector: pENTR223.1 with stop codon"
source      35 . . . 2383
            /organism = "Mus musculus"
            /mol_type = "other DNA"
            /db_xref = "taxon: 10090"
ORIGIN
   1 gtacaaaaaa gcagaagggc cgtcaaggcc caccatgctg gcggaaccag tccctgatgc

  61 cctggaacaa gagcatcccg gagcagtgaa gttggaggag gatgaagttg gcgaggagga

 121 tcccaggctc gcagagtcca ggcctaggcc tgaggtggcc caccagcttt tcagatgctt

 181 ccagtatcag gaagatatgg ggccacgggc atccctgggc cggctccggg aactctgcaa

 241 ccactggctg cgaccggctc tgcacaccaa gaagcagatc ctggagctgc tggtactgga

 301 gcagttcctg agtgtcctgc ccccgcatgt gctgagccgg ctgcacggcc aaccgctccg

 361 ggacggagag gaggtggtac agctattgga gggcgtgccc agagacatca gccacatggg

 421 gccactggat tttagcttca gtgctggcaa gaatgcccct gcagacatca tctcagagga

 481 acaaaatagc ccttcccagg tccccagcca cagcccccag acggagttgc cctcagaaga

 541 gattccagcc ctacatccac tgaatgagtt acctccacct cagccagcac ccataaggcc
```

-continued

```
 601 tgctgagcct gaggagtgga gactggcccc cagttcaaat tggccaatga gcccagagcc

 661 ccaggagata ctccaggacc cacgagaaag caacccttcc cagggccctt catggcttga

 721 ggaaaattcc agagaccaag agctggcggc tgtgttggag tccctcacct ttgaggatac

 781 ctcagagaag agagcttggc ctgcaaaccc tcttggattt ggaagcagaa tgcctgacaa

 841 tgaggaactt aaagttgaag agcctaaagt gactacttgg cctgtcgtca ttggagcaga

 901 gtcccagaca gagaaacctg aagttgcagg agagcctctt acgcaaactg tagggcagga

 961 gaccagcagc actggttggg gaggtactcc tgctgacggc agtgaagttg tgaaggttag

1021 aggagcttcc gatgccccag agccccaggg ggagatgcag ttcatatgta catattgtgg

1081 ggtaaacttc ccagagatgt ctcatctaca ggcccaccag ttacaatctc accccaactt

1141 gcaacctcac ccaagctctc gatccttccg atgtctgtgg tgtgggaaga cttttggacg

1201 cagctcgatc ctcaagctgc acatgcgcac tcacacagac gagcggccgc acgcctgtca

1261 tctctgcaac cgccgcttcc gccagagctc acacctgacg aagcacttgc taacgcattc

1321 ctctgagcct gccttccgat gcgccgagtg taaccagggt tttcagcgtc gctccagcct

1381 catgcagcac ctgctggcac atgcccaggg aaagaatctc acgccaaatc cagaaggcaa

1441 gacaaaagtg ccagagatgg cagctgtcct ctgttcccac tgcgggcaga ccttcaagcg

1501 gcgctctagc ttaaagcgtc acctgcgtaa ccatgccaag gacaaggacc atctgtcctc

1561 tgaagaccct ggcagcctta gctctagcca ggagagtaac ccctatgtgt gtagtgactg

1621 tggcaaggcc ttccgacaaa gcgagcaact aatgatccac actaggcgag tccatacccg

1681 tgaacgaccc ttctcctgcc aggtctgtgg ccgctgcttt acccaaaatt cccagctgat

1741 cagccaccag cagattcata cgggtgagaa gcctcacgcc tgtcctcagt gcagcaaacg

1801 ctttgtgaga cgagctggcc ttgctcggca tctgttgacc cacggtagcc tccggcctta

1861 ccactgtgcc caatgtggca aaagctttcg ccaaatgcga gacctaaccc gccacgtacg

1921 ctgccacacg ggggagaagc cctgccgatg caacgaatgt ggagaggggt tcacccagaa

1981 tgcccacctg gcacgccacc aacgcatcca cacgggggag aagccccacg cctgtgacat

2041 ctgtggtcac cgctttcgta acagctccaa cttggcccgc caccgccgca gccacactgg

2101 cgaacggccc tatagctgtc caacctgtgg ccgcagtttc cggcgcaatg cgcacctgca

2161 gcgccacctg atcacacaca cagggtcaaa gcaagaaaag gaagttcctc aggagtgccc

2221 tgagtgtggc aagagcttca atcgcagctg caacttgctg cgccacctgc tggttcacac

2281 cggtgcaagg ccttactcct gtgcactgtg tggccgcagc ttcagccgta attcacacct

2341 gctgcgccac ctgcgaaccc atgcccggga atcgctgtac tagggcctca tgggcccagc

2401 tttcttgtac

   1 atgctggcggaaccagtccctgatgccctggaacaagagcatccc
     M  L  A  E  P  V  P  D  A  L  E  Q  E  H  P

  46 ggagcagtgaagttggaggaggatgaagttggcgaggaggatccc
     G  A  V  K  L  E  E  D  E  V  G  E  E  D  P

  91 aggctcgcagagtccaggcctaggcctgaggtggcccaccagctt
     R  L  A  E  S  R  P  R  P  E  V  A  H  Q  L

 136 ttcagatgcttccagtatcaggaagatatggggccacgggcatcc
     F  R  C  F  Q  Y  Q  E  D  M  G  P  R  A  S

 181 ctgggccggctccgggaactctgcaaccactggctgcgaccggct
     L  G  R  L  R  E  L  C  N  H  W  L  R  P  A

 226 ctgcacaccaagaagcagatcctggagctgctggtactggagcag
     L  H  T  K  K  Q  I  L  E  L  L  V  L  E  Q
```

-continued

```
 271 ttcctgagtgtcctgcccccgcatgtgctgagccggctgcacggc
     F  L  S  V  L  P  P  H  V  L  S  R  L  H  G

 316 caaccgctccgggacggagaggaggtggtacagctattggagggc
     Q  P  L  R  D  G  E  E  V  V  Q  L  L  E  G

 361 gtgcccagagacatcagccacatggggccactggattttagcttc
     V  P  R  D  I  S  H  M  G  P  L  D  F  S  F

 406 agtgctggcaagaatgcccctgcagacatcatctcagaggaacaa
     S  A  G  K  N  A  P  A  D  I  I  S  E  E  Q

 451 aatagcccttcccaggtccccagccacagcccccagacggagttg
     N  S  P  S  Q  V  P  S  H  S  P  Q  T  E  L

 496 ccctcagaagagattccagccctacatccactgaatgagttacct
     P  S  E  E  I  P  A  L  H  P  L  N  E  L  P

 541 ccacctcagccagcacccataaggcctgctgagcctgaggagtgg
     P  P  Q  P  A  P  I  R  P  A  E  P  E  E  W

 586 agactggcccccagttcaaattggccaatgagcccagagccccag
     R  L  A  P  S  S  N  W  P  M  S  P  E  P  Q

 631 gagatactccaggacccacgagaaagcaacccttcccagggccct
     E  I  L  Q  D  P  R  E  S  N  P  S  Q  G  P

 676 tcatggcttgaggaaaattccagagaccaagagctggcggctgtg
     S  W  L  E  E  N  S  R  D  Q  E  L  A  A  V

 721 ttggagtccctcacctttgaggatacctcagagaagagagcttgg
     L  E  S  L  T  F  E  D  T  S  E  K  R  A  W

 766 cctgcaaaccctcttggatttggaagcagaatgcctgacaatgag
     P  A  N  P  L  G  F  G  S  R  M  P  D  N  E

 811 gaacttaaagttgaagagcctaaagtgactacttggcctgtcgtc
     E  L  K  V  E  E  P  K  V  T  T  W  P  V  V

 856 attggagcagagtcccagacagagaaacctgaagttgcaggagag
     I  G  A  E  S  Q  T  E  K  P  E  V  A  G  E

 901 cctcttacgcaaactgtagggcaggagaccagcagcactggttgg
     P  L  T  Q  T  V  G  Q  E  T  S  S  T  G  W

 946 ggaggtactcctgctgacggcagtgaagttgtgaaggttagagga
     G  G  T  P  A  D  G  S  E  V  V  K  V  R  G

 991 gcttccgatgccccagagccccagggggagatgcagttcatatgt
     A  S  D  A  P  E  P  Q  G  E  M  Q  F  I  C

1036 acatattgtggggtaaacttcccagagatgtctcatctacaggcc
     T  Y  C  G  V  N  F  P  E  M  S  H  L  Q  A

1081 caccagttacaatctcaccccaacttgcaacctcacccaagctct
     H  Q  L  Q  S  H  P  N  L  Q  P  H  P  S  S

1126 cgatccttccgatgtctgtggtgtgggaagacttttggacgcagc
     R  S  F  R  C  L  W  C  G  K  T  F  G  R  S

1171 tcgatcctcaagctgcacatgcgcactcacacagacgagcggccg
     S  I  L  K  L  H  M  R  T  H  T  D  E  R  P

1216 cacgcctgtcatctctgcaaccgccgcttccgccagagctcacac
     H  A  C  H  L  C  N  R  R  F  R  Q  S  S  H

1261 ctgacgaagcacttgctaacgcattcctctgagcctgccttccga
     L  T  K  H  L  L  T  H  S  S  E  P  A  F  R

1306 tgcgccgagtgtaaccagggttttcagcgtcgctccagcctcatg
     C  A  E  C  N  Q  G  F  Q  R  R  S  S  L  M

1351 cagcacctgctggcacatgcccagggaaagaatctcacgccaaat
     Q  H  L  L  A  H  A  Q  G  K  N  L  T  P  N

1396 ccagaaggcaagacaaaagtgccagagatggcagctgtcctctgt
     P  E  G  K  T  K  V  P  E  M  A  A  V  L  C

1441 tcccactgcgggcagaccttcaagcggcgctctagcttaaagcgt
     S  H  C  G  Q  T  F  K  R  R  S  S  L  K  R
```

-continued

```
1486 cacctgcgtaaccatgccaaggacaaggaccatctgtcctctgaa
     H  L  R  N  H  A  K  D  K  D  H  L  S  S  E

1531 gaccctggcagccttagctctagccaggagagtaacccctatgtg
     D  P  G  S  L  S  S  S  Q  E  S  N  P  Y  V

1576 tgtagtgactgtggcaaggccttccgacaaagcgagcaactaatg
     C  S  D  C  G  K  A  F  R  Q  S  E  Q  L  M

1621 atccacactaggcgagtccatacccgtgaacgacccttctcctgc
     I  H  T  R  R  V  H  T  R  E  R  P  F  S  C

1666 caggtctgtggccgctgctttacccaaaattcccagctgatcagc
     Q  V  C  G  R  C  F  T  Q  N  S  Q  L  I  S

1711 caccagcagattcatacgggtgagaagcctcacgcctgtcctcag
     H  Q  Q  I  H  T  G  E  K  P  H  A  C  P  Q

1756 tgcagcaaacgctttgtgagacgagctggccttgctcggcatctg
     C  S  K  R  F  V  R  R  A  G  L  A  R  H  L

1801 ttgacccacggtagcctccggccttaccactgtgcccaatgtggc
     L  T  H  G  S  L  R  P  Y  H  C  A  Q  C  G

1846 aaaagctttcgccaaatgcgagacctaacccgccacgtacgctgc
     K  S  F  R  Q  M  R  D  L  T  R  H  V  R  C

1891 cacacgggggagaagccctgccgatgcaacgaatgtggagagggg
     H  T  G  E  K  P  C  R  C  N  E  C  G  E  G

1936 ttcacccagaatgcccacctggcacgccaccaacgcatccacacg
     F  T  Q  N  A  H  L  A  R  H  Q  R  I  H  T

1981 ggggagaagccccacgcctgtgacatctgtggtcaccgctttcgt
     G  E  K  P  H  A  C  D  I  C  G  H  R  F  R

2026 aacagctccaacttggcccgccaccgccgcagccacactggcgaa
     N  S  S  N  L  A  R  H  R  R  S  H  T  G  E

2071 cggccctatagctgtccaacctgtggccgcagtttccggcgcaat
     R  P  Y  S  C  P  T  C  G  R  S  F  R  R  N

2116 gcgcacctgcagcgccacctgatcacacacacagggtcaaagcaa
     A  H  L  Q  R  H  L  I  T  H  T  G  S  K  Q

2161 gaaaaggaagttcctcaggagtgccctgagtgtggcaagagcttc
     E  K  E  V  P  Q  E  C  P  E  C  G  K  S  F

2206 aatcgcagctgcaacttgctgcgccacctgctggttcacaccggt
     N  R  S  C  N  L  L  R  H  L  L  V  H  T  G

2251 gcaaggccttactcctgtgcactgtgtggccgcagcttcagccgt
     A  R  P  Y  S  C  A  L  C  G  R  S  F  S  R

2296 aattcacacctgctgcgccacctgcgaacccatgcccgggaatcg
     N  S  H  L  L  R  H  L  R  T  H  A  R  E  S

2341 ctgtactag 2349
     L  Y  *
```

Human GPX2 Transcript mRNA

```
FEATURES         Location/Qualifiers
source           1 . . . 1105
                 /organism = "Homo sapiens"
                 /mol_type = "mRNA"
                 /db_xref = "taxon: 9606"
                 /chromosome = "14"
                 /map = "14q24.1"
ORIGIN
   1 cttgttcaaa cagcacttac aggtggggac ctgtttttgc taagtcatcc tggggatgct

  61 caaagctcca ttgttagatc ctttctgtcc tccttcctgg ctcctccttc ctccccaccc

 121 ctctaatagg ctcataagtg ggctcaggcc tctctgcggg gctcactctg cgcttcacca

 181 tggctttcat tgccaagtcc ttctatgacc tcagtgccat cagcctggat ggggagaagg
```

-continued

```
 241 tagatttcaa tacgttccgg ggcagggccg tgctgattga gaatgtggct tcgctctgag
 301 gcacaaccac ccgggacttc acccagctca acgagctgca atgccgcttt cccaggcgcc
 361 tggtggtcct tggcttccct tgcaaccaat ttggacatca ggagaactgt cagaatgagg
 421 agatcctgaa cagtctcaag tatgtccgtc ctgggggtgg ataccagccc accttcaccc
 481 ttgtccaaaa atgtgaggtg aatgggcaga acgagcatcc tgtcttcgcc tacctgaagg
 541 acaagctccc ctacccttat gatgacccat tttccctcat gaccgatccc aagctcatca
 601 tttggagccc tgtgcgccgc tcagatgtgg cctggaactt tgagaagttc ctcatagggc
 661 cggagggaga gcccttccga cgctacagcc gcaccttccc aaccatcaac attgagcctg
 721 acatcaagcg cctccttaaa gttgccatat agatgtgaac tgctcaacac acagatctcc
 781 tactccatcc agtcctgagg agccttagga tgcagcatgc cttcaggaga cactgctgga
 841 cctcagcatt cccttgatat cagtcccctt cactgcagag ccttgccttt cccctctgcc
 901 tgtttccttt tcctctccca accctctggt tggtgattca acttgggctc caagacttgg
 961 gtaagctctg ggccttcaca gaatgatggc accttcctaa accctcatgg gtggtgtctg
1021 agaggcgtga agggcctgga gccactctgc tagaagagac caataaaggg caggtgtgga
1081 aacggccaaa aaaaaaaaaa aaaaa
//
```

*Mus musculus* glutathione peroxidase 2 (Gpx2), mRNA
NCBI Reference Sequence: NM_030677.2
GenBank Graphics >gi|145275167|ref|NM_030677.2|*Mus musculus* glutathione peroxidase 2 (Gpx2), mRNA GCTACAGCCTTGTTCAAACAGTTCACAGGTGGGTACCTGTTTTTTGCT
AAGTCATCCCGGGAATGCTCAAAGGCCCTTTGTGAAGTCCTTTCGGTC
TTCTCCGGCTCCTCCTTTCTTCCCACCGGTCTAAAGGACTTAAGGAGG
CTCACAGAGCAGGGCAGGGCTCACTGCTCTTCAGCATGGCTTACATTG
CCAAGTCGTTCTACGATCTCAGTGCCGTTGGCCTGGATGGGGAGAAGA
TAGACTTCAATACGTTCAGAGGCAGGGCTGTGCTGATTGAGAATGTGG
CGTCACTCTGAGGAACAACTACCCGGGACTACAACCAGCTCAATGAGC
TGCAATGTCGCTTTCCCAGGCGCCTGGTAGTTCTCGGCTTCCCTTGCA
ACCAGTTCGGACATCAGGAGAACTGTCAGAACGAGGAGATCCTGAACA
GCCTCAAGTATGTCCGACCTGGGGGTGGGTACCAGCCCACCTTTAGTC
TTACCCAAAAGTGTGACGTCAATGGGCAGAACGAGCATCCTGTCTTTG
CCTACCTGAAAGACAAGCTGCCCTACCCTTATGATGACCCGTTCTCCC
TCATGACCGATCCCAAGCTCATCATATGGAGTCCCGTGCGCCGCTCAG
ACGTGTCCTGGAACTTTGAGAAGTTCCTCATAGGGCCAGAAGGGGAGC
CCTTCCGTCGCTACAGCCGCAGCTTCCAGACCATCAACATCGAGCCTG
ACATCAAACGGCTCCTCAAAGTTGCCATCTAGATGAGAGCTGCTCAGC
CCAGGAATCTCCCACTGTTTCCCCTGAGCAGTCTTCCTCAGGGCTCAG
TGTACCCTCGGGAGACCCTGGGAGACCAAGGCATTCCCTGAATATCGT
CCCCTTGCCTTCCCTACCGGCCATTTCCTTTAGCTCCCTCAAGGCTCT
TGGGGAGTTTGCTTGGGGCTCTAAGTCTGGGGTAGGTTCTGGGCCTTC
ACAGAATGATGGCATCTTCCTAAACCCTTCTGGGAGATGTCTGAGAAG -continued

TTGTGAAGGGTCCAGAGCCAGTCTGCTTTAGAGTCCAATAAAGTGTAG
GTGTGGCAATGAAAA

Human and Mouse GLUT3 DNA sequence
Human glut3 CDs

ATGGGGACACAGAAGGTCACCCCAGCTCTGATATTTGCCATCACAGTT
GCTACAATCGGCTCTTTCCAATTTGGCTACAACACTGGGGTCATCAAT
GCTCCTGAGAAGATCATAAAGGAATTTATCAATAAAACTTTGACGGAC
AAGGGAAATGCCCCACCCTCTGAGGTGCTGCTCACGTCTCTCTGGTCC
TTGTCTGTGGCCATATTTTCCGTCGGGGGTATGATCGGCTCCTTTTCC
GTCGGACTCTTCGTCAACCGCTTTGGCAGGCGCAATTCAATGCTGATT
GTCAACCTGTTGGCTGTCACTGGTGGCTGCTTTATGGGACTGTGTAAA
GTAGCTAAGTCGGTTGAAATGCTGATCCTGGGTCGCTTGGTTATTGGC
CTCTTCTGCGGACTCTGCACAGGTTTTGTGCCCATGTACATTGGAGAG
ATCTCGCCTACTGCCCTGCGGGGTGCCTTTGGCACTCTCAACCAGCTG
GGCATCGTTGTTGGAATTCTGGTGGCCCAGATCTTTGGTCTGGAATTC
ATCCTTGGGTCTGAAGAGCTATGGCCGCTGCTACTGGGTTTTACCATC
CTTCCTGCTATCCTACAAAGTGCAGCCCTTCCATTTTGCCCTGAAAGT
CCCAGATTTTTGCTCATTAACAGAAAAGAAGAGGAGAATGCTAAGCAG
ATCCTCCAGCGGTTGTGGGGCACCCAGGATGTATCCCAAGACATCCAG
GAGATGAAAGATGAGAGTGCAAGGATGTCACAAGAAAAGCAAGTCACC
GTGCTAGAGCTCTTTAGAGTGTCCAGCTACCGACAGCCCATCATCATT
TCCATTGTGCTCCAGCTCTCTCAGCAGCTCTCTGGGATCAATGCTGTG
TTCTATTACTCAACAGGAATCTTCAAGGATGCAGGTGTTCAAGAGCCC

-continued

ATCTATGCCACCATCGGCGCGGGTGTGGTTAATACTATCTTCACTGTA

GTTTCTCTATTTCTGGTGGAAAGGGCAGGAAGAAGGACTCTGCATATG

ATAGGCCTTGGAGGGATGGCTTTTTGTTCCACGCTCATGACTGTTTCT

TTGTTATTAAAGGATAACTATAATGGGATGAGCTTTGTCTGTATTGGG

GCTATCTTGGTCTTTGTAGCCTTCTTTGAAATTGGACCAGGCCCCATT

CCCTGGTTTATTGTGGCCGAACTCTTCAGCCAGGGCCCCCGCCCAGCT

GCGATGGCAGTGGCCGGCTGCTCCAACTGGACCTCCAACTTCCTAGTC

GGATTGCTCTTCCCCTCCGCTGCTCACTATTTAGGAGCCTACGTTTTT

ATTATCTTCACCGGCTTCCTCATTACCTTCTTGGCTTTTACCTTCTTC

AAAGTCCCTGAGACCCGTGGCAGGACTTTTGAGGATATCACACGGGCC

TTTGAAGGGCAGGCACACGGTGCAGATAGATCTGGAAAGGACGGCGTC

ATGGAGATGAACAGCATCGAGCCTGCTAAGGAGACCACCACCAATGTC

TAA

Mouse Glut3 CDs

ATGGGGACAACGAAGGTGACCCCATCTCTGGTGTTCGCCGTGACTGTT

GCCACGATCGGCTCTTTCCAGTTTGGCTACAACACTGGAGTCATCAAT

GCACCTGAGACAATCCTAAAGGACTTTCTTAACTACACTTTGGAAGAG

CGGTTAGAAGACCTACCAAGTGAGGGACTGCTGACTGCCCTCTGGTCC

TTATGTGTGGCCATCTTCTCTGTTGGTGGCATGATTGGCTCTTTTTCT

GTTGGACTCTTTGTCAACCGCTTTGGCAGACGCAACTCTATGCTTCTA

GTCAACTTGCTGGCCATCATTGCGGGCTGCCTTATGGGATTCGCCAAG

ATAGCGGAGTCTGTTGAAATGCTGATCCTGGGCCGCTTACTCATTGGC

-continued

ATTTTCTGTGGCCTGTGCACGGGCTTTGTGCCTATGTACATTGGAGAG

GTGTCTCCCACTGCCCTTCGGGGTGCATTTGGCACACTAAACCAGCTG

GGCATCGTTGTTGGGATTCTGGTAGCTCAGATCTTTGGTTTGGACTTT

ATTCTGGGCTCTGAAGAACTGTGGCCTGGGCTCCTTGGCTTAACCATC

ATTCCAGCTATCCTGCAAAGCGCAGCCCTTCCATTTTGCCCTGAGAGT

CCAAGATTCTTGCTCATTAACAAAAAGGAGGAAGACCAAGCTACAGAG

ATCCTGCAGCGCTTGTGGGGCACCTCGGACGTGGTCCAGGAGATCCAG

GAGATGAAGGATGAGAGTGTTCGGATGTCACAGGAGAAGCAGGTGACT

GTGCTGGAGCTCTTCAGGTCACCCAACTACGTCCAGCCGCTTCTCATC

TCCATTGTCCTCCAGCTGTCTCAGCAGCTCTCTGGGATCAATGCTGTG

TTCTATTACTCAACAGGAATCTTCAAGGACGCGGGTGTCCAGGAACCG

ATCTATGCCACGATTGGAGCAGGCGTGGTCAATACTATCTTCACTGTA

GTTTCTCTGTTCCTGGTGGAGAGGGCAGGGAGGAGAACCCTGCATATG

ATAGGCCTGGGAGGCATGGCTGTTTGCTCCGTTTTCATGACGATTTCG

CTGTTACTAAAGGATGACTATGAAGCCATGAGCTTTGTCTGTATTGTG

GCTATCTTGATCTACGTAGCCTTCTTTGAGATTGGACCTGGCCCCATT

CCCTGGTTTATTGTGGCTGAGCTCTTCAGCCAGGGCCCCCGCCCAGCT

GCCATTGCGGTGGCTGGCTGTTGTAACTGGACCTCCAACTTTCTGGTC

GGAATGCTCTTCCCCTCAGCTGCAGCCTACTTAGGAGCCTACGTTTTT

ATCATCTTCGCTGCCTTCCTCATCTTCTTCCTAATCTTCACCTTCTTC

AAAGTCCCGGAGACCAAAGGCAGGACTTTCGAGGACATTGCCCGGGCC

TTCGAGGGGCAGGCGCACTCTGGAAAAGGCCCTGCCGGTGTGGAGTTG

AACAGCATGCAGCCGGTCAAGGAGACCCCTGGCAACGCCTGA

Human GSS genomic DNA

```
LOCUS NG_008848 34366 bp DNA linear PRI
04-MAY-2014
DEFINITION    Homo sapiens glutathione synthetase (GSS),
RefSeqGene on chromosome 20.
ACCESSION     NG_008848
VERSION       NG_008848.1 GI: 209977061
KEYWORDS      RefSeq; RefSeqGene.
SOURCE        Homo sapiens (human)
ORGANISM      Homo sapiens
ORIGIN
      1 tcctcacttt gattccacag gcatttcctg agcagcaatg ctggcccagg cctgtgctag

     61 gggctggaag acagaggaat tccactctga atggccaaag cagtggcccc cagccaggtg

    121 gggagatggc ctcataaaca acagtatgag gcagggtgat atcactgcta aaaagagaca

    181 gtagccatgt gcacagatgc agaccatgtg tgatgcagac cctggggctg acagagatgt

    241 tccaatcaaa aggcacagtc cagtggctgg gtgcggtggc tcccgcctgt aatcccagca

    301 ctttgggagg ctgaggcggg tggatcacaa ggtcaggaga tcgagaccat cctggctaac

    361 acggtgaaac cccatctcta ctaaaaatag aaaaaattag gcgggcgtgg tggcaggcgc

    421 ctgtagtccc agctactcgg gaggctgagg taggagaatg gcatgaacac gggaggcgga

    481 gcttgcagtg agccaagatg gcgccactgc actctagcct gggctacaaa gcaagactcc

    541 atctcaaaaa aacaaaaaca aaaaaaaccc acagtccaga cttggagaga ggccctcgca

    601 gggagaaagg caagacacaa aattaaggga ttggcctcca ttcacagtga agtacatccc
```

-continued 661 tgcatacctt ttttcaccta attcagaccc aaatgttccc acaaacccca agaacagagg
721 atgaaattga ttcaacagtt agctttggga agtctgagcc catggcatgt cccaaggtac
781 atatgtggga acaccatggc tgacactgct gctgtgatct ttggcaagtc aggatacctc
841 ttcaagcctt cctttccccg gctgtaaaat ggaggctata aagatactga tgtgataggg
901 aggtaaggga aagtgagata acgactgtaa agtcattagc caagtacctg acacttagcg
961 accagatcaa taaagggtag ttattgttag gaaaaaacag atttcacttt gaaagtgagg
1021 aaagccaggc gcggtggctc acacctgtaa tcccagcact ttgggaggct gaggcaggca
1081 gatcacgagg tcaggagttc gagaccagcc tggacagcaa ggtgaaaccc tgtctccact
1141 aaaaatacaa aaaattagct gggcatggtg gcatgtgcct gtaatcccag ctactcggga
1201 gactgaggca ggagaattgc ctgaacccgg gaggcagagg ttgcagtgag ccaagatcgt
1261 gccactgcac tccagcctgg gtgacagaga gagactccat ctcaaaaaaa aaaaaaagaa
1321 agaaagaaaa aaaataaaat gaggaaagtg ggattcggag aggtgagatg acttctgcac
1381 agtcaggatt caaactcagg tctgagacac cagaggctca gggcaaatca tctccctctg
1441 ctccggaatc ttcagcaggt tccctacagt ccactacatg gactccatcc ttgccaggga
1501 gtgaggatcc agcaaaggcc tggggccaaa aagaccctgg gcaagttccc aatcctatg
1561 tgtcttgatc tgagatcccc aagtgagcct gagaaggtct gtgaattcct ccacgtagct
1621 gatgcaaaat tttatactaa tggatctcag acgagtctat agcctcaaaa gtaacaaacc
1681 acagacttga cctgacttag catggtttct tattcaccca atggagatac gatttctacc
1741 ttgaaaggct gtgaagggat taaatgaggt aatttgtgag aagtacttga aacatcctca
1801 gctttcatta aatgttggtt tccttctctt tctctctccc caaactattt ccatcagtta
1861 gcaaatatta ttgagcatct gccacgtggc aggcaccagt caggtcctgg gggtaaagtg
1921 gtgaacaaga cagacatggc ccattttcat ggggctcaca ttctagcaga gggaaacagc
1981 aaacaaataa aagcaacaat ttcagatatg aataactgct atgaagaaaa tacaaggccg
2041 ggcacggtgg ctcacgcctg taatcccagc actttgagag gcagaggcgg acggatcaca
2101 aggtcaggag tttgagacca gcctgatcaa catggtgaaa ccctgtctct cctaaaaata
2161 caaaaattag ccgggcatgg tggcacgtgc ctgtaatccc agctactcag gagactgagg
2221 caggagaatt gtttgaaccc aggagacaga ggttgcagtg agccaagatc gcaccactgc
2281 actccagcct gggcaacaga gtgagactcc atctcaaaaa aaagaaaagg ataacgtgat
2341 agacttatag ggtggggcag cctccaggga tgaaacatct gaatgaccaa aggagccagt
2401 catgccagga ttttggagga aagcacccag gcagagagtg cagaaagggc aaacgctccc
2461 tggaaagatt cttagtcaag agtccttcac tcccagtcct accacaaact gggtcacctt
2521 gaacaagtca cgtaacttct gaggctcagc tgccacatct acaaaatggg aataaagaca
2581 tcttacctgc cacattgtga gaggtttcaa ccaaagggct gttaaggtct gggatcctcc
2641 ccaaatctca ccatagacac ctgatactca tcacttggca cccgtcttgg aagaggggaa
2701 cctgcacaga gaaccctggg tcatgctttt gatttttaat ttcatgctgc actagaaata
2761 gcttcttttg ttcctggttg acccaggagc ctcttcctgc cacctggggc ctattctagt
2821 taacagctgc ttatcccctc aggtacaaaa gccaacgagg aaaggacatc aggaaacatt
2881 gttctgggaa taaccagaca cctatctgcc accatctccc cccatcccgt gaccacacac
2941 gggagactgg aggactcagc ctgtcctgta gtcagataat gtacatggtt tatttaaaga
3001 gtcaaaaggg gccgggcgca gtggctaacg cctgtaatcc tagcactctg ggaggctggg
3061 gcgggtggat cacctgagct caagagtttc agaccaatct ggccaacatg gtgaaaccct -continued 3121 gtctctacca aaaatacaaa aattagccgg gtgtggtggt ggacgcctgt aatcccagct 3181 acttgggagg ctgaggcagg agaattgctt gaacctggga agtggaggtt gcagtgagct 3241 gagatcgtgc cactgcactc cagcctgggc aacaacaacg aaaactccgt ctcaaaaaaa 3301 aaaaaaaaaa aaaagagtca aaggatctt ggtccctggg ttgggccact gatttacgat 3361 cactaggagt tctcactcct aaatttcttt gatctgttcg cttcgctcca tctccacagc 3421 tgctgcactg gctacagcct catgatctca catcttaact ctctctgctt tctctggccc 3481 atctccccac ttccaaacca tttgtcacgc tgtaaccagt gcctaacaca caaaactaac 3541 catgtccttc ccctgcttaa agcccttagc tcctgttgct cagtggaact ggcgtctgag 3601 gctacctctc caagcctaag cgcctaagtc ctgttgcaac cctcaggccc ttcctcatta 3661 tccacaccaa actcctcagt gtctgtaaaa caagccgagc aaccctcaga attatatgcc 3721 ttcgctgctc gtttgttttg tttttaggac agggtctcac gctgtcaccc aggcaggagt 3781 gctgcagcgt gatctcagct cacagcagcc tccgtctccg gggctcaaga attctcacgc 3841 cgcagcctcc cgagtagctg ggattacagg cacgggccaa cacacccggc taattcttgt 3901 atttctagta gagacggggt ttcgccatgt tgcccagcct ggtctccaac tcctgagctc 3961 aagtaatcca cctgcctcgg cctctcaaag tgctgggatt acaggtctga gccactgcac 4021 ccagccagcc tttgctgctt ttgttcctgc aatttggaac actgtcccca tcccagcctc 4081 tcacctctac ccctacctcc ttcactacct ataccttcct atccatcctt caagacccca 4141 aaaaccatcc ctgattcctt cagaaaggca gtttattgcc tatcttatca gactgaaagc 4201 agtggctgtg tcttatttat ggttaattcc ctagaagctg gactgataca ttccatttaa 4261 ctaaaattcg tatcaggtgc ttcggactgc agacaagcct atcacaaccc agaaggaaga 4321 aacagggaag gcacctgggg gctgccaagc aatgaggtgg ggggtaggaa tcatgaatcc 4381 gcatattttt aaaaactgcc ccagatcctg atgtaaacgg tacaagagag tctgagaaac 4441 acagggctcc cctcaaacag tcctgacttc agcattcctg gaaaaatgaa aatcctttcc 4501 ttttgcctct aatgctttcc ctgctggtat cccaggttaa aaaaaaatag ataaaatcag 4561 ggggattttt ctgggacttg gctgggctgg gaaacaagcc tgggttctaa tacaggctca 4621 gcccctgacg tactatgggc ccctgcccct ccttggggcc tccattacca cggccacccc 4681 cacccttatc aattgtgtgc ccctgaggta gtgactgtcc cgctctgagc attagtttcc 4741 ccatcttcca ctagtcgtcg tcagctctga cgctctatga gctatgcata cccgtagctc 4801 cccgccgacc ccgatggtcc cctcccctcc ttcccaaggt ccatccgcca gggtgcagcc 4861 gacgcactcc taatgctaag gccgccctct catcgaccgc cccttcctgg cctcgactca 4921 gcgccaaagg tatgggtctc tgccccgcct gctctttaag cctagccggg gcggtcagcg 4981 caagcgcact gggtcgcatc gaggccccgc cccctgagcc tgggtagcgg cgcgagggcc 5041 gggagaaccg ttcgcggagg aaaggcgaac tagtaggttg gggcggccac ggcggccggc 5101 atgggtcacg tttcctcggg aggaacgatg tgagggaggg gtctggcaag agattggaat 5161 tccggaggcc gggagacctt gtggctgaaa cccttcgtag gagcggggca actagtgtct 5221 agtgaggggg ttgggctggc gcgcactgat cccagacttt ccggatcttc tgcctttaga 5281 tcgggccggt gtcggggcat gtaggccagt gagactggag ccagttagag ctacaacggg 5341 gagcgattag ggccaaactt tgtccagggt ggaagcgagc gggcccgtga agtggggcca 5401 gcctgggcag ccgaccgtgt cgttgcctcg gggcctttcc aggcactggc ctaagtcctg 5461 gcgataaagt gcgaccgatt tccttgtggg cgttttgagg ctttcggtga tctgacccgt -continued

```
5521 ctgtcattca ttcttcattc attcatgtga tgaatgaata cagtactaag cgcggctaat
5581 tactaggtag agaagtgatc aagacaaaca ctgttcctac ggtacaggga aaagtgatgg
5641 gctgtagaat gtagaagccc ggggcggaga acagggacag cttccggaac gaaatcgcga
5701 gcccagatca ggagtggtgg cgagagttcc aaagagaaga cagcacgtgc caagtcctgg
5761 aagggggaca gaggccaaca tatcctggtc actgaagaca cctgactctg aatctgtttc
5821 acgcccaggg aagagatgac agtggccggg gctaggctac aaactctgga aatggagata
5881 aataaaggaa ttcaaagtac tatatactta ggcagcaaaa tccataggat ttggggagag
5941 tgagatgtag gaaacaagta ctcaaggctt gggtacctgg gtggggttca tcagagaaga
6001 agcagatttg tgggagacaa caacaaattc tattctggtt gtatggagac tcgcaggaaa
6061 aaattggata ttctagtttg aaggtaggaa agtattgctg tgaagatgta gatttgaatg
6121 tcatcagcaa aacataaata aagccaaggg agggttgagg ctgtagaatg agaaaaacaa
6181 agggcccact tagcaccttc atctgatttc ttttctttct ttcttttttt cttttttttt
6241 ttttttgaca gagctttgct cttgttgccc aggctggagt gcaatggcac gatctcggct
6301 cactacaacc tccacctcct gggttcaagc tattctcctg cctcagcctc ccaagtagct
6361 cggattacag gcatgcgcca ccaggcccgg ctaattttgt atttttagta gagatggggt
6421 ttctccatgt tggtgaggct ggtctcgaac tcccgacctc gggtgatccg cctgcctcgg
6481 cctcacaaag tgctgggatt acacgagtga gccaccacac ctggcccatg gtgattatct
6541 ttatgtctta tcctcctcca tatccccagt acctagtcaa gggagtggca ttaaatgcaa
6601 atcagtgttt gccaactaaa taaaagccca acagcaaaca gatgttggaa tttcagagtt
6661 gtggaacgat gggggctcat ggagggtttc attactctaa tgtcaaggta atgggttctt
6721 gtcctggctc tgccactagg cttctgtgtg acctctgaca agtctcctcc tacctataaa
6781 gagagtacag ccaaaaaatg gtctcatgta tagagcttca aacactgctg ataaatttca
6841 cactgatttt tctcttttaa tccacacagc aatcttactt gaaagggaag tcggctgggc
6901 ggggtggctc acgcctgtaa tcccagcact ttgggaggcc gagagtgggg gatcacgaga
6961 tcgagaccat cctggctaac acggtgaaac cccgtctcta ctaaaaatac aaaaaattag
7021 ccgggcatgg tggcaggtgc ctgtagtccc agctactcgg gaggctgagg caggagaatg
7081 gcatgaaccc aggaggcgga gcttgcagtg agccgagatc gtgcggctgc actccagcct
7141 gggcgacaga gccagactcc gtcaaaaaaa aaaaaaaaga aagaaagagg gagggagaga
7201 gagagaaaga aagaaaaaga aggaaggaag gaaggaaaga aggagggaag ggaaagggaa
7261 agggaaaagg aaggaaggaa agaagggaaa gggagaagtc gtattattat ggactcaaac
7321 ccaggtctgt ctgtctgtct gacttgaacc ttgttcttta ctatgattgc cctcatgtat
7381 gtctcactca acagggatat tatcaggacc ctcttgagat cacatgcgca ttctttcaaa
7441 gcattgtgct gaggctggca gactttcata attggcctgg cactggctct gtcatgggga
7501 caggggggaca gagctgaatg tgatggaggt ttcctattat tctctaactc ccttcctggg
7561 gaccactgag ttgggcaacc atgttctgtt aaatggcaac agggcagaac aaaattagtg
7621 actgtgtttc cagattttta cccagatctt aaactcctga ggcctgctga aaaatgaatg
7681 agtatcaggg tgtgagtttg tacacctctg tatgtctctg ggcaaccaat cagacaactt
7741 ctcctattac attggacact tgggtttcag caatttccat cttgctaatg tgatttctca
7801 aaaatatttt ctgtcttttg gtgctttgat gataaatgtc catatatgga atgtagtcat
7861 ttcctgctac taagattcct tctggtttgt ataagggagg agttcacctt attcgcattt
7921 catggtattc cacaaagagc tccctccccc ttcccatgta atttatttga gatctgctga
```

-continued 7981 catgagttgt tggagcttga agggaattaa taatgtactg cagtgactcc tatcccagga
8041 aaacttgtta aaaatacaaa gcctcggctg ggtgtgatgg ctcacgcctg taatcccagt
8101 actttgggag gtcgaggcgt gtggatcaca aggtcagaag atcaagatca tcctggctaa
8161 cacggtgaaa ccccgtctct actaaaatac aaaaaattag ccaggcgtgg tggtgtgtgc
8221 ctgtaatccc agctactcag ggaggctgag gcgggagaat tacttgaacc caggaggcgg
8281 aggttgcagt gagccaagat cgagccactg aactccagcc taggcgactg agtgagactc
8341 catatcaaaa aaaaaaaaat acaaagcctc aacccctcct tcccatcagg cctcttgcat
8401 cagagtctct gggatggggc ccaggaatct gtattctttc ccagctcccc agaatgttca
8461 gccaggtttg gaaactgatc tatccgattc ttcttgtttc acagttaggg aatctgtagc
8521 tctgggaagg gaaggaactt gccccagtca catctgatat tagtgcttct ttctccaatg
8581 aagagccttt aggctgggag tccagagaca tgggttcaag tccaggctat accagtcatc
8641 acctcgggca agtcatttca cctctccaag cctctgcttc cttactgtga gaataatgcc
8701 attgtgttgg gaatcaaaag agagagtggc aatggaaatg ctttgtcaag ctttctattt
8761 tgtgcacatg gaagttgtta agagctagaa ccagccagtg ttcactcctg tataccacgc
8821 tgttcccttc caacagaggt cagggtcctg ctgtgttggg ggtggccgcc agccagtttc
8881 ggtggttgct gggcttcagg ccatctgtta ccaactctct tctctccatc ttttgcaggt
8941 gttgggatgg ccaccaactg ggggagcctc ttgcaggata aacagcagct agaggagctg
9001 gcacggcagg ccgtggaccg ggccctggct gagggagtat tgctgaggac ctcacaggag
9061 cccacttcct cggaggtaag cccctagctc ctccccacag cattcaccat ggcccactgt
9121 ctggccccgg ccaggctgag ggtcactcct ttgcatcagg gaccatatct cttttgcctt
9181 atttttttcca gtaactaaaa ttgatctcta gaagtagaaa ataaaaaggc agtgtcctgg
9241 agtaatcaaa tttaaatatg gggtttgaag tgtgacttag gcaaattact taaccgctct
9301 cagctgcagt ttcttcaggt gtaaaaatgg gataataata ggacctacct cactggtttg
9361 gtaagagaat tacaggatga ttcatgtgaa gcactttgcc cagtgagcta ttactgaaaa
9421 ccccataatc actctacctt ctctgtaact ggtttgtgat atatgctttc aagcctttct
9481 ctgtgcattt atatacatag ataggtatat atagaaatac gtcttttta aaaaacaaat
9541 tgtatcatat atattattct atgatatgtt tttggttttt tatttgtctg tcttagaact
9601 ttctaatgcc ttctattagg gtcatcttca ttctgaggca tagtattcca gatgtgggtg
9661 tatcacagtt tagcttccct ctactcatgt ctatttaggt gatttctcat tattttatga
9721 ccataaatag cattataggg aacatccatg catatgtctg ttggggcacc tatgtgagtg
9781 tttctccagg ttcaatacgt aaaagtagaa ctgctgagtc caaaccacac ctttttaaaa
9841 cctcatcctt agggaagaaa aaaaaataaa aaaataaaat cttttttaat ttggtgacta
9901 ggtaagacat tttcatggtt caaattcaaa tggtacaaga gtttacccta atgcagcttg
9961 tgttttggtt tcttgttgat cctttcagat ggcttattca taacaagtaa ctaataacaa
10021 gtaaatatat tccttggggc ctcgctctgt tgcccaggct ggagtgtagt ggcacaatct
10081 tggctcactg caacctccgc ctcctgggtt caagcaattc tcccacctca gcctcccaag
10141 tagctgggac tacaggcatg tgccactacg cctggctaat tttttttttt tttttggtag
10201 ggacagggtt tcaccatgtt gtccaggctg gtctcaaact cctgacttca agtgatccac
10261 tggcctctgc cccccaaaat tgctgggatt acaggtgtga accaccgtgc ccagcctcct
10321 tttgcccact ttttttttctt taacttaaca gtacacctta agaccatatt ggtgactaaa -continued 10381 gagctgccaa catctcttct ttttttagcc agacccattc ttttttgtct ctgtgtgccc 10441 agaacctaca caggcctgat ggagtccaca ctcagtaatt gtttgctaag gcccaagtaa 10501 atgacaatgt ctgtcaccta aggcaggctg atggtatgga atagaattgc ttgggctgtg 10561 aacctagatt ttgtgaatta cttgtatgaa tctaaaatga agcattttct cttccacgct 10621 tttgtttctt ctgttaatca ataggtacca tgtgaagatc caacacttgg tctttctggg 10681 aggttatgga gcctagaaaa ggcgtaatcc acaatgagat ttctaatcca gaaaaaaagt 10741 cagaaagtgt acgtgtgtgt gtatgtgtgt gtgtgtgtgt gtgtgagaga gagagagaga 10801 gaatgatttt actccaaatc tttaccaaat gcctgctcta tgccgggcca ttgtaggcac 10861 tgaggacaga gaggtgagtc agccagagcc ctagcctctg gggctcctgg tctagttaga 10921 gaacatacca caaaacaaaa ttaaataaca tcagctctat gaggaaacac aggcagtctg 10981 ctacacaaag ttaactatca tttattgagt atttagtatg tgccaggcat tattctaaac 11041 actttggaat cactgactcc tcaccacaac agagataagg aaaccgaagc ccagagaggc 11101 taagtaacct acctgaggtt atttaaatgg taaaataatt ggcagagcca ggatgtgaac 11161 ccaaggaatt tggctcctga gtccatgctc tgaacatcca tgcttttttt cctctcccaa 11221 gatactatat aggacagctg gaagaaagag tagttcatta tgattagatg attgagatgg 11281 ggggtggtat ttgaactaga ccttaaaaga caaataggga aaaggaacag catagcaagg 11341 acccaaaagt aggaaaaggc aaaaaaaaaa aaaaatgttc aagagaatgc agctgaaatg 11401 cagggcgcat aagtggatat agtgggaaag aaggcaggcc agcgtcagac agccgcgggg 11461 ccttagctac tgggtggagg aggagtatga actttatcct gtagatcaga gctgcaaact 11521 agccatatct aggctgagta tttggctcct gcagtgtttg gggagttaat ttgtttttta 11581 caataagtaa tacgttcaaa tacatttgaa cagggcgcaa aattcaaaag ggtattcagt 11641 acagagtaag tccccttcct ccagccactg tttccctgac caggggcaag cattgttaac 11701 agttgttttc accagagtat ttttaaaaag tcagagccaa catttaaaaa aaaaaatcat 11761 gaaattaaaa caaaaaatct agcaacccaa cttgtcttga aaaattatat catctggcaa 11821 ctctggccta ctttcctgca tggcaacaat tggctagagc agagttctgg ctgcccccttt 11881 tagagaagat gcaagtactt ctttttgcca caattcctat cactccctgt tgcttcctgg 11941 ctacaaagca gaattttgtc atgcacgtgc tataggtttt tttaaatagt agaaaaatgt 12001 ttcttttttt ttttttgaga cagagtctca ctctgtcgcc aggctggagt gcagtggcac 12061 gatctcagct cactgcaacc tctgcctcct gggttcaagc gattctcctg cctcagcctc 12121 cagagcagct gggactacgg gtgtgtgcca ccacgcccag ctaatttttg tatttttagt 12181 agagatgggg tttcaccatg ttggccagga tggtctcgat ctcttgatct tgtgatctgc 12241 ccgcctcggc ctcccaaagt gctgggatta caggcatgag ccaccgtgcc cggccagtaa 12301 tgtcatttta tgttaatgtc tctatcaaaa gtgagaagac tgtgtgtttc agcctttagc 12361 ctgtagatag cagagaacag ctataaacta ttgatcctaa attcaggagg gcataatgag 12421 ccctgggaca gaggcagagg gatgtcttag cagaaaaact ctgagttttt gaggccaaga 12481 tgagacttgt tgggggcagc agagctctat gtgttcaagc caaggaaatg ctcctgtagt 12541 catcacatag ctactcaggg tattaggtca ccccttatgt aatctgcagt cattcccatt 12601 ctaactcata aaggcttcag actgaataaa ccttattctc acaaatagcc ttcctcagtt 12661 ttatcttaga tgctgaggcc agggcagtgg tacacacctg cagtctcagc tactggggag 12721 gctgagacag gaggattgct tgagcccagg aatttgaggc tatagtgcac tatgatggca 12781 cctatgaata gccactgtat tccagtctgg gcaacatagt aagaccccac tccaaaaaaa -continued 12841 aaaaaaaaag atgctgagaa gggtaattta gaaattatct accaaaattt aaaatagatt 12901 tacctgaatt acttgatatt tttactttta gaaatttaga atgtatggac tttctcatat 12961 atgaaaatat ctagaatgta tattctagga tacccattga aacattaatg gtaataggaa 13021 aataaagaaa ccacctatat actagattca ataaattatg gtatatccta agagtagaat 13081 aatatacagc aattaaaaat aatgaaaatg ctctatttga acatataagg aaatatttaa 13141 aaagcacaat gtagtatagt ttgctatggg ggtgaaaaaa agagaaaata tatgtgtata 13201 catatatatc aatacaaaga tgactggaag gatgtgtgag acactagtct gtcatttgcc 13261 tctggggagg agaactgggt ggctggggcc cagtcttttc cccaggagac tggaatgaga 13321 gtgagacata cttctcacta tatattctta tgtctctttt gaattttgta tcatgtattt 13381 gtattacctg ttaaaaaaat aataatattt tggctgggca tggtggctca tgcctgtaat 13441 cccaacactt tgggaggctg aggcaggcag atcacttgag gccaggtgtt tgagaccagc 13501 ctggacaaca cagtgaaacc ccatctctac taaaaataca aaaattacct gggtgtggtg 13561 gcacacacct gtagtctcag ctacttggga ggctgaggca ggagaattgc ttgaacccag 13621 gagatggagg ttgcagtgag ccgagattgt accactgcac tccagcctgg gcaacagagt 13681 gagactctac ctcaaaaaaa aaaatagtac tttaaaaata aatatctaaa taccaagttc 13741 taacaccgta aacttatacc accataatga caaactgata ttaactcaaa ggttaaactc 13801 aggaatgctt tataatacaa gtcacaagat tttcttttca tctcttaccc aagttctagt 13861 tcagttgttg gcagggatct cagaatgcac ttttcccttc tagaatcagt gtccttgatg 13921 gtatttgggt ttctcgtcta tgataaagtc caaagaatgc ggaatgcagc tgaactctag 13981 gcctgttaac ctgagtcacc atcactaaca ttggtggaaa aaacactcct ggcttctact 14041 aagggaacca gagttcactt gtcctaccca gtaaccaaat caaaatcaaa aggcaaggaa 14101 actggagtgt gagctcctga tgcatggaag ggcctgggct tgaacatcaa ccagcaagga 14161 gcaggcttcc atgtatgtat gtgtgtgttg tgtttagtaa ccatcctggt tcaaatccca 14221 gcaccccgtt actagctgaa tataattttg gatctgttaa ctgttctggt tcaaatccca 14281 gcaccagttc ctagctgaat ataattttgg atctgttaac ctctctttct caggtcccgt 14341 ctctgttaag tgtggataat aatagtatct tcctcacagg gctgaatgat gaatctatgt 14401 aaagtattta aaatagtacc ttgcacatag taagtgctca ataacttgtg ggtttctttt 14461 tgttatttgc attttgcttt tttgcttctc tctcttcaat acgtagagat aaactatcac 14521 agaatctgga agctctctgg gttccactct ccccccttcca ctctcccaag gtaaccacta 14581 atctacagtt ggtgtgtcct cagtaaatat aggccagact ttccatggga ttccatttgc 14641 aggaagacaa cccgttcaca ggtgccctac ccctgtccca ttctctcttc ttgatcacag 14701 gtggtgagct atgccccatt cacgctcttc ccctcactgg tccccagtgc cctgctggag 14761 caagcctatg ctgtgcagat ggacttcaac ctgctagtgg atgctgtcag ccagaacgct 14821 gccttcctgg agcaaactct ttccaggtag gggacagtga agcattgggg ggccaggagc 14881 tgccagagcc aaggaactgg aagattgcag agccgtgagg tgttactgtg tcagctgact 14941 tggtgggata gaggaaaggt acctccaaag aacaaaaagt cataggagtc aggaaagctg 15001 gcttctaatc ctggctcgac cagttattta tatggcctca agccactccc tttccttctc 15061 tgggcctaag gtttcttcat ctgaaaaatg aagagactgg cttaaatcca agatcccttt 15121 attgttgaca ttctgtaatc cgtgacaccc tactttgaag actgatattt ccatttggaa 15181 ttaggggaag tcagcctggt tttggaggaa aacagaggta gggaaggtta ttgggttaaa -continued 15241 gtcagatttt ctacttctcc taagcagcga cactttcttg tcacctcagg cctctcatct
15301 ttggatggga tggggtacag actgggccac actcagggca tgaggaagca acctctgaaa
15361 tggttcagcc catccgccct tctctgtctc tttcccttga tctttttttt tttttcttca
15421 gattctgggg caatttctta aaatttcttt atttatttta gaattaaata tatataggct
15481 gggcgcggtg gctcaggcct gtaatcccag cactttggga ggccgaggtg ggtggatcac
15541 ttaaggtcag gagtttgaga ccagcctggc caacatggtg aaaccccgtc tctactaaaa
15601 atataaaaaa attagctggg tgtggtggcg ggtgcctata atcccagcta cttgggaggc
15661 tgaggcagga gaatcgcttg aacccaggag gcagaggctg cagtaagcca agatcacgac
15721 actgtactcc agcctgggcg acagagcgag actccatctc aaaaaaaaag aaataataat
15781 acatatatat atgtatatat attcattgta gaattaaata tctagaaata ttatgtattt
15841 acatatacat gctagatgtg tatatactgt acaggttgag catccctaat ccaaaaatcc
15901 aaaagctgaa atgctccaaa attcaaaact tgttgaacac cacatgactc taccagtgga
15961 aaacgccacg cctgatgtca tgtgacaggt gcagtcaaaa cacagtcaaa agtttgtttc
16021 atgcacaaaa ttaattaaaa tattgtataa aataatcttc aggctatgag tataaggtgt
16081 atatgaaaca aatgaatttt gtgtttagac ttgagtccca tccccaagat gtctcattac
16141 gtatatgcaa atcttccaaa atccgaaaga cttctggtcc caagcatttc ggataaggga
16201 tatccaacct gtaattgcat gtctttgatt aatttttcaa cagaaattag acttttgttg
16261 gagacaaaat cttttaaaaa tgtgtgggtg aatatgagaa ggggtcataa tggtaagaag
16321 cttggaaacc attgacttgt agccaaaaac ccaatgagtc atgaatgtat gaatctgccc
16381 accaccttgc ccctgagctg tttcttggaa tgggcccagc tttgtacctg caatcctgga
16441 ttgtgggaaa catgagcagc ctggcttata accctaatga tgcaattatg aaggagactt
16501 gcagctcatc tttgcaaccc ctgccttctc tgttcctctc tcctctcata cacatataaa
16561 ccctagttcc taagggagaa gagcccccta caaaacatga aggggagcac ctcttcagaa
16621 aaaggaaagt gtgtctcaac ttccttggag gctgaagccc agctgggact ctcctcctaa
16681 ccaagggctg gcatgagaga gctcaccctt gggagagagc tggctgagga gcagaggaac
16741 ttcagggcag gcctgggcta cttggcttcc ccccactggt ctgctgtgac gtttctgtaa
16801 caaggtgatt caggcttgag caggtgtgca gaatccaccc tgaatctcaa agggcagtaa
16861 gtgtgatgtt aatcacctgt ggattccttc ttactgtggc tcttgttgag acttcagaaa
16921 accatactgg ataggcccct aacacatgtc acatgtcatg gcagtacact gagctgtgac
16981 gatgagcctg catagacaca gccattacct tcatgaggtt tatagtcaaa caggagagat
17041 gacactaatc atcacacaaa gaaaatgtaa aattgcaact gcagtcagtg ctgtaaagga
17101 gtggttctta gttctatgag aacacatagt agggggatct gactcagata gggaaggctt
17161 ccctgaggaa atcacatcat atgaggacta gttgaagaag aaacaaacaa acaaaaaaaa
17221 cccaggatat ttagcttggg tcagaaaaat cttattggtg cacagggcat aactgctgtc
17281 ttctaatctc caagggctgc tgtggaggag gaggagaagg ctcaccctgg gaggtcgcag
17341 agggtaggaa aagctatgga gagttagtat taggtcaacc agaaggcttg ccaaccatca
17401 gagctattca agtagaatag atacatcatg tcattttcta gctcttcttc ggtgcagtat
17461 gttcaattct ttgaatgtaa tatcttattg gctttttacc acaactctat gatataaata
17521 taattatatt ctccatttta aagatcagca aactgagaca cagagaggtg aaatgattcc
17581 ctgaggttgc ctactagtga gtggtagagc taggatttga acccaggtct agagttggat
17641 tcttagccac tgttctctac cacattgggg cggacattca agttttggcc agtagactca -continued 17701 gagaggattc aggagtcaat gactgaggat gggactcctt gaaattttag gtccaattaa 17761 gcctgcaaaa tgttctctgt ttcttcctcc agcaccatca aacaggatga ctttaccgct 17821 cgtctctttg acatccacaa gcaagtccta aaagagggca ttgcccaggt aaccattccc 17881 agccctactc cagtctgtaa cctgtccctc ccatctctgt ttgttttctg ttttgcttga 17941 agaatttggt ccaggccctc agctcatggg aatctgcctc tcactggtcc tcactgggtt 18001 tatcccagtg accaattcta ggatgaccag aagaatgatt ccactgggct tgggagtgtt 18061 tgctggtacc tctaatctct gtgtagagtt catggtacct gtgtgctctg tggctaggtc 18121 ctcagagtca gtccctgggc aggtactgtc agccttcagt tttccccaca gactgtgttc 18181 ctgggcctga atcgctcaga ctacatgttc cagcgcagcg cagatggctc cccagccctg 18241 aaacagatcg aaatcaacac catctctgcc agctttgggg gcctggcctc ccggacccca 18301 gctgtgcacc ggtgggtccc ctgggcagcc cccggcatac ctgtggggtg acatgctgat 18361 gggtgtacag tcactggcta ggccagggaa ctccagctat gattgtgctt tcctgggccc 18421 cgggtcacat gttgcccctg gccaccccga cagcagtttc cacttgtaat gagatccttg 18481 gtatgtcagg gagaaaaagg acctcatagc tcatctagtc ctgtccctcc attgtacagg 18541 cagagggaac aatatcttga gagccccaga gagaggaatg cagggacttc tgtctggggg 18601 ctgggcctgg tagcatccat ttctagccag cagtgatgct ccaggttgca atgattttag 18661 atggtctgca gcaggattcc agacagcacc tggaggccca gagtaagggg ctccagctca 18721 ctgggacact agggtaggtt ggggtgggga cagaggctct caggtctcct ccaggcatat 18781 acaccagggg ccaaggttag ggcagcccag catattccaa cctgaagtgg atcttacagg 18841 aatgtgatgg gaggatgctt tttagtgctc agctgattct cagagtcatg ttgctgtata 18901 tatgaggtca tgggcagagg ggtcttccag gtccatccaa ttactgaaca gccatctctc 18961 ttccaacaga catgttctca gtgtcctgag taagaccaaa gaagctggca agatcctctc 19021 taataatccc agcaagggac tggccctggg aattgccaaa gcctgggagc tctacggctc 19081 acccaagtaa gggtgtgaaa aggtagcagg aggatcctgc tttagtttca gcattcatgg 19141 gtttagcaac ttcttttctt gccagccatc attagagaat aaggggattt ttctaggaat 19201 agaaacttat acctttacat gccaaaatta ttttaaggtt tccttcttaa ataacagatg 19261 ctgactatga tttaactttt tcttattgag tggaggtcat cattatgact gtcaacaatt 19321 gcagcttgct gtaatacagt agtgctacct agggttagag aggcacgcaa ggctgtttgc 19381 ctgcgctaat agctctgact gctaggcttt aagttcttag tcatttcctt tttttttttt 19441 ttttgagaca gagtctcact ctctcaccca ggctggagtg cagtggtaca atcttggctt 19501 acttcaacct ccacctcccg ggttcaagca attcttctgc ctcagcctcc tgagtagctg 19561 ggatttcagg cgcatgctgc cacacctggc taatttttgt atttttagta gagacggggt 19621 ttcaccatgt tggtcatgct ggtctcgaac tcctgacctc gtgatccgcc caccttggcc 19681 tcccaaagtg ctgggattac aggcatgagc cactgcaccc ggcctctcat tcattttctt 19741 catagttttc ttgtctgttt cccaattctc agctcttact tttgactgct gttggtatgc 19801 ttgaatttgg aatcctccac cccccatgcc catgcctccc ttctgatttg ctgtggtttg 19861 ggaaaacaaa tgatccagat tgttatgatt gggtctgaag agtgtgaggg cctcttggat 19921 gagtaaatgc ataagctttg actacgaaat tttatggtat ccttttttaac tgcttagagg 19981 catttttttgc tttcttccta tttctcaagt gaagatgtta ggtaagtgat tttcagatca 20041 tcgaggggcc gctatactaa cagttattgc aatgttaata tagcattaat agtccttaat -continued

```
20101 gtacacttac tagtgctaca ccttgtgcta agctctgtac atacaggatc tcattgaatt
20161 ctcataataa gctctctgag gtcaatactg ttcaactccc tcattttaca gatgaggaaa
20221 ctgaggttct gagaaacgaa gtgaattgtt aaggctaagt gatgagttgg tggcagatcc
20281 caaagtctac ctccctctaa aacctccact cttaatcatg ctcttacctc caagggagcc
20341 tctctgtcct tgctaagcct cactaagccc aaagaaacct cagactgtaa gcatttagaa
20401 gtcatcagac aaatattctt tcaagtatat tggctaggtt gtattttaag agagtgaagc
20461 caggggatgg gtcagctggg gaactgctga cagacaaatg ctgcagaggg ttttgcctgc
20521 cagcctgtca gtaacgtgga cagaaaatac ttgtgtgtcc aaaattaggc actggtaggt
20581 aggagttatg tggcacctga gccagaactg gcttccccca ttgtgagagt gagataggtt
20641 cttctgctga catagcacat gaccttggca agttagttct tctctgagct tcagtttcct
20701 catttgtaaa ataggagtaa taataatacc taaaggggtg ttagtgagaa ttaaatgaga
20761 tcatggatct gaaaaatgtt tttaaaaatc tgtgtggatc attatgtggt actttcaata
20821 ataataatag gccgggtgca gtggctcaca cctctaatcc cagcactttg ggagaccgag
20881 gcgggtggat catcagaggt caggagttca aggccagcct ggccaacatg gtgaaacctt
20941 gtctctacta aaaaatacaa aaattagcca ggcatggtgg caggcacctg tagtcccagc
21001 tacttgggat gctgaggcag gagaatcact tgaacccggg aggtggaagt tgcagtggcc
21061 aagatcaccc cactgcactc cagcctgggc gacagagcga gactccatct caaaaaaaaa
21121 aaaaacaaaa aacaaaccca aataataata ataatagcta tcatttgaca agtattagtt
21181 ttaattcata caacagcaaa ctgaggctaa gagagtttga ataacttgcc caaagttaca
21241 caaccggtaa gtatagaatt catctgcctc taaagcctat gttctctcta cttccctatt
21301 ctgcctttaa gagatatggt tccacagtat tgactgaaaa actgcattgg tagagcagat
21361 taattttcgt caattatctc atgattttta aaatttctta aaaatggaag cctgcaaaat
21421 gacttacaat ttcaatttag acaaactctc aaagcatagg gcctgtggtt agaatgagta
21481 gaataagaaa aggggactac tggtgataaa agtttgggaa ctgtgatctt tttaacacca
21541 atttttttct ttttttttga gacagagttt cgtttttgtt gcccaggctg gagtgcaatg
21601 gcacgatctc ggctcactac atcctccacc ttccaggttc aagggatttt cctgccttag
21661 cctcccaagt aactgggatt acaggtgccc accaccacgc ctggctaatt ttgtattttt
21721 agtagaaacg gggtttctcc atgttggtca ggctggtctc aaactcccga cctcaggcaa
21781 tccgcccgcc tcggcctctt aaagtgctgg gactataggc gtgagctacc atgcccagcc
21841 ataacactct tattttatag atgggaaaac cagggcccaa ggaacgaaat tgccttaccc
21901 aagtcaatta ccaagacaca ctacaagtca ctggcagagc ctggactacc tacgactcag
21961 gggtcctcac ccccagcccg catgcgtcct tagctgacaa ctttcctact aggaaacaga
22021 ctgctgagaa ctgctcagaa ctgaaggcag gagaggtcaa atatgttttc tgagcccagc
22081 tctgattgtt tagcagttgg caggctgact taattagctg gggcgtgcag ttcctcttta
22141 acctccagct gccagccttc ctcctccgcc tctttttgga ggtgggccag cctgggccaa
22201 ctgcctccct cccacacaca ccctcaccca tgagcgggac agtttaggct gcaaagtgaa
22261 gagcaaagcc attggccctt aggactctct cagggcaaga tgacttgtga gagcaccact
22321 tttagtttgt ctctcaggca cccaactcaa agccaagact cagcttaaca tcacatctga
22381 cctcatgaga tttcaggcaa accaggagag gggacttact aagacctata ttttggctaa
22441 gcagaaagga gtcaggcaaa cagagtttag actaagaggt tcagccaagg tcaggagaag
22501 cagagataga caagagaggc taagcagagg aggtcaggga atacacactt agaatcctaa
```

-continued

```
22561 gccaaagcct agggttccat gggtctcagg aagaagccac agacacaaag cagtacagtc
22621 acagcaaaaa tggagtttgg aggctgagcg cagtggctca cacctgtaat gctaacactt
22681 tgggaggccg aggcgggcag atcacctgag gtcaggagtt cgagcccagc ctggccaaca
22741 tggtgaaacc ccatctctac tcaaactaca aaaattagcc ggcgggggtg gtgcacacct
22801 gaaatcccag ctacccggga ggctgaagca ggagaatcgc tggaacccag gggtggaggg
22861 ttgcagtgag cctagattgt gccactgcac tccagcctgg gcaacagggg gagactccgt
22921 ctcaaaaaaa taaataaaat aaaatgtaaa agaaaaaaaa tgcagtttgg tactgctgag
22981 cattagccct aggaatctct taggggactg gacctatctt tgacaacgga aatatgttag
23041 ctggcagcca aacagatagt tccctggcat aagcttttcc ctgagccctc aagcccctgc
23101 ctctttaaga aatacatgaa taatcagaga ggaagaagcc acataagccc tagtgatctc
23161 attaatacta tgagatcaaa tgtggccctg tgtacattat aggaatcttg ggagggccca
23221 ggagataatg tcgttgtttg tagttggccc tgtgggtttc tgtagggttc catcttgtgt
23281 aagaaccaca ttcctttatt gtatccttta caatctagta atagagccat tagccccgga
23341 ccccctgcat tgttctttta caaaatgttc ctcaatactc ccacttgttt attcttccag
23401 aaagatttta gaattatgtt aagttctaag aaaaagtcct cttgggtttt tgagatggtt
23461 ttaaatctaa attttaattt gcacagaaat tcatcaaccc atgacatcat tacaatattt
23521 catctgccca ctggagaagg gtcagaggca tcttcatttt tgaagttttc tattttcagg
23581 aaatcatatg tgatagcatc aggtgtctat gcctgaggta atctcaaggt tcctgagaga
23641 gggaacatct gttctttcag ggaagcggtg ttcttattct tattccagga ggtggggcgg
23701 tatgggggtt gaggggagaa acaaaagaag aacaagttct atagtagcct cgggccacct
23761 gtgctctttc cccagtgctc tggtgctact gattgctcaa gagaaggaaa gaaacatatt
23821 tgaccagcgt gccatagaga atgagctact ggccaggtaa gtaaaggaag ggggacttct
23881 aggtgtggct ccaggattag gggtggggca ctcagaacat agcatccatt ccctctggct
23941 cttgcccatt tttcccagga acatccatgt gatccgacga acatttgaag atatctctga
24001 aaaggggtct ctggaccaag accgaaggct gtttgtgtaa gcattcccaa gaatccagtg
24061 gaaggctggt ttatgaaact catcctgcca ccctcttccc caaaatgatt ctttcttctg
24121 ggagatgtga tggcttgctt ccttctctca taattcctga aatatctcat cctcccagga
24181 aattttggag aaagccagcc acgctgtgct tctatcagag ctgttgacat tctggatcag
24241 ggtctcctta gagatcatct tagttttcat atgccctaag ttcccaaaag ttttcttgcc
24301 tctcctagta aggtgaggtc aggcctgaga agctgagctg ggcagtcagg gaggaagagg
24361 agcagctggc tcatgctgtg attggtctgg atgccactgt ctgagctcga gcctggattt
24421 gtgttccaag ccaagcctta tccttttctc taggggccac caccaggtag atttggtgct
24481 acatatttgg gtagcattgc agcacatata tttagaccta gacctttgtg attgttaaaa
24541 ttaaaactgt ccatggaatt tcacaatacc actcactgtt tttcaaaatg tgcttttatc
24601 ataactaaac aaagtagtta atttactttt cagataaact agacaatatc aaataggtca
24661 aagaaaagga aaagacattt aaaaagcctg tgtcttaatc agactcatca ttttacatgt
24721 ttgcgttttc accttcaccc ctgccattaa aaattttttc attctggttt cagctgcttt
24781 aagcagtgga aatataaagt gtgttttact acacatggca gtatgattct gctgctcggt
24841 aatttcgagc caacatttgt atgcatttac caaatttgat tctagtgacc ttcttgttcc
24901 ttctggcctt cttagaatga ctctaaatct ggcatattct aaagtattct gtatggcaca
```

-continued 24961 cctccctgtt ttcagtggaa gccctggtag tgtggatatc tactttcact ggttccagtg 25021 aacccctgac caggctccca ctgtgggctg aattttgaaa aagccaaatt catcttgatg 25081 caccctgaaa tagattgaac cactgaacaa atcagttata atttaacaca gcagccttct 25141 ccatcctgtg ttccagggat ggccaggaaa ttgctgtggt ttacttccgg gatggctaca 25201 tgcctcgtca gtacagtcta caggttggta ttttctgtga gaccattctt tgcctcctgg 25261 gacccacaag agctccacag agacccaatt caggcttata acaacctggg ttttccgagt 25321 cctcacttca cttctttctc agggagcttg ctgctagaac ctcctatcct ccctcaagcc 25381 ttttgctacc tatcactcta cacagtcttc tagaatttga atcctcagga atccacagag 25441 cttcagccat ttacactgtt tccagagatg tgctggcaaa tgtttaacaa caatcagctc 25501 tcactggttg atataagcca gttccagcat actgctgacc attttttttc ctgccaactc 25561 ttacctttcc tttatctgaa tcagaaagtt ttatcatctc ctcattcatg ttaatgacag 25621 ttatatcacc tcattttgct atcctaccat gtagtttcat tagtttccac atccattatt 25681 tcatttaacc ctcacaacca ctcggtgagg catataatta tccccattat acagatggag 25741 aaactaacgt ttagagagat ggagaggctt ctctaaggcc ctacaggaag ttcccaggtt 25801 ttctgacttt caggccgatg gtattcccat tcttctcctc tgctcctaac atccacatca 25861 tggagaggct aagaagctct gctctcagct gggagatgat aaaggaggaa ataagtttag 25921 aaataccatg ggcagtgagc tggaggtcat gagcttgact gcctctgtgt gatgatgggc 25981 aagttcctga ccctttctag gtctgtttct atgagcgggg ggagctacac tagaaaactg 26041 agggggctcc ttctaggtct gtaattcatc taggactccc cccgagggtt gagctccaca 26101 tgaggaggct ctatagaggt ggtatctcga tagaacatcc ttttctttag ataggtggtt 26161 agcagtggtg gcaacttgct gactacagga gagataaact gtctattaga aaaataggtc 26221 taggccgggc acggtggttc acgcctataa tcccagcact ttgggaggcc aaggcaggtg 26281 gattacctga ggtcaggagt tcaagaccag cctggccaac atggtgaaac cccgtctcta 26341 ctaaaaatac aaaaattagc cgggcgtggt ggcatacccc tgtaatccca gctactcagg 26401 acgctgaggc aggagaattg cttgagcccg ggaggcagag gttgcagtaa gttgagatca 26461 tgccactgca ctccagcctg gctgacagag cgagactctg tctcaaaaaa aaaaaaaaga 26521 aatgggtcta gatttcaaaa cacgacaaag aaaacttaga agagtttgag ataacaagga 26581 aggaaagtag tgtttaaaga ggtagacttt tttttttttt tgagacagag ttttgctctt 26641 gttgaccagg ctggagtaca gtggtgcgat ctcggctcac tgcaaccttt gacttccagt 26701 ttcaagcgat tctcctgcct cggcctcctg agtagctggg attacaggca cccaccacca 26761 cacccagcta atttttgtat ttttaataga gacagggttt caccatgttg gccaggctgg 26821 tctcgaactc ctgaccttac gatccaccca ccttggcctc ccaaagtgct gggattacag 26881 gtgttagcca ccacacctgg ccaagaggta gacattttta gggaactgag cagctcagag 26941 caggtttaga catggagaga gatctagaag gcttagtgac ttactagatg accctgggca 27001 agtccttgct tatctttggt tttgctttcc tgcttctacc ataatggggt atttctctgg 27061 gtttatttct gatgttctgg tcacgtgtga ttctgcgtgg aatgccagac tagtagttgg 27121 gttcctgggg ttattgatga agatcaggtc aaggtgctac aggtggacca gtagtatcaa 27181 aggaaggaca gcattgggtg ggggtcacag gagagacctg atcctgctgt gtgcagtttg 27241 cagtggtctg gagccaagga cagactgtct ccccattgca tgagaatggg aaccagagtt 27301 gggaggcatg atcccctgct gtttccttgc cttttatacc ctcagctctt gtggtaataa 27361 accattcatc ctgtgatcat ccacttgaga cctgtgttca tattattctc ttagcctgag -continued 27421 tatcccttcc ctattgagtc tcacttgtca ggctctacct gtccttcaga accccactca 27481 aatttcaact tattcagcaa caacaacaaa tatttattga gcaactacaa agtgccagga 27541 actgtgttag acactggaga tacaacagaa aatgaggaaa atgataagag ccctgtgcta 27601 tggagctcac agtctggtca gagaaatggg catcagaaag taaacaaaaa tatggccatt 27661 tactgtggct cgtacctgta atcccagcac tttgggaggc ctaggtaggt ggattgcatg 27721 agctcaggag ttcaagacca gcctgggcaa catggcaaaa ccccatctct acaaataata 27781 caaaaattag ctgggtgtgg tggcgtgcac ctgtagtccc agctacttgg gaggctgagg 27841 agggaggatc acttgagccc aggaggtaga agttgcagtg agccaagatt gcgctgttgc 27901 actccagtct gggtgacaga gcaagaccca cgtctcaaaa gaaaaaaaaa gtaaacaaaa 27961 ataggaaaaa aaaattggga tttgtgtgtg tatgtttgtg tgcgtgtgcg tgtatgtgtg 28021 catgtgtgtg ttttagtctc aggtaactgc tttcaatgaa acaactgggt aaaaagagaa 28081 ttatgggaaa tccacattaa atagagtgga cagggaagcc ttctctgaaa aggtgacatt 28141 gagctgagat gtaaggatgg taaggatcca gctatgcatg ggaaaagccg aaaggaaggg 28201 ggtttcaggt tgagggaaaa gcagtgcagg ccctgaggag ggaaagagct ttgtgatttg 28261 aggaatgaca ggcctgtgtg agtagaatgg cagagactag gagtcaggga tggtacaagg 28321 ttgaaaaagt agacaggagc cagctcctga aggatcttga aggccatggt agggagtatg 28381 gaacacagtg ggaagctgag cacgtagaca aatgttctac ccttacacct tctattgttt 28441 cccacagatt gggggattct tgcctttgca ggggctcaca gtctggcaca atgatacata 28501 actacaacat atcacacctg gctcacaagg atgttagaat gatcctgggt gataatgagg 28561 gtgaagatac aaatcatgat acctggcacc taatggatgg atgttcagta aacgtcagct 28621 gaagtaaaat aaagtcgaat tccttttgtc ttcttccctc tgcagaattg ggaagcacgt 28681 ctactgctgg agaggtcaca tgctgccaag tgcccagaca ttgccaccca gctggctggg 28741 actaagaagg tgcagcagga gctaagcagg ccgggcatgc tggagatgtt gctccctggc 28801 cagcctgagg ctgtggcccg cctccgcgcc acctttgctg gcctctactc actggatgtg 28861 gtacgtgggc agcctgtttc tcctaccaca ggcctcctag gtggcagaga cctacagccc 28921 aatgtgttgg ggagggtgga gctggcattg tgacaagggg aaggtggagc tggcaaggtt 28981 ggtgatgctc tggagaaccc ctagaactct gagcagaagg gcagcctcat aatggaagga 29041 tgggggctgg aatccattgt aagctccctc agcaaaggta gagatgagga tggcaaccag 29101 agggaaggga ctaaggcagg tggcaagaat tgagaagtgt atcaggctgc ctgctgcaga 29161 gccctgagct gttgctaaag aaaggcctgt tctcattgca tcggctgctg caggggggttt 29221 gttgggagtg tcatccagat agtagcatcc tgcctgaagg aatttgtggc tgttctccct 29281 cctgctcttc ctctgatgct gctctgcata accagctgga cctaagcttc ttgcctcttt 29341 agcctttaaa cttttgataa ctgctttctg cctcctgcca gggtgaagaa ggggaccagg 29401 ccatcgccga ggcccttgct gcccctagcc ggtttgtgct aaagccccag agagagggtg 29461 gaggtaggtg gatctccctt tgcagggctc ctcaatgaga gggactagca ggctgtggcc 29521 agtgctcatt ggcacttact ctgggcacag tcccgggcat gggggaaact attggaactg 29581 acacaggcca catgttggac agtgtcccct aagaccctgt gaccaagtcc gggagcacag 29641 gggaatctga ttaaccagca ttgaagggtt tggacaagtt ttacctgagg tgcctgtggg 29701 tagattgttg ggaagtagag tagggtcata ttaggagact ggagagaata catgtctgtt 29761 ttcctttcta gtttgaaact ccttgaggtc aggggtcatg tctgcctctc cagaggagag -continued

```
29821 gatttttta atctttgtct taagaggtgg gtaggaattt cccaggtgga aaggaggaag
29881 agtgttccat acaaaaggga caacctcaag ccaaggcacc gggccatgaa agtgtgagat
29941 gtttggaggt taatgagaaa ctggtgaggc tggaggggga gctgggaggg gacagggatt
30001 taggctggaa aaatggtttg catcctgatt ataaagggcc ttgaatatat actgagaaat
30061 tggattttat cttaagggca gtgggaagcc attagggagt tttaagccag gaagggacac
30121 attgatccag gactcaagtg gttagcagtg gtgggaactt gcaaaactta cagtttctgc
30181 attgtagaag atgtcctgga atgaggggag acactggaag cagaaagacc gtggaagagg
30241 ctgatacagt tgttcagaag agcaacgtag aggcctgggc tagggctatg actatggggc
30301 caactggaga gacatgtcct agatagtgag agggtagtgg aagggaggag ttaaatatga
30361 ctcaggggta ccttttgcct gattgggagt aggaaggtcc aggaggggca ggttcaggca
30421 gaagtaataa gttctgcttg gacaagttga gtttgtttgg gggccagtca tatgatgtct
30481 aagcagggag cctgcattaa atatttggaa gttaacaatt tttttttttt ttttgagacg
30541 gattctcgct ctgtcaccag gctggagtgc agtggcatga tcttggctca ctgcaaccac
30601 tgcctcccag gttcaagcga ttctcctgcc tcagcctcct gagtagctgg gactacaggt
30661 gtgcgccacc acacccagct aatttttgta tttttagtag agatggggtt tcatcatatt
30721 ggccaggatg gtctcaatct cttgacctca tgatctgcct gcctcggcct cccaaagtgc
30781 tgggattaca ggcgtgagcc accatgcccg gccggaagtt aacaattttt agggtataga
30841 tggagactca ggaataggag agatctcctt gggaaaatgt acatggggga gagagcaagc
30901 gtggaggacc aattcccctg ggaccccagc atttaagaga aggagccagc aatggagctt
30961 gagaaggaac agctgtaggt aggaggagaa ccagggcaga acagtgtagt ggaagatgtg
31021 ttcactgcat gagtaagggc tctcctgtca aagtgagctt ccctcctgag aagccagata
31081 tgccctggct tcactgagcg ggtgccagga actgaggctg ctgacttgcc catgtggccc
31141 caaaagtgag ggcatgggat ggaggaggta ggcagagggt ccagggtgac tggccagttt
31201 cattgcaggt aacaacctat atggggagga aatggtacag gccctgaaac agctgaagga
31261 cagtgaggag agggcctcct acatcctcat ggagaagatc gaacctgagc cttttgagaa
31321 ttgcctgcta cggcctggca gccctgcccg agtggtccag tgcatttcag agctgggcat
31381 ctttggggtc tatgtcaggt gagccaatca ggagaagctc tttccactac ctgcttgcaa
31441 gagtgccagc caagtgagcc agcctagagg ggaacactgg aaagagtcag gaatcctggg
31501 cttcggtgcc agctctgcca atcactagct ttattacctg tttctttatc tattaaatga
31561 ggccaaggac ccaagacctg cccaccttac cagggtatca gatgaagccc tgatgagaag
31621 tcctttgcaa ccgtgaagga aactccaaat agcaccaaga ggactcagaa cacatggttt
31681 gacaacctag gactagaagg agactccaga gaggcataga gactctaaaa tcctagcact
31741 ttcttggtat agacagttac ccaggtactg ctcagctggg tccagggaag gtcctgggtt
31801 tggggctgag tccaggtgat gtgtgtcccc tgcctccatt tctataggca ggaaaagaca
31861 ctcgtgatga acaagcacgt ggggcatcta cttcgaacca aagccatcga gcatgcagat
31921 ggtggtgtgg cagcgggagt ggcagtcctg gacaacccat accctgtgtg agggcacaac
31981 caggccacgg gaccttctat cctctgtatt tgtcattcct ctcctagccc tcctgagggg
32041 tatcctccta aagacctcca aagtttttat ggaagggtaa atactggtac cttcccccag
32101 ctttccatct gaggaccaga aaagttgtgt ctcccttaga tgagatctag acgcccccaa
32161 atccttgaga tgtgggtata gctcagggta agctgctctg aggtaaaggt ccatgaaccc
32221 tgccccactc ctgtcagccc ctcatcagcc ttttcagcag gttccagtgc ctgacttggg
```

-continued 32281 ataggactga gtggtaggag gagggggagt ggaggggcat agcctttccc taattctgcc 32341 ttaaataaaa ctgcattgct gattcagtga tgattcctta cttcgtgcat agaggggagg 32401 cgggagctgt aatctacgtt agcccactta agatgtatta gagcagggaa gtgactggtc 32461 tgtaatcagg gtccccctag accagtctct acaggtggaa ccctgaagtt tcaatcctta 32521 gccacccact aatgctctta ctggatcaca gggaggaatg agagtccctg gcaggagccc 32581 aggagggaag gcaaccaaga tgggacatac ataacagttg tgaactggct tcagtcactt 32641 tcctgcttag ctcaggggct tgtcaaaggc cctgtcagtg aagcctcctt cgctctgccc 32701 aaaccaaaag ttctagaagg aagatattgg ggatagtcct aggaaatacc cctcccttcc 32761 catctgccac acaaatcaga gccactaatg aatatacagc ctcagggcac agatacctaa 32821 gaaaacaagt caccacttct tgagatcaca ggctttattc ctacaaccac agggcttgag 32881 cctgactggg gcaagaaaac agagtttcat ctgagaatgt ctcttatggg ctgggttctg 32941 ttcaggggag ggtgggaaca gaggacaagg aagacaagct cctctggccc taggaacaaa 33001 acacatttac tccttcaaag aagcagatga tctgaatacc ctctggagac tgaatctgcc 33061 catacagccc ctggagccaa tgggcagaca gtactggcat ctggcacaaa agggaattca 33121 gacccagaac agaagcagca aaatatttta aaaatagtaa attgttcctg gactcacaaa 33181 tcattgtttt taagggcaag tgcatgccca atataagtac tggggcttcc taagagagct 33241 gacataggat tacacagctg cctccctgct tcagtggagg ccctcacatc ccctttgaac 33301 acttaacttg ggtaggagag gtagcctttt cgtctctgtt ctgggttctg agagctctgc 33361 agtctggagg cacagcagac tgaggctgac ctgggccctg tcctttctgc ctggcagtca 33421 caggatgttg tctctacctg gagacaaagc tggtttccgg tcccagacag ctggtcaagg 33481 gagggtagtg tgggtcaaca ctggccctca gcactcctga gggggcaaag aggatgggca 33541 aagtttggag caggaggaat cctaggtaaa ggtcaggatc atgttcactg gatggtcagg 33601 cagcggtggc tgaagaggtg actgatgaca gatgggtcag ccacagtaga catgtccccg 33661 aggtcatggt cattctgagc aatcttccga agcactcgcc tcatgatttt ccctggggaa 33721 ccacagacct ctagttactt ggtgaaagca ctgacccacc ctagccctgc caaaggcttt 33781 catccacgca caccccacca ccaccaggcc tcagcccatc ccaatccatg gaggcctctg 33841 aacatacctg agcgggtttt aggcaagcca ggtgcattct ggatgtagtc tggtgtggca 33901 atggggccaa tcttttctct aactgtaacc aacaaatcat caagcatttc ttcagcaccc 33961 ttagccagac ttttcaaaaa tcaaagtaga gatggctttg ttccccacct gtttcctcct 34021 caagtccctg cccacagaga cagcctcagg ttcactgctt ctcttgctct caacacactt 34081 gtctctttac tctctcattt tatcttatgg aactcaggct gtagaatgag cctgctagag 34141 tttaaatgcc acctttctag cagtgtggcc ttgggcaagt gatttaactt ccatgagtct 34201 cagtttcatc atctttagca tgaaggtaac aataagatct gtttcatgga ggtgactcta 34261 gggattaagt ggggtaattc atttaaagca cttagcctag cggtggcaca aagtattcta 34321 gaaatgttgg ctattattat tatcctagtg ggagactagt ggagac
//

Human GSS Protein Sequence 1 matnwgsllq dkqqleelar qavdralaeg vllrtsqept ssevvsyapf tlfpslvpsa 61 lleqayavqm dfnllvdavs qnaafleqtl sstikqddft arlfdihkqv lkegiaqtvf 121 lglnrsdymf qrsadgspal kqieintisa sfgglasrtp avhrhvlsvl sktkeagkil -continued

```
181 snnpskglal giakawelyg spnalvllia qekernifdq raienellar nihvirrtfe
241 disekgsldq drrlfvdgqe iavvyfrdgy mprqyslqnw earlllersh aakcpdiatq
301 lagtkkvqqe lsrpgmleml lpgqpeavar lratfaglys ldvgeegdqa iaealaapsr
361 fvlkpqregg gnnlygeemv qalkqlkdse erasyilmek iepepfencl lrpgsparvv
421 qciselgifg vyvrqektlv mnkhvghllr tkaiehadgg vaagvavldn pypv
```

*Mus musculus* glutathione synthetase, mRNA (cDNA clone MGC:6012 IMAGE:3593913), complete cds

```
   1 cccacgcgtc cgcagctgga caacgagcga gttgggatgg ctaccagctg gggcagcatc
  61 ttgcaggatg agaagcagct ggaagaactg gcaaagcagg ccatagaccg ggccctggcc
 121 gagggcgtgt tgctgaggtc cgcacagcat cccagctcct ccgacgtggt gacatatgcc
 181 ccattcacgc ttttcccctc gccagtaccc agtgctctgc tggagcaggc ctatgctgtg
 241 cagatggact tcaacatact ggtggatgct gtcagccaga acccagcctt cctggagcaa
 301 acactgtcta gcaccatcaa aaaggacgac tatactgccc gtctctttga tatctacaaa
 361 caagtcctga aagagggcat tgcccagacc gtgttcctgg gcctgaatcg ctcagattac
 421 atgttccagt gcggcgcaga cggctccaaa gccctgaaac agatcgagat caacactatc
 481 tctgccagct ttgggggcct ggcctcccgg actccagctg tgcaccgaca cgttctcaat
 541 gtcctgaata agaccaaaga agcttccaag atcctgtcca ataaccccag caagggactg
 601 gccctgggga tcgccaaagc ctgggagctc tatggctcag ctaatgcggt ggtgctactg
 661 attgctcaag agaaggaaag gaacatattt gaccagcgtg ccgtagagaa cgagctgcta
 721 gacaggaaga tccatgtcat ccgtggaaga tttgaagatg tctctgaaag gggttctctg
 781 gaccaaaacc gaaggctgtt tatggatgac caggaagttg ctgtggtgta cttccgagat
 841 ggctacatgc ccagtcagta taattcacag aactgggaag cacgcctgat gctagagaga
 901 tctcgtgctg ccaagtgtcc agacattgcc atacagctgg ctgggactaa gaaggtgcag
 961 caggaactga gcagggtggg tctgctggaa gcactgctcc cgggccagcc cgaggctgtg
1021 gcccgcctcc gagccacctt tgctggcctc tattcactgg acatgggtga agaaggggac
1081 caggccattg ctgaggccct tgctgctcct agccactttg tgctgaagcc ccagagagag
1141 ggtggaggta acaacttata cggggaagaa atggtacaag ctctggagca gctgaaggac
1201 agtgaggaga gagcctccta catcctcatg gagaagattg aacctgagcc ttttaggaat
1261 tgcttgctac ggcctggcag ccctgcccaa gtggtccagt gtatctcgga gctgggtatt
1321 tttggagtct atgtcagaca gggaacaaca ctggtgatga acaagcatgt ggggcacctg
1381 cttcgaacca aagccgtgga gcatgcagac ggaggtgtgg cggcaggagt ggcagtcctg
1441 gacaacccct accctgtgtg aaggcgccat ctggacttca ctcaggaggc cttctatccc
1501 ctgtacttgg cactcctctt ctgaggggtt gcccctgtcc ctatcttagg ggagcttgtc
1561 tcttccatag acctccaaaa cttcagggaa gggaaaaccc agggtatctt ccctcagcag
1621 ccttccagcc gaggaccaga aaagctatga ttccattaga agacttctgg aggtccccag
1681 atctttggag tgtgggaatg gaagctgctt tgaggcaaag gctcataaac cctgcaagtc
1741 ttcatggtct tctcaccagc ctttccagca ggttctagtg ccttgacctg gggtaggacc
1801 gagtgaagga ggaagagggt aaaagggcac agacttcccc agctctgccc taaataaaat
1861 aacaatgctg attcaaaaaa aaaaaaaaa
```

Glutathione synthetase (GSS) [*Mus musculus*] Protein Sequence 1 matswgsilq dekqleelak qaidralaeg vllrsaqhps ssdvvtyapf tlfpspvpsa 61 lleqayavqm dfnilvdavs qnpafleqtl sstikkddyt arlfdiykqv lkegiaqtvf 121 lglnrsdymf qcgadgskal kqieintisa sfgglasrtp avhrhvlnvl nktkeaskil 181 snnpskglal giakawelyg sanavvllia qekernifdq ravenelldr kihvirgrfe 241 dvsergsldq nrrlfmddqe vavvyfrdgy mpsqynsqnw earlmlersr aakcpdiaiq 301 lagtkkvqqe lsrvglleal lpgqpeavar lratfaglys ldmgeegdqa iaealaapsh 361 fvlkpqregg gnnlygeemv qaleqlkdse erasyilmek iepepfrncl lrpgspaqvv 421 qciselfifg vyvrqgttlv mnkhvghllr tkavehadgg vaagvavldn pypv

---

The invention claimed is:

1. A method for producing induced pluripotent stem cells generated from somatic cells of aged donors (A-iPSCs), the method comprising: supplementing somatic cells of aged donors prior to the initiation of reprogramming, during reprogramming, and/or after reprogramming of the somatic cells with an effective amount of pluripotency factor ZSCAN10, thereby producing A-iPSCs with at least one of DNA damage response, apoptosis response, glucose metabolism, and genomic stability levels approximating those of induced pluripotent stem cells from young donors (Y-iPSCs), wherein the supplementation is carried out by adding ZSCAN10 to a culture medium in which the somatic cells are maintained or by transfecting the somatic cells with a vector harboring a nucleic acid sequence encoding ZSCAN10.

2. The method of claim 1, further comprising reducing expression of A-iPSC glutathione peroxidase 2 (GPX2) or glutathione synthase (GSS) by supplementing the A-iPSC with an effective amount of ZSCAN10, thereby rescuing one or more of DNA damage response, apoptosis, and genomic stability in the A-iPSC.

3. The method of claim 1, wherein the supplementation:

is sufficient to restore ZSCAN10 levels in the A-iPSCs to about 50% or more of the respective levels of embryonic stem cells (ESCs);

is sufficient to reduce oxidation capacity of glutathione in the A-iPSCs to about 80% to about 120% of that of ESCs;

is sufficient to restore genomic stability of the A-iPSCs to approximately that of Y-iPSCs;

is sufficient to restore apoptosis rate of the A-iPSCs to approximately that of Y-iPSCs;

is sufficient to restore DNA damage response of the A-iPSCs to approximately that of Y-iPSCs;

is sufficient to reduce oxidation capacity of glutathione in the A-iPSCs to approximately that of Y-iPSCs; and/or is sufficient to reduce GPX2 levels in the A-iPSCs to approximately those of Y-iPSCs.

4. The method of claim 3, wherein the genomic stability is measured by incidence of aneuploid clones; the apoptosis rate is measured by DNA fragmentation assay in response to a DNA damaging agent; and the DNA damage response is measured by ATM or H2AX phosphorylation in response to a DNA damaging agent.

5. A method for reducing the oncogenic potential of induced pluripotent stem cells (iPSCs) or A-iPSCs, the cells having one or more of genomic instability, a defect in apoptosis, a defect in DNA damage response, and a defect in glucose metabolism, and exhibiting excessive glutathione-mediated H2O2 scavenging activity compared to embryonic stem cells (ESCs) or induced pluripotent stem cells from young donors (Y-iPSCs), the method comprising supplementing iPSCs or A-iPSCs with pluripotency factor ZSCAN10 as an adjunct to reprogramming to substantially restore the at least one of DNA damage response, apoptosis response, glucose metabolism and genomic stability to levels substantially the same as those of Y-iPSC or ESC, wherein the supplementation is carried out by adding ZSCAN10 to a culture medium in which the iPSCs or A-iPSCs are maintained, or by transfecting the iPSCs or A-iPSCs with a vector harboring a nucleic acid sequence encoding ZSCAN10.

6. The method of claim 5, wherein the supplementation:

is sufficient to restore ZSCAN10 levels in the iPSCs or A-iPSCs to about 50% or more of the respective levels of embryonic stem cells (ESCs);

is sufficient to reduce oxidation capacity of glutathione in the iPSCs or A-iPSCs to about 80% to about 120% of that of ESCs;

is sufficient to restore genomic stability of the iPSCs or A-iPSCs to approximately that of Y-iPSCs;

is sufficient to restore apoptosis rate of the iPSCs or A-iPSCs to approximately that of Y-iPSCs; and/or is sufficient to restore DNA damage response of the iPSCs or A-iPSCs to approximately that of Y-iPSCs.

7. The method of claim 6, wherein the genomic stability is measured by incidence of aneuploid clones; the apoptosis rate is measured by DNA fragmentation assay in response to a DNA damaging agent; and the DNA damage response is measured by ATM or H2AX phosphorylation in response to a DNA damaging agent.

8. The method of claim 1, wherein the reprogramming of the somatic cells is carried out with Yamanaka factors OCT4, SOX2, KLF4, and MYC.

9. The method of claim 1, wherein the reprogramming of the somatic cells is carried out with pluripotency factors selected from the group of those of Yamanaka wherein one or more of OCT4, SOX2, KLF4 and MYC are replaced as follows: Nanog and Lin28 replace Klf4 and MYC; esrb replaces Klf4; SV40 LT (T) replaces Klf4, MYC lin28 and Nanog; BIX-01294 replaces SOX2, OCT4; VPA replaces Klf4 and MYC.

10. An iPSC derived from a somatic cell of an aged donor (A-iPSC) where the A-iPSC has been engineered to express ZSCAN10 by transfecting the iPSC with a vector harboring nucleic acid for ZSCAN10 at levels comparable to an iPSC derived from a healthy young donor (Y-iPSC) or an embryonic stem cell (ESC), wherein the iPSC comprises the vector harboring nucleic acid for ZSCAN10, and wherein the iPSC originally displayed reduced ZSCAN10 expression levels compared to a Y-iPSC or ESC control.

11. The iPSC of claim 10, wherein the iPSC in the absence of ZSCAN10 supplementation was first deficient in ZSCAN10 expression, expressing either no ZSCAN10 or a level of ZSCAN10 substantially lower than that of a control iPSC derived from a healthy young donor (Y-iPSC) or embryo (ESC).

12. An A-iPSC produced by the method of claim 1, wherein the A-iPSC in the absence of ZSCAN10 supplementation was first deficient in ZSCAN10 expression, expressing either no ZSCAN10 or a level of ZSCAN10 substantially lower than that of a control iPSC derived from a healthy young donor (Y-iPSC) or embryo (ESC), and wherein the A-iPSC comprises a vector harboring nucleic acid for ZSCAN10.

13. An A-iPSC produced by the method of claim 1, wherein the A-iPSC is characterized by ZSCAN10 expression levels, oncogenic potential, GPX2 expression levels, and/or GSS expression levels comparable to those of a control Y-iPSC or embryonic stem cell (ESC).

14. An iPSC or A-iPSC produced by the method of claim 5, wherein the iPSC or A-iPSC exhibits increased ZSCAN10 expression relative to an untreated control iPSC or A-iPSC, and wherein the iPSC or A-iPSC comprises a vector harboring nucleic acid for ZSCAN10.

15. The iPSC or A-iPSC of claim 14, wherein the iPSC or A-iPSC further exhibits decreased GPX2 expression relative to an untreated control iPSC or A-iPSC.

* * * * *